US012747286B2

(12) United States Patent
Schmidt et al.

(10) Patent No.: US 12,747,286 B2
(45) Date of Patent: Sep. 29, 2026

(54) MEANS FOR SPECIFICALLY ELIMINATING PERILIPIN-1 FRAGMENT PRESENTING ADIPOCYTES

(71) Applicant: ALYTAS THERAPEUTICS GMBH, Jena (DE)

(72) Inventors: Martin Schmidt, Jena (DE); Cornelius Alfred Rudolf Lemke, Jena (DE); Ulrich-Eckehard Baumann, Jena (DE)

(73) Assignee: ALYTAS THERAPEUTICS GMBH, Jena (DE)

( * ) Notice: Subject to any disclaimer, the term of this patent is extended or adjusted under 35 U.S.C. 154(b) by 1240 days.

(21) Appl. No.: 17/429,548

(22) PCT Filed: Feb. 13, 2020

(86) PCT No.: PCT/EP2020/053801

§ 371 (c)(1),
(2) Date: Aug. 9, 2021

(87) PCT Pub. No.: WO2020/165366

PCT Pub. Date: Aug. 20, 2020

(65) Prior Publication Data

US 2022/0153822 A1 May 19, 2022

(30) Foreign Application Priority Data

Feb. 13, 2019 (EP) .................................... 19156940

(51) Int. Cl.

| | |
|---|---|
| ***C07K 16/00*** | (2006.01) |
| ***A61K 39/00*** | (2006.01) |
| ***A61P 3/04*** | (2006.01) |
| ***C07K 16/18*** | (2006.01) |

(52) U.S. Cl.

CPC ................ *C07K 16/18* (2013.01); *A61P 3/04* (2018.01); *A61K 2039/505* (2013.01); *C07K 2317/21* (2013.01); *C07K 2317/33* (2013.01); *C07K 2317/34* (2013.01); *C07K 2317/565* (2013.01); *C07K 2317/734* (2013.01); *C07K 2317/92* (2013.01)

(58) Field of Classification Search

None

See application file for complete search history.

(56) References Cited

U.S. PATENT DOCUMENTS

| | | | | |
|---|---|---|---|---|
| 5,585,462 A * | 12/1996 | Londos | C07K 14/47 530/359 |
| 2012/0087862 A1* | 4/2012 | Hood | G01N 33/6845 424/9.1 |
| 2015/0153356 A1* | 6/2015 | Meng | C12N 5/163 506/26 |
| 2017/0211043 A1 | 7/2017 | Guenantin et al. | |

FOREIGN PATENT DOCUMENTS

| | | | |
|---|---|---|---|
| JP | 2002-510965 | A | 4/2002 |
| JP | 2017-522889 | A | 8/2017 |
| WO | 98/41640 | A1 | 9/1998 |
| WO | 02/28410 | A1 | 4/2002 |
| WO | 03/019142 | A2 | 3/2003 |

OTHER PUBLICATIONS

Fenton et al. Rheostat positions: A new classification of protein positions relevant to pharmacogenomics Medicinal Chemistry Research 29:1133-1146; (2020). (Year: 2020).*

Bhattacharya et al. Impact of genetic variation on three dimensional structure and function of proteins PLoS ONE 12(3): e0171355; (2017). (Year: 2017).*

Al Qaraghuli et al. Antibody-protein binding and conformational changes: identifying allosteric signaling pathways to engineer a better effector response. Nature Scientific Reports 10:13969, (2020). (Year: 2020).*

Edwards et al. The remarkable flexibility of the human antibody repertoire; isolation of over one thousand different antibodies to a single protein, BLyS. Journal of Molecular Biology 334:103-118; 2003). (Year: 2003).*

Lloyd et al. Modelling the human immune response: performance of a 10(11) human antibody repertoire against a broad panel of therapeutically relevant antigens. Protein Engineering, Eng. Design & Selection 22(3): 159-168; (2009). (Year: 2009).*

Goel et al. (Plasticity within the antigen-combining site may manifest as molecular mimicry in the humoral immune response. J. Immunol. 173: 7358-7367; (2004). (Year: 2004).*

Khan et al. Adjustable locks and flexible keys: plasticity of epitope-paratope interactions in germline antibodies. J. Immunol. 192:5398-5405; (2014). (Year: 2014).*

Bedouelle et al. Diversity and junction residues as hotspots of binding energy in an antibody neutralizing the dengue virus Febs J. Jan. 2006;273(1):34-46. (Year: 2006).*

(Continued)

*Primary Examiner* — Bridget E Bunner
*Assistant Examiner* — Regina M DeBerry
(74) *Attorney, Agent, or Firm* — SALIWANCHIK, LLOYD & EISENSCHENK

(57) ABSTRACT

The present invention relates to an antigen-binding peptide specifically binding to at least one perilipin-1 epitope as defined herein. The present invention further relates to an antigen-binding peptide for use in the prevention or treatment of obesity. Furthermore, the present invention relates to a bispecific antigen-binding peptide comprising a first binding site specifically binding to a perilipin-1 epitope and a second binding site, and use thereof. The present invention also relates to a pharmaceutical composition, comprising an antigen-binding peptide or a bispecific antigen-binding peptide, for use in the prevention or treatment of obesity. The present invention further relates to an isolated nucleic acid encoding for an antigen-binding peptide or a bispecific antigen-binding peptide. Furthermore, the present invention relates to a recombinant cell comprising said nucleic acid and to a method of producing a means for specifically targeting perilipin-1 fragment presenting adipocytes.

17 Claims, 27 Drawing Sheets

Specification includes a Sequence Listing.

(56) References Cited

OTHER PUBLICATIONS

Brown et al. Tolerance of single, but not multiple, amino acid replacements in antibody VH CDR 2: a means of minimizing B cell wastage from somatic hypermutation? J Immunol. May 1, 1996;156(9):3285-91. (Year: 1996).*

Rudikoff et al. Single amino acid substitution altering antigen-binding specificity Proc. Natl. Acad. Sci. USA, 79(6):1979-1983, Mar. 1982. (Year: 1982).*

Speakman et al. Animal models of obesity. Obesity Reviews vol. 8, Suppl 1:55-61 (2007) (Year: 2007).*

Corvillo, Fernando et al., "Autoantibodies Against Perilipin 1 as a Cause of Acquired Generalized Lipodystrophy," Frontiers in Immunology, vol. 9, Article 2142, pp. 1-13, Sep. 19, 2018.

Deng, Xiaoxiang et al., "Enhancing antibody patent protection using epitope mapping information," MABS, vol. 10, No. 2, pp. 204-209, Dec. 7, 2017.

Dickinson, Keith et al., "Antibody-Induced Lysis of Isolated Rat Epididymal Adipocytes and Complement Activation In Vivo," Obesity Research, vol. 10, No. 2, pp. 122-127, Feb. 1, 2002.

Greenberg, Andrew S. et al., "Perilipin, a Major Hormonally Regulated Adipocyte-specific Phosphoprotein Associated with the Periphery of Lipid Storage Droplets*," The Journal of Biological Chemistry, vol. 266, No. 17, pp. 11341-11346, Jun. 15, 1991.

Mathieson, Peter W. et al., "Complement-mediated Adipocyte Lysis by Nephritic Factor Sera," J. Exp. Med., vol. 177, No. 6, pp. 1827-1831, Jun. 1, 1993.

Wang, Yanxin et al., "Perilipin Expression in Human Adipose Tissues: Effects of Severe Obesity, Gender, and Depost," Obesity Research, vol. 11, No. 8, pp. 930-936, Aug. 1, 2003.

* cited by examiner

B

| Spot-Nr. | Acc. Nr. | Name of protein | MR (kDa) | Mascot-Score | Sequence Coverage (%) |
|---|---|---|---|---|---|
| 1 | NP_037226 | Perilipin A (*R. norvegicus*) | 55.6 | 125 | 53.2 |
| 2 | NP_037226 | Perilipin A (*R. norvegicus*) | 55.6 | 149 | 51.1 |
| 3 | AAA41831 | Perilipin B (*R. norvegicus*) | 42.4 | 99 | 43.9 |
| 4 | NP_037226 | Perilipin A (*R. norvegicus*) | 55.6 | 89 | 31.5 |
| 5 | AAA41831 | Perilipin B (*R. norvegicus*) | 42.4 | 73 | 31.2 |

A Human pAb aF-AK, 10 µg/ml

B Human polyclonal antibody aF-AK, 1 µg/ml and 10 µg/ml

A

Figure 10, continued
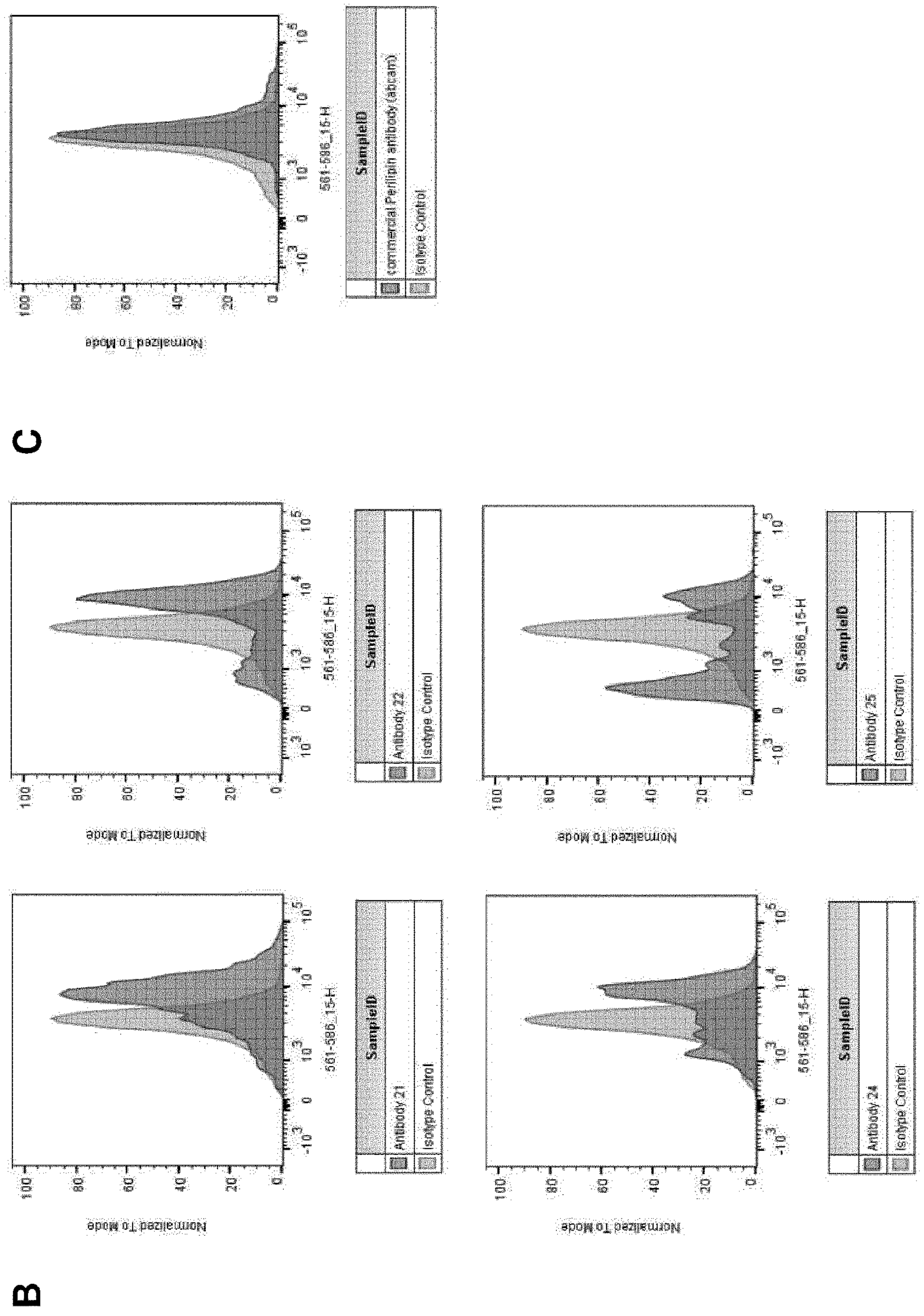

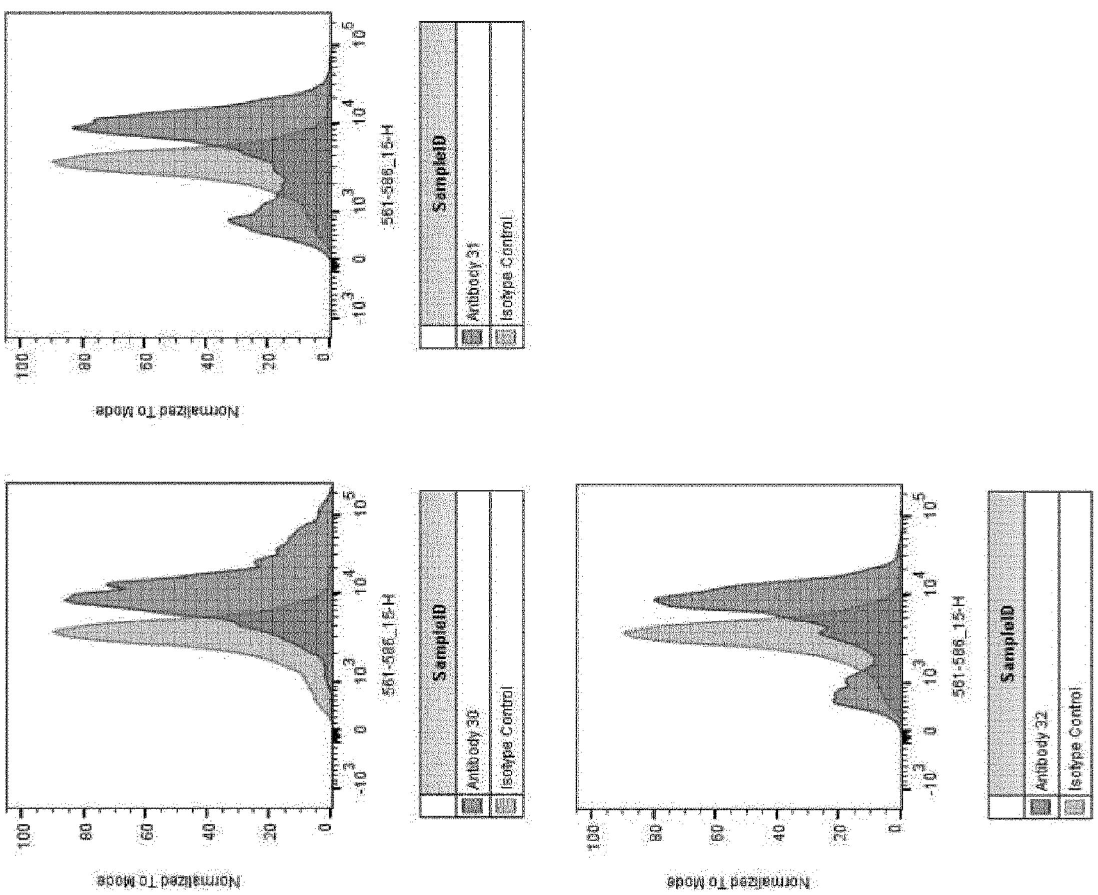
Figure 11, continued

A

Figure 12, continued
B
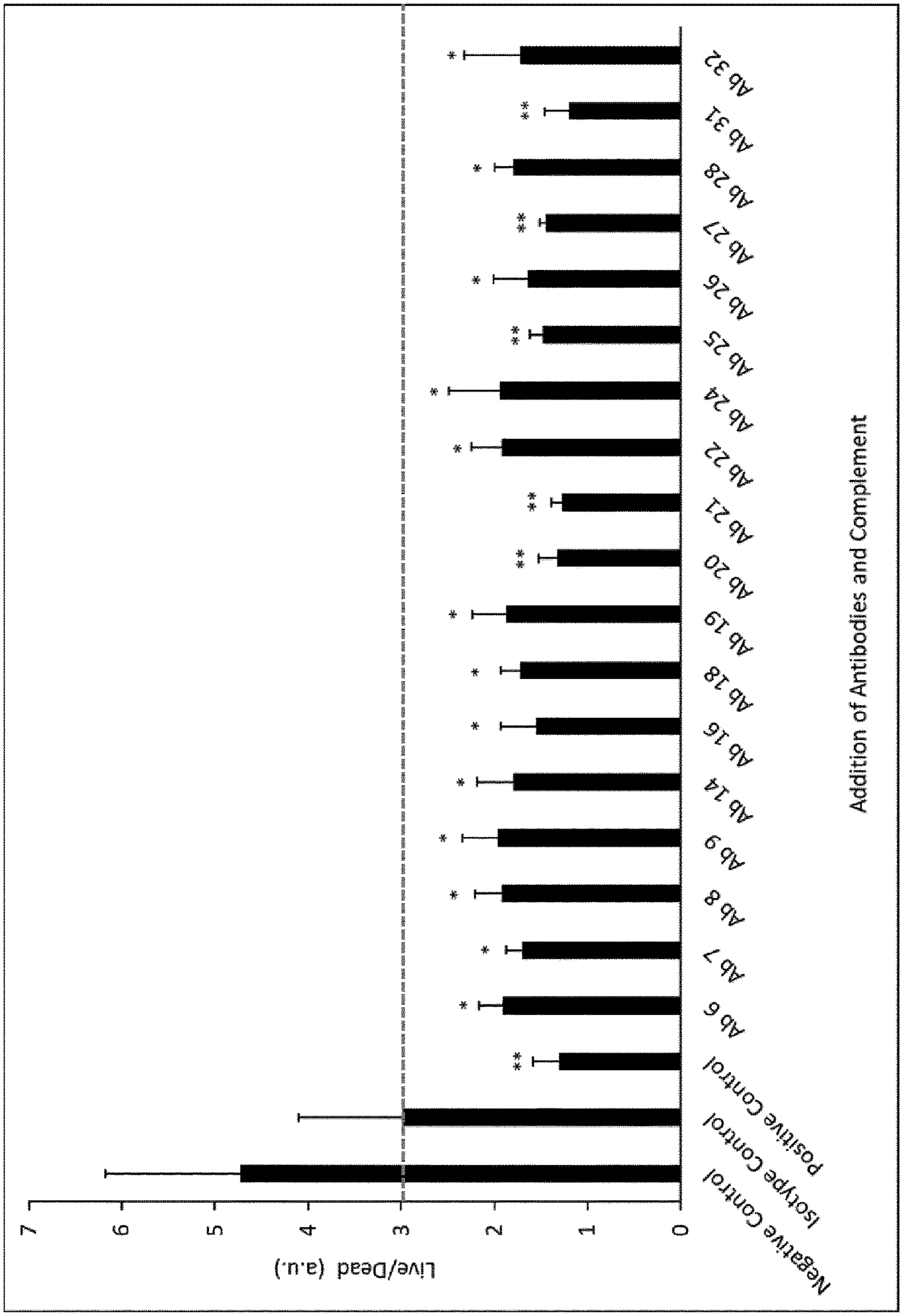

A

No Antibody

Isotype Control Antibody

Figure 13, continued
B
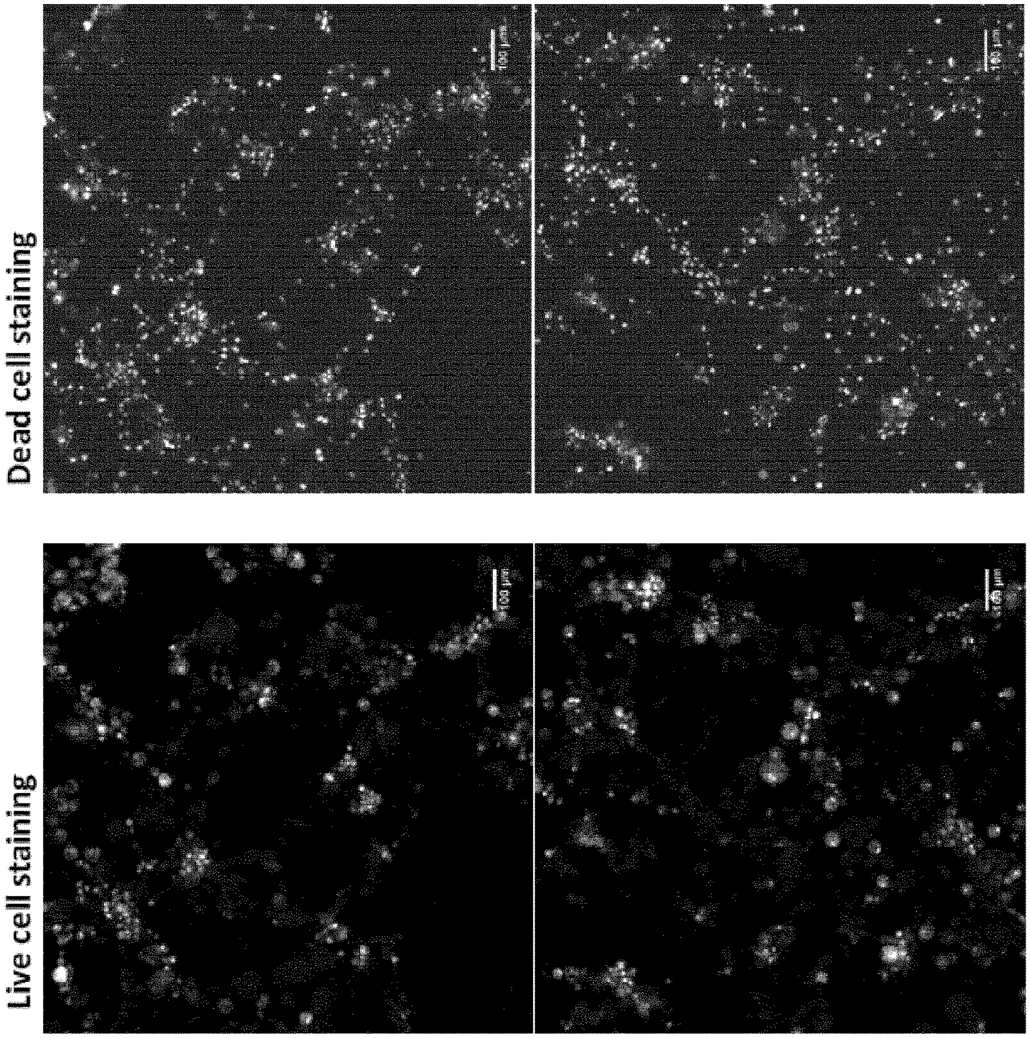
Antibody 20
Antibody 25

A

B

Figure 15, continued
C
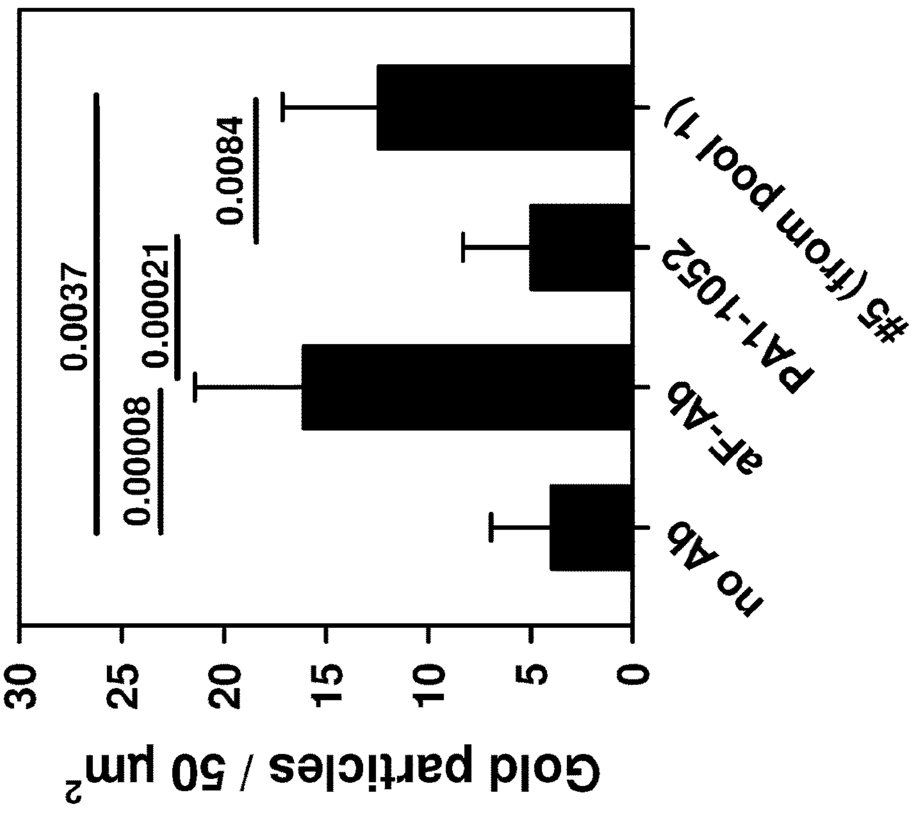

Figure 16

| Antibody No. | HCDR | LCDR |
|---|---|---|
| 5 | SYAMH_VISYDGSNKYYADSVKG_IAAAGPFDY | SGSSSNIGNNAVN_YDDLLPS_AAWDDSLNGVV |
| 6 | SYAMS_AISGSGGSTYYADSVKG_GFRRLFDP | TGTSSDVGGYNYVS_DVSNRPS_SSYTSSSTHVV |
| 7 | SYAMH_VISYDGSNKYYADSVKG_FASIAARPFDY | SGSSSNIGSNTVN_SNNQRPS_AAWDDSLNGRYV |
| 8 | SYGIS_WISAYNGNTNYAQKLQG_GGSSSNY | TGTSSDVGGYNYVS_EVSNRPS_SSYTSSSTLV |
| 9 | SYGMH_VISYDGSNKYYADSVKG_NPSSGADY | SGSSSNIGSNYVY_RNNQRPS_AAWDDSLSGAWV |
| 10 | SYAIS_GIIPIFGTANYAQKFQG_SHSSGWEW | SGSSSNIGSNYVY_RNNQRPS_AAWDDSLSGVV |
| 11 | SYGIS_WISAYNGNTNYAQKLQG_LYCSGGSCYSALDP | TGSSSNIGAGYDVH_GNSNRPS_QSYDSSLRYVV |
| 13 | DYAMH_GISWNSGSIGYADSVKG_EDGSYALDY | RASQSISSYLN_AASSLQS_QQSYSTPPT |
| 14 | DYAMH_GISWNSGSIGYADSVKG_EGYGNDAFDI | RASQSISSYLN_AASSLQS_QQSYSTPPT |
| 16 | SYGMH_AISYDGSNKYYADSVKG_DMGLSWYGEFDY | SGSSSNIGNNAVS_YDDLLPS_AAWDDSLNWV |
| 17 | SYGMH_VISYDGSNKYYADSVKG_DIFMDV | TGTSSDVGGYNYVS_DVSNRPS_SSYTSSSTLVV |
| 18 | DYGMH_VISYDGSNKYYADSVKG_AYGEGGFDP | TGTSSDVGGYNYVS_EVSNRPS_SSYTSSSTTWV |
| 19 | SYAMH_VISYDGSNKYYADPVKG_GGDGYNWDAFDI | SGSSSNIGSNTVN_SNNQRPS_AAWDDSLNALV |
| 20 | DYAMH_GISWNSGSIGYADSVKG_EGRYGGFDY | QASQDISNYLN_DASNLET_QQYDNLPLT |
| 21 | DYAMH_GISWNSGSIGYADSVKG_EGEYSYGGGEFDP | TGTSSDVGGYNYVS_DVSNRPS_SSYTSSSTWV |
| 22 | SYGMH_VISYDGSNKYYADSVKG_TPGGLTPFDY | SGSSSNIGGNTVN_SNNQRPS_AAWDDSLNGPNVV |
| 23 | DYAMH_GISWNSGSIGYADSVKG_DIAGGDYPVFDY | RASQSISSWLA_KASSLES_QQYNSYSPWT |
| 24 | SYAMS_AISGSGGSTYYADSVKG_ESYYDSSGYTT | TGSSSNIGAGYDVH_GNSNRPS_QSYDSSLSGYV |
| 25 | DYAMH_GISWNSGSIGYADSVKG_AQYYYDSSGSYVGESFDY | RASQSISSYLN_AASSLQS_QQSYSTPT |
| 26 | SYAMH_VISYDGSNKYYADSVKG_ELYYGPGGMDV | TGSSSNIGAGYDVH_GNSNRPS_QSYDSSLSGSV |
| 27 | NYAMS_AISGSGGSTYYADSVKG_VEVSSWYENWFDP | RASQSISSYLN_AASSLQS_QQSYSTPLT |
| 28 | SYAMH_VISYDGSNKYYADSVKG_DSGVVMDY | TGTSSDVGGYNYVS_DVSNRPS_SSYTSSSTLV |
| 29 | SYAMS_AISGSGGSAYYADSVKG_VGMVQGARNWFDP | RASQSISSYLN_AASSLQS_QQSYSTPLT |
| 30 | SYAMS_AISGSGGSTYYADSVKG_VRVSDGRFDY | KSSQSVLYSSNNKNYLA_WASTRES_QQYYSTPT |
| 31 | SYAMH_VISYDGSNKYYADSVKG_DTILID | RSSQSLLYSNGYNYLD_LGSNRAS_MQALQTPIT |
| 32 | SYAMH_VISYDGSNKYYADSVKG_DVHHPDYGGNSAFDY | QASQDISNYLN_DASNLET_QQYDNLPLT |

Figure 16, continued

| Antibody No. | HCDR | LCDR |
|---|---|---|
| 33 | SYAMH_VISYDGSNKYYADSVKG_DRYGDYDGSAFDI | QASQDISNYLN_DASNLET_QQYDNLPLT |
| 34 | DYAMH_GISWNSGSIGYADSVKG_EGGDSDFDY | RASQSISSYLN_AASSLQS_QQSYSTPVT |
| 35 | DYYMH_LVDPEDGETLYAEKFQG_EPQMVQGPSPPDY | TGTSSDVGGYSYVS_DVSNRPS_SSYTSSSTLL |
| 36 | SYAMH_VISYDGSNKYYADSVKG_DPLYGMDV | TGTSSDVGNYNYVS_EVSKRPS_ASYADSNNLYV |
| 37 | SYYMH_IINPSGGSTSYAQKFQG_DSYYDSSGYYYADAFDI | TGSSSNIGAGYDVH_GNSNRPS_QSYDSSLSGDVV |
| 38 | SYYMH_IINPSGGSTSYAQKFQG_NVPGDYEVGFDY | TGSSSNIGAGYDVH_GNSNRPS_QSYDSSLSAVV |
| 39 | DYAMH_GISWNSGSIGYADSVKG_DTTWGGSYPYFDY | RASQSISSWLA_KASSLES_QQYNSYSPLA |
| 40 | DYYMS_YISSSSSYTNYADSVKG_LSTVTRAFDI | RASQGISSWLA_AASSLQS_QQANSFPPT |
| 41 | NAWMS_AISGSGGSTYYADSVKG_NEGGDAFDI | RSSQSLVYSDGNTYLN_KVSNRDS_MQGTHWPLT |
| 42 | NYAMH_VISYDGSKKYYADSVKG_EDPRRGGIDY | TGSSSNIGAGYDVH_GNSNRPS_QSYDSSLSGYV |
| 43 | SYAIS_GIIPIFGTANYAQKSQG_ESGSGNRIPYGMDV | TGSSSNIGAGYDVH_GNSNRPS_QSYDSSLSGPVV |
| 44 | SYAMH_VISYDGSNKYYADSVKG_DALYNYYGSGSHFDY | QASQDISNYLN_DASNLET_QQYDNLPLT |
| 45 | SYAMH_VISYDGSNKYYADSVKG_DKGDSSFDY | TGSSSNIGAGYDVH_GNSNRPS_QSYDSSLSGVV |
| 46 | SYAMH_VISYDGSNKYYADSVKG_DQYDILTGYGGTALDY | TGTSSDVGGYNYVS_EVSKRPS_SSYAGSNNLV |
| 47 | SYAMH_VISYDGSNKYYADSVKG_EAGEGVDY | TGSSSNIGAGYDVH_GNSNRPS_QSYDSSLSGYV |
| 48 | SYAMH_VISYDGSNKYYADSVKG_ESAYSSSWSGLRFDP | TGSSSNIGAGYDVH_GNSNRPS_QSYDSSLSGYV |
| 49 | SYAMH_VISYDGSNKYYADSVKG_GGAVAGGWYFDY | RASQGISSWLA_AASSLQS_QQANSFPPT |
| 50 | SYAMH_VISYDGSNKYYADSVKG_SGSYFGFDY | RSSQSLLHSNGYNYLD_LGSNRAS_MQALQTPLT |
| 51 | SYAMH_VISYDGSNKYYAGSVKG_DWRGVYFDY | TGTSSDVGGYNYVS_EVSNRPS_SSYTSSSTLV |
| 52 | SYGIS_WISAYNGNTNYAQKLQG_WGVVGGMDV | RASQGISSWLA_AASSLQS_QQANSFPLT |
| 53 | SYGMH_VISYDGSNKYYADSVKG_DFSDAFDI | SGSSSNIGNNYVS_DNNKRPS_GTWDSSLSAVV |
| 54 | SYGMH_VISYDGSNKYYADSVKG_GSGWYFDY | RASQSISSWLA_KASSLES_QQYNSYSWT |
| 55 | SYYMH_IINPSGGSTSYAQKFQG_DDYGDY | TGTSSDVGGYNYVS_EVSNRPS_SSYTSSSFS |
| 56 | SYYMH_IINPSGGSTSYAQKFQG_DSSSGWSSYFDY | QASQDISNYLN_DASNLET_QQYDNLPLT |
| 57 | SYYMH_IINPSGGSTSYAQKFQG_MTTSLGFDY | RASQGISNWLA_AASSLQS_QQANSLPLT |
| 58 | SYYMH_IINPSGGSTSYAQKFQG_SRGGSAFDI | RSSQSLLHSNGYNYLD_LGSNRAS_MQALQTPLT |

Figure 17

| Antibody No. | AA of VH | AA of VL |
|---|---|---|
| 5 | QVQLVESGGGVVQPGRSLRLSCAASGFTFSSYAMHWVRQAPG<br>KGLEWVAVISYDGSNKYYADSVKGRFTISRDNSKNTLYLQMNSL<br>RAEDTAVYYCARIAAAGPFDYWGQGTLVTVSS | SYVLTQPPSVSEAPRQRVTISCSGSSSNIGNNAVNWYQQ<br>LPGKAPKLLIYYDDLLPSGVSDRFSGSKSGTSASLAISGL<br>QSEDEADYYCAAWDDSLNGVVFGGGTKLTVL |
| 6 | EVQLLESGGGLVQPGGSLRLSCAASGFTFSSYAMSWVRQAPG<br>KGLEWVSAISGSGGSTYYADSVKGRFTISRDNSKNTLYLQMNSL<br>RAEDTAVYYCANGFRRLFDPWGQGTLVTVSS | QSALTQPASVSGSPGQSITISCTGTSSDVGGYNYVSWYQ<br>QHPGKAPKLMIYDVSNRPSGVSNRFSGSKSGNTASLTIS<br>GLQAEDEADYYCSSYTSSSTHVVFGGGTKLTVL |
| 7 | QVQLVQSGGSVVQPGRSLRLSCAASGFTFSSYAMHWVRQAPG<br>KGLEWVAVISYDGSNKYYADSVKGRFTISRDNSKNTLYLQMNSL<br>RAEDTAVYYCARFASIAARPFDYWGQGTLVTVSS | QSVLTQPPSASGTPGQRVTISCSGSSSNIGSNTVNWYQQ<br>LPGTAPKLLIYSNNQRPSGVPDRFSGSKSGTSASLAISGL<br>QSEDEADYYCAAWDDSLNGRYVFGTGTKLTVL |
| 8 | QVQLVESGAEVKKPGASVKVSCKASGYTFTSYGISWVRQAPGQ<br>GLEWMGWISAYNGNTNYAQKLQGRVTMTTDTSTSTAYMELRSL<br>RSDDTAVYYCARGGSSSNYWGQGTLVTVSS | QSALTQPASVSGSPGQSITISCTGTSSDVGGYNYVSWYQ<br>QHPGKAPKLMIYEVSNRPSGVSNRFSGSKSGNTASLTIS<br>GLQAEDEADYYCSSYTSSSTLVFGGGTKLTVL |
| 9 | QVQLVQSGGGVVQPGRSLRLSCAASGFTFSSYGMHWVRQAPG<br>KGLEWVAVISYDGSNKYYADSVKGRFTISRDNSKNTLYLQMNSL<br>RAEDTAVYYCANNPSSGADYWGQGTLVTVSS | QSVLTQPPSASGTPGQRVTISCSGSSSNIGSNYVYWYQQ<br>LPGTAPKLLIYRNNQRPSGVPDRFSGSKSGTSASLAISGL<br>RSEDEADYYCAAWDDSLSGAWVFGGGTKLTVL |
| 10 | EVQLVQSGAEVKKPGSSVKISCKASGGTFSSYAISWVRQAPGQ<br>GLEWMGGIIPIFGTANYAQKFQGRVTITADESTSTAYMELSSLRS<br>EDTAVYYCARSHSSGWEWWGQGTLVTVSS | QSVLTQPPSASGTPGQRVTISCSGSSSNIGSNYVYWYQQ<br>LPGTAPKLLIYRNNQRPSGVPDRFSGSKSGTSASLAISGL<br>RSEDEADYYCAAWDDSLSGVVFGGGTKLTVL |
| 11 | QVQLVQSGAEVKKPGASVKVSCKASGYTFTSYGISWVRQAPGQ<br>GLEWMGWISAYNGNTNYAQKLQGRVTMTTDTSTSTAYMELRSL<br>RSDDTAVYYCASLYCSGGSCYSALDPWGQGTLVTVSS | QSVLTQPPSVSGAPGQRVTISCTGSSSNIGAGYDVHWY<br>QQLPGTAPKLLIYGNSNRPSGVPDRFSGSKSGTSASLAIT<br>GLQAEDEADYYCQSYDSSLRYVVFGGGTKVTVL |
| 13 | QVQLVQSGGGLVQPGRSLRLSCAASGFTFDDYAMHWVRQAPG<br>KGLEWVSGISWNSGSIGYADSVKGRFTISRDNAKNSLYLQMNSL<br>RAEDTALYYCAKEDGSYALDYWGQGTLVTVSS | DIQMTQSPSSLSASVGDRVTITCRASQSISSYLNWYQQK<br>PGKAPKLLIYAASSLQSGVPSRFSGSGSGTDFTLTISSLQ<br>PEDFATYYCQQSYSTPPTFGGGTKLEIK |
| 14 | QVQLVESGGGLVQPGRSLRLSCAASGFTFDDYAMHWVRQAPG<br>KGLEWVSGISWNSGSIGYADSVKGRFTISRDNAKNSLYLQMNSL<br>RAEDTALYYCAKEGYGNDAFDIWGQGTMVTVSS | DIVMTQSPSSLSASVGDRVTITCRASQSISSYLNWYQQKP<br>GKAPKLLIYAASSLQSGVPSRFSGSGSGTDFTLTISSLQP<br>EDFATYYCQQSYSTPPTFGQGTKVEIK |
| 16 | QVQLVEFGGGVVQPGRSLRLSCAASGFTFSSYGMHWVRQAPG<br>KGLEWVAAISYDGSNKYYADSVKGRFTISRDNSKNTLYLQMNSL<br>RAEDTAVYYCAKDMGLSWYGEFDYWGQGTLVTVSS | QSVLTQPPSVSEAPRQRVTISCSGSSSNIGNNAVSWYQQ<br>LPGKAPKLLIYYDDLLPSGVSDRFSGSKSGTSASLAISGL<br>QSEDEADYYCAAWDDSLNWVFGGGTKLTVL |
| 17 | EVQLVQSGGGVVQPGRSLRLSCAASGFTFSSYGMHWVRQAPG<br>KGLEWVAVISYDGSNKYYADSVKGRFTISRDNSKNTLYLQMNSL<br>RAEDTAVYYCAKDIFMDVWGQGTMVTVSS | QSALTQPASVSGSPGQSITISCTGTSSDVGGYNYVSWYQ<br>QHPGKAPKLMIYDVSNRPSGVSNRFSGSKSGNTASLTIS<br>GLQAEDEADYYCSSYTSSSTLVVFGGGTKLTVL |

Figure 17, continued

| Antibody No. | AA of VH | AA of VL |
|---|---|---|
| 18 | EVQLLESGGGLVQPGRSLRLACVASGFTFDDYGMHWVRQAPGKGLEWVAVISYDGSNKYYADSVKGRFTISRDNSKNTLYLQMNSLRAEDTAVYYCAKAYGEGGFDPWGQGTLVTVSS | QSALTQPASVSGSPGQSITISCTGTSSDVGGYNYVSWYQQHPGKAPKLMIYEVSNRPSGVSNRFSGSKSGNTASLTISGLQAEDEADYYCSSYTSSSTTWVFGGGTKVTVL |
| 19 | QVQLVQSGGGVVQPRRSLRLSCAASGFTFSSYAMHWVRQAPGKGLEWVAVISYDGSNKYYADPVKGRFTISRDNSKNTLYLQMNSLRAEDTAVYYCARGGDGYNWDAFDIWGQGTMVTVSS | SYVLTQPPSASGTPGQRVTISCSGSSSNIGSNTVNWYQQLPGTAPKLLIYSNNQRPSGVPDRFSGSKSGTSASLAISGLQSEDEADYYCAAWDDSLNALVFGGGTKLTVL |
| 20 | EVQLVESGGGLVQPGRSLRLSCAASGFTFDDYAMHWVRQAPGKGLEWVSGISWNSGSIGYADSVKGRFTISRDNAKNSLYLQMNSLRAEDTALYYCAKEGRYGGFDYWGQGTLVTVSS | DIQMTQSPSSLSASVGDRVTITCQASQDISNYLNWYQQKPGKAPKLLIYDASNLETGVPSRFSGSGSGTDFTFTISSLQPEDIATYYCQQYDNLPLTFGGGTKVEIK |
| 21 | QVQLVESGGGLVQPGRSLRLSCAASGFTFDDYAMHWVRQAPGKGLEWVSGISWNSGSIGYADSVKGRFTISRDNAKNSLYLQMNSLRAEDTALYYCAKEGEYSYGGGEFDPWGQGTLVTVSS | QSALTQPASVSGSPGQSITISCTGTSSDVGGYNYVSWYQQHPGKAPKLMIYDVSNRPSGVSNRFSGSKSGNTASLTISGLQAEDEADYYCSSYTSSSTWVFGGGTKLTVL |
| 22 | QVQLVESGGGVVQPGRSLRLSCAASGFTFSSYGMHWVRQAPGKGLEWVAVISYDGSNKYYADSVKGRFTISRDNSKNTLYLQMNSLRAEDTAVYYCANTPGGLTPFDYWGQGTLVTVSS | QSVLTQPPSASGTPGQRVTISCSGSSSNIGGNTVNWYQQLPGTAPKLLIYSNNQRPSGVPDRFSGSKSGTSASLAISGLQSEDEADYYCAAWDDSLNGPNVVFGGGTKLTVL |
| 23 | QVQLVQSGGGLVQPGRSLRLSCAASGFTFDDYAMHWVRQAPGKGLEWVSGISWNSGSIGYADSVKGRFTISRDNAKNSLYLQMNSLRAEDTALYYCAKDIAGGDYPVFDYWGQGTLVTVSS | DIQLTQSPSTLSASVGDRVTITCRASQSISSWLAWYQQKPGKAPKLLIYKASSLESGVPSRFSGSGSGTEFTLTISSLQPDDFATYYCQQYNSYSPWTFGQGTKLEIK |
| 24 | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKESYYDSSGYTTWGQGTLVTVSS | QSVLTQPPSVSGAPGQRVTISCTGSSSNIGAGYDVHWYQQLPGTAPKLLIYGNSNRPSGVPDRFSGSKSGTSASLAITGLQAEDEADYYCQSYDSSLSGYVFGTGTKLTVL |
| 25 | QVQLVQSGGGLVQPGRSLRLSCAASGFTFDDYAMHWVRQAPGKGLEWVSGISWNSGSIGYADSVKGRFTISRDNAKNSLYLQMNSLRAEDTAVYYCAKAQYYYDSSGSYVGESFDYWGQGTLVTVSS | DIVMTQSPSSLSASVGDRVTITCRASQSISSYLNWYQQKPGKAPKLLIYAASSLQSGVPSRFSGSGSGTDFTLTISSLQPEDFATYYCQQSYSTPTFGQGTKVEIK |
| 26 | EVQLLESGGGVVQPGRSLRLSCAASGFTFSSYAMHWVRQAPGKGLEWVAVISYDGSNKYYADSVKGRFTISRDNSKNTLYLQMNSLRAEDTAVYYCARELYYGPGGMDVWGQGTLVTVSS | QSVLTQPPSVSGAPGQRVTISCTGSSSNIGAGYDVHWYQQLPGTAPKLLIYGNSNRPSGVPDRFSGSKSGTSASLAITGLQAEDEADYYCQSYDSSLSGSVFGGGTKLTVL |
| 27 | EVQLLESGGGLVQPGGSLRLSCAASGITFSNYAMSWVRQAPGKGLEWVSAISGSGGSTYYADSVKGRFTISRDNSKNTLYLQMNSLRAEDTAVYYCAKVEVSSWYENWFDPWGQGTLVTVSS | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTRLEIK |
| 28 | QVQLVQSGGGVVQPGRSLRLSCAASGFTFSSYAMHWVRQAPGKGLEWVAVISYDGSNKYYADSVKGRFTISRDNSKNTLYLQMNSLRAEDTAVYYCARDSGVVMDYWGQGTLVTVSS | QSALTQPASVSGSPGQSITISCTGTSSDVGGYNYVSWYQQHPGKAPKLMIYDVSNRPSGVSNRFSGSKSGNTASLTISGLQAEDEADYYCSSYTSSSTLVFGGGTKVTVL |

Figure 17, continued

| Antibody No. | AA of VH | AA of VL |
|---|---|---|
| 29 | EVQLLESGGGLVQPGGSLRLSCAASGFTFSSYAMSWVRQAPGKGLEWVSAISGSGGSAYYADSVKGRFTISRDNSKNTLYLQMNSLRAEDTAVYYCAKVGMVQGARNWFDPWGQGTTVTVSS | DIVMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIK |
| 30 | EVQLVQSGGGLVQPGGSLRLSCAASGFTFSSYAMSWVRQAPGKGLEWVSAISGSGGSTYYADSVKGRFTISRDNAKNSLYLQMNSLRAEDTAVYYCARVRVSDGRFDYWGQGTLVTVSS | DIVMTQSPDSLAVSLGERATINCKSSQSVLYSSNNKNYLAWYQQKPGQPPKLLIYWASTRESGVPDRFSGSGSGTDFTLTISSLQAEDVAVYYCQQYYSTPTFGGGTKLEIK |
| 31 | EVQLLESGGGVVQPGRSLRLSCAASGFTFSSYAMHWVRQAPGKGLEWVAVISYDGSNKYYADSVKGRFTISRDNSKNTVSLQMSSLRADDTAIYYCVKDTILIDWGQGTLVTVSS | DIVMTQSPLSLPVTPGEPASISCRSSQSLLYSNGYNYLDWYLQKPGQSPQLLIYLGSNRASGVPDRFSGSGSGTDFTLKISRVEAEDVGIYYCMQALQTPITFGQGTRLEIK |
| 32 | EVQLLESGGGVVQPGRSLRLSCAASGFTFSSYAMHWVRQAPGKGLEWVAVISYDGSNKYYADSVKGRFTISRDNSKNTLYLQMDSLRAEDTAVYYCARDVHHPDYGGNSAFDYWGQGTLVTVSS | DIVMTQSPSSLSASVGDRVTITCQASQDISNYLNWYQQKPGKAPKLLIYDASNLETGVPSRFSGSGSGTDFTFTISSLQPEDIATYYCQQYDNLPLTFGGGTKLEIK |
| 33 | EVQLLESGGGVVQPGRSLRLSCAASGFTFSSYAMHWVRQAPGKGLEWVAVISYDGSNKYYADSVKGRFTISRDNSKNTLYLQMNSLRAEDTAVYYCARDRYGDYDGSAFDIWGQGTMVTVSS | DIVMTQSPSSLSASVGDRVTITCQASQDISNYLNWYQQKPGKAPKLLIYDASNLETGVPSRFSGSGSGTDFTFTISSLQPEDIATYYCQQYDNLPLTFGGGTRLEIK |
| 34 | QVQLVESGGGLVQPGRSLRLSCAASGFTFDDYAMHWVRQAPGKGLEWVSGISWNSGSIGYADSVKGRFTISRDNAKNSLYLQMNSLRAEDTALYYCAKEGGDSDFDYWGQGTLVTVSS | DIVMTQSPSSLSASVGDRVTITCRASQSISSYLNWYQQKPGKAPKLLIYAASSLQSGVPSRFSGSGSGTDFTLTISSLQPEDFATYYCQQSYSTPVTFGGGTKVDIK |
| 35 | QVQLVQSGAEVKKPGTTVKISCKVSGYSFTDYYMHWVQQAPGKGLEWMGLVDPEDGETLYAEKFQGRVTITVDTSTDTAYMELSSLRSEDTAVYYCAAEPQMVQGPSPPDYWGQGTLVTVSS | QSALTQPASVSGSPGQSITISCTGTSSDVGGYSYVSWYQQHPGKAPKLMIYDVSNRPSGVSNRFSGSKSGNTASLTISGLQAEDEADYYCSSYTSSSTLLFGGGTKLTVL |
| 36 | EVQLVESGGGVVQPGRSLRLSCAASGFTFSSYAMHWVRQAPGKGLEWVAVISYDGSNKYYADSVKGRFTISRDNSKNTLYLQMNSLRAEDTAVYYCARDPLYGMDVWGQGTLVTVSS | QSVLTQPPSASGSPGQSVTISCTGTSSDVGNYNYVSWFQQHPGKAPKLMIYEVSKRPSGVPDRFSGSKSGNTASLTVSGLQAEDEADYYCASYADSNNLYVFGTGTKLTVL |
| 37 | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARDSYYDSSGYYYADAFDIWGQGTMVTVSS | QSVLTQPPSVSGAPGQRVTISCTGSSSNIGAGYDVHWYQQLPGTAPKLLIYGNSNRPSGVPDRFSGSKSGTSASLAITGLQAEDEADYYCQSYDSSLSGDVVFGGGTKLTVL |
| 38 | EVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARNVPGDYEVGFDYWGQGTLVTVSS | QSVLTQPPSVSGAPGQRVTISCTGSSSNIGAGYDVHWYQQLPGTAPKLLIYGNSNRPSGVPDRFSGSKSGTSASLAITGLQAEDEADYYCQSYDSSLSAVVFGGGTKLTVL |

Figure 17, continued

| Antibody No. | AA of VH | AA of VL |
|---|---|---|
| 39 | QVQLVESGGGLVQPGRSLRLSCAASGFTFDDYAMHWVRQAPGKGLEWVSGISWNSGSIGYADSVKGRFTISRDNAKNSLYLQMNSLRAEDTALYYCAKDTTWGGSYPYFDYWGQGTLVTVSS | DIQLTQSPSTLSASVGDRVTITCRASQSISSWLAWYQQKPGKAPKLLIYKASSLESGVPSRFSGSGSGTEFTLTISSLQPDDFATYYCQQYNSYSPLAFGGGTKLEIK |
| 40 | EVQLLESGGGLVKPGGSLRLSCAASGFTFSDYYMSWIRQAPGKGLEWVSYISSSSSYTNYADSVKGRFTISRDNAKNSLYLQMNSLRAEDTAVYYCARLSTVTRAFDIWGQGTMVTVSS | DIQLTQSPSSVSASVGDRVTITCRASQGISSWLAWYQQKPGKAPKLLIYAASSLQSGVPSRFSGSGSGTDFTLTISSLQPEDFATYYCQQANSFPPTFGQGTKLEIK |
| 41 | QVQLVQSGGGVVQPGRSQRLSCAASGFTFSNAWMSWVRQAPGKGLEWVSAISGSGGSTYYADSVKGRFTISRDNSKNTLYLQMNSLRAEDTAVYYCAANEGGDAFDIWGQGTMVTVSS | DVVMTQSPLSLPVTLGQPASISCRSSQSLVYSDGNTYLNWFQQRPGQSPRRLIYKVSNRDSGVPDRFSGSGSGTDFTLKISRVEAEDVGVYYCMQGTHWPLTFGGGTKLEIK |
| 42 | QVQLVESGGGVVQPGRSLRLSCAASGFTFSNYAMHWVRQAPGKGLEWVAVISYDGSKKYYADSVKGRFTISRDNSKNTLYLQMNSLGAEDMAVYYCAREDPRRGGIDYWGQGTLVTVSS | QSVLTQPPPVSGAPGQRVTISCTGSSSNIGAGYDVHWYQQLPGTAPKLLIYGNSNRPSGVPDRFSGSKSGTSASLAITGLQAEDEADYYCQSYDSSLSGYVFGTGTKVTVL |
| 43 | QVQLVQSGAEVKKPGSSVKVSCKASGGTFSSYAISWVRQAPGQGLEWMGGIIPIFGTANYAQKSQGRVTITADESTSTAYMELSSLRSEDTAVYYCARESGSGNRIPYGMDVWGQGTMVTVSS | QSVLTQPPSVSGAPGQRVTISCTGSSSNIGAGYDVHWYQQLPGTAPKLLIYGNSNRPSGVPDRFSGSKSGTSASLAITGLQAEDEADYYCQSYDSSLSGPVVFGGGTQVTVL |
| 44 | QVQLVESGGGVVQPGRSLRLSCAASGFTFSSYAMHWVRQAPGKGLEWVAVISYDGSNKYYADSVKGRFTISRDNSKNTLYLQMNSLRAEDTAVYYCARDALYNYYGSGSHFDYWGQGTLVTVSS | DIVMTQSPSSLSASVGDRVTITCQASQDISNYLNWYQQKPGKAPKLLIYDASNLETGVPSRFSGSGSGTDFTFTISSLQPEDIATYYCQQYDNLPLTFGGGTRLEIK |
| 45 | QVQLVESGGGVVQPGRSLRLSCAASGFTFSSYAMHWVRQAPGKGLEWVAVISYDGSNKYYADSVKGRFTISRDNSKNTLYLQMNSLRAEDTAVYYCARDKGDSSFDYWGQGTLVTVSS | QSVLTQPPSVSGAPGQRVTISCTGSSSNIGAGYDVHWYQQLPGTAPKLLIYGNSNRPSGVPDRFSGSKSGTSASLAITGLQAEDEADYYCQSYDSSLSGVVFGGGTKVTVL |
| 46 | QVQLVQSGGGVVQPGRSLRLSCAASGFTFSSYAMHWVRQAPGKGLEWVAVISYDGSNKYYADSVKGRFTISRDNSKNTLYLQMNSLRAEDTAVYYCARDQYDILTGYGGTALDYWGQGTLVTVSS | QSALTQPPSASGSPGQSVTISCTGTSSDVGGYNYVSWYQQHPGEAPKLMIYEVSKRPSGVPDRFSGSKSGNTASLTVSGLQAEDEADYYCSSYAGSNNLVFGGGTKLTVL |
| 47 | QVQLVQSGGGVVQPGRSLRLSCAASGFTFSSYAMHWVRQAPGKGLEWVAVISYDGSNKYYADSVKGRFTISRDNSKNTLYLQMNSLRAEDTAVYYCAREAGEGVDYWGQGTLVTVSS | QSVLTQPPSVSGAPGQRVTISCTGSSSNIGAGYDVHWYQQLPGTAPKLLIYGNSNRPSGVPDRFSGSKSGTSASLAITGLQAEDEADYYCQSYDSSLSGYVFGTGTKLTVL |
| 48 | EVQLVQSGGGVVQPGRSLRLSCAASGFTFSSYAMHWVRQAPGKGLEWVAVISYDGSNKYYADSVKGRFTISRDNSKNTLYLQMNSLRAEDTAVYYCAAESAYSSSWSGLRFDPWGQGTLVTVSS | QSVLTQPPSVSGAPGQRVTISCTGSSSNIGAGYDVHWYQQLPGTAPKLLIYGNSNRPSGVPDRFSGSKSGTSASLAITGLQAEDEADYYCQSYDSSLSGYVFGTGTKLTVL |

Figure 17, continued

| Antibody No. | AA of VH | AA of VL |
|---|---|---|
| 49 | EVQLVESGGGVVQPGRSLRLSCAASGFTFSSYAMHWVRQAPGKGLEWVAVISYDGSNKYYADSVKGRFTISRDNSKNTLYLQMNSLRAEDTAVYYCARGGAVAGGWYFDYWGQGTLVTVSS | DIVMTQSPSSVSASVGDRVTITCRASQGISSWLAWYQQKPGKAPKLLIYAASSLQSGVPSRFSGSGSGTDFTLTISSLQPEDFATYYCQQANSFPPTFGQGTKLEIK |
| 50 | QVQLVESGGGVVQPGRSLRLSCAASGFTFSSYAMHWVRQAPGKGLEWVAVISYDGSNKYYADSVKGRFTISRDNSKNTLYLQMNSLRAEDTAVYYCARSGSYFGFDYWGQGTLVTVSS | DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPLTFGGGTKLEIK |
| 51 | QVQLQESGGGVVQPGRSLRLSCAASGFTFSSYAMHWVRQAPGKGLEWVAVISYDGSNKYYAGSVKGRFTISRDNSKNTLYLQMNSLRAEDTAVYYCARDWRGVYFDYWGQGTLVTVSS | QSALTQPASVSGSPGQSITISCTGTSSDVGGYNYVSWYQQHPGKAPKLMIYEVSNRPSGVSNRFSGSKSGNTASLTISGLQAEDEADYYCSSYTSSSTLVFGGGTKLTVL |
| 52 | QVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCASWGVVGGMDVWGQGTLVTVSS | DIQMTQSPSSVSASVGDRVTITCRASQGISSWLAWYQQKPGKAPKLLIYAASSLQSGVPSRFSGSGSGTDFTLTISSLQPEDFATYYCQQANSFPLTFGGGTKVDIK |
| 53 | QVQLVQSGGGVVQPGRSLRLSCAASGFTFSSYGMHWVRQAPGKGLEWVAVISYDGSNKYYADSVKGRFTISRDNSKNTLYLQMNSLRAEDTAVYYCAKDFSDAFDIWGQGTMVTVSS | QSVLTQPPSVSAAPGQKVTISCSGSSSNIGNNYVSWYQQLPGTAPKLLIYDNNKRPSGIPDRFSGSKSGTSATLGITGLQTGDEADYYCGTWDSSLSAVVFGGGTKVTVL |
| 54 | EVQLLESGGGVVQPGRSLRLSCAASGFTFSSYGMHWVRQAPGKGLEWVAVISYDGSNKYYADSVKGRFTISRDNSKNTLYLQMNSLRAEDTAVYYCAKGSGWYFDYWGQGTLVTVSS | DIVMTQSPSTLSASVGDRVTITCRASQSISSWLAWYQQKPGKAPKLLIYKASSLESGVPSRFSGSGSGTEFTLTISSLQPDDFATYYCQQYNSYSWTFGQGTKLEIK |
| 55 | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARDDYGDYWGQGTLVTVSS | QSALTQPASVSGSPGQSITIPCTGTSSDVGGYNYVSWYQQHPGKAPKLMIYEVSNRPSGVSNRFSGSKSGNTASLTISGLQAEDEADYYCSSYTSSSFSFGTGTKLTVL |
| 56 | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARDSSSGWSSYFDYWGQGTLVTVSS | DIQLTQSPSSLSASVGDRVTITCQASQDISNYLNWYQQKPGKAPKLLIYDASNLETGVPSRFSGSGSGTDFTFTISSLQPEDIATYYCQQYDNLPLTFGGGTKVEIK |
| 57 | QVQLVESGAEVKKPGASVKVSCKASGYTFTSYYMHWVRQAPGQGLEWMGIINPSGGSTSYAQKFQGRVTMTRDTSTSTVYMELSSLRSEDTAVYYCARMTTSLGFDYWGQGTLVTVSS | DIQLTQSPSSVSASVGDKVTITCRASQGISNWLAWYQLKPGKAPKLLVYAASSLQSGVPSRFSGSGSGTDFTLTISNLQPEDFATYYCQQANSLPLTFGGGTRLEIK |
| 58 | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARSRGGSAFDIWGQGTLVTVSS | DVVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPLTFGGGTKVDIK |

MEANS FOR SPECIFICALLY ELIMINATING PERILIPIN-1 FRAGMENT PRESENTING ADIPOCYTES

CROSS REFERENCE TO RELATED APPLICATIONS

This application is a National Stage Application of International Application Number PCT/EP2020/053801, filed Feb. 13, 2020; which claims priority to European Patent Application No. 19156940.9, filed Feb. 13, 2019.

The Sequence Listing for this application is labeled "SeqList-27Jul21-ST25.txt", which was created on Jul. 27, 2021 and is 178 KB. The entire content is incorporated herein by reference in its entirety.

FIELD OF THE INVENTION

The present invention relates to an antigen-binding peptide specifically binding to at least one perilipin-1 epitope as defined herein. The present invention further relates to an antigen-binding peptide for use in the prevention or treatment of obesity. Furthermore, the present invention relates to a bispecific antigen-binding peptide comprising a first binding site specifically binding to a perilipin-1 epitope and a second binding site, and use thereof. The present invention also relates to a pharmaceutical composition, comprising an antigen-binding peptide or a bispecific antigen-binding peptide, for use in the prevention or treatment of obesity. The present invention further relates to an isolated nucleic acid encoding for an antigen-binding peptide or a bispecific antigen-binding peptide. Furthermore, the present invention relates to a recombinant cell comprising said nucleic acid and to a method of producing a means for specifically targeting perilipin-1 fragment presenting adipocytes.

BACKGROUND OF THE INVENTION

Obesity is a worldwide problem and according to the World Health Organization, more than 1.9 billion are overweight. People suffering from obesity are commonly predisposed to a variety of medical conditions. Surgical intervention is presently a successful therapeutic approach, however, complications often arise with subsequent gastrointestinal problems. Thus, surgical intervention is considered acceptable merely in patients, which are highly obese with high comorbidity. Pharmacotherapies that were relatively promising had to be withdrawn from the market because of serious side effect profiles. The pleiotropic nature of the signaling mechanisms involved caused unacceptable side effects. Accordingly, there is a lack of therapeutic approaches which are successful in long-term and which have negligible side effects.

The harmful long-term effects of excess body fat are widely known. However, there is also a medical condition resulting in loss of body fat, namely lipodystrophy. Although metabolic complications vary with regard to the degree of fat loss, common consequences of lipodystrophy are insulin resistance or diabetes mellitus, absence of ketosis, increased metabolic rates, hyperlipidemia, as well as hepatomegaly including fatty liver. These implications result from the absence of metabolically active adipocytes irrespective of the underlying cause of adipocyte loss, as shown in various animal models. Lipodystrophy widely gained interest as a common side effect of some anti-retroviral drugs, which cause partial redistribution of fat.

Perilipin-1 is specifically expressed in adipocytes, but not in other cells storing triacylglycerols such as hepatocytes [1]. In such other cells, other members of the lipid droplet associated proteins, such as adipophilin and TIP47, occur instead of perilipin-l. As perilipin-1 shields the lipid storage droplets in adipocytes from the activity of lipolytic enzymes, any mechanism leading to depletion of lipid storage droplet-associated perilipin-1 may result in increased lipolysis and release of lipids stored in droplets (and thereby aggravate the metabolic situation).

Accordingly, a reduction of fat mass is expected at the expense of an unfavourable metabolic situation. Said unfavourable metabolic situation can be prevented by completely eliminating said adipocytes. Since other types of lipid storing cells do not present perilipin-1, targeting perilipin-1 for activation of an immune-effector mechanism against adipocytes may allow for specific elimination of adipocytes. WO 02/028410 A1 discloses that perilipin may be a target for regulation of body weight, muscle mass and diabetes. Greenberg et al. (J. Biol. Chem., 1991, vol. 266, no. 17, pp. 11341-11346) describes perilipin-1 and discloses that it is intracellularly present on the surface of lipid droplets within adipocytes, such as lipid storage droplets.

The autoimmune reaction against adipocytes leads to almost complete loss of adipose tissue as observed in generalized acquired lipoatrophy (AGL) [2]. There is broad clinical evidence for an autoimmune etiology in most cases of the classical acquired lipodystrophies. In a patient with acquired generalized lipodystrophy, serum autoantibodies against adipose tissue were found [2]. Particularly, autoantibodies against perilipin-1 were found to be associated with acquired generalized lipodystrophy [3].

Accordingly, effector systems which cause fat loss in lipodystrophy patients could be used to specifically target fat tissue in patients suffering from obesity. However, such specific effector systems, which may, for example, be antibodies or antigen-binding fragments, or cytotoxic T cells, have not been provided. Particularly, despite many efforts, no adipocyte-specific epitopes have been identified so far which could potentially be targeted as specific therapeutic targets [4].

Accordingly, the present invention aims to provide means for specifically targeting and/or eliminating adipocytes, such as an antigen-binding peptide or a cytotoxic T cell. Furthermore, the present invention aims to provide a method of producing a means for specifically targeting adipocytes.

SUMMARY OF THE INVENTION

The present invention relates to epitopes of perilipin-1, which are molecular target structures to specifically target and/or eliminate adipocytes. Particularly, the herein disclosed epitopes are target structures of the intracellular protein perilipin-1 which are presented on the surface of adipocytes. Antigen-binding peptides that target the herein disclosed epitopes can be used alone or in combination with any therapeutic agent to target and/or eliminate adipocytes by activating an immune effector system, such as an exogenous effector system or an endogenous effector system. The herein disclosed epitopes are also useful for generating perilipin-1 specific cytotoxic T cells, which are capable of targeting perilipin-1 fragment presenting adipocytes.

The present inventors disclose perilipin-1 as the autoantigen targeted by autoantibodies from the serum of a patient with AGL. Furthermore, the present inventors disclose various epitopes of perilipin-1 having any of SEQ ID Nos. 1-6, 330-333 and provide antibodies and antigen-binding fragments targeting said epitopes which are useful in the treatment of obesity. The present inventors have surprisingly found that perilipin-1 and/or fragments thereof are present on the surface(s) of adipocytes, rather than merely coating or surrounding intracellular lipid droplets within such adipocytes, such as lipid storage droplets. Without wishing to be bound by any theory, the inventors have found that perilipin-1 and/or fragments thereof become presented or are otherwise present on the surface(s) of adipocytes and thus may be specifically targeted.

The present invention further relates to producing a means to specifically target adipocytes. These means to specifically target adipocytes are useful in treating or preventing a disease and/or a medical condition related to obesity.

The present invention aims at using an exogenous or endogenous effector system of the immune system to specifically target and/or eliminate adipocytes. Such an exogenous effector system may be, for example, ex vivo or in vitro generated and/or amplified antibodies and/or cytotoxic T cells. The herein disclosed epitopes of perilipin-1, which are SEQ ID NOs. 1-6, 330-333, allow for specifically targeting adipocytes via perilipin-1 fragments presented on said adipocytes, in particular present on the surface(s) of said adipocytes. Targeting said adipocytes via perilipin-1 using an antigen-binding peptide specific for any of SEQ ID NOs. 1-6, 330-333 marks said adipocytes for an effector system such as the complement system, which results in the activation of the complement system, and/or Fc-receptors, such as FcRIII (CD16), Fc-RII (CD32), Fc-RI (CD64), or others, which results in the recruitment and activation of effector systems such as ADCC (antibody dependent cellular cytotoxicity) by NK (natural killer) cells or ADCP (antibody dependent cellular phagocytosis) by macrophages, neutrophils, or any other effector system carrying the respective Fc-receptor. The recruitment of one of those effector systems leads consequently to the targeting and/or elimination of said adipocytes. Alternatively, said adipocytes can be directly targeted by cytotoxic T cells specific for perilipin-1, particularly specific for any of SEQ ID NOs. 1-6, 330-333, which then eliminate said adipocytes presenting at least one of those perilipin-1 epitopes. Accordingly, a means to specifically target and/or eliminate an adipocyte according to the present invention may either directly eliminate said adipocyte, in case of ADCP, and thus be a direct elimination means, or may indirectly eliminate said adipocyte by targeting said adipocyte resulting in an activation of an effector system such as the complement system or ADCC or cytotoxic T cells, and thus be an indirect elimination means.

The cell type specificity of the effector reaction is secured by the specificity of the cellular antigen, namely perilipin-1, particularly the epitopes having an amino acid sequence according to any of SEQ ID NOs. 1-6, 330-333. Accordingly, the present invention provides a means to specifically target and/or eliminate adipocytes without off-target effects on other cells, and thus with only negligible side effects.

Furthermore, the targeting of adipocytes for an immune effector system using an antigen-binding peptide allows for systemic application, e.g. by an infusion, and/or allows for fine-tuned, targeted administration to eliminate certain fat depots by administration into the respective fat depot, such as by injection into a target fat depot.

The present invention uses the adipocyte specific presentation of a fragment of a typically intracellular protein, i.e. of a protein which so far had only been known to be present intracellularly, on the surface of an adipocyte, namely a perilipin-1 fragment, perilipin-1 being essential for storage of lipids in adipocytes. The present inventors disclose herein six peptide sequences which are epitopes on perilipin-1, which were identified by analyzing the binding pattern of an anti-perilipin-1 autoantibody of a patient having lipoatrophy. The present inventors also disclose further peptide sequences which are variations of such epitopes which variations of epitopes comprise additional residues, and which may equally well serve as epitopes. The plurality of the identified epitopes is highly conserved in the perilipin-1 sequences of mice and humans.

The target antigen epitopes of perilipin-1 disclosed herein allow for a) immunizing an animal with said target structures to produce polyclonal or monoclonal antibodies and/or antigen-binding fragments against perilipin-1 peptides presented by adipocytes,
b) screening a recombinant antibody library and/or small molecule libraries to identify specific antibodies, antigen-binding fragments, or other suitable affinity ligands against perilipin-1 peptides presented by adipocytes, and/or
c) isolating and/or generating cytotoxic T cells in vitro, which are specific for perilipin-1 peptides presented by adipocytes.

With the antibodies, antibody fragments, or other suitable affinity ligands produced by a method in accordance with a) or b), it is possible to induce a specific immune effector reaction by marking said adipocytes in vivo. Furthermore, with the cytotoxic T cells produced by a method in accordance with c), adipocytes are indirectly eliminable in vivo.

In the following, the elements of the invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine two or more of the explicitly described embodiments or which combine the one or more of the explicitly described embodiments with any number of the disclosed and/or preferred elements. Furthermore, any permutations and combinations of all described elements in this application should be considered disclosed by the description of the present application unless the context indicates otherwise.

In a first aspect, the present invention relates to an antigen-binding peptide specifically binding to at least one perilipin-1 epitope selected from the following amino acid sequences: LTLLDGDLPE (SEQ ID NO. 1), EKIASELK (SEQ ID NO. 2), VPIASTSDKV (SEQ ID NO. 3), PAPGHQQAQK (SEQ ID NO. 4), PSLLSRVGALTN (SEQ ID NO. 5), and PWLHSLAA (SEQ ID NO. 6). In one embodiment, said at least one perilipin-1 epitope is selected from the following amino acid sequences: NKGLTLLDGDLPEQE (SEQ ID NO: 330), QYPPEKIASELKDTI (SEQ ID NO:331), AKPSLLSRVGALTNT (SEQ ID NO: 332), and EVRVPWLHSLAAAQE (SEQ ID NO:333).

In one embodiment, said antigen-binding peptide binds to more than one of SEQ ID NO. 1-6 and SEQ ID NO: 330-333.

In one embodiment, said perilipin-1 epitope is a human perilipin-1 epitope.

In one embodiment, said antigen-binding peptide is not a perilipin-1 targeting autoantibody of a human patient having lipoatrophy, and wherein preferably said antigen-binding peptide is not a perilipin-1 targeting anti-PLIN1 antibody directed to the peptide spanning Thr8-Ala145 having catalog #AF6615 from manufacturer R&D.

In one embodiment, said antigen-binding peptide competes for binding with a perilipin-1 targeting autoantibody of a human patient having lipoatrophy.

In one embodiment, said antigen-binding peptide binds to perilipin-1 in a binding assay with an affinity ($K_D$) of at least $10^{-4}$ M.

In one embodiment, said antigen-binding peptide is an antibody, preferably a monoclonal antibody.

In one embodiment, said antigen-binding peptide is a polyclonal antibody.

In one embodiment, said antigen-binding peptide, in particular said antibody, when incubated in the presence of complement, with 3T3-L1-cells that have been differentiated into adipocytes, causes a complement-mediated cell death of said 3T3-L1-cells and/or said differentiated adipocytes.

In one embodiment, said complement-mediated cell death is determined, preferably numerically determined, by determining the ratio of live vs. dead cells, using an appropriate dye or mixture of dyes, such as a fluorescent dye or mixture of fluorescent dyes. Typically, such dye or mixture of dyes distinguishes between live and dead cells. An example for such mixture of dyes is the dye commercially available as "FluoroQuench™ Staining/Quenching Reagent" from ThermoFisher. Preferably, said 3T3-L1-cells have been differentiated into adipocytes using an appropriate differentiation medium, such as a serum-free differentiation (SFD) medium, supplemented with insulin, and optionally further supplemented with dexamethasone and/or isobutyl-1-methylxanthine.

In one embodiment, said complement is selected from a mammal complement, preferably human complement or rodent complement. In one embodiment, said rodent complement is rabbit complement or mouse complement. Complement is commercially available through a variety of companies such as BAG Diagnostics GmbH, BAG Health Care, or Bio-Rad. Alternatively, blood serum or plasma may serve as a source of complement.

In one embodiment, said antigen-binding peptide, in particular said antibody, binds to the surface(s) of adipocytes, when said antigen-binding peptide, in particular said antibody, is incubated with said adipocytes. In one embodiment, said binding of said antigen-binding peptide, preferably of said antibody, to the surface(s) of said adipocytes is determined by incubating said adipocytes with the respective antigen-binding peptide, preferably with the respective antibody, and thereafter detecting the respective antigen-binding peptide, preferably the respective antibody, when bound to said adipocytes, using an appropriate detection technique, such as an immunochemical detection, alone or in combination with flow cytometry.

The "surface(s)" of said adipocytes, as used herein, typically refers to the outside surface(s) of such adipocytes, i.e. the extracellular surface(s) exposed to the surrounding of said adipocyte(s).

In one embodiment, said antigen-binding peptide, in particular said antibody, when incubated in the presence of complement, with 3T3-L1-cells that have been differentiated into adipocytes, causes a complement-mediated cell death of said 3T3-L1-cells and/or said differentiated adipocytes, and also, upon incubation with adipocytes, binds to the surface(s) of said adipocytes.

In one embodiment, said antigen-binding peptide is an antigen-binding peptide, preferably an antibody, i. comprising a heavy chain CDR1 region comprising the amino acid sequence of SEQ ID NO:18, a heavy chain CDR2 region comprising the amino acid sequence of SEQ ID NO:19, a heavy chain CDR3 region comprising the amino acid sequence of SEQ ID NO:20, a light chain CDR1 region comprising the amino acid sequence of SEQ ID NO:21, a light chain CDR2 region comprising the amino acid sequence of SEQ ID NO:22, and a light chain CDR3 region comprising the amino acid sequence of SEQ ID NO:23; or ii. comprising a heavy chain CDR1 region comprising the amino acid sequence of SEQ ID NO:24, a heavy chain CDR2 region comprising the amino acid sequence of SEQ ID NO:25, a heavy chain CDR3 region comprising the amino acid sequence of SEQ ID NO:26, a light chain CDR1 region comprising the amino acid sequence of SEQ ID NO:27, a light chain CDR2 region comprising the amino acid sequence of SEQ ID NO:28, and a light chain CDR3 region comprising the amino acid sequence of SEQ ID NO:29; or iii. comprising a heavy chain CDR1 region comprising the amino acid sequence of SEQ ID NO:30, a heavy chain CDR2 region comprising the amino acid sequence of SEQ ID NO:31, a heavy chain CDR3 region comprising the amino acid sequence of SEQ ID NO:32, a light chain CDR1 region comprising the amino acid sequence of SEQ ID NO:33, a light chain CDR2 region comprising the amino acid sequence of SEQ ID NO:34, and a light chain CDR3 region comprising the amino acid sequence of SEQ ID NO:35; or iv. comprising a heavy chain CDR1 region comprising the amino acid sequence of SEQ ID NO:36, a heavy chain CDR2 region comprising the amino acid sequence of SEQ ID NO:37, a heavy chain CDR3 region comprising the amino acid sequence of SEQ ID NO:38, a light chain CDR1 region comprising the amino acid sequence of SEQ ID NO:39, a light chain CDR2 region comprising the amino acid sequence of SEQ ID NO:40, and a light chain CDR3 region comprising the amino acid sequence of SEQ ID NO:41; or v. comprising a heavy chain CDR1 region comprising the amino acid sequence of SEQ ID NO:42, a heavy chain CDR2 region comprising the amino acid sequence of SEQ ID NO:43, a heavy chain CDR3 region comprising the amino acid sequence of SEQ ID NO:44, a light chain CDR1 region comprising the amino acid sequence of SEQ ID NO:45, a light chain CDR2 region comprising the amino acid sequence of SEQ ID NO:46, and a light chain CDR3 region comprising the amino acid sequence of SEQ ID NO:47; or vi. comprising a heavy chain CDR1 region comprising the amino acid sequence of SEQ ID NO:48, a heavy chain CDR2 region comprising the amino acid sequence of SEQ ID NO:49, a heavy chain CDR3 region comprising the amino acid sequence of SEQ ID NO:50, a light chain CDR1 region comprising the amino acid sequence of SEQ ID NO:51, a light chain CDR2 region comprising the amino acid sequence of SEQ ID NO:52, and a light chain CDR3 region comprising the amino acid sequence of SEQ ID NO:53; or vii. comprising a heavy chain CDR1 region comprising the amino acid sequence of SEQ ID NO:54, a heavy chain CDR2 region comprising the amino acid sequence of SEQ ID NO:55, a heavy chain CDR3 region comprising the amino acid sequence of SEQ ID NO:56, a light chain CDR1 region comprising the amino acid sequence of SEQ ID NO:57, a light chain CDR2 region comprising the amino acid sequence of SEQ ID NO:58, and a light chain CDR3 region comprising the amino acid sequence of SEQ ID NO:59; or viii. comprising a heavy chain CDR1 region comprising the amino acid sequence of SEQ ID NO:60, a heavy chain CDR2 region comprising the amino acid sequence of SEQ ID NO:61, a heavy chain CDR3 region comprising the amino acid sequence of SEQ ID NO:62, a light chain CDR1 region comprising the amino acid sequence of SEQ ID NO:63, a light chain CDR2 region comprising the amino acid sequence of SEQ ID NO:64, and a light chain CDR3 region comprising the amino acid sequence of SEQ ID NO:65; or ix. comprising a heavy chain CDR1 region comprising the amino acid sequence of SEQ ID NO:66, a heavy chain CDR2 region comprising the amino acid sequence of SEQ ID NO:67, a heavy chain CDR3 region comprising the amino acid sequence of SEQ ID NO:68, a light chain CDR1 region comprising the amino acid sequence of SEQ ID NO:69, a light chain CDR2 region comprising the amino acid sequence of SEQ ID NO:70, and a light chain CDR3 region comprising the amino acid sequence of SEQ ID NO:71; or x. comprising a heavy chain CDR1 region comprising the amino acid sequence of SEQ ID NO:72, a heavy chain CDR2 region comprising the amino acid sequence of SEQ ID NO:73, a heavy chain CDR3 region comprising the amino acid sequence of SEQ ID NO:74, a light chain CDR1 region comprising the amino acid sequence of SEQ ID NO:75, a light chain CDR2 region comprising the amino acid sequence of SEQ ID NO:76, and a light chain CDR3 region comprising the amino acid sequence of SEQ ID NO:77; or xi. comprising a heavy chain CDR1 region comprising the amino acid sequence of SEQ ID NO:78, a heavy chain CDR2 region comprising the amino acid sequence of SEQ ID NO:79, a heavy chain CDR3 region comprising the amino acid sequence of SEQ ID NO:80, a light chain CDR1 region comprising the amino acid sequence of SEQ ID NO:81, a light chain CDR2 region comprising the amino acid sequence of SEQ ID NO:82, and a light chain CDR3 region comprising the amino acid sequence of SEQ ID NO:83; or xii. comprising a heavy chain CDR1 region comprising the amino acid sequence of SEQ ID NO:84, a heavy chain CDR2 region comprising the amino acid sequence of SEQ ID NO:85, a heavy chain CDR3 region comprising the amino acid sequence of SEQ ID NO:86, a light chain CDR1 region comprising the amino acid sequence of SEQ ID NO:87, a light chain CDR2 region comprising the amino acid sequence of SEQ ID NO:88, and a light chain CDR3 region comprising the amino acid sequence of SEQ ID NO:89; or xiii. comprising a heavy chain CDR1 region comprising the amino acid sequence of SEQ ID NO:90, a heavy chain CDR2 region comprising the amino acid sequence of SEQ ID NO:91, a heavy chain CDR3 region comprising the amino acid sequence of SEQ ID NO:92, a light chain CDR1 region comprising the amino acid sequence of SEQ ID NO:93, a light chain CDR2 region comprising the amino acid sequence of SEQ ID NO:94, and a light chain CDR3 region comprising the amino acid sequence of SEQ ID NO:95; or xiv. comprising a heavy chain CDR1 region comprising the amino acid sequence of SEQ ID NO:96, a heavy chain CDR2 region comprising the amino acid sequence of SEQ ID NO:97, a heavy chain CDR3 region comprising the amino acid sequence of SEQ ID NO:98, a light chain CDR1 region comprising the amino acid sequence of SEQ ID NO:99, a light chain CDR2 region comprising the amino acid sequence of SEQ ID NO:100, and a light chain CDR3 region comprising the amino acid sequence of SEQ ID NO:101; or xv. comprising a heavy chain CDR1 region comprising the amino acid sequence of SEQ ID NO:102, a heavy chain CDR2 region comprising the amino acid sequence of SEQ ID NO:103, a heavy chain CDR3 region comprising the amino acid sequence of SEQ ID NO:104, a light chain CDR1 region comprising the amino acid sequence of SEQ ID NO:105, a light chain CDR2 region comprising the amino acid sequence of SEQ ID NO:106, and a light chain CDR3 region comprising the amino acid sequence of SEQ ID NO:107; or xvi. comprising a heavy chain CDR1 region comprising the amino acid sequence of SEQ ID NO:108, a heavy chain CDR2 region comprising the amino acid sequence of SEQ ID NO:109, a heavy chain CDR3 region comprising the amino acid sequence of SEQ ID NO:110, a light chain CDR1 region comprising the amino acid sequence of SEQ ID NO:111, a light chain CDR2 region comprising the amino acid sequence of SEQ ID NO:112, and a light chain CDR3 region comprising the amino acid sequence of SEQ ID NO:113; or xvii. comprising a heavy chain CDR1 region comprising the amino acid sequence of SEQ ID NO:114, a heavy chain CDR2 region comprising the amino acid sequence of SEQ ID NO:115, a heavy chain CDR3 region comprising the amino acid sequence of SEQ ID NO:116, a light chain CDR1 region comprising the amino acid sequence of SEQ ID NO:117, a light chain CDR2 region comprising the amino acid sequence of SEQ ID NO:118, and a light chain CDR3 region comprising the amino acid sequence of SEQ ID NO:119; or xviii. comprising a heavy chain CDR1 region comprising the amino acid sequence of SEQ ID NO:120, a heavy chain CDR2 region comprising the amino acid sequence of SEQ ID NO:121, a heavy chain CDR3 region comprising the amino acid sequence of SEQ ID NO:122, a light chain CDR1 region comprising the amino acid sequence of SEQ ID NO:123, a light chain CDR2 region comprising the amino acid sequence of SEQ ID NO:124, and a light chain CDR3 region comprising the amino acid sequence of SEQ ID NO:125; or xix. comprising a heavy chain CDR1 region comprising the amino acid sequence of SEQ ID NO:126, a heavy chain CDR2 region comprising the amino acid sequence of SEQ ID NO:127, a heavy chain CDR3 region comprising the amino acid sequence of SEQ ID NO:128, a light chain CDR1 region comprising the amino acid sequence of SEQ ID NO: 129, a light chain CDR2 region comprising the amino acid sequence of SEQ ID NO:130, and a light chain CDR3 region comprising the amino acid sequence of SEQ ID NO:131; or xx. comprising a heavy chain CDR1 region comprising the amino acid sequence of SEQ ID NO:132, a heavy chain CDR2 region comprising the amino acid sequence of SEQ ID NO:133, a heavy chain CDR3 region comprising the amino acid sequence of SEQ ID NO:134, a light chain CDR1 region comprising the amino acid sequence of SEQ ID NO:135, a light chain CDR2 region comprising the amino acid sequence of SEQ ID NO:136, and a light chain CDR3 region comprising the amino acid sequence of SEQ ID NO:137; or xxi. comprising a heavy chain CDR1 region comprising the amino acid sequence of SEQ ID NO:138, a heavy chain CDR2 region comprising the amino acid sequence of SEQ ID NO:139, a heavy chain CDR3 region comprising the amino acid sequence of SEQ ID NO:140, a light chain CDR1 region comprising the amino acid sequence of SEQ ID NO:141, a light chain CDR2 region comprising the amino acid sequence of SEQ ID NO:142, and a light chain CDR3 region comprising the amino acid sequence of SEQ ID NO:143; or xxii. comprising a heavy chain CDR1 region comprising the amino acid sequence of SEQ ID NO:144, a heavy chain CDR2 region comprising the amino acid sequence of SEQ ID NO: 145, a heavy chain CDR3 region comprising the amino acid sequence of SEQ ID NO:146, a light chain CDR1 region comprising the amino acid sequence of SEQ ID NO:147, a light chain CDR2 region comprising the amino acid sequence of SEQ ID NO:148, and a light chain CDR3 region comprising the amino acid sequence of SEQ ID NO:149; or xxiii. comprising a heavy chain CDR1 region comprising the amino acid sequence of SEQ ID NO:150, a heavy chain CDR2 region comprising the amino acid sequence of SEQ ID NO:151, a heavy chain CDR3 region comprising the amino acid sequence of SEQ ID NO:152, a light chain CDR1 region comprising the amino acid sequence of SEQ ID NO:153, a light chain CDR2 region comprising the amino acid sequence of SEQ ID NO:154, and a light chain CDR3 region comprising the amino acid sequence of SEQ ID NO:155; or xxiv. comprising a heavy chain CDR1 region comprising the amino acid sequence of SEQ ID NO:156, a heavy chain CDR2 region comprising the amino acid sequence of SEQ ID NO:157, a heavy chain CDR3 region comprising the amino acid sequence of SEQ ID NO:158, a light chain CDR1 region comprising the amino acid sequence of SEQ ID NO:159, a light chain CDR2 region comprising the amino acid sequence of SEQ ID NO:160, and a light chain CDR3 region comprising the amino acid sequence of SEQ ID NO:161; or xxv. comprising a heavy chain CDR1 region comprising the amino acid sequence of SEQ ID NO:162, a heavy chain CDR2 region comprising the amino acid sequence of SEQ ID NO:163, a heavy chain CDR3 region comprising the amino acid sequence of SEQ ID NO:164, a light chain CDR1 region comprising the amino acid sequence of SEQ ID NO:165, a light chain CDR2 region comprising the amino acid sequence of SEQ ID NO:166, and a light chain CDR3 region comprising the amino acid sequence of SEQ ID NO:167; or xxvi. comprising a heavy chain CDR1 region comprising the amino acid sequence of SEQ ID NO:168, a heavy chain CDR2 region comprising the amino acid sequence of SEQ ID NO:169, a heavy chain CDR3 region comprising the amino acid sequence of SEQ ID NO:170, a light chain CDR1 region comprising the amino acid sequence of SEQ ID NO:171, a light chain CDR2 region comprising the amino acid sequence of SEQ ID NO:172, and a light chain CDR3 region comprising the amino acid sequence of SEQ ID NO:173; or xxvii. comprising a heavy chain CDR1 region comprising the amino acid sequence of SEQ ID NO:174, a heavy chain CDR2 region comprising the amino acid sequence of SEQ ID NO:175, a heavy chain CDR3 region comprising the amino acid sequence of SEQ ID NO:176, a light chain CDR1 region comprising the amino acid sequence of SEQ ID NO:177, a light chain CDR2 region comprising the amino acid sequence of SEQ ID NO:178, and a light chain CDR3 region comprising the amino acid sequence of SEQ ID NO:179; or xxviii. comprising a heavy chain CDR1 region comprising the amino acid sequence of SEQ ID NO:180, a heavy chain CDR2 region comprising the amino acid sequence of SEQ ID NO:181, a heavy chain CDR3 region comprising the amino acid sequence of SEQ ID NO:182, a light chain CDR1 region comprising the amino acid sequence of SEQ ID NO:183, a light chain CDR2 region comprising the amino acid sequence of SEQ ID NO:184, and a light chain CDR3 region comprising the amino acid sequence of SEQ ID NO:185; or xxix. comprising a heavy chain CDR1 region comprising the amino acid sequence of SEQ ID NO:186, a heavy chain CDR2 region comprising the amino acid sequence of SEQ ID NO:187, a heavy chain CDR3 region comprising the amino acid sequence of SEQ ID NO:188, a light chain CDR1 region comprising the amino acid sequence of SEQ ID NO:189, a light chain CDR2 region comprising the amino acid sequence of SEQ ID NO:190, and a light chain CDR3 region comprising the amino acid sequence of SEQ ID NO:191; or xxx. comprising a heavy chain CDR1 region comprising the amino acid sequence of SEQ ID NO:192, a heavy chain CDR2 region comprising the amino acid sequence of SEQ ID NO:193, a heavy chain CDR3 region comprising the amino acid sequence of SEQ ID NO:194, a light chain CDR1 region comprising the amino acid sequence of SEQ ID NO:195, a light chain CDR2 region comprising the amino acid sequence of SEQ ID NO:196, and a light chain CDR3 region comprising the amino acid sequence of SEQ ID NO:197; or xxxi. comprising a heavy chain CDR1 region comprising the amino acid sequence of SEQ ID NO:198, a heavy chain CDR2 region comprising the amino acid sequence of SEQ ID NO:199, a heavy chain CDR3 region comprising the amino acid sequence of SEQ ID NO:200, a light chain CDR1 region comprising the amino acid sequence of SEQ ID NO:201, a light chain CDR2 region comprising the amino acid sequence of SEQ ID NO:202, and a light chain CDR3 region comprising the amino acid sequence of SEQ ID NO:203; or xxxii. comprising a heavy chain CDR1 region comprising the amino acid sequence of SEQ ID NO:204, a heavy chain CDR2 region comprising the amino acid sequence of SEQ ID NO:205, a heavy chain CDR3 region comprising the amino acid sequence of SEQ ID NO:206, a light chain CDR1 region comprising the amino acid sequence of SEQ ID NO:207, a light chain CDR2 region comprising the amino acid sequence of SEQ ID NO:208, and a light chain CDR3 region comprising the amino acid sequence of SEQ ID NO:209; or xxxiii. comprising a heavy chain CDR1 region comprising the amino acid sequence of SEQ ID NO:210, a heavy chain CDR2 region comprising the amino acid sequence of SEQ ID NO:211, a heavy chain CDR3 region comprising the amino acid sequence of SEQ ID NO:212, a light chain CDR1 region comprising the amino acid sequence of SEQ ID NO:213, a light chain CDR2 region comprising the amino acid sequence of SEQ ID NO:214, and a light chain CDR3 region comprising the amino acid sequence of SEQ ID NO:215; or xxxiv. comprising a heavy chain CDR1 region comprising the amino acid sequence of SEQ ID NO:216, a heavy chain CDR2 region comprising the amino acid sequence of SEQ ID NO:217, a heavy chain CDR3 region comprising the amino acid sequence of SEQ ID NO:218, a light chain CDR1 region comprising the amino acid sequence of SEQ ID NO:219, a light chain CDR2 region comprising the amino acid sequence of SEQ ID NO:220, and a light chain CDR3 region comprising the amino acid sequence of SEQ ID NO:221; or xxxv. comprising a heavy chain CDR1 region comprising the amino acid sequence of SEQ ID NO:222, a heavy chain CDR2 region comprising the amino acid sequence of SEQ ID NO:223, a heavy chain CDR3 region comprising the amino acid sequence of SEQ ID NO:224, a light chain CDR1 region comprising the amino acid sequence of SEQ ID NO:225, a light chain CDR2 region comprising the amino acid sequence of SEQ ID NO:226, and a light chain CDR3 region comprising the amino acid sequence of SEQ ID NO:227; or xxxvi. comprising a heavy chain CDR1 region comprising the amino acid sequence of SEQ ID NO:228, a heavy chain CDR2 region comprising the amino acid sequence of SEQ ID NO:229, a heavy chain CDR3 region comprising the amino acid sequence of SEQ ID NO:230, a light chain CDR1 region comprising the amino acid sequence of SEQ ID NO:231, a light chain CDR2 region comprising the amino acid sequence of SEQ ID NO:232, and a light chain CDR3 region comprising the amino acid sequence of SEQ ID NO:233; or xxxvii. comprising a heavy chain CDR1 region comprising the amino acid sequence of SEQ ID NO:234, a heavy chain CDR2 region comprising the amino acid sequence of SEQ ID NO:235, a heavy chain CDR3 region comprising the amino acid sequence of SEQ ID NO:236, a light chain CDR1 region comprising the amino acid sequence of SEQ ID NO:237, a light chain CDR2 region comprising the amino acid sequence of SEQ ID NO:238, and a light chain CDR3 region comprising the amino acid sequence of SEQ ID NO:239; or xxxvii. comprising a heavy chain CDR1 region comprising the amino acid sequence of SEQ ID NO:240, a heavy chain CDR2 region comprising the amino acid sequence of SEQ ID NO:241, a heavy chain CDR3 region comprising the amino acid sequence of SEQ ID NO:242, a light chain CDR1 region comprising the amino acid sequence of SEQ ID NO:243, a light chain CDR2 region comprising the amino acid sequence of SEQ ID NO:244, and a light chain CDR3 region comprising the amino acid sequence of SEQ ID NO:245; or xxxix. comprising a heavy chain CDR1 region comprising the amino acid sequence of SEQ ID NO:246, a heavy chain CDR2 region comprising the amino acid sequence of SEQ ID NO:247, a heavy chain CDR3 region comprising the amino acid sequence of SEQ ID NO:248, a light chain CDR1 region comprising the amino acid sequence of SEQ ID NO:249, a light chain CDR2 region comprising the amino acid sequence of SEQ ID NO:250, and a light chain CDR3 region comprising the amino acid sequence of SEQ ID NO:251; or xl. comprising a heavy chain CDR1 region comprising the amino acid sequence of SEQ ID NO:252, a heavy chain CDR2 region comprising the amino acid sequence of SEQ ID NO:253, a heavy chain CDR3 region comprising the amino acid sequence of SEQ ID NO:254, a light chain CDR1 region comprising the amino acid sequence of SEQ ID NO:255, a light chain CDR2 region comprising the amino acid sequence of SEQ ID NO:256, and a light chain CDR3 region comprising the amino acid sequence of SEQ ID NO:257; or xli. comprising a heavy chain CDR1 region comprising the amino acid sequence of SEQ ID NO:258, a heavy chain CDR2 region comprising the amino acid sequence of SEQ ID NO:259, a heavy chain CDR3 region comprising the amino acid sequence of SEQ ID NO:260, a light chain CDR1 region comprising the amino acid sequence of SEQ ID NO:261, a light chain CDR2 region comprising the amino acid sequence of SEQ ID NO:262, and a light chain CDR3 region comprising the amino acid sequence of SEQ ID NO:263; or xlii. comprising a heavy chain CDR1 region comprising the amino acid sequence of SEQ ID NO:264, a heavy chain CDR2 region comprising the amino acid sequence of SEQ ID NO:265, a heavy chain CDR3 region comprising the amino acid sequence of SEQ ID NO:266, a light chain CDR1 region comprising the amino acid sequence of SEQ ID NO:267, a light chain CDR2 region comprising the amino acid sequence of SEQ ID NO:268, and a light chain CDR3 region comprising the amino acid sequence of SEQ ID NO:269; or xliii. comprising a heavy chain CDR1 region comprising the amino acid sequence of SEQ ID NO:270, a heavy chain CDR2 region comprising the amino acid sequence of SEQ ID NO:271, a heavy chain CDR3 region comprising the amino acid sequence of SEQ ID NO:272, a light chain CDR1 region comprising the amino acid sequence of SEQ ID NO:273, a light chain CDR2 region comprising the amino acid sequence of SEQ ID NO:274, and a light chain CDR3 region comprising the amino acid sequence of SEQ ID NO:275; or xliv. comprising a heavy chain CDR1 region comprising the amino acid sequence of SEQ ID NO:276, a heavy chain CDR2 region comprising the amino acid sequence of SEQ ID NO:277, a heavy chain CDR3 region comprising the amino acid sequence of SEQ ID NO:278, a light chain CDR1 region comprising the amino acid sequence of SEQ ID NO:279, a light chain CDR2 region comprising the amino acid sequence of SEQ ID NO:280, and a light chain CDR3 region comprising the amino acid sequence of SEQ ID NO:281; or xlv. comprising a heavy chain CDR1 region comprising the amino acid sequence of SEQ ID NO:282, a heavy chain CDR2 region comprising the amino acid sequence of SEQ ID NO:283, a heavy chain CDR3 region comprising the amino acid sequence of SEQ ID NO:284, a light chain CDR1 region comprising the amino acid sequence of SEQ ID NO:285, a light chain CDR2 region comprising the amino acid sequence of SEQ ID NO:286, and a light chain CDR3 region comprising the amino acid sequence of SEQ ID NO:287; or xlvi. comprising a heavy chain CDR1 region comprising the amino acid sequence of SEQ ID NO:288, a heavy chain CDR2 region comprising the amino acid sequence of SEQ ID NO:289, a heavy chain CDR3 region comprising the amino acid sequence of SEQ ID NO:290, a light chain CDR1 region comprising the amino acid sequence of SEQ ID NO:291, a light chain CDR2 region comprising the amino acid sequence of SEQ ID NO:292, and a light chain CDR3 region comprising the amino acid sequence of SEQ ID NO:293; or xlvii. comprising a heavy chain CDR1 region comprising the amino acid sequence of SEQ ID NO:294, a heavy chain CDR2 region comprising the amino acid sequence of SEQ ID NO:295, a heavy chain CDR3 region comprising the amino acid sequence of SEQ ID NO:296, a light chain CDR1 region comprising the amino acid sequence of SEQ ID NO:297, a light chain CDR2 region comprising the amino acid sequence of SEQ ID NO:298, and a light chain CDR3 region comprising the amino acid sequence of SEQ ID NO:299; or xlviii. comprising a heavy chain CDR1 region comprising the amino acid sequence of SEQ ID NO:300, a heavy chain CDR2 region comprising the amino acid sequence of SEQ ID NO:301, a heavy chain CDR3 region comprising the amino acid sequence of SEQ ID NO:302, a light chain CDR1 region comprising the amino acid sequence of SEQ ID NO:303, a light chain CDR2 region comprising the amino acid sequence of SEQ ID NO:304, and a light chain CDR3 region comprising the amino acid sequence of SEQ ID NO:305; or xlix. comprising a heavy chain CDR1 region comprising the amino acid sequence of SEQ ID NO:306, a heavy chain CDR2 region comprising the amino acid sequence of SEQ ID NO:307, a heavy chain CDR3 region comprising the amino acid sequence of SEQ ID NO:308, a light chain CDR1 region comprising the amino acid sequence of SEQ ID NO:309, a light chain CDR2 region comprising the amino acid sequence of SEQ ID NO:310, and a light chain CDR3 region comprising the amino acid sequence of SEQ ID NO:311; or l. comprising a heavy chain CDR1 region comprising the amino acid sequence of SEQ ID NO:312, a heavy chain CDR2 region comprising the amino acid sequence of SEQ ID NO:313, a heavy chain CDR3 region comprising the amino acid sequence of SEQ ID NO:314, a light chain CDR1 region comprising the amino acid sequence of SEQ ID NO:315, a light chain CDR2 region comprising the amino acid sequence of SEQ ID NO:316, and a light chain CDR3 region comprising the amino acid sequence of SEQ ID NO:317; or li. comprising a heavy chain CDR1 region comprising the amino acid sequence of SEQ ID NO:318, a heavy chain CDR2 region comprising the amino acid sequence of SEQ ID NO:319, a heavy chain CDR3 region comprising the amino acid sequence of SEQ ID NO:320, a light chain CDR1 region comprising the amino acid sequence of SEQ ID NO:321, a light chain CDR2 region comprising the amino acid sequence of SEQ ID NO:322, and a light chain CDR3 region comprising the amino acid sequence of SEQ ID NO:323; or lii. comprising a heavy chain CDR1 region comprising the amino acid sequence of SEQ ID NO:324, a heavy chain CDR2 region comprising the amino acid sequence of SEQ ID NO:325, a heavy chain CDR3 region comprising the amino acid sequence of SEQ ID NO:326, a light chain CDR1 region comprising the amino acid sequence of SEQ ID NO:327, a light chain CDR2 region comprising the amino acid sequence of SEQ ID NO:328, and a light chain CDR3 region comprising the amino acid sequence of SEQ ID NO:329;

or wherein said antigen-binding peptide is a peptide, preferably an antibody, the heavy chain CDR1, CDR2, CDR3, regions of which and the light chain CDR1, CDR2, CDR3 regions of which comprise amino acid sequences which have at least 90% identity, preferably at least 95% identity, more preferably at least 98% identity, even more preferably 99% identity to any of the sequences indicated for i.-lii.

In one embodiment, said antigen-binding peptide is an antigen-binding peptide, preferably an antibody, i. comprising the amino acid sequence of SEQ ID NO: 334 and/or comprising the amino acid sequence of SEQ ID NO: 335; or ii. comprising the amino acid sequence of SEQ ID NO: 336 and/or comprising the amino acid sequence of SEQ ID NO: 337; or iii. comprising the amino acid sequence of SEQ ID NO: 338 and/or comprising the amino acid sequence of SEQ ID NO: 339; or iv. comprising the amino acid sequence of SEQ ID NO: 340 and/or comprising the amino acid sequence of SEQ ID NO: 341; or v. comprising the amino acid sequence of SEQ ID NO: 342 and/or comprising the amino acid sequence of SEQ ID NO: 343; or vi. comprising the amino acid sequence of SEQ ID NO: 344 and/or comprising the amino acid sequence of SEQ ID NO: 345; or vii. comprising the amino acid sequence of SEQ ID NO: 346 and/or comprising the amino acid sequence of SEQ ID NO: 347; or viii. comprising the amino acid sequence of SEQ ID NO: 348 and/or comprising the amino acid sequence of SEQ ID NO: 349; or ix. comprising the amino acid sequence of SEQ ID NO: 350 and/or comprising the amino acid sequence of SEQ ID NO: 351; or x. comprising the amino acid sequence of SEQ ID NO: 352 and/or comprising the amino acid sequence of SEQ ID NO: 353; or xi. comprising the amino acid sequence of SEQ ID NO: 354 and/or comprising the amino acid sequence of SEQ ID NO: 355; or xii. comprising the amino acid sequence of SEQ ID NO: 356 and/or comprising the amino acid sequence of SEQ ID NO: 357; or xiii. comprising the amino acid sequence of SEQ ID NO: 358 and/or comprising the amino acid sequence of SEQ ID NO: 359; or xiv. comprising the amino acid sequence of SEQ ID NO: 360 and/or comprising the amino acid sequence of SEQ ID NO: 361; or xv. comprising the amino acid sequence of SEQ ID NO: 362 and/or comprising the amino acid sequence of SEQ ID NO: 363; or xvi. comprising the amino acid sequence of SEQ ID NO: 364 and/or comprising the amino acid sequence of SEQ ID NO: 365; or xvii. comprising the amino acid sequence of SEQ ID NO: 366 and/or comprising the amino acid sequence of SEQ ID NO: 367; or xviii. comprising the amino acid sequence of SEQ ID NO: 368 and/or comprising the amino acid sequence of SEQ ID NO: 369; or xix. comprising the amino acid sequence of SEQ ID NO: 370 and/or comprising the amino acid sequence of SEQ ID NO: 371; or xx. comprising the amino acid sequence of SEQ ID NO: 372 and/or comprising the amino acid sequence of SEQ ID NO: 373; or xxi. comprising the amino acid sequence of SEQ ID NO: 374 and/or comprising the amino acid sequence of SEQ ID NO: 375; or xxii. comprising the amino acid sequence of SEQ ID NO: 376 and/or comprising the amino acid sequence of SEQ ID NO: 377; or xxiii. comprising the amino acid sequence of SEQ ID NO: 378 and/or comprising the amino acid sequence of SEQ ID NO: 379; or xxiv. comprising the amino acid sequence of SEQ ID NO: 380 and/or comprising the amino acid sequence of SEQ ID NO: 381; or xxv. comprising the amino acid sequence of SEQ ID NO: 382 and/or comprising the amino acid sequence of SEQ ID NO: 383; or xxvi. comprising the amino acid sequence of SEQ ID NO: 384 and/or comprising the amino acid sequence of SEQ ID NO: 385; or xxvii. comprising the amino acid sequence of SEQ ID NO: 386 and/or comprising the amino acid sequence of SEQ ID NO: 387; or xxviii. comprising the amino acid sequence of SEQ ID NO: 388 and/or comprising the amino acid sequence of SEQ ID NO: 389; or xxix. comprising the amino acid sequence of SEQ ID NO: 390 and/or comprising the amino acid sequence of SEQ ID NO: 391; or xxx. comprising the amino acid sequence of SEQ ID NO: 392 and/or comprising the amino acid sequence of SEQ ID NO: 393; or xxxi. comprising the amino acid sequence of SEQ ID NO: 394 and/or comprising the amino acid sequence of SEQ ID NO: 395; or xxxii. comprising the amino acid sequence of SEQ ID NO: 396 and/or comprising the amino acid sequence of SEQ ID NO: 397; or xxxiii. comprising the amino acid sequence of SEQ ID NO: 398 and/or comprising the amino acid sequence of SEQ ID NO: 399; or xxxiv. comprising the amino acid sequence of SEQ ID NO: 400 and/or comprising the amino acid sequence of SEQ ID NO: 401; or xxxv. comprising the amino acid sequence of SEQ ID NO: 402 and/or comprising the amino acid sequence of SEQ ID NO: 403; or xxxvi. comprising the amino acid sequence of SEQ ID NO: 404 and/or comprising the amino acid sequence of SEQ ID NO: 405; or xxxvii. comprising the amino acid sequence of SEQ ID NO: 406 and/or comprising the amino acid sequence of SEQ ID NO: 407; or xxxviii. comprising the amino acid sequence of SEQ ID NO: 408 and/or comprising the amino acid sequence of SEQ ID NO: 409; or xxxix. comprising the amino acid sequence of SEQ ID NO: 410 and/or comprising the amino acid sequence of SEQ ID NO: 411; or xl. comprising the amino acid sequence of SEQ ID NO: 412 and/or comprising the amino acid sequence of SEQ ID NO: 413; or xli. comprising the amino acid sequence of SEQ ID NO: 414 and/or comprising the amino acid sequence of SEQ ID NO: 415; or xlii. comprising the amino acid sequence of SEQ ID NO: 416 and/or comprising the amino acid sequence of SEQ ID NO: 417; or xliii. comprising the amino acid sequence of SEQ ID NO: 418 and/or comprising the amino acid sequence of SEQ ID NO: 419; or xliv. comprising the amino acid sequence of SEQ ID NO: 420 and/or comprising the amino acid sequence of SEQ ID NO: 421; or xlv. comprising the amino acid sequence of SEQ ID NO: 422 and/or comprising the amino acid sequence of SEQ ID NO: 423; or xlvi. comprising the amino acid sequence of SEQ ID NO: 424 and/or comprising the amino acid sequence of SEQ ID NO: 425; or xlvii. comprising the amino acid sequence of SEQ ID NO: 426 and/or comprising the amino acid sequence of SEQ ID NO: 427; or xlviii. comprising the amino acid sequence of SEQ ID NO: 428 and/or comprising the amino acid sequence of SEQ ID NO: 429; or xlix. comprising the amino acid sequence of SEQ ID NO: 430 and/or comprising the amino acid sequence of SEQ ID NO: 431; or l. comprising the amino acid sequence of SEQ ID NO: 432 and/or comprising the amino acid sequence of SEQ ID NO: 433; or li. comprising the amino acid sequence of SEQ ID NO: 434 and/or comprising the amino acid sequence of SEQ ID NO: 435; or lii. comprising the amino acid sequence of SEQ ID NO: 436 and/or comprising the amino acid sequence of SEQ ID NO: 437;

or wherein said antigen-binding peptide is a peptide, preferably an antibody, comprising an amino acid sequence which has at least 90% identity, preferably at least 95% identity, more preferably at least 98% identity, even more preferably 99% identity to any of the sequences indicated for i.-lii.

The respective sequences are also outlined in table 5 and shown in detail in the sequence listing and FIG. 16 (HCDR1-3 sequences and LCDR1-3 sequences) and FIG. 17 (VH- and VL-sequences).

The term "comprising", when used in connection with an amino acid sequence of a SEQ ID NO:, herein, is typically meant to allow for the presence of additional residues adjacent to such sequence, which additional residues are not listed in the respective SEQ ID NO:. The term "comprising" is, however, also meant to include the possibility that such sequence does not include any additional residues (not listed in the respective SEQ ID NO:), in which case, such term "comprising" is used in the sense of and to be understood as "consisting of". As an example, a region which "comprises" an amino acid sequence of SEQ ID NO:xyz, includes the sequence that is listed in SEQ IDxyz, but may also include additional adjacent residues that are not listed in SEQ ID NO:xyz; such terminology does, however, also include the possibility that the region merely "consists of" the amino acid sequence of SEQ ID NO:xyz, in which case no additional adjacent residues are meant to be encompassed by and present in said region.

In one embodiment, said antigen-binding peptide is an antibody selected from the antibodies shown in table 5, further below.

In one embodiment, said antigen-binding peptide is a human antibody, a humanised antibody, or a chimeric-human antibody.

In one embodiment, said antigen-binding peptide is an intact antibody, a substantially intact antibody, a Fab fragment, a $F(ab')_2$ fragment or a single chain Fv fragment.

In one embodiment, said antigen-binding peptide is capable of binding to a perilipin-1 fragment presented on an adipocyte, and said binding of said antigen-binding peptide to a perilipin-1 fragment on said adipocyte activates an immune effector system to target and/or eliminate said adipocyte.

In one embodiment, said antigen-binding peptide comprises an Fc region, preferably an Fc region which is optimized by protein engineering for higher binding affinity to an effector cell compared to a binding affinity of an Fc region which has not been optimized.

In one embodiment, said antigen-binding peptide does not cross-react with any other perilipin protein, such as perilipin-2 -3, -4, or -5.

In a further aspect, said antigen-binding peptide is an antigen-binding peptide for use in the prevention or treatment of obesity.

Said antigen-binding peptide is as defined above and elsewhere herein.

In a further aspect, the present invention relates to a bispecific antigen-binding peptide comprising (i) a first binding site specifically binding to a perilipin-1 epitope having any of SEQ ID NO. 1-6, 330-333; and (ii) a second binding site.

In one embodiment, said second binding site binds to a perilipin-1 epitope having any of SEQ ID NO. 1-6, 330-333, wherein said epitope is equal to or different from the epitope of said first binding site; to a white adipocyte-specific surface marker, for example the neutral amino acid transporter ASC-1; or to an immune cell specific receptor molecule, such as a T cell specific receptor molecule or a natural killer cell specific receptor molecule.

Said epitope is as defined in any of the embodiments above and elsewhere herein.

In a further aspect, said bispecific antigen-binding peptide is a bispecific antigen-binding peptide for use in the prevention or treatment of obesity.

In a further aspect, the present invention also relates to a composition comprising an antigen-binding peptide according to the present invention as defined herein, and/or a bispecific antigen-binding peptide according to the present invention as defined herein.

In one embodiment, the composition comprises more than one antigen-binding peptide according to the present invention as defined herein, and/or more than one bispecific antigen-binding peptide according to the present invention as defined herein.

In one embodiment, where the composition comprises more than one antigen-binding peptide, and/or more than one bispecific antigen-binding peptide, said more than one antigen-binding peptide are a set of peptides, each of which peptides bind to a different perilipin-1 epitope, and said more than one bispecific antigen-binding peptide are a set of bispecific peptides, each of which bispecific peptides bind to a different perilipin-1 epitope.

In one embodiment, the composition comprises at least two or at least three or at least four or at least five or at least six antigen-binding peptides according to the present invention as defined herein, each of which peptides bind to a different perilipin-1 epitope, and/or comprises at least two or at least three or at least four or at least five or at least six bispecific antigen-binding peptides according to the present invention as defined herein, each of which bispecific antigen-binding peptides bind to a different perilipin-1 epitope.

In a further aspect, the present invention also relates to a composition comprising more than one antigen-binding peptide according to the present invention as defined herein, and/or more than one bispecific antigen-binding peptide according to the present invention as defined herein, for use as a pharmaceutical composition in the prevention or treatment of obesity.

In a further aspect, the present invention relates to a pharmaceutical composition, comprising said antigen-binding peptide and/or said bispecific antigen-binding peptide, for use in the prevention or treatment of obesity.

Said antigen-binding peptide and said bispecific antigen-binding peptide are as defined in any of the embodiments above and elsewhere herein.

In a further aspect, the present invention relates to an isolated nucleic acid encoding for said antigen-binding peptide or encoding for said bispecific antigen-binding peptide.

Said antigen-binding peptide and said bispecific antigen-binding peptide are as defined in any of the embodiments above and elsewhere herein.

In a further aspect, the present invention relates to a recombinant cell comprising said nucleic acid, wherein said recombinant cell is preferably a recombinant autologous effector cell or a recombinant host cell.

Said nucleic acid is as defined in any of the embodiments above and elsewhere herein.

In a further aspect, the present invention relates to a method of producing a means for specifically targeting perilipin-1 fragment presenting adipocytes, comprising:

a) Inoculating a non-human animal with an antigen comprising at least one perilipin-1 specific epitope selected from SEQ ID NO. 1-6, 330-333; and screening and producing an antigen-binding peptide specifically binding to the at least one perilipin-1 specific epitope from the inoculated animal, preferably by harvesting cells expressing an antigen-binding peptide from the spleen of said non-human animal, preparing a hybridoma cell therefrom, expressing said antigen-binding peptide, and screening said antigen-binding peptide expressed by said hybridoma cell to identify an antigen-binding peptide specifically binding to any of SEQ ID NO. 1-6, 330-333, and isolation thereof; or b) providing and screening a recombinant antigen-binding peptide library, such as a library of antibodies, scFv molecules, Camel antibodies, Anticalins, or DARPins, to identify an antigen-binding peptide specifically binding to any of SEQ ID NO. 1-6, 330-333, and isolation thereof; or c) providing and screening a cell pool comprising cytotoxic T cells, such as by Tetramer-staining or Dextramer-Technology, to identify a cytotoxic T cell having specificity to any of SEQ ID NO. 1-6, 330-333, and isolation thereof; or d) providing a blood sample of a patient and obtaining T cells therefrom, genetically modifying said T cells by introducing a nucleic acid as defined above and elsewhere herein, and obtaining chimeric antigen receptor expressing T cells; or e) providing and screening a pool of T cell receptors to identify a T cell receptor having specificity to any of SEQ ID NO. 1-6, 330-333, and isolation thereof.

In one embodiment, said means targets perilipin-1 and is selected from an antigen-binding peptide and a cytotoxic T cell.

Said antigen-binding peptide and said epitopes are as defined in any of the embodiments above and elsewhere herein.

In a further aspect, the present invention also relates to the use of an antigen-binding peptide or a bispecific antigen-binding peptide in the manufacture of a pharmaceutical composition for the treatment or prevention of obesity.

Said antigen-binding peptide, said bispecific antigen-binding peptide, and said pharmaceutical composition are as defined above and elsewhere herein.

In a further aspect, the present invention also relates to the use of an antigen-binding peptide, a bispecific antigen-binding peptide, or a specific cytotoxic T cell in the manufacture of a preparation, preferably a pharmaceutical preparation, for the treatment or prevention of obesity.

Said antigen-binding peptide, said bispecific antigen-binding peptide, and said specific cytotoxic T cell are as defined above and elsewhere herein.

In a further aspect, the present invention also relates to a method of preventing or treating obesity comprising administering an antigen-binding peptide, a bispecific antigen-binding peptide, and/or a cytotoxic T cell, specifically binding to any of the perilipin-1 epitopes having SEQ ID Nos. 1-6, 330, 333, to a patient in need thereof.

In one embodiment, said patient is a human.

Said antigen-binding peptide, said bispecific antigen-binding peptide, and said cytotoxic T cell are as defined above and elsewhere herein.

In a further aspect, the present invention relates to the use of at least one perilipin-1 epitope having any of SEQ ID NOs. 1-6, 330-333, for the identification of an antigen-binding peptide, a bispecific antigen-binding peptide, and/or a cytotoxic T cell that is specific for adipocytes and/or may be used in a method for the treatment or prevention of obesity.

Said antigen-binding peptide, said bispecific antigen-binding peptide, and said cytotoxic T cell are as defined above and elsewhere herein.

DETAILED DESCRIPTION

The term "antigen-binding peptide", as used herein, relates to a peptide which specifically binds to an antigen, preferably a peptide which binds to a perilipin-1 epitope selected from any of SEQ ID NOs. 1-6. In one embodiment, said perilipin-1 epitope is selected from any of SEQ ID NOs. 1-6, 330-333. In one embodiment, an antigen-binding molecule is based on an immunoglobulin, such as a polyclonal or monoclonal antibody, or based on a protein scaffold structure having antigen-binding capacity, such as an anticalin protein, an Affilin, an Affimer, an Affitin, an Alphabody, a nanobody, or a DARPin. In one embodiment, an antigen-binding peptide relates to an antibody or an antibody fragment. In one embodiment, when referring to an antibody or antibody fragment, it is referred to an antigen-binding peptide. There are several classes of antibodies, particularly human antibodies, such as IgA, IgG, IgM, IgD and IgE, as well as subclasses, such as IgG1, IgG2, IgG3, and IgG4. An antibody is a protein produced mainly by plasma cells of the immune system to neutralize pathogens. Antibodies are grouped into classes, also referred to as isotypes, as determined genetically by the constant region. Human constant light chains are classified as kappa (CK) and lambda (CA) light chains. Human heavy chains are classified as mu, delta, gamma, alpha, or epsilon, and define the antibody's isotype as IgM, IgD, IgG, IgA, and IgE, respectively. The IgG class is the most commonly used for therapeutic purposes. "IgG", as used herein, relates to a polypeptide belonging to the class of antibodies that are substantially encoded by a recognized immunoglobulin gamma gene. In humans this class comprises subclasses IgG1, IgG2, IgG3, and IgG4. In mice this class comprises subclasses IgG1, IgG2a, IgG2b and IgG3. IgA has several subclasses, including but not limited to IgA1 and IgA2. Thus, "isotype", as used herein, relates to any of the classes or subclasses of immunoglobulins defined by the chemical and antigenic characteristics of their constant regions. The known human immunoglobulin isotypes are IgG1, IgG2, IgG3, IgG4, IgA1, IgA2, IgM, IgD, and IgE. Also useful for the invention may be IgGs that are hybrid compositions of the natural human IgG isotypes. Effector functions such as ADCC, ADCP, CDC, and serum half-life differ significantly between the different classes of antibodies, including for example human IgG1, IgG2, IgG3, IgG4, IgA1, IgA2, IgD, IgE, and IgM. In one embodiment, an antigen-binding peptide may comprise a domain of any of the above mentioned antibody classes, subclasses, and/or chains. In one embodiment, the amino acid sequence of an antigen-binding peptide may be modified by protein engineering, e.g. to comprise constant regions from other immunoglobulin classes mediating improved effector function properties. Such engineered hybrid IgG compositions may provide improved effector function properties, including improved ADCC, phagocytosis, CDC, and serum half-life.

According to the present invention, an antigen-binding peptide may relate, for example, to human antibodies, human-chimeric antibodies, humanized antibodies, and antibody fragments. An antibody recognizes an antigen via the Fab fragment variable region comprising a paratope. Said paratope specifically targets an epitope on an antigen. In one embodiment, an antigen-binding peptide according to the present invention binds to any of the epitopes having SEQ ID NOs. 1-6, 330-333, on perilipin-l. In one embodiment, said binding of an antigen-binding peptide to a perilipin-1 fragment presented on the cell surface of an adipocyte results in activation of an immune effector system to eliminate said adipocyte. Furthermore, the term "antigen-binding peptide", as used herein, relates to a peptide that specifically binds to a target antigen, such as to one or more epitope(s) displayed by or present on a target antigen. The antigen bound by an antigen-binding peptide of the present invention is perilipin-1, or in the case of bispecific molecules perilipin-1 and optionally another antigen, such as an antigen on an effector cell, such as an antigen on a cytotoxic T cell, or an antigen presented on an adipocyte other than a perilipin-1 fragment, or an antigen presented by any component of fat tissue. In one embodiment, a bispecific molecule comprises a first binding site binding for one of the perilipin-1 epitopes having any of SEQ ID NO. 1-6, 330-333, and a second binding site for the same perilipin-1 epitope as the first binding site or for a perilipin-1 epitope having any of SEQ ID NO. 1-6, 330-333, different from the epitope of the first binding site. In one embodiment, a bispecific molecule comprises a first binding site binding for one of the perilipin-1 epitopes having any of SEQ ID NO. 1-6, 330-333, and a second binding site for an antigen different from perilipin-1.

In one embodiment, an antigen-binding peptide is a TCR-derived antigen-binding peptide and relates to a T cell receptor specific for any of SEQ ID NOs. 1-6, 330-333, or to a fragment of a T cell receptor specific for any of SEQ ID NOs. 1-6, 330-333. In one embodiment, said T cell receptor may be a soluble T cell receptor or may be expressed on the surface of a genetically modified cell, preferably a T cell. In one embodiment, said TCR-derived antigen-binding peptide is used for an adoptive T cell receptor transfer. In one embodiment, an antigen binding peptide relates to a peptide expressed on the surface of a genetically modified cell, particularly a T cell or NK cell, wherein said genetically modified cell is genetically modified to express said antigen-binding peptide, resulting in a CAR-T cell or CAR-NK cell, respectively.

According to the present invention, an antigen-binding peptide may further relate to a fragment of an antibody, such as a substantially intact antibody, a Fab fragment, a $F(ab')_2$ fragment, a diabody, a single chain Fv fragment, a tetrabody, a triabody, a disulfide bond-stabilized Fv (dsFv), or a heavy chain VHH fragment from camels. However, other forms of an antigen-binding peptide are also envisioned by the present invention. For example, the antigen-binding peptide may be another (non-antibody) receptor protein derived from small and robust non-immunoglobulin scaffolds, such as those equipped with binding functions for example by using methods of combinatorial protein design. Such a non-antibody antigen-binding peptide may be, for example, an Affibody molecule, an Affilin, an Affimer, an Affitin, an Alphabody, an Anticalin, a nanobody, or a DARPin. An antigen-binding peptide may also relate to other antibody-mimetic molecules such as a dual-affinity re-targeting antibody (DART). In one embodiment, an antigen-binding peptide preferably relates to an antibody or an antibody fragment. In one embodiment, an antigen-binding peptide may relate to any antibody-mimetic molecule which mimics the binding properties of an antibody to an antigen but which is structurally distinct from a naturally occurring antibody.

In one embodiment, an antigen-binding peptide may be optimized by protein engineering methods known to a person skilled in the art, such as directed evolution, phage display, or ribosome display, to have improved properties such as higher binding affinity and longer serum half-life compared to a non-optimized antigen-binding peptide. In one embodiment, an antigen-binding peptide may be modified by protein engineering methods known to a person skilled in the art to have the capacity to induce certain effector functions, such as by comprising an Fc region to be targeted by an effector cell. In one embodiment, said optimized antigen-binding peptide may be engineered by specific amino acid exchanges in the amino acid sequence of said Fc region to increase the response of effector systems to said Fc region. In one embodiment, said optimized antigen-binding peptide may be optimized to have an improved serum half-life, for example by modification of a CH3 region of an IgG domain. In one embodiment, an antigen-binding peptide may be modified by protein engineering methods known to a person skilled in the art to improve the capacity to induce certain effector functions, such as stronger effector responses by the complement system or cytotoxic T cells when recognizing said optimized antigen-binding peptide bound to an epitope having any of SEQ ID NOs. 1-6, 330-333, presented on or present on the surface of an adipocyte compared to a non-optimized antigen-binding peptide bound to an epitope having any of SEQ ID NOs. 1-6, 330-333, presented on or present on the surface of an adipocyte. In one embodiment, an antigen-binding peptide is a bispecific antigen-binding peptide.

The terms "complementarity determining region", "CDR", and "hypervariable region", as used herein, relate to one or more of the hypervariable or complementarity determining regions (CDRs) found in the variable regions of light or heavy chains of antibodies. The CDRs in each chain are held in close proximity by framework regions and contribute to the formation of the antigen-binding site together with the CDRs from the other chain. In one embodiment, an antigen-binding peptide comprises at least one, preferably all, CDR(s) of an antibody specifically binding to a perilipin-1 fragment, preferably specifically binding to a perilipin-1 epitope having any of SEQ ID NO. 1-6, 330-333. In one embodiment, an antigen-binding peptide comprises a peptide scaffold and at least one, preferably all, CDR(s) of an antibody specifically binding to a perilipin-1 fragment, wherein said peptide scaffold may be an antibody fragment or any non-antibody peptide scaffold such as an anticalin, an Affilin, an Affimer, an Affitin, an Alphabody, an a nanobody, or a DARPin.

The term "bispecific antigen-binding peptide", as used herein, relates to an artificial protein which comprises a first binding site specifically binding to a perilipin-1 epitope having any of SEQ ID NO. 1-6, 330-333, and a second binding site. A bispecific antigen-binding peptide can simultaneously bind to two target structures, such as to two different types of antigens. In one embodiment, said bispecific antigen-binding peptide is immunoglobulin-based. In one embodiment, said bispecific antigen-binding peptide comprises two different immunoglobulin-based binding fragments having binding specificity to an antigen, and said two fragments are connected by a linker fragment such as a linker peptide sequence and/or an antibody scaffold structure. In one embodiment, said binding fragments of a bispecific antigen-binding peptide may be specific for different antigens, or for different epitopes on the same antigen, or for the same epitope on the same antigen. In one embodiment, a bispecific antigen-binding peptide according to the present invention binds to a first perilipin-1 epitope and to a second, but different non-overlapping perilipin-1 epitope. In one embodiment, a bispecific antigen-binding peptide according to the present invention binds to a perilipin-1 epitope and to a different antigen. In one embodiment, said different antigen is a surface marker of an effector cell, such as a T cell or a natural killer cell. In one embodiment, said different antigen may also be an antigen presented on an adipocyte other than a perilipin-1 fragment, such as a neutral amino acid transporter ASC-l. In one embodiment, said different antigen may also be an antigen presented by any component of fat tissue other than perilipin-l. In one embodiment, a bispecific antigen-binding peptide is a fusion protein comprising a TCR-derived antigen-binding peptide. In one embodiment, a bispecific antigen-binding peptide comprises a TCR-derived antigen-binding peptide as first binding site and a second binding site derived from a molecule selected from an antibody fragment, an anticalin, a DARPin, an aptamer, an Affibody molecule, an Affilin, an Affimer, an Affitin, an Alphabody, and a nanobody. In one embodiment, said second binding site binds specifically to a receptor on immune cells such as T cells or natural killer cells, preferably to receptors capable of activating the immune cell or of stimulating an immune response of the immune cell, in which the immune response is preferably a cytotoxic immune response. In one embodiment, said receptor is preferably a receptor molecule such as CD3, CD3δ/ε, CD3γ/ε, TCR, TCRα, TCRβ, CD2, CD5, CD28, OX40, 4-1BB, CD16, Ly49, NKp30 (CD337), NKp44 (CD336), NKp46 (NCR1), or CD3ζ (CD247). In one embodiment, said second binding site of the bispecific antigen-binding peptide binds specifically to a second perilipin-1 epitope having any of SEQ ID NO. 1-6, 330-33, and said second perilipin-1 epitope is different from and non-overlapping with the perilipin-1 epitope of said first binding site.

The present invention also relates to compositions of one or several antigen-binding peptides and/or bispecific antigen-binding peptides in accordance with the present invention, as well as use(s) of such compositions. For example such a composition may be a composition comprising one antigen-binding peptide, e.g. antibody, in accordance with the present invention, and/or one bispecific antigen-binding peptide in accordance with the present invention. As another example such a composition may be a composition comprising a plurality of different antigen-binding peptides, e.g. antibodies, in accordance with the present invention, and/or a plurality of different bispecific antigen-binding peptides in accordance with the present invention. Such a composition of a plurality of different antigen-binding peptides, e.g. antibodies, and/or different bispecific antigen-binding peptides in accordance with the present invention, is herein also sometimes referred to as a "pool" of different antigen-binding peptides, e.g. antibodies, and/or of different bispecific antigen-binding peptides. Typically, in such "pool", each of the different antigen-binding peptides, e.g. antibodies, and/or each of the different bispecific antigen-binding peptides, bind to a different perilipin-1 epitope, as defined herein, For example, such a pool may be a pool of different antibodies, each of which different antibodies bind to a different perilipin-1 epitope, as defined herein. Perilipin-1 epitopes, as defined herein, are preferably epitopes having an amino acid sequence selected from SEQ ID NO: 1-6, 330-333.

The term "autoantibody", as used herein, relates to an antibody which is produced by the immune system of a patient and which is directed against one or more of the patient's own proteins. Many autoimmune diseases are caused by such autoantibodies. In one embodiment, an anti-perilipin-1 autoantibody is involved in acquired generalized lipodystrophy. In one embodiment, said anti-perilipin-1 autoantibody triggers complement mediated destruction of adipocytes in acquired generalized lipodystrophy.

The term "lipodystrophy", as used herein, relates to a medical condition in which a body is unable to produce and maintain healthy adipose tissue. There are different types of lipodystrophies, such as congenital lipodystrophy syndromes and acquired lipodystrophy syndromes. The term "Lipoatrophy" typically describes the (almost) complete loss of adipose tissue from one area of the body or from the whole body. In one embodiment, lipodystrophy is used synonymously with lipoatrophy. In one embodiment, lipodystrophy relates to acquired generalized lipoatrophy (AGL). In one embodiment, the present invention discloses an anti-perilipin-1 autoantibody involved in lipodystrophy.

The term "perilipin-1", as used herein, is also known as lipid droplet-associated protein and relates to a protein associated with the surface of lipid droplets. Perilipin-1 belongs to the family of perilipins which are a family of proteins associated with lipid droplet surfaces. Perilipin-1 expression is elevated in obese humans. Perilipin-1 protects lipid droplets from lipases involved in lipolysis. In humans, there are three perilipin-1 isoforms, namely perilipin-A, perilipin-B, and perilipin-C. The human amino acid sequence of perilipin-1 is in accordance with SEQ ID NO. 7. In one embodiment, the term "perilipin-1" relates to a full-length perilipin-1 protein and/or a fragment thereof.

The term "epitope", as used herein, relates to the part of an antigen that is recognized by the immune system, specifically by antibodies, B cells, or T cells. In one embodiment, epitope is used synonymously with antigenic determinant. The part of an antibody that binds to the epitope is a paratope. An epitope may be a conformational epitope or a linear epitope, depending on the structure and interaction with the paratope. In one embodiment, antigen perilipin-1 comprises six epitopes, wherein said epitopes have any of the sequences as disclosed in SEQ ID NOs. 1-6, 330-333. An antibody or antigen-binding fragment according to the present invention may bind to one or more of SEQ ID NOs. 1-6, 330-333. In one embodiment, an antibody or antigen-binding fragment according to the present invention may also bind to a sequence having at least 85% identity with any of SEQ ID NOs. 1-6, 330-333.

The term "antigen", as used herein, relates to a molecule capable of inducing an immune response in an organism. An antigen may be targeted by an antibody. The antigenic determinant of an antigen is a distinct surface feature, namely an epitope. Most antigens are potentially bound by multiple antibodies, each of which is typically specific to one of the antigen's epitopes. An autoantigen is a normal protein of an organism that is recognized by the immune system of said organism suffering from a specific autoimmune disease. In one embodiment, an antigen relates to a perilipin-1 protein and/or a fragment thereof. In one embodiment, the antigen, particularly a perilipin-1 fragment, is presented by an MHC molecule on the surface of an adipocyte. In one embodiment, said MHC molecule is an MHC-I or MHC-II molecule.

The term "targeting", as used herein, relates to the capacity of a molecular structure, such as an antibody, an antigen-binding peptide, or a surface molecule of a cytotoxic T cell, to bind to a certain structure, such as an antigen, specifically an epitope, by specific interaction. In one embodiment, a perilipin-1 fragment on the surface of an adipocyte is targeted by an antigen-binding peptide, which results in activation of an effector system, which in turn results in the elimination of said adipocyte, such as, for example, via a caspase cascade. In one embodiment, a perilipin-1 fragment on the surface of an adipocyte is targeted by a cytotoxic T cell, which specifically binds to said perilipin-1, preferably resulting in cell death of said adipocyte. In one embodiment, the terms "targeting" and "recognizing" are used interchangeably. In one embodiment, an antigen-binding peptide of the present invention targets a perilipin-1 protein and/or a perilipin-1 fragment, preferably via an epitope having any of SEQ ID NOs. 1-6, 330-333. In one embodiment, an antigen-binding peptide of the present invention targets a perilipin-1 fragment presented by an MHC on a cell surface, or such perilipin-1 fragment may be present or presented on the cell surface, due to another mechanism. In one embodiment, an antigen-binding peptide targets at least one of the perilipin-1 epitopes having any of SEQ ID NOs. 1-6, 330-333. In one embodiment, targeting of a perilipin-1 fragment presented on an adipocyte using an antigen-binding peptide preferably results in elimination of said adipocyte via an effector/elimination mechanism. In one embodiment, if said antigen-binding peptide binds to more than one of SEQ ID NO. 1-6 and SEQ ID NO: 330-333, said antigen-binding peptide preferably binds to any of the following double or triple combinations a)-s):

a) SEQ ID NO.s 1 and 2; b) SEQ ID NO.s 1 and 5; c) SEQ ID NO.s 1 and 6; d) SEQ ID NO.s 2 and 5; e) SEQ ID NO.s 2 and 6; f) SEQ ID NO.s 5 and 6; g) SEQ ID NO.s 1, 2 and 5; h) SEQ ID NO.s 1, 2 and 6; i) SEQ ID NO.s 2, 5 and 6; k) SEQ ID NO.s 330 and 331; 1) SEQ ID NO.s 330 and 332; m) SEQ ID NO.s 330 and 333; n) SEQ ID NO.s 331 and 332; o) SEQ ID NO.s 331 and 333; p) SEQ ID NO.s 332 and 333; q) SEQ ID NO.s 330, 331, and 332; r) SEQ ID NO.s 330, 331, and 333; and s) SEQ ID NO.s 331, 332, and 333.

Alternatively, the invention also envisages that binding to more than one perilipin-1 epitope can be achieved by providing a composition (or "pool") of several, different, antigen-binding peptides in accordance with the present invention as defined herein, each of which antigen-binding peptides binds to a single perilipin-1 epitope that is different from the perilipin-1 epitopes to which the other antigen-binding peptides in such composition (or "pool") bind. Accordingly, in one embodiment, such composition may e.g. comprise two or three antigen-binding peptides, which preferably bind to the any of the aforementioned double or triple combinations a)-s).

The term "eliminating", as used herein, relates to targeting a target cell and inducing cell destruction, for example by a complement cascade, or by recruitment of NK cells, or by attack from a cytotoxic T cell, and preferably further comprises degradation and/or removal of the resulting cell debris. In one embodiment, an antigen-binding peptide of the present invention triggers elimination of an adipocyte via an effector mechanism. In one embodiment, a target adipocyte cell presenting a perilipin-1 fragment on its surface is eliminated by induction of apoptosis via a cytotoxic T cell, or by lysis of said cell via a complement cascade. In one embodiment, the term "eliminating" may refer to damaging a cell, destroying a cell, degrading a cell, and/or phagocytosing a cell. In one embodiment, eliminating a cell refers to damaging a cell in a manner sufficient to terminate the cell's ability to survive and/or sufficient to terminate the cell's ability to maintain its cell function. In many of the embodiments, elimination preferably relates to complete removal of an adipocyte. In many of the embodiments, "eliminating" preferably relates to destruction and complete degradation of an adipocyte without remaining extracellular cell debris, preferably by phagocytosis of said adipocyte. In one embodiment, a perilipin-1 presented on an adipocyte is targeted using an antigen-binding peptide to eliminate said adipocyte. In one embodiment, elimination of an adipocyte may be triggered by one effector mechanism, by several effector mechanisms simultaneously, or by a cascade of effector mechanisms.

The term "effector mechanism", as used herein, relates to a mechanism which is involved in and/or results in the elimination of a target cell. An effector mechanism, as used herein, may relate to various mechanisms of action involved in the destruction of a target cell, such as activation of a death pathway in a target cell, blockade of necessary growth factor/growth factor receptor interaction, induction of antibody-dependent cellular cytotoxicity (ADCC), a complement-dependent cytotoxicity (CDC) response, and/or of antibody-dependent cell phagocytosis (ADCP). In one embodiment, an effector mechanism is an immune effector mechanism which is a mechanism of the immune system to eradicate cells such as infected cells. In one embodiment, "effector mechanism" is used interchangeably with "effector system". In one embodiment, the term effector mechanism may refer to an individual effector mechanism involved in eliminating an adipocyte or to a group of several effector mechanisms which are involved simultaneously or as a cascade of mechanisms in eliminating an adipocyte.

In one embodiment, the interaction of an antigen-binding peptide with complement initiates a complement-dependent cytotoxicity (CDC) response. In one embodiment, binding of an antigen-binding peptide to a perilipin-1 fragment presented on a surface of an adipocyte mediates apoptosis of said adipocyte. In one embodiment, an antigen-binding peptide comprises an Fc (fragment crystallisable)-derived region which mediates an effector function such as antibody-dependent cell-mediated cytotoxicity (ADCC), complement-dependent cytotoxicity (CDC), and/or antibody-dependent cellular phagocytosis (ADCP), preferably via interaction with Fc receptors expressed by effector cells and/or interaction with components of the complement system such as complement component 1q (C1q). In one embodiment, an antigen-binding peptide comprises an Fc region which contributes to long half-life of said antigen-binding peptide mediated by binding to the salvage receptor FcRn. In one embodiment, glycosylation of the antigen-binding peptide may alter the intensity of an effector function mediated by said antigen-binding peptide. In one embodiment, effector cells such as NK cells, monocytes, macrophages, and granulocytes recognize an antigen-binding peptide of the present invention bound to a target cell, preferably an adipocyte, said recognition being carried out for example via a receptor FcγR of said effector cell and an Fc domain of said antigen-binding peptide, and this recognition triggers effector cells to release cytoplasmic perforin, granulysin, and granzymes that induce apoptosis and/or lysis of said target cell. In one embodiment, an effector mechanism resulting in the destruction of an adipocyte may also comprise a cytotoxic drug, a toxin, or a radionuclide that is delivered to said adipocyte by an antigen-binding peptide of the present invention, such as by conjugation of said cytotoxic drug, toxin, or radionuclide to said antigen-binding peptide, or by delivering said cytotoxic drug, toxin, or radionuclide using a liposome which is labeled with an antigen-binding peptide.

In one embodiment, an effector mechanism may also involve a chimeric antigen receptor (CAR) which is a receptor protein that has been engineered to give a T cell the ability to target a specific protein. Particularly, T cells are harvested from a patient, genetically altered to comprise a chimeric antigen receptor including an antigen-binding peptide of the present invention, e.g. by transforming said T cells with a plasmid/virus comprising the genetic information for a fusion protein including an antigen-binding peptide, such as a TCR-derived antigen-binding peptide, as well as a transmembrane domain and a cytoplasmic effector domain, and then said genetically altered T cells are administered as CAR-T cells to said patient to attack adipocytes. In one embodiment, said CAR-T cells may be derived from T cells of the patient's own blood (autologous cells) or derived from T cells of another healthy individual (allogenic cells). In one embodiment, said CAR comprises an antigen-binding peptide specific for any of SEQ ID NOs. 1-6, 330-333 as ectodomain, as well as a transmembrane domain and an endodomain. In one embodiment, said antigen-binding peptide specific for any of SEQ ID NOs. 1-6, 330-333 may be a T cell receptor or may be a domain of a T cell receptor. In one embodiment, an effector mechanism may involve a T cell genetically altered to be specific for any of SEQ ID NOs. 1-6, 330-333 and/or a T cell naturally specific for any of SEQ ID NOs. 1-6, 330-333 which is selected from a pool of T cells obtained from a donor and amplified in vitro, wherein said donor may be autologous or allogenic.

The term “effector cell”, as used herein, refers to a cell, preferably an immune cell, which is involved in an effector system and/or effector mechanism resulting in the destruction and/or elimination of a target cell. In one embodiment, an effector cell may be a monocyte, macrophage, neutrophil, NK cell, NKT cell, or a cytotoxic T cell. In one embodiment, an effector cell recognizes and/or binds to an antigen-binding peptide of the present invention bound to a perilipin-1 fragment presented on an adipocyte, recognizes and/or binds to a perilipin-1 fragment presented on an adipocyte, or recognizes and/or binds to a complex thereof. In one embodiment, said recognizing and/or binding induces an effector mechanism resulting in the elimination/destruction of said adipocyte. In one embodiment, an effector cell such as a T cell recognizes an adipocyte target cell and induces cell death of said target cell. In one embodiment, an effector cell such as a NK cell, a monocyte, a macrophage, or a granulocyte recognizes an antigen-binding peptide of the present invention bound to an adipocyte, and this recognition triggers induction of apoptosis or lysis of said adipocyte, and/or phagocytosis of said adipocyte.

The term “adipocyte”, as used herein, relates to a fat cell which is specialized in storing fat. Adipose tissue is primarily composed of adipocytes. There are different types of fat tissue, namely white fat, brown fat, beige fat and marrow fat, and accordingly also different types of fat cells. White fat cells are monovacuolar cells containing one large lipid droplet surrounded by a layer of cytoplasm. Brown fat cells are plurivacuolar and are typically in a polygonal shape. Beige fat comprises white fat cells and brown fat cells, which make beige fat metabolically more desirable than white fat. There are also adipocytes in marrow adipose tissue which also seemed to have a role in obesity. In one embodiment, the terms “perilipin-1 presenting adipocyte” and “perilipin-1 fragment presenting adipocyte” are used interchangeably. In one embodiment, an adipocyte preferably presents a fragment of perilipin-1 on its surface. In one embodiment, said fragment of perilipin-1 presented on a surface of an adipocyte preferably comprises any of SEQ ID NOs. 1-6, 330-333.

The term “direct elimination mechanism”, as used herein, relates to a process and/or a capacity of an immune effector system to directly destruct a target cell and remove its constituents. In one embodiment, a target cell is destroyed and its constituents are removed via the activation of a macrophage by Fc-receptor mediated binding of an antigen-binding peptide to perilipin-1 or fragments thereof. In one embodiment, a direct elimination mechanism involves neutrophils (neutrophilic polymorphonuclear granulocytes) by Fc-receptor mediated binding of an antibody or antigen-binding fragment to perilipin-1 or fragments thereof. In one embodiment, a direct elimination mechanism preferably comprises macrophages and/or neutrophils binding to an antigen-binding peptide bound to a perilipin-1 fragment on the surface of an adipocyte, wherein said binding results in phagocytosis of said adipocyte, wherein said binding is preferably mediated via an Fc receptor.

The term “indirect elimination mechanism”, as used herein, relates to a process and/or a capacity of an immune effector system to target a target cell and involve another system to destroy said target cell and/or to remove the cell remnants. In one embodiment, an indirect elimination mechanism involves binding of an antigen-binding peptide to a target structure such as perilipin-1 or fragments thereof on the surface of an adipocyte. In one embodiment, said binding triggers destruction of said adipocyte via the activation of a complement cascade. In one embodiment, this mechanism is complement dependent cytotoxicity (CDC). In one embodiment, an indirect elimination mechanism involves antibody-dependent cell-mediated cytotoxicity (ADCC) which involves lysis of a target cell by an effector cell of the immune system, such as a natural killer cell. In one embodiment, an indirect elimination involves antibody-dependent cellular phagocytosis (ADCP) which involves phagocytosis of an adipocyte by an effector cell of the immune system, such a macrophage. In one embodiment, an indirect elimination mechanism involves cytotoxic T-cell-mediated cytotoxicity which involves lysis of an adipocyte by an effector cell which directly binds to perilipin-1-fragments presented via an MHC on that adipocyte. Said destruction of an adipocyte then triggers the activation of another system that results in elimination of the debris of said destroyed adipocyte, such as phagocytosis. In one embodiment, an indirect elimination mechanism involves phagocytosis of target cell remnants by macrophages or neutrophils (neutrophilic polymorphonuclear granulocytes). In one embodiment, a means for specifically targeting and/or eliminating adipocytes may have both a direct elimination capacity and an indirect elimination capacity. In one embodiment, macrophages and neutrophils are both a direct elimination means, such as by Fc receptor dependent binding to a target adipocyte and phagocytosis thereof, and an indirect elimination means, such as by phagocytosis of debris of destroyed adipocytes which have been targeted by a different elimination means such as complement-mediated opsonization. In one embodiment, direct elimination mechanisms and indirect elimination mechanisms may occur concurrently and/or their scope may overlap. In one embodiment, the term “effector mechanism” may refer to both indirect and direct elimination mechanisms. In one embodiment, the terms “effector mechanism” and “elimination mechanism” may be used synonymously.

The term “effector system” or “immune effector system”, as used herein, relates to any system involved in the immune system that can potentially contribute to an immune response. An immune effector system may, for example, relate to the complement system, to a T cell such as a cytotoxic T cell or a regulatory T cell, to a natural killer cell, to a B cell, to a plasma cell, or to macrophage. In one embodiment, an effector system relates to the complement system, macrophages, neutrophils, NK cells, NKT cells, and/or to cytotoxic T cells. In one embodiment, an effector system is triggered by the binding of an antigen-binding peptide to perilipin-1 presented on an adipocyte, and said triggering results in the elimination of said adipocyte.

The term “endogenous effector system”, as used herein, relates to an immune effector system which is endogenous. An endogenous effector system may be, for example, the complement system which is capable of triggering targeted cell destruction upon activation, such as via opsonization. An endogenous effector system may also relate to endogenous cytotoxic T cells which are activated by specific antigens. An endogenous effector system may also relate to a macrophage, or a neutrophil such a neutrophilic polymorphonuclear granulocyte, or to a NK cell.

The term "exogenous effector system", as used herein, relates to an immune effector system which is exogenous. An exogenous effector system may be, for example, cytotoxic T cells, which are amplified ex vivo and subsequently administered to a patient. Such ex vivo amplified cytotoxic T cells may either derive from said patient or from a donor, or may derive from the commercially available source. In one embodiment, said exogenous effector system may relate to a chimeric antigen receptor T cell (CAR-T cell), which is a genetically modified T cell that expresses a T cell receptor specific for any of SEQ ID NOs. 1-6, 330-333. In one embodiment, an exogenous effector system may also relate to an exogenous T cell receptor (TCR), wherein said exogenous TCR may be a soluble TCR or a TCR expressed by an effector cell such as a T cell, preferably a T cell transformed to express a TCR specific for any of SEQ ID NOs. 1-6, 330-333.

The term "complement system", as used herein, relates to a part of the innate immune system that enhances the ability of antibodies and phagocytic cells to clear damaged cells from an organism. More than thirty proteins are involved in the complement system. The complement system is capable of triggering different immune functions, such as phagocytosis by opsonizing antigens, inflammation by attracting macrophages and neutrophils, and membrane attack. The classical complement pathway typically requires antigen-antibody complexes for activation. The complement system may involve a membrane attack complex, which forms a transmembrane channel causing osmotic lysis of the target cell. Furthermore, macrophages help to clear complement-coated target cells.

The term "cytotoxic T cell", as used herein, relates to a T lymphocyte which is able to kill a cancer cell, an infected cell or a cell which is damaged in another way. A T cell typically expresses a T cell receptor (TCR) that specifically recognizes an antigen. Such an antigen is typically presented on the surface of a cell by an MHC-I molecule. If the T cell receptor of a cytotoxic T cell is specific for an antigen, it binds to the complex of the antigen and the MHC-I molecule and destroys the cell. The interaction of a T cell with the complex of an antigen and a MHC-I molecule of a target cell typically also involves a co-receptor, namely CD8. In one embodiment, when a T cell binds to such a complex on a target cell, it releases any of the cytotoxins perforin, granzyme, and granulysin. In one embodiment, through the action of perforin, granzymes enter the cytoplasm of the target cell and their serine protease function triggers a caspase cascade leading to apoptosis of said target cell. In one embodiment, apoptosis of said target cells may also be induced by cell-surface interaction between the cytotoxic T cell and the target cell, such as by a Fas-Fas ligand interaction.

The term "means for specifically targeting perilipin-1 fragment presenting adipocytes", as used herein, relates to any means which is capable of specifically targeting a perilipin-1 fragment presented on the surface of an adipocyte and which is capable of triggering the elimination of said adipocyte directly and/or indirectly. In one embodiment, said means for specifically targeting perilipin-1 fragment presenting adipocytes relates to an antigen-binding peptide capable of recognizing a perilipin-1 fragment specifically, preferably via an epitope having any of SEQ ID NOs. 1-6, 330-333. In one embodiment, said means for specifically targeting perilipin-1 fragment presenting adipocytes comprises and/or induces an effector mechanism which triggers elimination of said adipocyte. In one embodiment, said means for specifically targeting perilipin-1 fragment presenting adipocytes relates to cytotoxic T cells which have a T cell receptor specific for perilipin-1, preferably specific for an epitope of perilipin-1 having any of SEQ ID NOs. 1-6, 330-333. In one embodiment, said means for specifically targeting perilipin-1 fragment presenting adipocytes triggers an indirect elimination mechanism and/or a direct elimination mechanism. In one embodiment, a means for specifically targeting perilipin-1 fragment presenting adipocytes is preferably a means for specifically eliminating perilipin-1 fragment presenting adipocytes. In one embodiment, said means is capable of eliminating perilipin-1 presenting adipocytes and/or is capable of inducing an effector mechanism which eliminates perilipin-1 presenting adipocytes.

The term "specific" or "specifically binding", as used herein, means in accordance with this invention that the antibody or immune receptor fragment is capable of specifically interacting with and/or binding to a specific antigen or a set of specific antigens but does not essentially bind to other antigens. Such binding may be exemplified by the specificity of a lock-and-key-principle.

The term "nucleic acid", as used herein, relates to a nucleotide sequence, such as ribonucleic acid or deoxyribonucleic acid. In one embodiment, said nucleic acid encodes for an antigen-binding peptide in accordance with other embodiments of the present invention. In one embodiment, said nucleic acid encodes for a sequence which is at least 50%, preferably at least 85% identical to a nucleic acid sequence encoding for an antigen-binding peptide in accordance with other embodiments of the present invention. In one embodiment, said nucleic acid at least 50%, preferably at least 85% identical to a nucleic acid sequence encoding for an antigen-binding peptide results in the same peptide product as a 100% identical sequence, due to the redundancy of the genetic code.

The term "non-human animal", as used herein, relates to an animal which is not human, preferably to a mammal.

The term "inoculating", as used herein, relates to administration of an antigen, preferably having at least one epitope having a sequence according to any of SEQ ID NOs. 1-6, 330-333, for immunization and production of an antibody or antigen-binding fragment specific for said antigen.

The term "screening", as used herein, relates to analyzing certain candidates of molecules or cells with regard to their binding specificity for a certain antigen, preferably perilipin-1. The aim of such a screening is to identify molecules, such as an antigen-binding peptide, or cells, such as cytotoxic T cells, which bind to a certain antigen, preferably perilipin-1, specifically and with high affinity, preferably with an affinity of at least $10^{-9}$M, or, with regard to TCR-derived antigen-binding fragments, preferably with an affinity of at least $10^{-4}$M. In one embodiment, the best candidates identified by screening are subsequently amplified, for example by cell culture expansion, preferably in vitro.

The term "host cell", as used herein, relates to a cell which may be used to produce an antigen-binding peptide of the present invention. In one embodiment, said host cell allows for production of an antibody or antigen-binding fragment, such as a yeast cell or a Chinese hamster ovary (CHO) cell. In one embodiment, a host cell is transformed to comprise a nucleic acid encoding an antigen-binding peptide of the present invention and said transformed host cell is referred to as recombinant cell. In one embodiment, said host cell is an autologous or allogenic effector cell, such as a T cell or NK cell, which may be transformed into a CAR-T cell or CAR-NK cell, respectively. In one embodiment, such a cell is a genetically modified cell which comprises a nucleic acid encoding for an antigen-binding peptide specific for perilipin-1.

The term “obesity”, as used herein, relates to a medical condition in which excess body fat has accumulated in a body to the extent that it may have negative effects on the health of said body. In one embodiment, a means for specifically eliminating perilipin-1 fragment presenting adipocytes, such as a perilipin-1 fragment specific antigen-binding peptide, or a perilipin-1 specific cytotoxic T cell is used to target and/or eliminate adipocytes in a patient having obesity.

The term “binding assay”, as used herein, relates to an assay or an analytic procedure used to study the binding of an antigen-binding peptide to an antigen. In one embodiment, a binding assay may refer to flow-cytometry, tetramer staining, western blot, fluorescence assay, surface plasmon resonance, or other binding assays known to a person skilled in the art. In one embodiment, a binding assay (e.g. tetramer staining) may also relate to an assay used to study the binding of a cytotoxic T cell, preferably that T cell receptor of said cytotoxic T cell, to an antigen. In one embodiment, a binding assay may relate to a surface plasmon resonance measurement.

The term “Kp”, as used herein, relates to the dissociation constant, which is the inverse of the association constant. In one embodiment, an antigen-binding peptide of the present invention binds to an antigen with an affinity ($K_D$) of at least $10^{-4}$ M. In one embodiment, said antigen-binding peptide is a peptide selected from an antibody, an antibody-derived fragment, and a non-antibody antigen-binding peptide such as an anticalin or a DARPin, and binds to an antigen with an affinity ($K_D$) of at least $10^{-7}$M, preferably of at least $10^{-9}$ M, more preferably of at least $10^{-11}$ M. In one embodiment, said antigen-binding peptide is a TCR-derived antigen-binding peptide and binds to an antigen and/or an MHC-antigen-complex with an affinity ($K_D$) of at least $10^{-4}$ M. In one embodiment, the term “an affinity ($K_D$) of at least $10^{-4}$ M” is meant to refer to a Kp value that is $10^{-4}$ M or smaller, such as $10^{-5}$ M, 106 M, or $10^{-7}$M.

The term “monoclonal antibody” or “mAB”, as used herein, relates to an antibody which is obtained from a population of substantially identical antibodies based on their amino acid sequence. Monoclonal antibodies are typically highly specific. Furthermore, in contrast to a polyclonal antibody preparation which typically includes different antibodies directed against different epitopes of an antigen, a mAb is typically directed against a single epitope on the antigen. In addition to their specificity, mAbs are advantageous in that they can be synthesized by cell culture, such as by a hybridoma cell culture or recombinant host cells uncontaminated by other immunoglobulins. In one embodiment, a mAb relates to a chimeric, a humanized or a human antibody or an antibody fragment. In one embodiment, a monoclonal antibody may be an optimized monoclonal antibody having an Fc region which is engineered to have improved binding properties to be targeted by an effector cell. In one embodiment, said optimized monoclonal antibody may be engineered by specific amino acid exchanges in the amino acid sequence of the Fc region. In one embodiment, said optimized monoclonal antibody may also be optimized to have an improved serum half-life, for example by modification of a CH3 region of an IgG.

The term “human antibody”, as used herein, relates to an antibody which only comprises human sequences, or a fragment thereof. In one embodiment, a human antibody is produced by a display technique, such as by phage display or ribosome display.

The term “humanized antibody”, as used herein, relates to an immunoglobulin chain or fragment thereof, such as a Fab fragment, a Fab' fragment, a $F(ab')_2$ fragment, a Fv fragment, or an other antigen-binding fragment of an antibody, which contain a sequence from non-human immunoglobulin. In one embodiment, a humanized antibody is a human antibody in which certain CDR residues are replaced by CDR residues from a non-human having desired specificity and affinity properties.

The term “chimeric-human antibody”, as used herein, relates to an artificial antibody which has been designed by genetic engineering or protein engineering by combining sequences of different species, such as mouse and human. In one embodiment, a human-chimeric antibody is a hybrid protein of the antigen-binding domain from a mouse antibody and the constant domain of a human antibody.

The term “substantially intact antibody”, as used herein, relates to an antibody which is not fragmented, truncated or otherwise shortened, and which has retained its capability of specifically binding to an antigen.

The term “cross-react”, as used herein, relates to off-target binding to a structure which is not the target structure. In one embodiment, “cross-reacting” relates to binding of an antibody, an antigen-binding fragment, or a cytotoxic T cell, to a protein which is not perilipin-1, such as to perilipin-2, -3, -4, or -5.

The term “(%) sequence identity”, as used herein, relates to the percentage of pair-wise identical residues with regard to a homology alignment of a sequence of a polypeptide/nucleic acid of the present invention with a sequence in question.

The term “patient”, as used herein, may relate to a human or an animal. A blood sample for obtaining T cells and/or antibodies may be an autologous sample or an allogenic sample.

The term “recombinant antigen-binding peptide library”, as used herein, relates to a pool of antigen-binding peptides produced by protein engineering technology methodologies known to a person skilled in the art. For example, such a pool of antigen-binding peptides may be produced and screened by phage display, yeast display, mRNA display or ribosome display. Display libraries display single-chain variable-domain antigen-binding fragments such as scFvs or Fab fragments, and contain the encoding DNA or RNA. The genetic diversity of these libraries is commonly generated by cloning the repertoire of the immunoglobulin heavy-chain and light-chain variable gene segments from naïve or immunized individuals, or by using synthetic DNA to randomize the antigen-binding fragments, or by a combination of these approaches, optionally in combination with error-prone PCR. In one embodiment, antigen-binding peptides may be optimized to enhance an effector function and/or half-life of said antigen-binding peptide.

The term “optimized”, as used herein, relates to enhanced properties of a peptide, which has been modified by protein engineering compared to said peptide in unmodified form. In one embodiment, an antigen-binding peptide is optimized with regard to the strength and/or the type of effector functions it evokes by means of an effector system, e.g. by designing said antigen-binding peptide to comprise an Fc region which is recognized by an Fc receptor of a macrophage, a monocyte, a neutrophil, a NK cell, or another effector cell. In one embodiment, said Fc region is optimized by genetic engineering to contain amino acid exchanges and/or an altered glycosylation compared to an unmodified Fc region. In one embodiment, the serum half-life of an antigen-binding peptide is increased by designing said peptide to comprise a CH3 region of an IgG domain increasing half-life or by modification of said antigen-binding peptide with other half-life increasing molecules.

BRIEF DESCRIPTION OF THE FIGURES

The present invention is now further described by reference to the following figures.

With the exception of the fluorescence labeling visualisation was accomplished using 10 nm gold particles in electron microscopy (EM) and with 1 nm gold in light microscopy (LM).

A) Light microscopy of univacuolar fat cells of human white adipose tissue. Silver-enhanced gold particles only appear at the membranes of fat vacuoles, which cannot be distinguished from the plasma membrane at this magnification. The loose connective tissue between the fat cells is free of staining. Bar 25 μm.

B) Fluorescence microscopy of multivacuolar 3T3-L1 cells. Labeling was visualized by the cyanine dye Cy3. Bar 50 μm.

C, D) Transmission electron microscopy (TEM) of 3T3-L1 cells. The surface of lipid storage droplets is tightly labeled with gold particles. There are only sporadic gold particles at the plasma membrane (white arrowheads), whereas no gold particles appear at the nuclear envelope. Bar 1 μm.

E) There is no labeling in 3T3-L1 cells at the preadipocyte stage. Bar 1 μm.

F) Freeze-fracture replica of a 3T3-L1 cell. The gold label appears at the phospholipid layer (P-face, white arrowhead). There is no labeling at the convex inner droplet surface (E-face equivalent, black arrowhead) and in the core of the LSD. Bar 0.3 μm.

G) Freeze-fracture replica of the exoplasmic fracture face of the plasma membrane of a 3T3-L1 cell characterized by elevated caveolae. Gold particles are not visible. Bar 0.2 μm.

H) TEM of mouse adipose tissue. Gold particles are deposited at the surface of the LSD (white arrowheads). Dashed line indicates adipocyte plasma membrane. In the neighborhood there is a tissue eosinophil granulocyte.

C, caveolae; core, lipid core of LSDs; EF, exoplasmic fracture face; EOSG, eosinophil granule; LSD, lipid storage droplet; N, nucleus; PM, plasma membrane. Bar 0.5 μm. Images shown are representative for at least 3 independent experiments.

Figure 2:
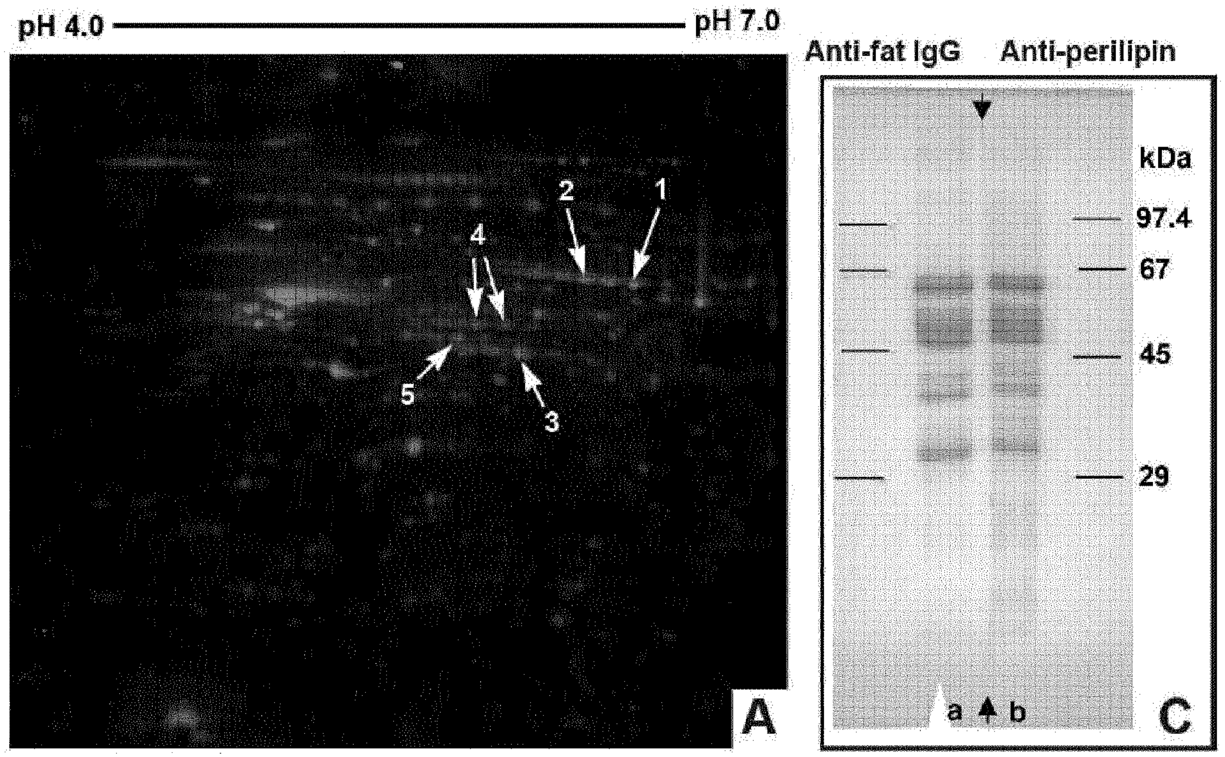

FIG. 2: The human anti-fat autoantibody reacts with multiple Perilipin-1 variants.

A) Two-dimensional separation of proteins of rat fat cell membranes. Proteins were separated in a linear pH gradient IPG strip (pH 4-7) in the first dimension. In the second dimension proteins were separated using 10% (w/v) homogeneous SDS PAGE gels. In the overlay spots detected by Coomassie staining are shown in green. Spots detected by anti-fat autoantibody on a parallel blot are color coded in red. Immunoreactive spots are identified by their yellow color (marked with arrows). Spot numbers refer to the identifications listed in table B.

B) Summary of the peptide mass fingerprint (PMF) analysis of protein spots. Three out of five analyzed spots were clearly identified as Perilipin A (spots 1, 2 and 4) and two spots as Perilipin B (spots 4 and 5), respectively, which result from differential splicing of the Perilipin-1 transcripts. Acc.-Nr. is the sequence identification number in GenBank. Theoretical molecular masses denoted in the fourth column were calculated from the amino acid sequence. PMF spectra were submitted for identification using Mascot interface (MASCOT 2.1.03) and Mascot scores are depicted (P=0.05).

C) Comparison of the human anti-fat IgG with a commercial anti-Perilipin-1 antibody (Affinity BioReagents, Golden, CO, USA). 10 μg of membrane proteins were subjected to SDS-PAGE and immunoblotting was performed after cutting the PVDF membrane between two lanes of membrane proteins (1). Incubation with the patient's autoantibody and with anti-Perilipin-1 antibody demonstrates an identical pattern of positive bands.

Figure 3:
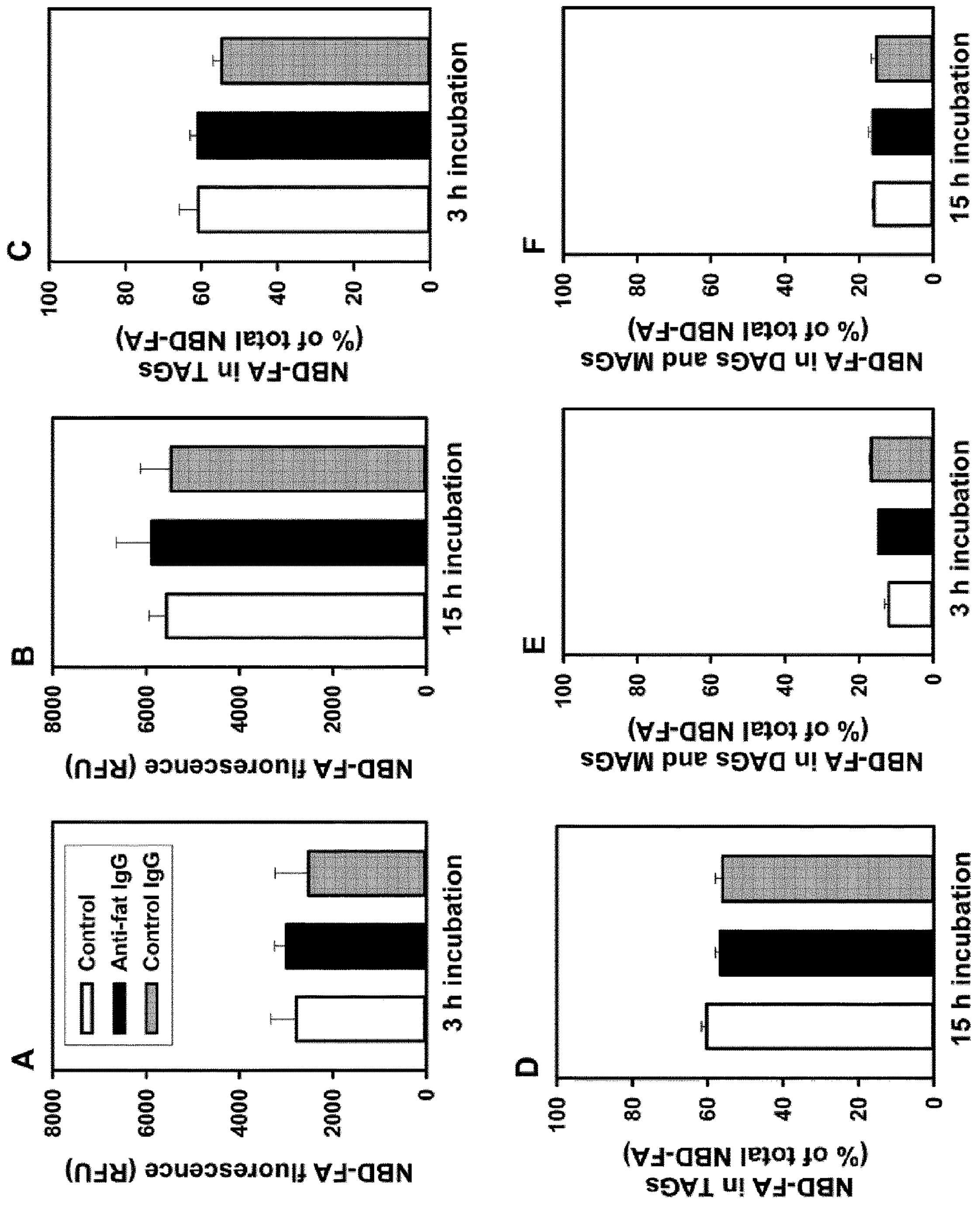

FIG. 3: The autoantibody does not interfere with homeostasis of lipid storage in differentiated human preadipocytes.

Human preadipocytes were induced for adipose conversion and allowed to accumulate triacylglycerols over 14 days. These cells were loaded with a fluorescently labeled fatty-acid (NBD-FA) for 3 h in the presence of 10 nM insulin. After washing to eliminate excess NBD-FA the cells were incubated for an additional 3 h (A, C, E) or 15 h (B, D, F) in the absence of antibodies (white bars) or in the presence of anti-fat IgG (black bars) or control IgG (grey bars), respectively, in the presence of 10 nM insulin. Cells were harvested, total lipids were extracted and aliquots analyzed by thin-layer chromatography with subsequent quantification of labeled intracellular lipids by fluorescence scanning. The results shown are means±SEM of 4 experiments.

A, B) Anti-fat IgG does not interfere with accumulation of the NBD-FA in the total cellular lipid pool, presented as relative fluorescence units (RFU).

C, D) The autoantibody has no effect on the distribution of incorporated NBD-FA between the pools of storage triacylglycerols E, F) The autoantibody has no effect on the distribution of incorporated NBD-FA between the pools of intermediates of lipid synthesis and degradation, diacylglycerols (DAGs) and monoacylglycerols (MAGs).

Figure 4:
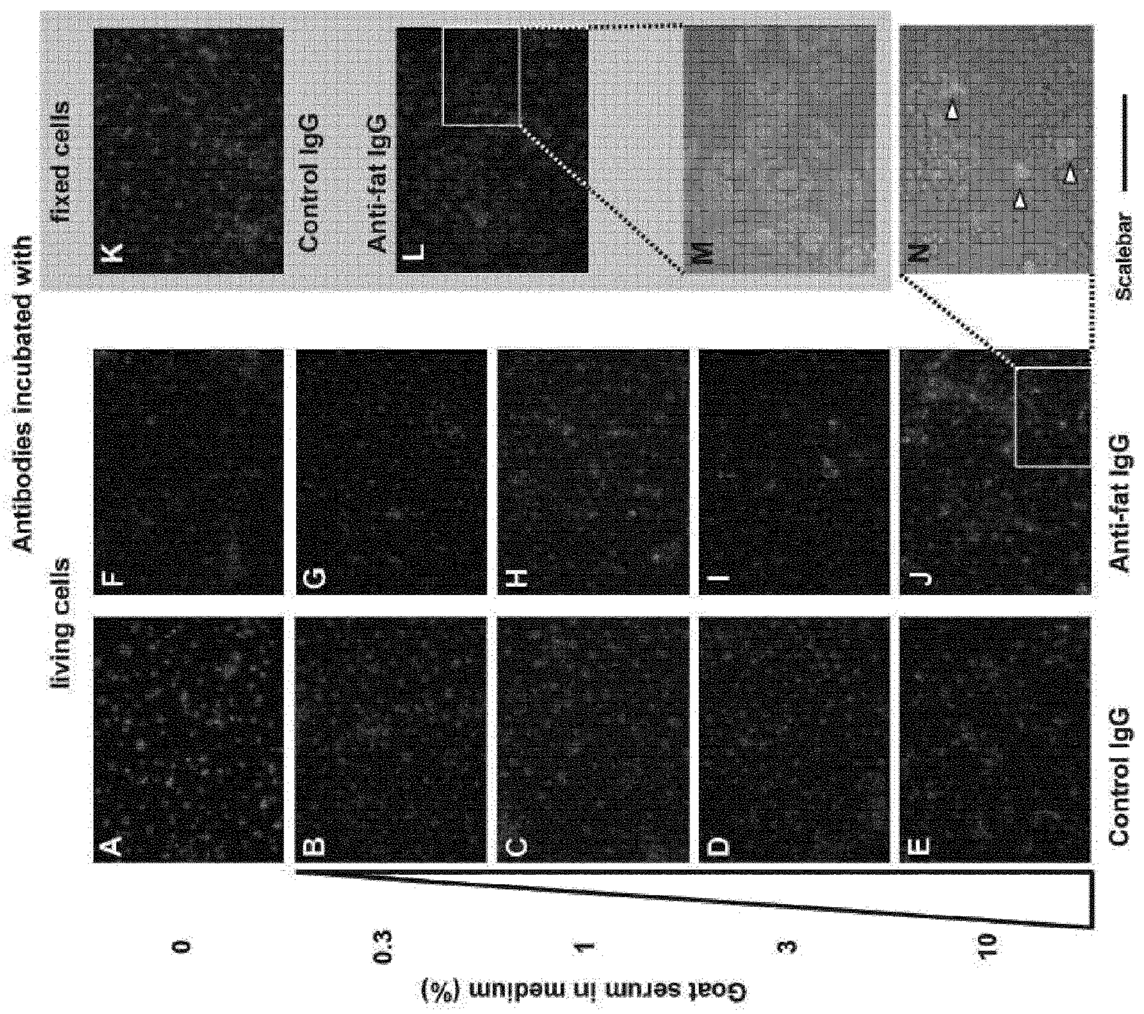

FIG. 4. The anti-fat autoantibody accumulates in cells with atypical morphology (dead cells) in the presence of serum.

Exposure of 3T3-L1-adipocytes to neither control IgG nor anti-fat IgG in serum-free culture medium resulted in almost undetectable labeling of the cells, when the cells were washed extensively before fixation and immunofluorescence detection (A, F). However, anti-fat IgG (G-J) but not control IgG (B-E) resulted in immunoreactivity of a significant proportion of cells in the presence of goat serum (not heat-inactivated). This effect was strongly dose-dependent. Closer examination revealed that under these conditions anti-fat IgG did not visibly accumulate on the surface of lipid droplets (N), but in cells with atypical morphology (arrowheads; staining not associated with lipid droplets, condensed chromatin), which are only rarely found in normal cultures of 3T3-L1-adipocytes. Note the typical staining pattern of lipid droplets around the nucleus for cells fixed and stained according to the normal protocol (L, M). (K) No immunoreactivity in fixed cells with control IgG. (A-J, N)

Live cells incubated with primary antibodies, (K-M) fixed cells incubated with primary antibodies. (M, N) Overlay of the indicated areas of the fluorescence images (J and L, respectively) and the corresponding phase contrast images; red channel set to two-fold intensity for better visibility in the overlay image. Scalebar: 250 μm (A-L) or 100 μm (M-N).

Figure 5:
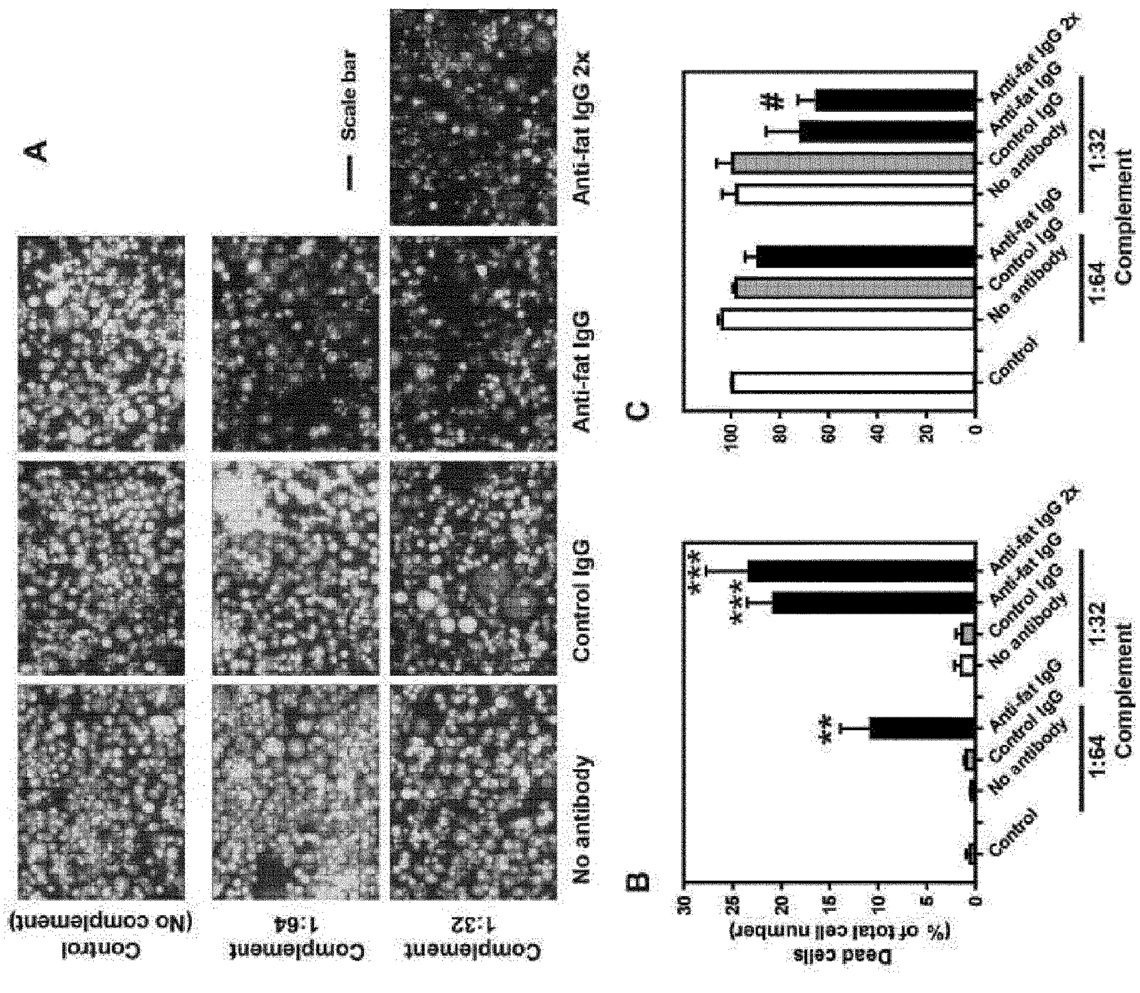

FIG. 5. The anti-fat autoantibody triggers complement dependent cell-death in 3T3-LI-cells.

3T3-L1-adipocytes were generated in a serum-free differentiation system and allowed to accumulate lipids until day 8 after induction of differentiation. Cells were pre-incubated with anti-fat IgG or control IgG for 40 min as indicated. Then, medium without (control) or with rabbit complement (final dilution either 1:64 or 1:32) was added as noted in the figure. In the presence of complement 1:32 anti-fat IgG was additionally tested in twice the concentration normally used (anti-fat IgG 2x).

A) Cells were fixed and stained with Fluoro Quench AO/EB reagent, which results in green staining of living cells and in orange staining of dying and dead cells (in flat adipocytes the lipid droplets appear unstained, whereas in rounded adipocytes they are merely visible). Scale bar 100 μm for all images.

B) The quantification of 3 independent experiments indicates significant numbers of dead cells in the presence of anti-fat IgG plus complement, but not under control conditions. Significant differences versus all respective controls were identified by ANOVA ($P<0.005$) with Student-Newman-Keuls all pairwise multiple comparisons; , $P<0.01$; *, $P<0.001$.

C) Percentage of viable cells in relation to corresponding untreated controls after 1 hour (Student's t-test; #, $P<0.05$).

Figure 6:
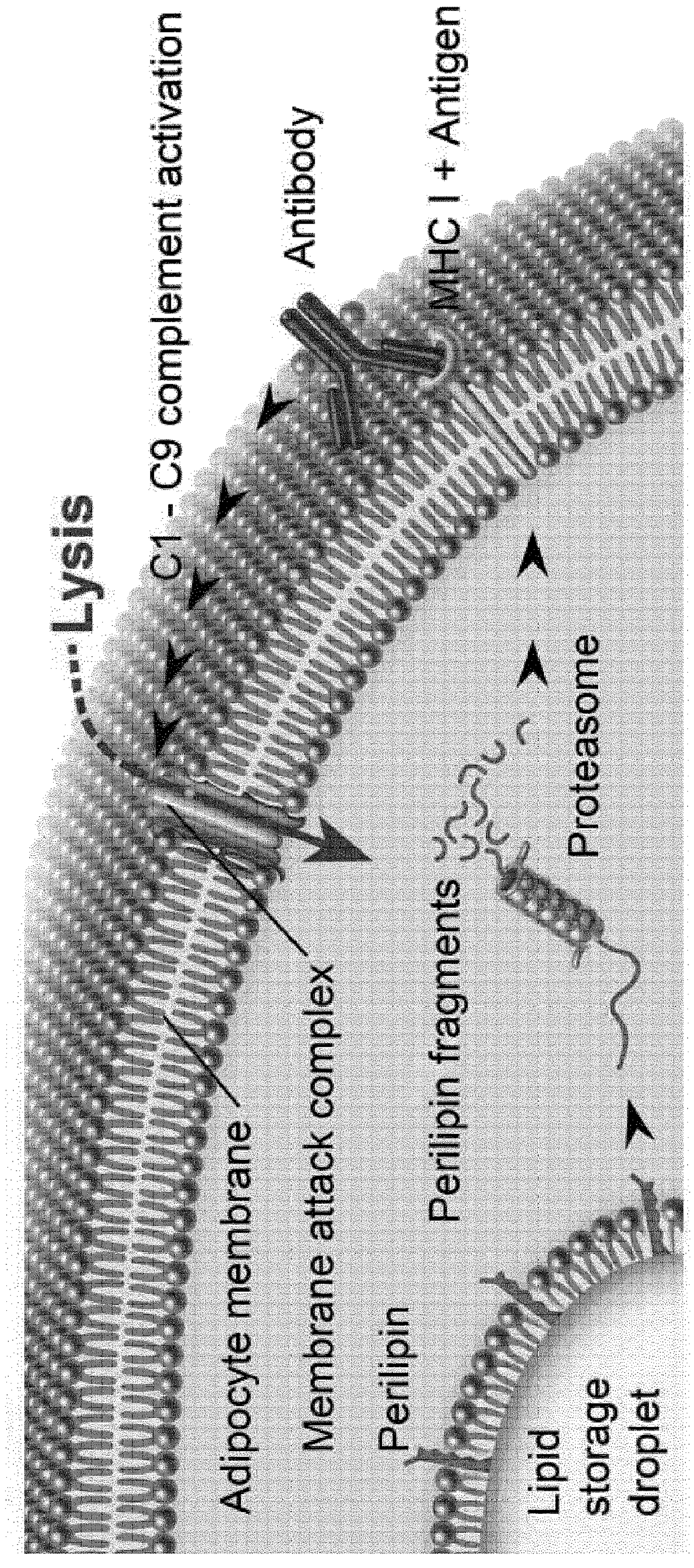

FIG. 6. Scheme of perilipin-1-dependent antibody-induced complement activation.

Mechanism of action of an induced complement reaction against adipocytes which is mediated by anti-perilipin-1 antibodies. Perilipin-1 peptides are degraded by the proteasome and the resulting perilipin-1 fragments are presented by an MHC on the cell surface of adipocytes. Antibodies targeting a peptide sequence, i.e. an epitope having any of SEQ ID NOs. 1-6, 330-333, as disclosed herein, specifically target adipocytes and allow for specific elimination of adipocytes by complement activation (indirect elimination mechanism). Alternatively, cytotoxic T cells specific for at least one perilipin-1 epitope may eliminate adipocytes presenting said perilipin-1 by an indirect elimination mechanism.

In addition, other effector systems which may be activated by antibodies binding to perilipin-1 fragment-loaded MHC may employ a direct elimination mechanism. These effector systems, which are activated by Fc-receptor mediated binding to the said adipocyte bound antibodies, may be macrophages or neutrophils (neutrophilic polymorphonuclear granulocytes).

Figure 7:
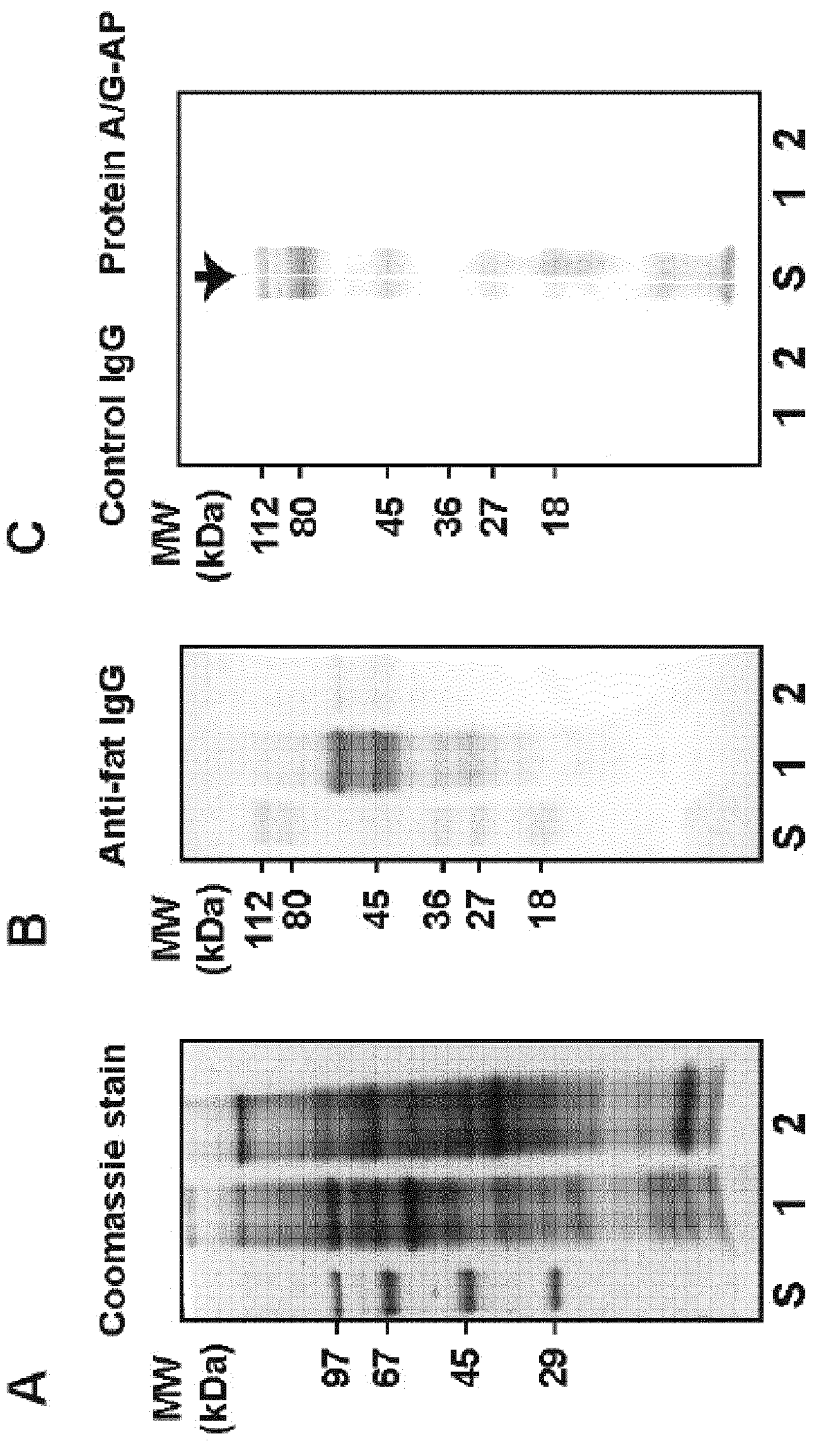

FIG. 7. The anti-fat autoantibody binds to lipid associated proteins.

Lipid associated (1) and cytosolic proteins (2) from isolated fat cells of rat fat pads were separated by SDS-PAGE and either stained with Coomassie blue (A) or transferred to a PVDF membrane (B). The anti-fat IgG reacts with two major and several minor bands of the preparation containing lipid associated proteins. (C) A control membrane was cut along the molecular weight standard lane (1) and incubated with either a control serum and subsequently with protein A/G-AP (Control IgG) or with protein A/G-AP alone (Protein A/G-AP), indicating that recognition of bands in (B) was specific for the anti-fat antibody. S, molecular weight standard. Data are representative for 5 experiments with rat fat pads and similar results were obtained with in vitro differentiated human adipocytes and mouse 3T3-L1-cells.

Figure 8:
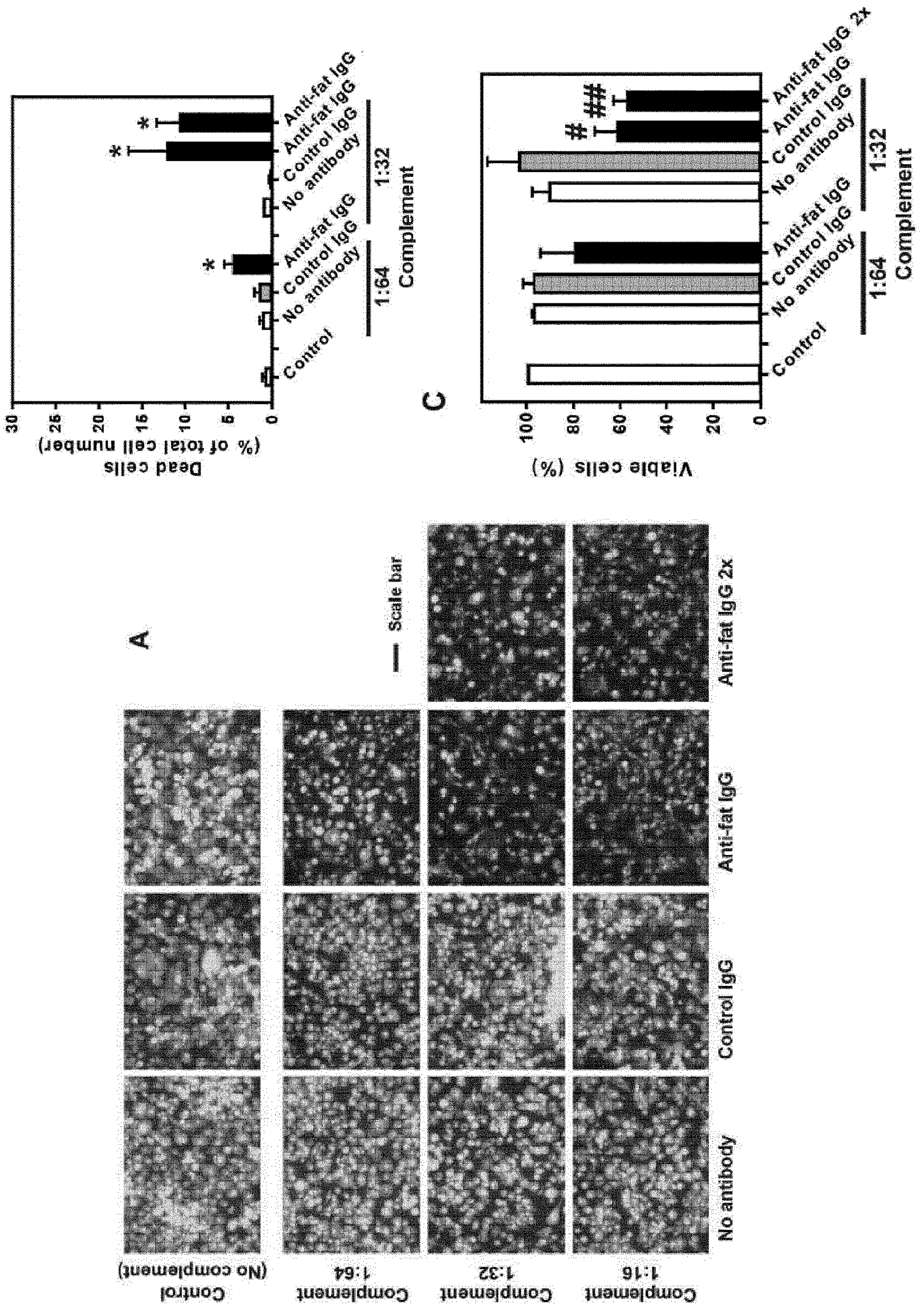

FIG. 8. Only a fraction of cells is susceptible to autoantibody triggered cell death.

Cells were treated in parallel to the experiments summarized in FIG. 5, but incubations lasted 24 hours. In addition, data obtained with a higher complement concentration (final dilution 1:16) are shown (A). The quantification of 3 independent experiments indicates significant loss of cells in the presence of anti-fat IgG plus complement, but not under control conditions. When comparing numbers for dead cells (B) and viable cells (C), there is a remarkable difference due to detachment of dead cells. (B) Significant differences versus all respective controls were identified by ANOVA ($p=0.016$) with Student-Newman-Keuls all pairwise multiple comparisons; *, $P<0.05$. (C) Percentage of viable cells in relation to corresponding untreated controls after 24 hours (Student's t-test; #, $P<0.05$; ##, $P<0.005$).

Figure 9:
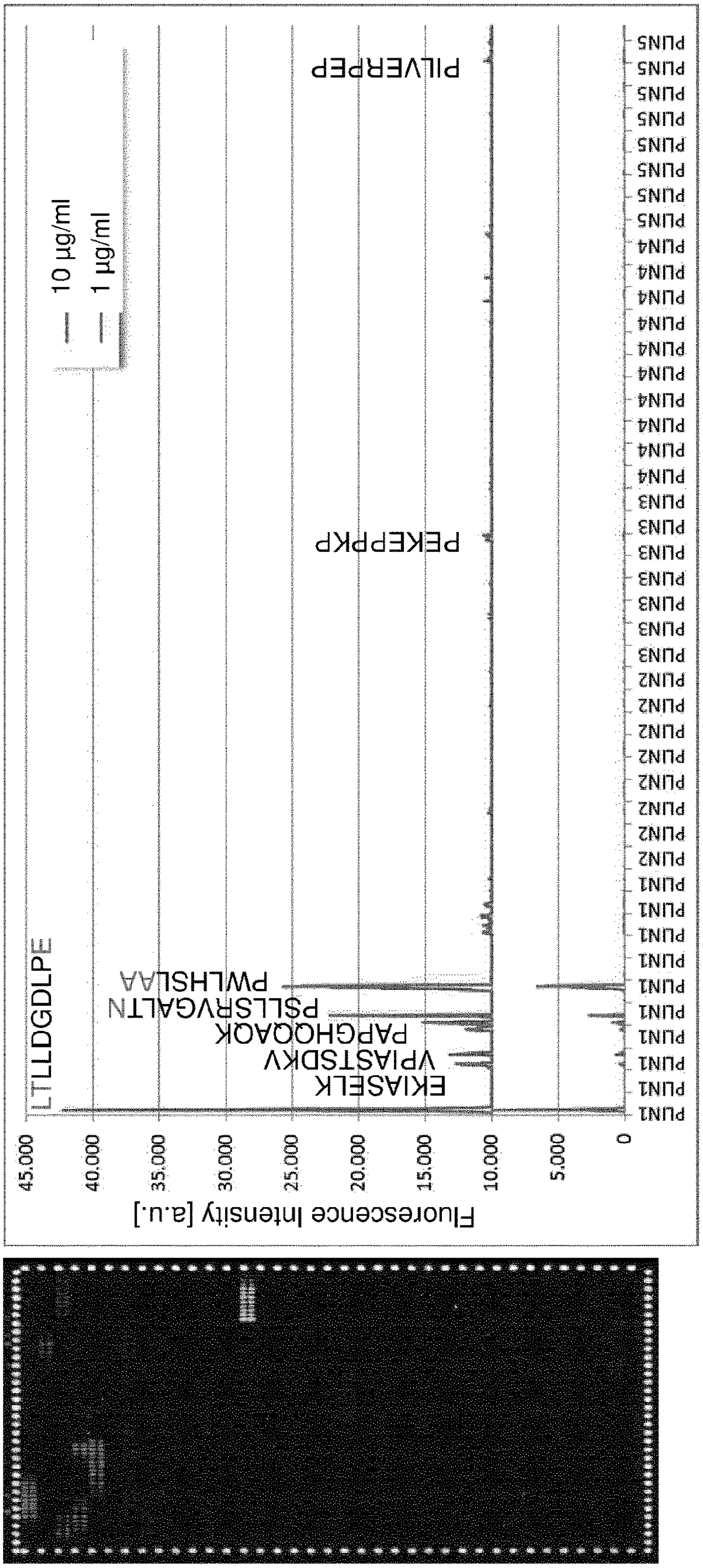

FIG. 9. Peptide array for perilipin-1 epitopes.

Perilipin-1 epitopes having any of SEQ ID NOs. 1-6, 330-333 were identified using peptide arrays (PEPperPRINT, PEPperMAP) with perilipin-1 autoantibodies. Sequences of human perilipins 1-5 were elongated with neutral linker sequences at the N- and C-terminal ends to prevent shortened peptides. The elongated antigen sequences were translated into peptide sequences having 15 amino acids each, wherein said peptide sequences had an overlap of 14 amino acids each. The thus produced peptide array was screened with the perilipin-1 autoantibody described in the previous examples. The antibody specificity was verified by screening all possible 15mer peptide sequences of perilipin-1 related proteins perilipin-2,-3,-4- and 5, which are involved in different functions of lipid storage and/or in other cells. Accordingly, cross-reactivity with other members of the perilipin family was excluded.

A) Analysis of a peptide array using a human anti-perilipin-1 autoantibody to identify perilipin-1 epitopes. Only perilipin-1 peptides are bound specifically and with high affinity.

B) Quantification of the antibody binding. Six peptides were bound with high affinity. The binding of the peptide depicted on the right (PEKEPPKP from perilipin-3 and PILVERPEP from perilipin-5) was negligible.

The plurality of the identified peptides (epitopes) is highly conserved in the mouse sequence and human sequence.

Figure 10:
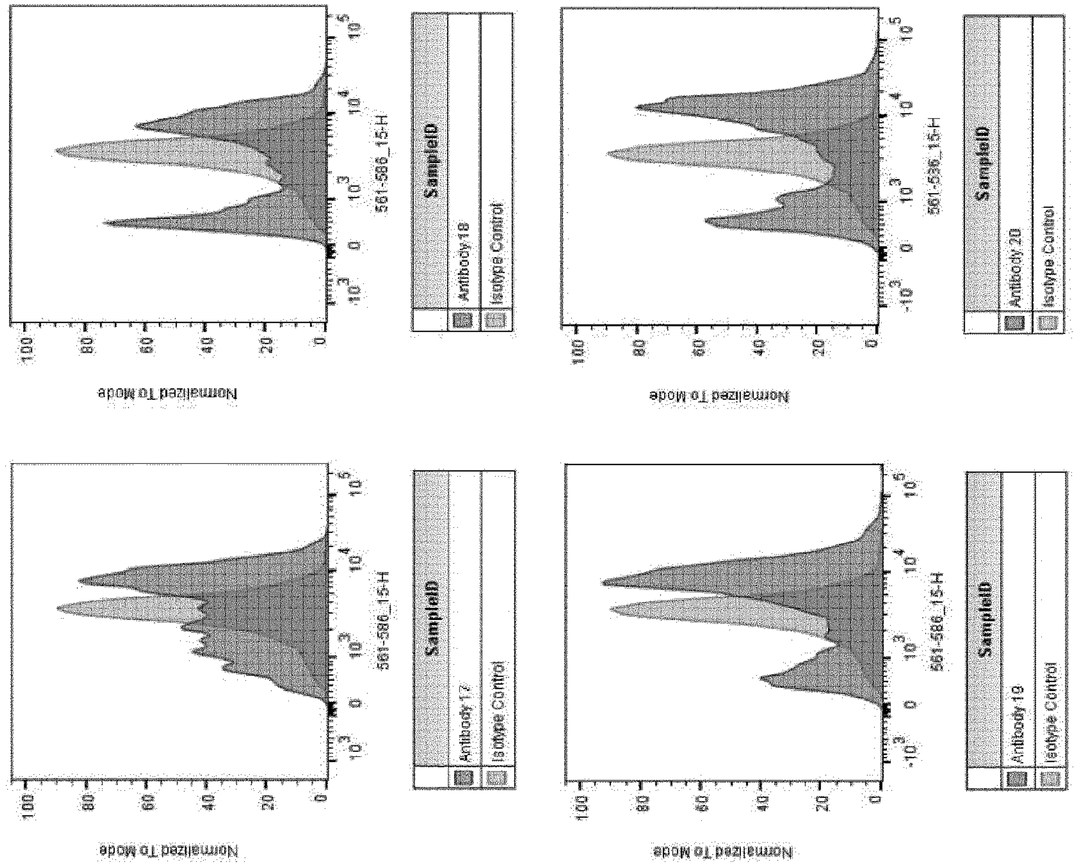

FIG. 10. Representative flow cytometry fluorescence histograms of anti-perilipin antibodies binding to primary adipocytes (dark gray profiles).

Antibodies 17-20 (A), 21, 22, 24, and 25 (B) were analyzed. Controls represent cells treated with isotype control and the secondary antibodies (light gray profiles). As a control, commercially available antibody for perilipin-1 from Abcam (ab192716) was used (C). The overlapping histograms observed using the commercial antibody (C) indicate that the commercial anti-perilipin-1 antibody does not bind specifically to adipocytes. In contrast thereto, antibodies of the present invention show binding to adipocytes (rightward shift of histograms) compared to isotope control (A, B).

Figure 11:
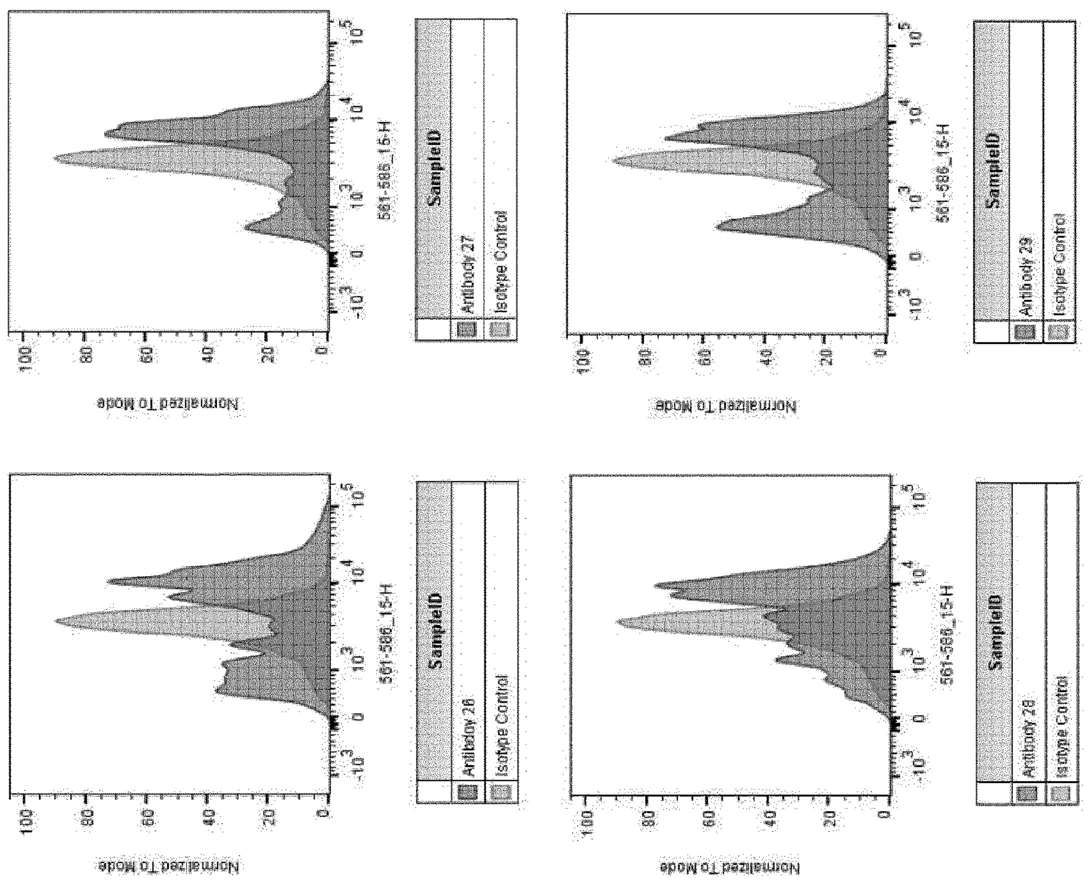

FIG. 11. Representative flow cytometry fluorescence histograms of anti-perilipin antibodies binding to primary adipocytes (dark gray profiles).

Antibodies 26-32 of the present invention were analyzed. Controls represent cells treated with isotype control and the secondary antibodies (light gray profiles). Antibodies of the present invention effectively bind to adipocytes compared to isotope control.

Figure 12:
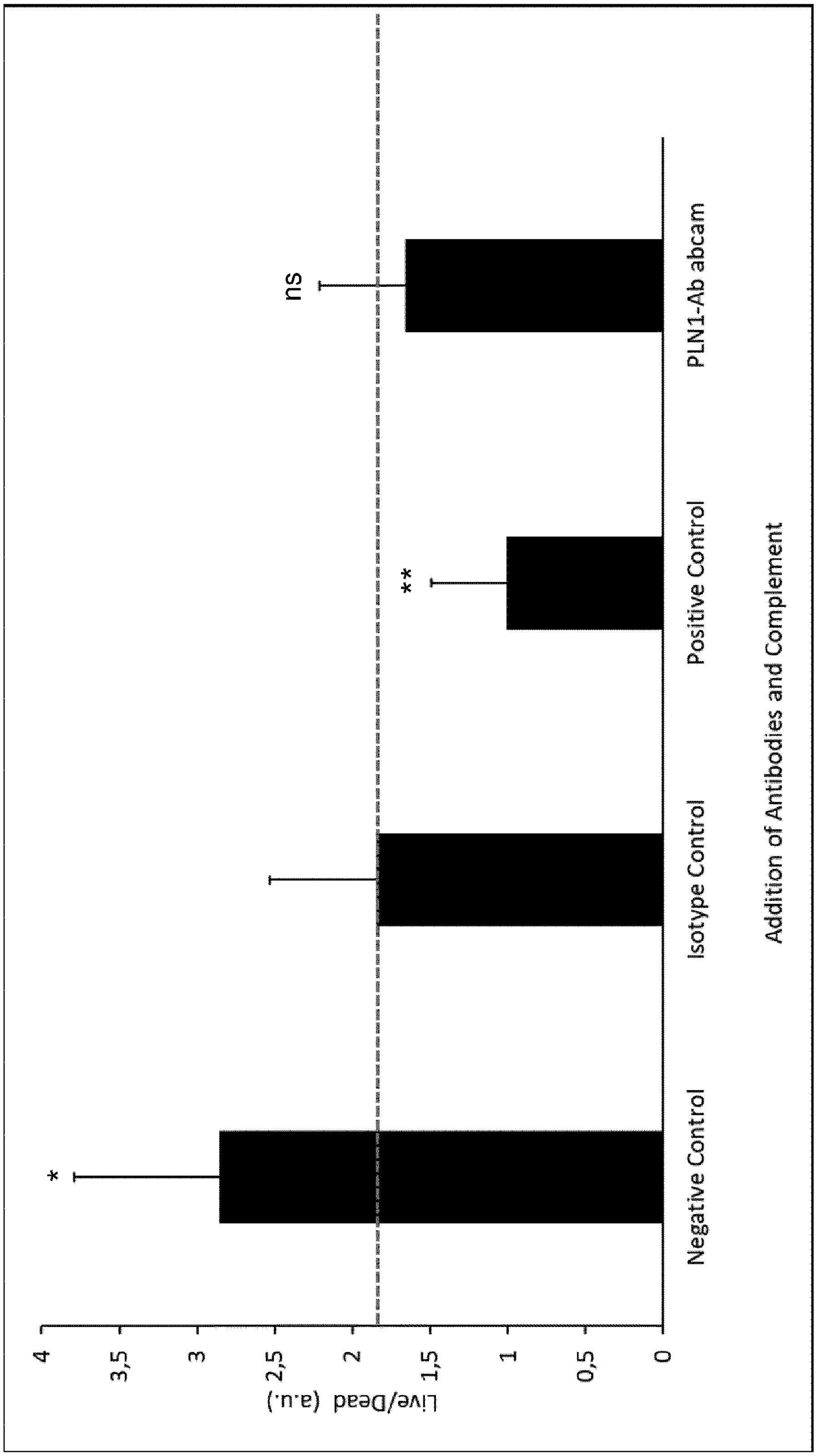

FIG. 12. Complement-mediated cell death mediated by anti-perilipin antibodies.

Complement-mediated cell death of 3T3-L1 cells differentiated into adipocytes after addition of commercially available antibody for perilipin-1 from Abcam (ab192716) compared to controls (A) and after addition of single anti-perilipin antibodies (B). The Live/Dead cell ratio was calculated from fluorescence intensities of fluorescence dye, staining only alive cells, divided by fluorescence intensity of dye, staining dead cells. Detected signals are compared to the signals of the isotope control. The signal obtained for the isotope control is indicated by the dashed line. The tested commercially available antibody (PLN1-Ab abcam) is not significantly different from the signal of the isotype control and does not show significant (not significant: ns complement mediated cell death (A). In contrast thereto, antibodies of the present invention show significant (*: $p<0.05$; : $p<0.01$) mediation of complement-mediated cell death (FIG. 12 panel (B)). FIG. 12** panel (B) also shows again the signal obtained in this experiment for the isotope control as indicated by the dashed line. The indicated antibodies and their target epitopes as well as their respective SEQ ID NO:s are listed in table 5.

Figure 13:
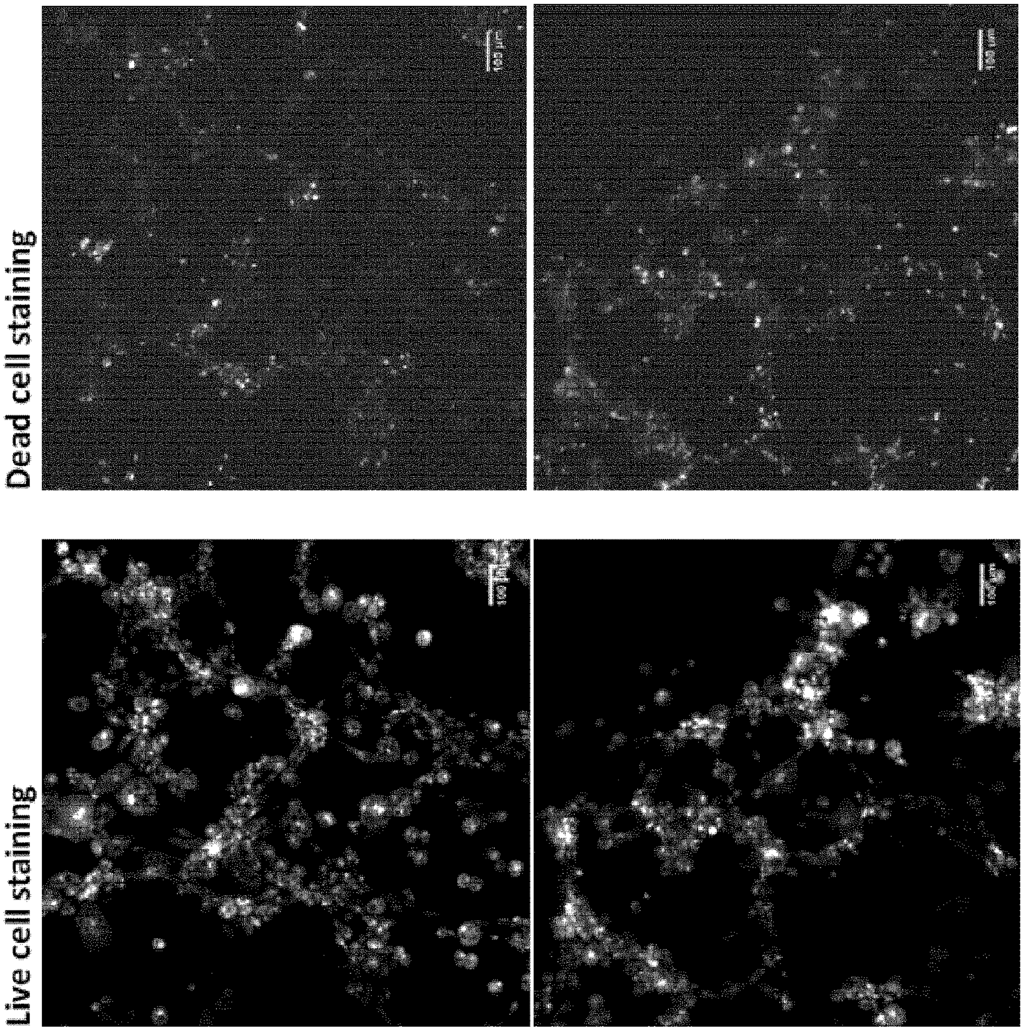

FIG. 13. Complement-mediated cell death mediated by anti-perilipin antibodies. Images from fluorescence microscopy of complement-mediated cell death of 3T3-L1 cells differentiated into adipocytes, compared to negative control (addition of no antibody) and an isotype control antibody (A), after addition of anti-perilipin antibodies, such as antibodies no. 20 and 25 (B). In the presence of an anti-perilipin antibody of the present invention, particularly antibody no. 20 or 25, the intensity of live cell staining is decreased and the number of dead cells is increased. Antibodies of the present invention thus show effective complement-mediated cell death.

Figure 14:
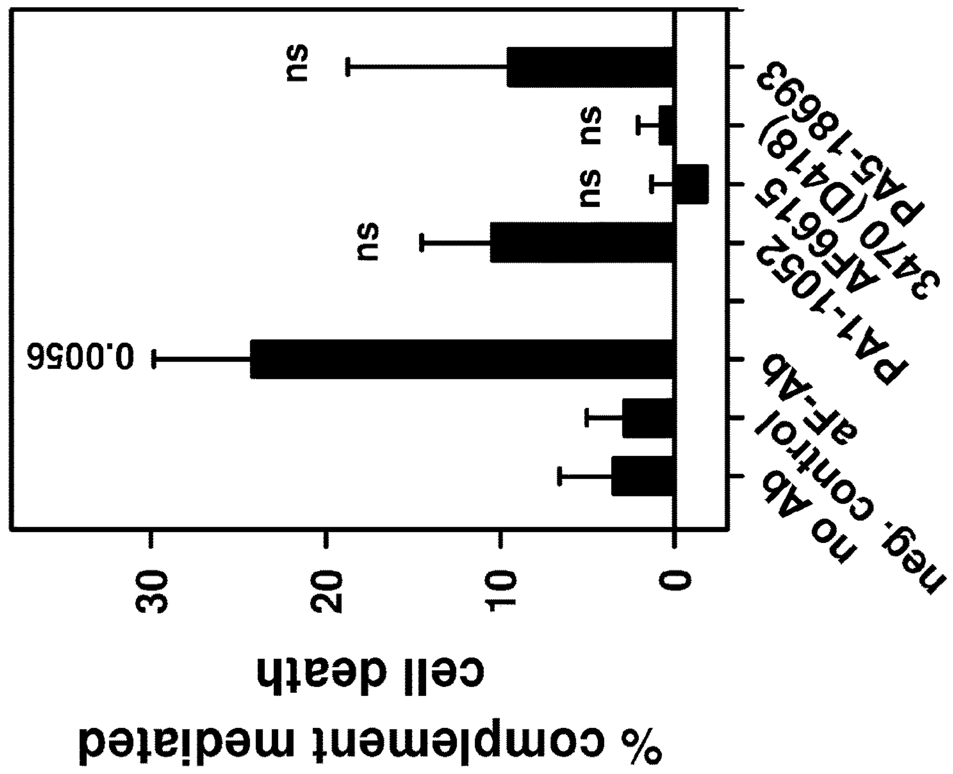

FIG. 14. Complement-mediated cell death compared to commercially available antibodies.

Mean values (plus SEM) for the differences in the numbers of dead cells determined with and without complement are shown; numbers on top of bars indicate P-values of 2-sided Student's t-tests; with the exception of aF-Ab (patient derived polyclonal antibody), all tested commercial available antibodies showed non-significant results. The tested commercially available anti-perilipin antibodies were PA1-1052 (ThermoFisher), AF6615 (R&D Systems), CST antibody #3470 (D418), and PA5-18693 (ThermoFisher). Accordingly, commercially available antibodies do not show mediation of complement-mediated cell death.

Figure 15:
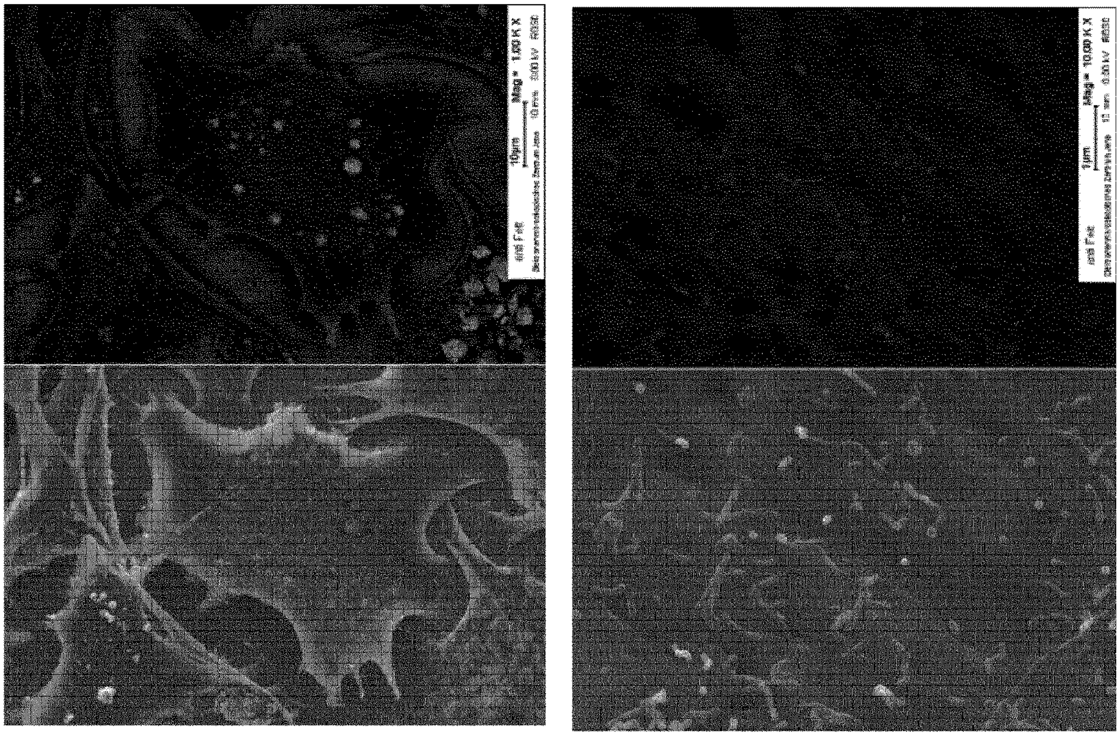

FIG. 15. The patient-derived anti-fat antibody (aF-AB) and antibody #5 bind to adipocyte surfaces, whereas the commercial antibody PA1-1052 does not bind.

(A) Total cell overview on the left and differently contrasted to the representation of lipid vacuoles on the right, shows that adipocytes are considered. (B) 10-fold magnification of a 50 $\mu m^2$ counting section. Left: microvilli, right: AB-bound immunogold particles (white dots). (A+B) for a cell incubated with aF-AB. At least 7-8 different cells are included for counting. (C) Quantitative evaluation. ANOVA (P=0.00002) with multiple comparisons (Holm-Sidak, P-values in the figure). Increased binding of gold particles, compared to control, is observed for the patient derived anti-fat antibody (aF-AB) and for antibodies of the present invention, such as antibody no. 5. In contrast thereto, significantly increased binding of gold particles, compared to control, is not observed for the commercially available antibody PA1-1052. Antibodies of the present invention thus show better binding effectiveness to adipocytes than commercially available anti-perilipin antibodies.

FIG. 16. Exemplary antigen-binding peptides, particularly antibodies, of the present invention and the respective CDR sequences.

CDR amino acid sequences of antibodies having antibody no. 5-11, 13-14, 16-58 are depicted. CDR sequences of the heavy chain (HCDR) and of the light chain (LCDR) are shown. CDRs 1, 2, and 3 of the heavy chain (HCDR) are depicted from left to right and are each separated by a "_". CDRs 1, 2 and 3 of the light chain (LCDR) are depicted from left to right and are each separated by a "_". The depicted CDR sequences correspond to the sequences having SEQ ID NOs. 18-329.

FIG. 17. Exemplary antigen-binding peptides, particularly antibodies, of the present invention and the respective VH and VL sequences.

VH and VL amino acid sequences of antibodies having antibody no. 5-11, 13-14, 16-58 are depicted. The depicted VH and VL sequences correspond to the sequences having SEQ ID NOs. 334-437.

EXAMPLES

Example 1: Isolation of Autoantibodies Targeting Perilipin-1

Written informed consent was obtained from all donors of tissue samples according to a protocol, which was approved by the ethics committee of the Jena University Hospital. The stromal vascular fractions of cells from adipose tissue samples (referred to as human preadipocytes) were isolated and cultured in medium 199 containing 10% (v/v) fetal calf serum until confluence [5]. 3T3-L1 cells were obtained from the ATCC and were maintained in DMEM containing 10% (v/v) fetal calf serum until confluence. All experiments involving differentiation or stimulation of 3T3-L1-cells were done in a serum-free medium consisting of DMEM and Ham's F12 medium in a ratio of 3:1 (without phenol-red and with 7.5 mM HEPES, pH 7.2), which was supplemented with gentamycin (40 μg/ml), fetuin (300 μg/ml), transferrin (2 μg/ml), pantothenate (17 μM), biotin (1 μM), and insulin (1 μM) [6]. For adipose conversion of 3T3-L1-cells this medium was further supplemented with dexamethasone (100 nM) and 3-isobutyl-1-methylxanthine (500 μM). Except indicated otherwise, all experiments involving anti-fat IgG and live cells (including the complement activation assay) were done in the absence of serum. Immunoglobulin G (IgG) from 5 ml patients' serum (anti-fat IgG) or control serum (control IgG) was purified on thiophilic agarose (AFFI-TTM; Kem-En-Tec, Taastrup, Denmark) according to manufacturers' instructions.

Example 2: Preparation and Analysis of Fat Cell Lipid Associated Proteins

Male Wistar rats were used. The fat cell suspension in PBS was extensively shaken with half the volume chloroform. Centrifugation (2500×g) at 25° C. for 5 min separated lipids dissolved in chloroform from supernatant cytoplasmic proteins and lipid associated proteins in the fat cake at the interface of the organic and aqueous phases. Extraction of the fat cake by chloroform was repeated twice. Proteins of the supernatant were precipitated with acetone at −20° C. for 1 h. Lipid associated proteins were suspended by vortexing in PBS. Residual chloroform in the final pellet was evaporated in vacuo. 100 μg lipid associated proteins or cytoplasmic proteins from fat cells were solubilized with 100 μl sample buffer containing 8 M urea. 10 μl samples were separated on minigels at 4° C. Gels were either fixed and stained with Coomassie blue or proteins were transferred onto PVDF membranes (Immobilon-P, 0.45 μm, Millipore, Bedford) for 2 h at 1 $mA/cm^2$ at 8° C. using a semi-dry blotting unit. After staining with Ponceau S for 2 min membranes were washed with 0.1 N NaOH, rinsed with water, blocked overnight in 0.2% I-block (TROPIX, Bedford, MA) in Tris buffered saline-Tween 20 (TBS-T), and incubated with the primary antibodies for 1 h: anti-fat IgG and control-IgG were used at a dilution of 1:1000, polyclonal rabbit anti-Perilipin-1 at 1:1250. The protein G-alkaline phosphatase (AP) was diluted 1:5000. Anti-rabbit IgG-AP was diluted 1:1250. Blots were developed with the Nitro blue tetrazolium method. Proteomic analysis of fat cake proteins was performed.

Example 3: Assessment of Storage Lipid Metabolism

Confluent monolayers of human preadipocytes were induced for adipose conversion in serum-free medium containing 1 μM insulin, 1 μM cortisol, 500 μM 3-isobutyl-1-methylxanthine, and 1 μM rosiglitazone for 8 days and subsequently allowed to accumulate triacylglycerols in the presence of insulin alone until day 14. The cellular pool of fatty acid containing lipids, mainly triacylglycerols, was labeled with the fluorescent fatty acid analog 12-(N-(7-nitrobenz-2-oxa-1,3-diazol-4-yl)amino) dodecanoic acid (NBD-FA) and analyzed by thin-layer chromatography and fluorescence imaging. Briefly, labeling was done in serum-free medium containing 1% (w/v) fatty acid free bovine serum albumin and 100 μM NBD-FA. After washing to remove excess NBD-FA the cells were incubated in the absence or presence of antibodies for various times. Incubations were terminated by removal of media and immediate extraction of lipids with 2-propanol.

Figure 1:
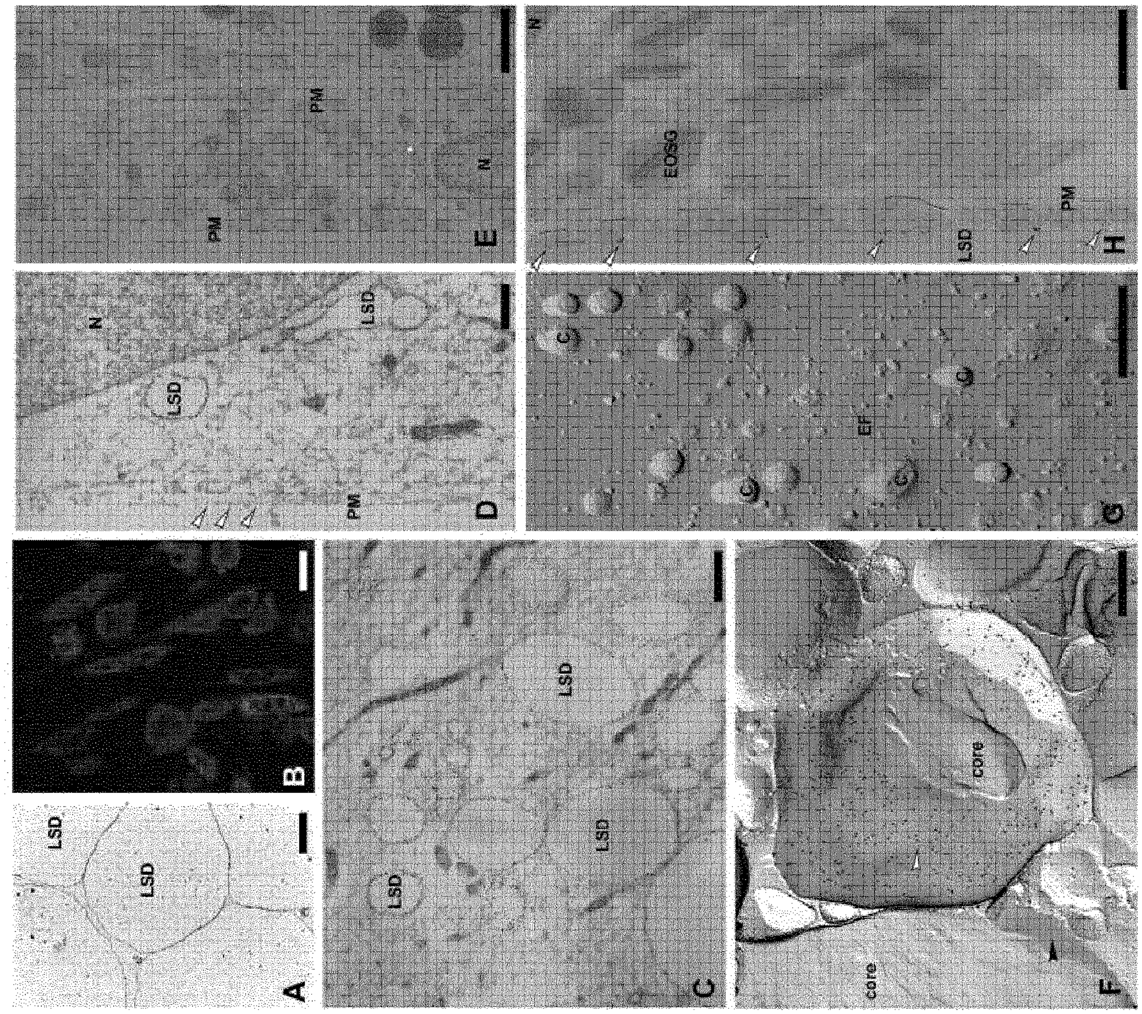
FIG. 1: Labeling of the membrane of lipid droplets with the IgG autoantibody from a patient with Lawrence Syndrome/AGL.

Example 4: Labeling of the Membrane of Lipid Droplets with the IgG Autoantibody from a Patient with Lipoatrophy The serum containing autoantibodies against adipose tissue from a patient with AGL was used to identify the target autoantigen. The purified IgG-fraction of the autoimmune serum (anti-fat IgG) exclusively labeled adipose tissue, but not other tissues tested. Labeling was confined to adipocytes in tissue sections analyzed by immunohistochemistry (FIG. 1A). Besides human univacuolar adipocytes, anti-fat IgG stained adipocytes from all other mammalians tested, but not from chicken and carp (data not shown). Immunofluorescent staining of in vitro differentiated 3T3-L1 mouse adipocytes containing multiple lipid storage droplets (LSDs) (FIG. 1B) suggested a specific reaction of the anti-fat IgG with the surface of LSDs. This specific labeling of the LSD surface was confirmed by transmission electron microscopy on immunogold labeled ultrathin sections of differentiated 3T3-L1-cells (FIG. 1 C). Adipocyte plasma membranes were labeled only sporadically (FIG. 1 D), undifferentiated cells showed no labeling at all (FIG. 1 E), suggesting that the expression of the autoantigen is almost exclusively limited to the LSDs of adipocytes. These findings were confirmed in ultrathin sections from mouse adipose tissue (FIG. 1 H).

Example 5: The Anti-Fat Autoantibody Reacts with Lipid Associated Proteins Identified as Multiple Perilipin-1 Variants Isolated fat cells of rat epididymal fat pads were used to prepare a delipidized fraction of lipid-associated proteins and a cytosolic fraction. In western blot experiments with the anti-fat IgG a characteristic pattern of two major and several minor bands was found almost exclusively in the fraction of lipid-associated proteins (FIG. 7 B). As neither IgG of a healthy control nor protein A/G-AP alone reacted with these bands (FIG. 7 C), recognition of this band pattern is specific for the anti-fat autoantibody. Thus, fractionation of rat adipocytes confirmed the results of the microscopic analyses. Having confirmed that the anti-fat IgG specifically labels (a) putative autoantigen(s) from adipocytes, we set out for identifying the autoantigen(s). After separation of the lipid associated protein fraction by two-dimensional electrophoresis several groups of immuno-reactive spots were identified by the anti-fat IgG (FIG. 2A). These spots were isolated, subjected to tryptic digestion and peptides were subsequently analyzed by MALDI-TOF-MS. Searches in the NCBI protein data base using the mass spectrometry data identified all immuno-reactive spots as variants of Perilipin-1 (FIG. 2 B). Direct comparison of the anti-fat IgG and a commercial anti-Perilipin-1 antibody revealed identical staining patterns in western analysis, confirming Perilipin-1 as an adipocyte-specific autoantigen in AGL (FIG. 2 C).

Example 6: The Anti-Fat Autoantibody Accumulates in Cells with Atypical Morphology in the Presence of Serum In order to obtain information regarding the mechanism by which the anti-fat IgG causes adipocyte loss, it was assessed whether the anti-fat IgG disturbs storage lipid metabolism in intact cells. Therefore, cells were labeled with a fluorescent fatty-acid (NBD-FA), which is a substrate for both, lipogenic and lipolytic, enzymes. Neither control IgG nor the anti-fat IgG did alter the total amount of labeled lipids during 3 h or 15 h incubations (FIG. 3A, B). More specific examination of storage triacylglycerols (FIG. 3 C, D) and intermediary products of lipolysis, diacylglycerols and monoacylglycerols, (FIG. 3 E, F) also revealed no effect of the anti-fat IgG in in vitro differentiated human adipocytes. Thus, in accordance with the almost exclusive localization of Perilipin-1 at the surface of LSDs (FIG. 1) it is unlikely that interference of the anti-fat IgG with the normal function of Perilipin-1 causes adipocyte loss. However, when living 3T3-L1-adipocytes were incubated with antibodies in the absence or presence of increasing amounts of goat serum, a dose dependent increase of the number of labeled cells could be detected when anti-fat IgG was present (FIG. 4 F-J), but not when control IgG was used (FIG. 4A-E). Examination of the stained cells revealed association of the anti-fat IgG with cells presenting atypical morphology (dying or dead cells) (FIG. 4 J, N). The serum dose dependent increase of such atypical cells indicated that serum factor(s) might cooperate with anti-fat IgG to induce cell-death. This is the classical hallmark of the complement system.

Example 7: Complement Activation Assay

3T3-L1-cells were induced for differentiation under serum-free conditions in 96-well plates and allowed to accumulate lipids until day 8. Then cells were pre-incubated in serum-free medium without or with antibodies in a total volume of 60 µl for 40 min, thereafter 20 µl of various dilutions of rabbit complement (BAG, Lich, Germany) in serum-free medium were added. To terminate the reactions, 40 µl Fluoro Quench AO/EB reagent (OneLambda, Canoga Park, USA) were added. 15 min later, the fluorescence images were captured using a FITC-filter (longpass emission). Complement dilutions were prepared fresh and checked for activity before each individual experiment.

Example 8: The Anti-Fat Autoantibody Triggers Complement Dependent Cell-Death in 3T3-LI-Cells It was tested whether the anti-fat IgG directs a complement-mediated reaction towards intact adipocytes. Complement alone or in the presence of control IgG was without effect on staining of dead or viable cells, respectively (FIG. 5). In contrast, within one hour anti-fat IgG induced a massive increase of the dead cell number in the presence of complement (FIG. 5A, B). A higher complement concentration led to an additional increase in the number of dead cells, which was mirrored by a significant loss of viable cells (FIG. 5 C). Extension of the incubation times to 24 hours did not affect cell viability or dead cell numbers in the absence of anti-fat IgG but induced an even more pronounced loss of viable cells in the presence of anti-fat IgG (FIG. 8). Obviously, the low density of epitope(s) targeted by the anti-Perilipin-1 autoantibody in adipocyte plasma membranes (see FIG. 1 D) was sufficient to trigger complement mediated cell death. Interestingly, after treatment with complement plus anti-fat IgG the remaining viable cell populations consisted mainly of preadipocytes lacking LSDs and Perilipin-1, again indicating the necessity of Perilipin-1 expression in target cells of the anti-fat IgG induced complement reaction.

Example 9: Anti-Perilipin-1 Autoantibodies Trigger Complement-Mediated Destruction of Adipocytes in Acquired Generalized Lipodystrophy Generalized lipodystrophies are associated with severe metabolic complications. Familial types were tracked down to defects of key genes of adipocyte function. Pathogenesis of the acquired lipodystrophies is less understood, but often accompanied by chronic infections or autoimmune markers. From serum of a patient with AGL we isolated autoantibodies against adipose tissue as described in the previous examples. The immunoglobulin G-fraction of patient serum, but not that of normal sera, specifically stained the lipid accumulating adipocytes in tissue sections and in vitro, indicating a direct immune reaction against adipocytes involved in the etiology of AGL. The lipodystrophy-associated autoantibodies react with an intracellular autoantigen, which is exclusively expressed in adipocytes, located at the surface of lipid storage droplets, and said antigen was identified as Perilipin-1 by two-dimensional electrophoresis coupled with mass spectrometry. The autoantibodies did not alter cellular lipid homeostasis and did not enter intact cells. In the presence of serum factors or complement, however, the autoantibodies induced cell death in cultured adipocytes. The present invention discloses a cellular target, namely Perilipin-1, which has a key role in the selective loss of adipocytes in AGL via a complement mediated reaction.

The present inventors disclose that lipodystrophy-associated autoantibodies react with an autoantigen, which is exclusively expressed in adipocytes, located at the surface of lipid storage droplets, identified as perilipin-l. The autoantibodies do not alter cellular lipid homeostasis and do not enter intact cells. In the presence of serum factors or complement, however, the autoantibodies induce cell death in cultured adipocytes. The anti-perilipin-1 autoantibodies are responsible for targeting a complement reaction against adipocytes.

Example 10: Antibody Preparation

A naïve human antibody-phage library was used for the antibody selection of perilipin-1 specific antibodies. First, the library was cleared from unspecific or cross-reactive antibody-phage (campaign a). For that purpose, the library was incubated in presence of immobilized streptavidin, magnetic streptavidin beads and BSA. Antibody-phage that bound to the negative antigens were removed from further selection.

After that, the cleared library was screened for target antigen specific antibodies. The following peptide antigens were used for the antibody selection:

```
Perilipin epitope 1:
                          (SEQ ID NO. 330)
NKGLTLLDGDLPEQE

Perilipin epitope 2:
                          (SEQ ID NO. 331)
QYPPEKIASELKDTI

Perilipin epitope 5:
                          (SEQ ID NO. 332)
AKPSLLSRVGALTNT

Perilipin epitope 6:
                          (SEQ ID NO. 333)
EVRVPWLHSLAAAQE
```

The peptides were synthesized with a Biotin-PEG Spacer and a GGSGGS Linker (SEQ ID NO. 438) at the N-terminus. Additionally, peptides were also synthesized with a Biotin-PEG Spacer and an AAAAA Linker (SEQ ID NO. 439) at the C-terminus. Both peptide variants were polished by HPLC purification.

First, the target peptides (with N-terminal biotin) were added to the cleared library preparations. Antibody-phage that bound to the biotinylated target antigen were captured and recovered from the solution using magnetic streptavidin beads. The beads were washed multiple times with a BSA solution (containing 0.05% Tween20) and PBS in order to remove unspecific or weakly bound antibody-phage particles. Antigen-specific antibody phage were eluted from the beads by trypsin treatment and rescued by *E. coli* infection. After short propagation, the bacteria were co-infected with a M13K07 helper phage and antibody-phage amplification was induced. The amplified phage were used for two more selection cycles as described above. An overview of the antibody selection strategies is given below. Selection strategies were performed for perilipin epitopes 1, 2, 5 and 6. Each strategy was performed with a lambda and kappa antibody library separately from each other.

TABLE 1

Selection strategy.

| Negative selection in selection cycle 1-3 (campaign a) | Positive selection in selection cycle 1 (campaign a) | Positive selection in selection cycle 2 (campaign a) | Positive selection in selection cycle 3 (campaign a) |
|---|---|---|---|
| Immobilized Streptavidin, magnetic Streptavidin-Beads, BSA | Perilipin epitope 1 (N-terminal biotin) | Perilipin epitope 1 (C-terminal biotin) | Perilipin epitope 1 (N-terminal biotin) |
| Immobilized Streptavidin, magnetic Streptavidin-Beads, BSA | Perilipin epitope 2 (N-terminal biotin) | Perilipin epitope 2 (C-terminal biotin) | Perilipin epitope 2 (N-terminal biotin) |
| Immobilized Streptavidin, magnetic Streptavidin-Beads, BSA | Perilipin epitope 5 (N-terminal biotin) | Perilipin epitope 5 (C-terminal biotin) | Perilipin epitope 5 (N-terminal biotin) |
| Immobilized Streptavidin, magnetic Streptavidin-Beads, BSA | Perilipin epitope 6 (N-terminal biotin) | Perilipin epitope 6 (C-terminal biotin) | Perilipin epitope 6 (N-terminal biotin) |

In order to direct the antibody-phage selection towards cell binding antibodies, the antibody-phage, after selection cycle 2 from campaign a, were additionally used for selection on cells (campaign b). For that purpose, the amplified phage were incubated in presence HEK293 cells. Antibody-phage that bound to the HEK cell surface were removed from further selection. After that, the cleared antibody-phage were selected for target antigen specific antibodies by incubation on living adipocytes. The cells were washed multiple times in order to remove unspecific or weakly bound antibody-phage particles. Antigen-specific antibody phage were rescued by *E. coli* infection. An overview of the antibody selection strategies is given below. Each strategy was performed with the lambda and kappa antibody-phage separately from each other.

TABLE 2

Selection strategy.

| Input | Negative selection in selection cycle 3 (campaign b) | Positive selection in selection cycle 3 (campaign b) |
|---|---|---|
| Amplified antibody-phage after selection cycle 2 (campaign a) against perilipin epitope 1 | HEK293 cells | Adipocytes |
| Amplified antibody-phage after selection cycle 2 (campaign a) against perilipin epitope 2 | HEK293 cells | Adipocytes |
| Amplified antibody-phage after selection cycle 2 (campaign a) against perilipin epitope 5 | HEK293 cells | Adipocytes |
| Amplified antibody-phage after selection cycle 2 (campaign a) against perilipin epitope 6 | HEK293 cells | Adipocytes |

Example 11: Antibody Screening

After three rounds of antibody selection, the binding characteristics of monoclonal antibody clones were analyzed. Firstly, 384 single colonies from each perilipin selection strategy (perilipin epitopes 1, 2, 5, and 6) were used for scFv antibody production (campaign a and b, respectively). These scFv productions were tested for their binding specificity by ELISA on:

Streptavidin+target peptide (N-terminal biotin),

Streptavidin+target peptide (C-terminal biotin),

Streptavidin.

Antibody clones were identified as antigen specific, if:

Signal/noise (S/N) between streptavidin+target peptide (N-terminal biotin) and streptavidin ≥5, i.e. (streptavidin+target peptide (N-terminal biotin))/(streptavidin) ≥5;

S/N between streptavidin+target peptide (C-terminal biotin) and streptavidin ≥5, i.e. (streptavidin+target peptide (C-terminal biotin))/(streptavidin) ≥5.

From campaign a, a total of 827 Hits was identified. From campaign b, a total of 146 Hits were identified. Sequence analysis of those clones was performed to identify clones with a unique antibody sequence (≥1 AA difference in the CDRs of VH and VL). An overview of the unique antibodies is given below:

TABLE 3

Hits identified in the screening.

| | campaign a | | campaign b | |
|---|---|---|---|---|
| strategy | identified hits | antibodies with unique sequences | identified hits | antibodies with unique sequences |
| perilipin epitope 1 | 216 Hits | 130 | 25 Hits | 9 |
| perilipin epitope 2 | 84 Hits | 33 | 3 Hits | 2 |
| perilipin epitope 5 | 251 Hits | 185 | 36 Hits | 26 |
| perilipin epitope 6 | 276 Hits | 219 | 82 Hits | 65 |
| total | 827 Hits | 567 | 146 Hits | 102 |

In campaign b, 18 antibodies were identified that were, in parallel, identified in campaign a:

TABLE 4

Identified antibodies with unique sequences.

| strategy | antibodies with unique sequences |
|---|---|
| S1 (perilipin epitope 1) | 8 |
| S3 (perilipin epitope 2) | 2 |
| S9 (perilipin epitope 5) | 5 |
| S11 (perilipin epitope 6) | 3 |
| total | 18 |

Based on selection campaign, peptide specificity, and sequence similarity of the antibodies, lead antibodies were selected for further testing.

Example 12: Antibody Conversion

The VH and VL genes were amplified from the phagemid DNA by PCR, and purified. The VH gene was inserted into a mammalian human IgG1 heavy chain expression vector. The VL gene was inserted into a mammalian human IgG1 light chain lambda or kappa expression vector. The IgG expression vectors were transformed into *E. coli.* Single colonies were selected for plasmid propagation. After isolation of transfection-grade DNA, HEK cells were transiently co-transfected with the heavy chain and the light chain expression vector DNA of one antibody clone.

The antibodies were produced by the HEK cells and secreted into the culture medium for 7 days. After clearance of the culture supernatant from cells by centrifugation, the IgG antibodies were purified by protein A affinity chromatography. After adjustment of the buffer to PBS, the protein concentration of the antibodies was determined by UV/VIS spectrometry. Integrity and purity of the antibodies was assessed by SDS-PAGE under reducing conditions. The functional binding activity of the antibodies to the target peptide was measured by ELISA. Various antibodies were produced and tested for their functional characteristics. Particularly, binding characteristics and functional characteristics of antibodies with various VH and VL regions were tested (SEQ ID NO.s 334-437).

Example 13: Exemplary Anti-Perilipin-1 Antibodies of the Present Invention

Various antibodies of the present invention were tested in binding assays and functional assays. Particularly, hIgG1 antibodies directed against a perilipin-1 epitope having any of SEQ ID NO. 1 (perilipin epitope 1), 2 (perilipin epitope 2), 5 (perilipin epitope 5), and 6 (perilipin epitope 6), particularly having any of SEQ ID NO. 330, 331, 332, and 333, respectively, were tested.

TABLE 5

Various exemplary perilipin-antibodies of the present invention and the respective CDRs, VH regions, and VL regions.

| Antibody No. | Sample ID | Epitope Binding | CDRs - SEQ ID NO. | VH - SEQ ID NO. | VL - SEQ ID NO. |
|---|---|---|---|---|---|
| 5 | 438-G12 | Perilipin epitope 1 | 18-23 | 334 | 335 |
| 6 | 448-B03 | Perilipin epitope 1 | 24-29 | 336 | 337 |
| 7 | 448-D02 | Perilipin epitope 1 | 30-35 | 338 | 339 |
| 8 | 448-E03 | Perilipin epitope 1 | 36-41 | 340 | 341 |
| 9 | 448-G01 | Perilipin epitope 1 | 42-47 | 342 | 343 |
| 10 | 439-E10 | Perilipin epitope 2 | 48-53 | 344 | 345 |
| 11 | 447-D12 | Perilipin epitope 2 | 54-59 | 346 | 347 |
| 13 | 432-G09 | Perilipin epitope 5 | 60-65 | 348 | 349 |
| 14 | 432-H10 | Perilipin epitope 5 | 66-71 | 350 | 351 |
| 16 | 447-B05 | Perilipin epitope 5 | 72-77 | 352 | 353 |
| 17 | 447-C04 | Perilipin epitope 5 | 78-83 | 354 | 355 |
| 18 | 447-D03 | Perilipin epitope 5 | 84-89 | 356 | 357 |
| 19 | 447-D04 | Perilipin epitope 5 | 90-95 | 358 | 359 |
| 20 | 447-E02 | Perilipin epitope 5 | 96-101 | 360 | 361 |
| 21 | 447-G03 | Perilipin epitope 5 | 102-107 | 362 | 363 |
| 22 | 447-H03 | Perilipin epitope 5 | 108-113 | 364 | 365 |
| 23 | 435-B08 | Perilipin epitope 6 | 114-119 | 366 | 367 |
| 24 | 447-C09 | Perilipin epitope 6 | 120-125 | 368 | 369 |
| 25 | 447-C10 | Perilipin epitope 6 | 126-131 | 370 | 371 |
| 26 | 447-D06 | Perilipin epitope 6 | 132-137 | 372 | 373 |
| 27 | 447-E11 | Perilipin epitope 6 | 138-143 | 374 | 375 |
| 28 | 447-F08 | Perilipin epitope 6 | 144-149 | 376 | 377 |
| 29 | 448-C06 | Perilipin epitope 6 | 150-155 | 378 | 379 |
| 30 | 448-E04 | Perilipin epitope 6 | 156-161 | 380 | 381 |
| 31 | 448-E06 | Perilipin epitope 6 | 162-167 | 382 | 383 |

TABLE 5-continued

Various exemplary perilipin-antibodies of the present invention and the respective CDRs, VH regions, and VL regions.

| Antibody No. | Sample ID | Epitope Binding | CDRs - SEQ ID NO. | VH - SEQ ID NO. | VL - SEQ ID NO. |
|---|---|---|---|---|---|
| 32 | 448-F04 | Perilipin epitope 6 | 168-173 | 384 | 385 |
| 33 | 434-F08 | Perilipin epitope 6 | 174-179 | 386 | 387 |
| 34 | 447-B01 | Perilipin epitope 5 | 180-185 | 388 | 389 |
| 35 | 447-E03 | Perilipin epitope 5 | 186-191 | 390 | 391 |
| 36 | 447-B03 | Perilipin epitope 5 | 192-197 | 392 | 393 |
| 37 | 447-F02 | Perilipin epitope 5 | 198-203 | 394 | 395 |
| 38 | 447-A05 | Perilipin epitope 5 | 204-209 | 396 | 397 |
| 39 | 448-H05 | Perilipin epitope 6 | 210-215 | 398 | 399 |
| 40 | 447-F11 | Perilipin epitope 6 | 216-221 | 400 | 401 |
| 41 | 447-E10 | Perilipin epitope 6 | 222-227 | 402 | 403 |
| 42 | 447-B06 | Perilipin epitope 6 | 228-233 | 404 | 405 |
| 43 | 447-A07 | Perilipin epitope 6 | 234-239 | 406 | 407 |
| 44 | 448-G04 | Perilipin epitope 6 | 240-245 | 408 | 409 |
| 45 | 447-E08 | Perilipin epitope 6 | 246-251 | 410 | 411 |
| 46 | 447-B07 | Perilipin epitope 6 | 252-257 | 412 | 413 |
| 47 | 447-A08 | Perilipin epitope 6 | 258-263 | 414 | 415 |
| 48 | 447-B08 | Perilipin epitope 6 | 264-269 | 416 | 417 |
| 49 | 448-H04 | Perilipin epitope 6 | 270-275 | 418 | 419 |
| 50 | 448-D05 | Perilipin epitope 6 | 276-281 | 420 | 421 |
| 51 | 447-E05 | Perilipin epitope 6 | 282-287 | 422 | 423 |
| 52 | 448-F05 | Perilipin epitope 6 | 288-293 | 424 | 425 |
| 53 | 447-G07 | Perilipin epitope 6 | 294-299 | 426 | 427 |
| 54 | 447-C12 | Perilipin epitope 6 | 300-305 | 428 | 429 |
| 55 | 447-C08 | Perilipin epitope 6 | 306-311 | 430 | 431 |
| 56 | 448-A06 | Perilipin epitope 6 | 312-317 | 432 | 433 |
| 57 | 447-H10 | Perilipin epitope 6 | 318-323 | 434 | 435 |
| 58 | 447-B12 | Perilipin epitope 6 | 324-329 | 436 | 437 |

The respective sequences are detailed in the sequence listing as well as in FIGS. 16 (CDR-sequences) and 17 (VH- and VL-sequences).

Example 14: Anti-Perilipin Antibody Binding Assay

Adipocytes were freshly isolated from WT untreated mice and stained with selected antibodies. Particularly, adipocytes were isolated through collagenase digestion of fat tissue from old male mice (white fat from around liver, intestine, kidney and testicles) [7,8]. The collagenase digestions was performed using a digestion buffer (Krebs-Ringers-HEPES; 2.5 mM glucose; 2% fetal bovine serum albumine; 200 μM adenosine (Sigma, 01890-5G); 1 mg/ml collagenase (Sigma, C2139), pH 7.4, wherein Krebs-Ringers-HEPES comprised 120 mM NaCl, 4.7 mM KCl, 2.2 mM CaCl2, 10 mM HEPES, 1.2 mM KH2PO4, and 1.2 mM MgSO4). The isolated adipocytes where first blocked with mouse FcR-blocking reagent. Then, the adipocytes were incubated with the selected primary antibodies in a concentration of 1 μg/ml (anti-perilipin antibodies or control). As controls, to exclude unspecific binding of antibodies, isotype control antibodies (human IgG1) were used. Additionally, one control sample was incubated with secondary antibodies only without an addition of a primary antibody. After washing, the adipocytes were incubated with secondary antibodies (goat anti-human Alexa 568) recognizing the primary antibodies. After incubation and another washing step, the DNA stain Hoechst 33342 was added in a 1:1000 dilution to identify intact cells in flow cytometry. The binding of anti-perilipin antibodies to the adipocytes was then analyzed using flow cytometry.

For signal detection, anti-human Alexa 568 recognizing primary antibodies were used (FIGS. 10 and 11). Isotype control antibodies (human IgG1) were used to exclude unspecific binding of tested antibodies to cell surfaces, namely by analyzing fluorescence intensities of anti-perilipin antibodies compared to isotype controls. Histograms of the tested antibodies of the present invention showed enhanced binding of antibodies of the present invention to adipocytes compared to binding of isotype controls to adipocytes. Furthermore, antibodies of the present invention showed enhanced binding to adipocytes compared to commercially available anti-perilipin antibodies (FIGS. 10 and 11).

Various antibodies of the present invention were tested for binding efficiency on adipocyte cell surfaces. Binding of antibodies of the present invention was further analyzed using gold nanoparticles and electron microscopy basically according to a published protocol [9], with modifications described below. Differentiated adipocytes on coverslips were fixed with 4% formaldehyde and 1% glutaraldehyde in PBS, pH 7.4, for 30 min. Subsequently, fixed cell-layers were incubated at 4° C. overnight without primary antibody or with 1 μg per coverslip of each antibody tested. After washing, coverslips were incubated for 5 h at 4° C. with bridging-antibodies: rabbit anti human IgG (DAKO; catalog no. A 0423; for all human or humanized primary antibodies) or polyclonal mouse anti rabbit (H+L) (Invitrogen; catalog no. 31213; for the commercial rabbit anti-perilipin-1 polyclonal antibody PA1-1052 from Invitrogen). After washing, coverslips were incubated with gold-labelled antibodies overnight at 4° C. (Britisch Biocell International; goat anti rabbit Au-20 nm; catalog no. EMGAR20; for human or humanized primary antibodies; or goat anti mouse Au-20 nm; catalog no. EMGAM20; for the commercial primary antibody). After final washing intact adipocytes were identified by their lipid vacuoles and microvilli, and bound gold particles were detected in the field emission scanning electron microscopy mode.

Successful binding of antibodies of the present invention to adipocytes was observed. Binding of an antibody of the present invention, for example antibody 5, to adipocytes is shown in FIG. 15. Similar results were also observed for other antibodies of the present invention, e.g. antibodies 11, 17, 20, 29 and 31 (data not shown). In contrast thereto, electron microscopy did not show binding of commercially available antibody Invitrogen PA1-1052 to adipocytes.

Example 15: Anti-Perilipin Antibody Functional Assay

The effect of anti-perilipin antibodies on complement-mediated cell death was tested in a microscopy-based cell assay. 3T3-L1 cells were differentiated to adipocytes using an insulin-based serum-free differentiation protocol [6]. Particularly, 3T3-LI cells were incubated with Serum-free differentiation Media (SFD-Media) supplemented with insulin (1 μM), dexamethasone (0.1 μM), and 3-isobutyl-1-methylxanthine (500 μM) for 3 days. SFD-Media comprised DMEM/HAM's F12 (1:1) Media with 15 mM HEPES, mixed 1:1 with DMEM (1 g/l Glucose, without $NaHCO_3$), 1.2 g/l $NaHCO_3$, 17 μM D-Pantothenic acid, 1 μM Biotin, 2.0 mg/l apo-Transferrin, 300 mg/l Fetuin, 1% Penicillin/Streptomycin, at pH 7,2. Cells were kept with SFD-Media supplemented with only insulin (1 μM) for 4 days. For the complement assay [10], the cells were incubated with selected antibodies (anti-perilipin antibodies and isotype control antibodies) with a final concentration between 0.017 and 0.05 mg/ml in 60 μl SFD-Media (pooled antibodies respectively in a concentration of 0.0017 mg/ml per antibody in 60 μl SFD-Media). Commercially available lyophilized rabbit complement (BAG Diagnostics GmbH) was reconstituted in water, then 20 μl of an 1:32-dilution of complement was added on top of the cells. After incubating for 1 hour, the cells were stained with FluoroQuench™ AE and the cell death was monitored using microscopy analysis.

Successful differentiation was assessed based on cellular morphological changes such as appearance of fat vacuoles and cell enlargement. The differentiated cells were incubated with selected antibodies and complement. Cell death was monitored using microscopy analysis and a commercially available FluoroQuench™ Staining/Quenching Reagent from Thermo Fisher Scientific Inc.

Antibodies of the present invention showed efficient complement-mediated cell death (FIG. 12B and FIG. 13B). Various antibodies of the present invention were tested for their functional effectiveness, and showed effective complement-mediated cell death (FIG. 12B), e.g. antibodies 6, 7, 8, 9, 14, 16, 18, 19, 20, 21, 22, 24, 25, 26, 27, 28, 31, and 32. The tested commercially available anti-perilipin antibodies did not show significant complement-mediated cell death compared to the controls (FIGS. 12A, 14, and FIG. 15C).

Example 16: Further Evaluation of Exemplary Antibodies of the Present Invention Various antibodies of the present invention were further investigated with regard to their adipocyte binding effectiveness and their effectiveness in complement-mediated cell death (Table 6).

TABLE 6

Functional characterization of various antibodies ("+" indicates effectiveness in at least one test, "++" indicates effectiveness in at least two tests).

| Antibody No. | Surface Binding | Complement-mediated cell death |
|---|---|---|
| 5 | + | |
| 6 | | + |
| 7 | | + |
| 8 | | + |
| 9 | | + |
| 10 | + | |
| 11 | + | + |
| 13 | | + |
| 14 | | + |
| 16 | | + |
| 17 | ++ | |
| 18 | + | + |
| 19 | + | + |
| 20 | ++ | ++ |
| 21 | ++ | ++ |
| 22 | + | ++ |
| 23 | | + |
| 24 | + | ++ |
| 25 | + | + |
| 26 | + | + |
| 27 | + | + |
| 28 | + | ++ |
| 29 | ++ | |
| 30 | ++ | |
| 31 | + | ++ |
| 32 | + | + |

Furthermore, complement assays were performed with antibody pools to investigate the synergy of targeting several perilipin epitopes (Table 7).

TABLE 7

Analysis of complement-mediated cell death using antibody pools (+, ++, and +++ indicate low, medium and high induction of complement-mediated cell death, respectively).

| Antibody pool | Antibody No. | Epitope(s) | Complement-mediated cell death |
|---|---|---|---|
| 1 | 5-9 | perilipin epitope 1 | + |
| 2 | 10-11 | perilipin epitope 2 | ++ |
| 3 | 13-14, 16-22 | perilipin epitope 5 | +++ |
| 4 | 23-32 | perilipin epitope 6 | +++ |
| 5 | 5-11 | perilipin epitopes 1 and 2 | +++ |
| 6 | 5-9, 13-14, 16-22 | perilipin epitopes 1 and 5 | ++ |
| 7 | 5-9, 23-32 | perilipin epitopes 1 and 6 | ++ |
| 8 | 10-11, 13-14, 16-22 | perilipin epitopes 2 and 5 | +++ |
| 9 | 13-14, 16-32 | perilipin epitopes 5 and 6 | +++ |
| 10 | 10-11, 23-32 | perilipin epitopes 2 and 6 | + |
| 11 | 5-11, 13-14, 16-22 | perilipin epitopes 1, 2, and 5 | ++ |
| 12 | 5-11, 23-32 | perilipin epitopes 1, 2, and 6 | ++ |
| 13 | 10-11, 13-14, 16-32 | perilipin epitopes 2, 5, and 6 | ++ |

REFERENCES

[1] Greenberg A S, Egan J J, Wek S A, Moos M C, Jr., Londos C, Kimmel AR. Isolation of cDNAs for perilipins A and B: sequence and expression of lipid droplet associated proteins of adipocytes. Proc Natl Acad Sci USA, 1993; 90:12035-9.

[2] Hübler A, Abendroth K, Keiner T, Stöcker W, Kauf E, Hein G et al. Dysregulation of insulin-like growth factors in a case of generalized acquired lipoatrophic diabetes mellitus (Lawrence Syndrome) connected with autoantibodies against adipocyte membranes. Exp Clin Endocrinol Diabetes, 1998; 106:79-84.

[3] Corvillo F, Aparicio V, Lopez-Lera A, Garrido S, Araujo-Vilar D, et al. Autoantibodies against perilipin 1 as a cause of acquired generalized lipodystrophy. Front Immunol, 2018; 9:2142.

[4] Misra A, Garg A. Clinical features and metabolic derangements in acquired generalized lipodystrophy: case reports and review of the literature. Medicine (Baltimore), 2003; 82:129-46.

[5] Schmidt M, Löffler G. Induction of aromatase activity in human adipose tissue stromal cells by extracellular nucleotides—evidence for P2-purinoceptors in adipose tissue. Eur J Biochem, 1998; 252:147-54.

[6] Schmidt W, Pöll-Jordan G, Löffler G. Adipose conversion of 3T3-L1 cells in a serum-free culture system depends on epidermal growth factor, insulin-like growth factor I, corticosterone, and cyclic AMP. J Biol Chem, 1990; 265:15489-95.

[7] Rodbell M. Metabolism of isolated fat cells. I. Effects of hormones on glucose metabolism and lipolysis. J Biol Chem, 1964; 239:375-80.

[8] Schödel J, Weise I, Klinger R, Schmidt M. Stimulation of lipogenesis in rat adipocytes by ATP, a ligand for P2-receptors. Biochem Biophys Res Commun, 2004; 321:767-73.

[9] Kaufmann R, Rahn S, Pollrich K, Hertel J, Dittmar Y, Hommann M, Henklein P, Biskup C, Westermann M, Hollenberg M D, Settmacher U. Thrombin-mediated hepatocellular carcinoma cell migration: cooperative action via proteinase-activated receptors 1 and 4. J Cell Physiol, 2007; 211:699-707.

[10] Terasaki P I, McClelland J D. Microdroplet assay of human serum cytotoxins. Nature, 1964; 204:998-1000.

The features of the present invention disclosed in the specification, the claims, and/or in the accompanying figures may, both separately and in any combination thereof, be material for realizing the invention in various forms thereof.

The invention claimed is:

1. An antigen-binding peptide specifically binding to at least one perilipin-1 epitope selected from the group consisting of amino acid sequences LTLLDGDLPE (SEQ ID NO: 1), EKIASELK (SEQ ID NO: 2), PSLLSRVGALTN (SEQ ID NO: 5), and PWLHSLAA (SEQ ID NO: 6);

wherein said antigen-binding peptide comprises (i) a heavy chain CDR1 region comprising the amino acid sequence of SEQ ID NO:18, a heavy chain CDR2 region comprising the amino acid sequence of SEQ ID NO:19, a heavy chain CDR3 region comprising the amino acid sequence of SEQ ID NO:20, a light chain CDR1 region comprising the amino acid sequence of SEQ ID NO:21, a light chain CDR2 region comprising the amino acid sequence of SEQ ID NO:22, and a light chain CDR3 region comprising the amino acid sequence of SEQ ID NO:23; or (ii) a heavy chain CDR1 region comprising the amino acid sequence of SEQ ID NO:24, a heavy chain CDR2 region comprising the amino acid sequence of SEQ ID NO:25, a heavy chain CDR3 region comprising the amino acid sequence of SEQ ID NO:26, a light chain CDR1 region comprising the amino acid sequence of SEQ ID NO:27, a light chain CDR2 region comprising the amino acid sequence of SEQ ID NO:28, and a light chain CDR3 region comprising the amino acid sequence of SEQ ID NO:29; or (iii) a heavy chain CDR1 region comprising the amino acid sequence of SEQ ID NO:30, a heavy chain CDR2 region comprising the amino acid sequence of SEQ ID NO:31, a heavy chain CDR3 region comprising the amino acid sequence of SEQ ID NO:32, a light chain CDR1 region comprising the amino acid sequence of SEQ ID NO:33, a light chain CDR2 region comprising the amino acid sequence of SEQ ID NO:34, and a light chain CDR3 region comprising the amino acid sequence of SEQ ID NO:35; or (iv) a heavy chain CDR1 region comprising the amino acid sequence of SEQ ID NO:36, a heavy chain CDR2 region comprising the amino acid sequence of SEQ ID NO:37, a heavy chain CDR3 region comprising the amino acid sequence of SEQ ID NO:38, a light chain CDR1 region comprising the amino acid sequence of SEQ ID NO:39, a light chain CDR2 region comprising the amino acid sequence of SEQ ID NO:40, and a light chain CDR3 region comprising the amino acid sequence of SEQ ID NO:41; or (v) a heavy chain CDR1 region comprising the amino acid sequence of SEQ ID NO:42, a heavy chain CDR2 region comprising the amino acid sequence of SEQ ID NO:43, a heavy chain CDR3 region comprising the amino acid sequence of SEQ ID NO:44, a light chain CDR1 region comprising the amino acid sequence of SEQ ID NO:45, a light chain CDR2 region comprising the amino acid sequence of SEQ ID NO:46, and a light chain CDR3 region comprising the amino acid sequence of SEQ ID NO:47; or (vi) a heavy chain CDR1 region comprising the amino acid sequence of SEQ ID NO:48, a heavy chain CDR2 region comprising the amino acid sequence of SEQ ID NO:49, a heavy chain CDR3 region comprising the amino acid sequence of SEQ ID NO:50, a light chain CDR1 region comprising the amino acid sequence of SEQ ID NO:51, a light chain CDR2 region comprising the amino acid sequence of SEQ ID NO:52, and a light chain CDR3 region comprising the amino acid sequence of SEQ ID NO:53; or (vii) a heavy chain CDR1 region comprising the amino acid sequence of SEQ ID NO:54, a heavy chain CDR2 region comprising the amino acid sequence of SEQ ID NO:55, a heavy chain CDR3 region comprising the amino acid sequence of SEQ ID NO:56, a light chain CDR1 region comprising the amino acid sequence of SEQ ID NO:57, a light chain CDR2 region comprising the amino acid sequence of SEQ ID NO:58, and a light chain CDR3 region comprising the amino acid sequence of SEQ ID NO:59; or (viii) a heavy chain CDR1 region comprising the amino acid sequence of SEQ ID NO:60, a heavy chain CDR2 region comprising the amino acid sequence of SEQ ID NO:61, a heavy chain CDR3 region comprising the amino acid sequence of SEQ ID NO:62, a light chain CDR1 region comprising the amino acid sequence of SEQ ID NO:63, a light chain CDR2 region comprising the amino acid sequence of SEQ ID NO:64, and a light chain CDR3 region comprising the amino acid sequence of SEQ ID NO:65; or (ix) a heavy chain CDR1 region comprising the amino acid sequence of SEQ ID NO:66, a heavy chain CDR2 region comprising the amino acid sequence of SEQ ID NO:67, a heavy chain CDR3 region comprising the amino acid sequence of SEQ ID NO:68, a light chain CDR1 region comprising the amino acid sequence of SEQ ID NO:69, a light chain CDR2 region comprising the amino acid sequence of SEQ ID NO:70, and a light chain CDR3 region comprising the amino acid sequence of SEQ ID NO:71; or (x) a heavy chain CDR1 region comprising the amino acid sequence of SEQ ID NO:72, a heavy chain CDR2 region comprising the amino acid sequence of SEQ ID NO:73, a heavy chain CDR3 region comprising the amino acid sequence of SEQ ID NO:74, a light chain CDR1 region comprising the amino acid sequence of SEQ ID NO:75, a light chain CDR2 region comprising the amino acid sequence of SEQ ID NO:76, and a light chain CDR3 region comprising the amino acid sequence of SEQ ID NO:77; or (xi) a heavy chain CDR1 region comprising the amino acid sequence of SEQ ID NO:78, a heavy chain CDR2 region comprising the amino acid sequence of SEQ ID NO:79, a heavy chain CDR3 region comprising the amino acid sequence of SEQ ID NO:80, a light chain CDR1 region comprising the amino acid sequence of SEQ ID NO:81, a light chain CDR2 region comprising the amino acid sequence of SEQ ID NO:82, and a light chain CDR3 region comprising the amino acid sequence of SEQ ID NO:83; or (xii) a heavy chain CDR1 region comprising the amino acid sequence of SEQ ID NO:84, a heavy chain CDR2 region comprising the amino acid sequence of SEQ ID NO:85, a heavy chain CDR3 region comprising the amino acid sequence of SEQ ID NO:86, a light chain CDR1 region comprising the amino acid sequence of SEQ ID NO:87, a light chain CDR2 region comprising the amino acid sequence of SEQ ID NO:88, and a light chain CDR3 region comprising the amino acid sequence of SEQ ID NO:89; or (xiii) a heavy chain CDR1 region comprising the amino acid sequence of SEQ ID NO:90, a heavy chain CDR2 region comprising the amino acid sequence of SEQ ID NO:91, a heavy chain CDR3 region comprising the amino acid sequence of SEQ ID NO:92, a light chain CDR1 region comprising the amino acid sequence of SEQ ID NO:93, a light chain CDR2 region comprising the amino acid sequence of SEQ ID NO:94, and a light chain CDR3 region comprising the amino acid sequence of SEQ ID NO:95; or (xiv) a heavy chain CDR1 region comprising the amino acid sequence of SEQ ID NO:96, a heavy chain CDR2 region comprising the amino acid sequence of SEQ ID NO:97, a heavy chain CDR3 region comprising the amino acid sequence of SEQ ID NO:98, a light chain CDR1 region comprising the amino acid sequence of SEQ ID NO:99, a light chain CDR2 region comprising the amino acid sequence of SEQ ID NO:100, and a light chain CDR3 region comprising the amino acid sequence of SEQ ID NO:101; or (xv) a heavy chain CDR1 region comprising the amino acid sequence of SEQ ID NO:102, a heavy chain CDR2 region comprising the amino acid sequence of SEQ ID NO:103, a heavy chain CDR3 region comprising the amino acid sequence of SEQ ID NO:104, a light chain CDR1 region comprising the amino acid sequence of SEQ ID NO:105, a light chain CDR2 region comprising the amino acid sequence of SEQ ID NO:106, and a light chain CDR3 region comprising the amino acid sequence of SEQ ID NO:107; or (xvi) a heavy chain CDR1 region comprising the amino acid sequence of SEQ ID NO:108, a heavy chain CDR2 region comprising the amino acid sequence of SEQ ID NO:109, a heavy chain CDR3 region comprising the amino acid sequence of SEQ ID NO:110, a light chain CDR1 region comprising the amino acid sequence of SEQ ID NO:111, a light chain CDR2 region comprising the amino acid sequence of SEQ ID NO:112, and a light chain CDR3 region comprising the amino acid sequence of SEQ ID NO:113; or (xvii) a heavy chain CDR1 region comprising the amino acid sequence of SEQ ID NO:114, a heavy chain CDR2 region comprising the amino acid sequence of SEQ ID NO:115, a heavy chain CDR3 region comprising the amino acid sequence of SEQ ID NO:116, a light chain CDR1 region comprising the amino acid sequence of SEQ ID NO:117, a light chain CDR2 region comprising the amino acid sequence of SEQ ID NO:118, and a light chain CDR3 region comprising the amino acid sequence of SEQ ID NO:119; or (xviii) a heavy chain CDR1 region comprising the amino acid sequence of SEQ ID NO:120, a heavy chain CDR2 region comprising the amino acid sequence of SEQ ID NO:121, a heavy chain CDR3 region comprising the amino acid sequence of SEQ ID NO:122, a light chain CDR1 region comprising the amino acid sequence of SEQ ID NO:123, a light chain CDR2 region comprising the amino acid sequence of SEQ ID NO:124, and a light chain CDR3 region comprising the amino acid sequence of SEQ ID NO:125; or (xix) a heavy chain CDR1 region comprising the amino acid sequence of SEQ ID NO:126, a heavy chain CDR2 region comprising the amino acid sequence of SEQ ID NO:127, a heavy chain CDR3 region comprising the amino acid sequence of SEQ ID NO:128, a light chain CDR1 region comprising the amino acid sequence of SEQ ID NO:129, a light chain CDR2 region comprising the amino acid sequence of SEQ ID NO:130, and a light chain CDR3 region comprising the amino acid sequence of SEQ ID NO:131; or (xx) a heavy chain CDR1 region comprising the amino acid sequence of SEQ ID NO:132, a heavy chain CDR2 region comprising the amino acid sequence of SEQ ID NO:133, a heavy chain CDR3 region comprising the amino acid sequence of SEQ ID NO:134, a light chain CDR1 region comprising the amino acid sequence of SEQ ID NO:135, a light chain CDR2 region comprising the amino acid sequence of SEQ ID NO:136, and a light chain CDR3 region comprising the amino acid sequence of SEQ ID NO:137; or (xxi) a heavy chain CDR1 region comprising the amino acid sequence of SEQ ID NO:138, a heavy chain CDR2 region comprising the amino acid sequence of SEQ ID NO:139, a heavy chain CDR3 region comprising the amino acid sequence of SEQ ID NO:140, a light chain CDR1 region comprising the amino acid sequence of SEQ ID NO:141, a light chain CDR2 region comprising the amino acid sequence of SEQ ID NO:142, and a light chain CDR3 region comprising the amino acid sequence of SEQ ID NO:143; or (xxii) a heavy chain CDR1 region comprising the amino acid sequence of SEQ ID NO:144, a heavy chain CDR2 region comprising the amino acid sequence of SEQ ID NO:145, a heavy chain CDR3 region comprising the amino acid sequence of SEQ ID NO:146, a light chain CDR1 region comprising the amino acid sequence of SEQ ID NO:147, a light chain CDR2 region comprising the amino acid sequence of SEQ ID NO: 148, and a light chain CDR3 region comprising the amino acid sequence of SEQ ID NO:149; or (xxiii) a heavy chain CDR1 region comprising the amino acid sequence of SEQ ID NO:150, a heavy chain CDR2 region comprising the amino acid sequence of SEQ ID NO:151, a heavy chain CDR3 region comprising the amino acid sequence of SEQ ID NO:152, a light chain CDR1 region comprising the amino acid sequence of SEQ ID NO:153, a light chain CDR2 region comprising the amino acid sequence of SEQ ID NO:154, and a light chain CDR3 region comprising the amino acid sequence of SEQ ID NO:155; or (xxiv) a heavy chain CDR1 region comprising the amino acid sequence of SEQ ID NO:156, a heavy chain CDR2 region comprising the amino acid sequence of SEQ ID NO:157, a heavy chain CDR3 region comprising the amino acid sequence of SEQ ID NO:158, a light chain CDR1 region comprising the amino acid sequence of SEQ ID NO:159, a light chain CDR2 region comprising the amino acid sequence of SEQ ID NO:160, and a light chain CDR3 region comprising the amino acid sequence of SEQ ID NO:161; or (xxv) a heavy chain CDR1 region comprising the amino acid sequence of SEQ ID NO:162, a heavy chain CDR2 region comprising the amino acid sequence of SEQ ID NO: 163, a heavy chain CDR3 region comprising the amino acid sequence of SEQ ID NO:164, a light chain CDR1 region comprising the amino acid sequence of SEQ ID NO:165, a light chain CDR2 region comprising the amino acid sequence of SEQ ID NO: 166, and a light chain CDR3 region comprising the amino acid sequence of SEQ ID NO:167; or (xxvi) a heavy chain CDR1 region comprising the amino acid sequence of SEQ ID NO:168, a heavy chain CDR2 region comprising the amino acid sequence of SEQ ID NO:169, a heavy chain CDR3 region comprising the amino acid sequence of SEQ ID NO:170, a light chain CDR1 region comprising the amino acid sequence of SEQ ID NO:171, a light chain CDR2 region comprising the amino acid sequence of SEQ ID NO:172, and a light chain CDR3 region comprising the amino acid sequence of SEQ ID NO:173; or (xxvii) a heavy chain CDR1 region comprising the amino acid sequence of SEQ ID NO:174, a heavy chain CDR2 region comprising the amino acid sequence of SEQ ID NO:175, a heavy chain CDR3 region comprising the amino acid sequence of SEQ ID NO:176, a light chain CDR1 region comprising the amino acid sequence of SEQ ID NO:177, a light chain CDR2 region comprising the amino acid sequence of SEQ ID NO:178, and a light chain CDR3 region comprising the amino acid sequence of SEQ ID NO:179; or (xxviii) a heavy chain CDR1 region comprising the amino acid sequence of SEQ ID NO: 180, a heavy chain CDR2 region comprising the amino acid sequence of SEQ ID NO: 181, a heavy chain CDR3 region comprising the amino acid sequence of SEQ ID NO: 182, a light chain CDR1 region comprising the amino acid sequence of SEQ ID NO: 183, a light chain CDR2 region comprising the amino acid sequence of SEQ ID NO: 184, and a light chain CDR3 region comprising the amino acid sequence of SEQ ID NO: 185; or (xxix) a heavy chain CDR1 region comprising the amino acid sequence of SEQ ID NO:186, a heavy chain CDR2 region comprising the amino acid sequence of SEQ ID NO:187, a heavy chain CDR3 region comprising the amino acid sequence of SEQ ID NO:188, a light chain CDR1 region comprising the amino acid sequence of SEQ ID NO:189, a light chain CDR2 region comprising the amino acid sequence of SEQ ID NO: 190, and a light chain CDR3 region comprising the amino acid sequence of SEQ ID NO:191; or (xxx) a heavy chain CDR1 region comprising the amino acid sequence of SEQ ID NO:192, a heavy chain CDR2 region comprising the amino acid sequence of SEQ ID NO:193, a heavy chain CDR3 region comprising the amino acid sequence of SEQ ID NO:194, a light chain CDR1 region comprising the amino acid sequence of SEQ ID NO:195, a light chain CDR2 region comprising the amino acid sequence of SEQ ID NO:196, and a light chain CDR3 region comprising the amino acid sequence of SEQ ID NO:197; or (xxxi) a heavy chain CDR1 region comprising the amino acid sequence of SEQ ID NO:198, a heavy chain CDR2 region comprising the amino acid sequence of SEQ ID NO:199, a heavy chain CDR3 region comprising the amino acid sequence of SEQ ID NO:200, a light chain CDR1 region comprising the amino acid sequence of SEQ ID NO:201, a light chain CDR2 region comprising the amino acid sequence of SEQ ID NO:202, and a light chain CDR3 region comprising the amino acid sequence of SEQ ID NO:203; or (xxxii) a heavy chain CDR1 region comprising the amino acid sequence of SEQ ID NO:204, a heavy chain CDR2 region comprising the amino acid sequence of SEQ ID NO:205, a heavy chain CDR3 region comprising the amino acid sequence of SEQ ID NO:206, a light chain CDR1 region comprising the amino acid sequence of SEQ ID NO:207, a light chain CDR2 region comprising the amino acid sequence of SEQ ID NO:208, and a light chain CDR3 region comprising the amino acid sequence of SEQ ID NO:209; or (xxxiii) a heavy chain CDR1 region comprising the amino acid sequence of SEQ ID NO: 210, a heavy chain CDR2 region comprising the amino acid sequence of SEQ ID NO: 211, a heavy chain CDR3 region comprising the amino acid sequence of SEQ ID NO: 212, a light chain CDR1 region comprising the amino acid sequence of SEQ ID NO: 213, a light chain CDR2 region comprising the amino acid sequence of SEQ ID NO: 214, and a light chain CDR3 region comprising the amino acid sequence of SEQ ID NO: 215; or (xxxiv) a heavy chain CDR1 region comprising the amino acid sequence of SEQ ID NO: 216, a heavy chain CDR2 region comprising the amino acid sequence of SEQ ID NO: 217, a heavy chain CDR3 region comprising the amino acid sequence of SEQ ID NO: 218, a light chain CDR1 region comprising the amino acid sequence of SEQ ID NO: 219, a light chain CDR2 region comprising the amino acid sequence of SEQ ID NO: 220, and a light chain CDR3 region comprising the amino acid sequence of SEQ ID NO: 221; or (xxxv) a heavy chain CDR1 region comprising the amino acid sequence of SEQ ID NO:222, a heavy chain CDR2 region comprising the amino acid sequence of SEQ ID NO:223, a heavy chain CDR3 region comprising the amino acid sequence of SEQ ID NO:224, a light chain CDR1 region comprising the amino acid sequence of SEQ ID NO:225, a light chain CDR2 region comprising the amino acid sequence of SEQ ID NO:226, and a light chain CDR3 region comprising the amino acid sequence of SEQ ID NO:227; or (xxxvi) a heavy chain CDR1 region comprising the amino acid sequence of SEQ ID NO: 228, a heavy chain CDR2 region comprising the amino acid sequence of SEQ ID NO: 229, a heavy chain CDR3 region comprising the amino acid sequence of SEQ ID NO: 230, a light chain CDR1 region comprising the amino acid sequence of SEQ ID NO: 231, a light chain CDR2 region comprising the amino acid sequence of SEQ ID NO: 232, and a light chain CDR3 region comprising the amino acid sequence of SEQ ID NO: 233; or (xxxvii) a heavy chain CDR1 region comprising the amino acid sequence of SEQ ID NO: 234, a heavy chain CDR2 region comprising the amino acid sequence of SEQ ID NO: 235, a heavy chain CDR3 region comprising the amino acid sequence of SEQ ID NO: 236, a light chain CDR1 region comprising the amino acid sequence of SEQ ID NO: 237, a light chain CDR2 region comprising the amino acid sequence of SEQ ID NO: 238, and a light chain CDR3 region comprising the amino acid sequence of SEQ ID NO: 239; or (xxxviii) a heavy chain CDR1 region comprising the amino acid sequence of SEQ ID NO: 240, a heavy chain CDR2 region comprising the amino acid sequence of SEQ ID NO: 241, a heavy chain CDR3 region comprising the amino acid sequence of SEQ ID NO: 242, a light chain CDR1 region comprising the amino acid sequence of SEQ ID NO: 243, a light chain CDR2 region comprising the amino acid sequence of SEQ ID NO: 244, and a light chain CDR3 region comprising the amino acid sequence of SEQ ID NO: 245; or (xxxix) a heavy chain CDR1 region comprising the amino acid sequence of SEQ ID NO: 246, a heavy chain CDR2 region comprising the amino acid sequence of SEQ ID NO: 247, a heavy chain CDR3 region comprising the amino acid sequence of SEQ ID NO: 248, a light chain CDR1 region comprising the amino acid sequence of SEQ ID NO: 249, a light chain CDR2 region comprising the amino acid sequence of SEQ ID NO: 250, and a light chain CDR3 region comprising the amino acid sequence of SEQ ID NO: 251; or (xl) a heavy chain CDR1 region comprising the amino acid sequence of SEQ ID NO:252, a heavy chain CDR2 region comprising the amino acid sequence of SEQ ID NO:253, a heavy chain CDR3 region comprising the amino acid sequence of SEQ ID NO:254, a light chain CDR1 region comprising the amino acid sequence of SEQ ID NO:255, a light chain CDR2 region comprising the amino acid sequence of SEQ ID NO:256, and a light chain CDR3 region comprising the amino acid sequence of SEQ ID NO:257; or (xli) a heavy chain CDR1 region comprising the amino acid sequence of SEQ ID NO:258, a heavy chain CDR2 region comprising the amino acid sequence of SEQ ID NO:259, a heavy chain CDR3 region comprising the amino acid sequence of SEQ ID NO:260, a light chain CDR1 region comprising the amino acid sequence of SEQ ID NO:261, a light chain CDR2 region comprising the amino acid sequence of SEQ ID NO:262, and a light chain CDR3 region comprising the amino acid sequence of SEQ ID NO:263; or (xlii) a heavy chain CDR1 region comprising the amino acid sequence of SEQ ID NO:264, a heavy chain CDR2 region comprising the amino acid sequence of SEQ ID NO:265, a heavy chain CDR3 region comprising the amino acid sequence of SEQ ID NO:266, a light chain CDR1 region comprising the amino acid sequence of SEQ ID NO:267, a light chain CDR2 region comprising the amino acid sequence of SEQ ID NO:268, and a light chain CDR3 region comprising the amino acid sequence of SEQ ID NO:269; or (xliii) a heavy chain CDR1 region comprising the amino acid sequence of SEQ ID NO:270, a heavy chain CDR2 region comprising the amino acid sequence of SEQ ID NO:271, a heavy chain CDR3 region comprising the amino acid sequence of SEQ ID NO:272, a light chain CDR1 region comprising the amino acid sequence of SEQ ID NO:273, a light chain CDR2 region comprising the amino acid sequence of SEQ ID NO:274, and a light chain CDR3 region comprising the amino acid sequence of SEQ ID NO:275; or (xliv) a heavy chain CDR1 region comprising the amino acid sequence of SEQ ID NO:276, a heavy chain CDR2 region comprising the amino acid sequence of SEQ ID NO:277, a heavy chain CDR3 region comprising the amino acid sequence of SEQ ID NO:278, a light chain CDR1 region comprising the amino acid sequence of SEQ ID NO:279, a light chain CDR2 region comprising the amino acid sequence of SEQ ID NO:280, and a light chain CDR3 region comprising the amino acid sequence of SEQ ID NO:281; or (xlv) a heavy chain CDR1 region comprising the amino acid sequence of SEQ ID NO:282, a heavy chain CDR2 region comprising the amino acid sequence of SEQ ID NO:283, a heavy chain CDR3 region comprising the amino acid sequence of SEQ ID NO:284, a light chain CDR1 region comprising the amino acid sequence of SEQ ID NO:285, a light chain CDR2 region comprising the amino acid sequence of SEQ ID NO:286, and a light chain CDR3 region comprising the amino acid sequence of SEQ ID NO:287; or (xlvi) a heavy chain CDR1 region comprising the amino acid sequence of SEQ ID NO:288, a heavy chain CDR2 region comprising the amino acid sequence of SEQ ID NO:289, a heavy chain CDR3 region comprising the amino acid sequence of SEQ ID NO:290, a light chain CDR1 region comprising the amino acid sequence of SEQ ID NO:291, a light chain CDR2 region comprising the amino acid sequence of SEQ ID NO:292, and a light chain CDR3 region comprising the amino acid sequence of SEQ ID NO:293; or (xlvii) a heavy chain CDR1 region comprising the amino acid sequence of SEQ ID NO:294, a heavy chain CDR2 region comprising the amino acid sequence of SEQ ID NO:295, a heavy chain CDR3 region comprising the amino acid sequence of SEQ ID NO:296, a light chain CDR1 region comprising the amino acid sequence of SEQ ID NO:297, a light chain CDR2 region comprising the amino acid sequence of SEQ ID NO:298, and a light chain CDR3 region comprising the amino acid sequence of SEQ ID NO:299; or (xlviii) a heavy chain CDR1 region comprising the amino acid sequence of SEQ ID NO:300, a heavy chain CDR2 region comprising the amino acid sequence of SEQ ID NO:301, a heavy chain CDR3 region comprising the amino acid sequence of SEQ ID NO:302, a light chain CDR1 region comprising the amino acid sequence of SEQ ID NO:303, a light chain CDR2 region comprising the amino acid sequence of SEQ ID NO:304, and a light chain CDR3 region comprising the amino acid sequence of SEQ ID NO:305; or (xlix) a heavy chain CDR1 region comprising the amino acid sequence of SEQ ID NO:306, a heavy chain CDR2 region comprising the amino acid sequence of SEQ ID NO:307, a heavy chain CDR3 region comprising the amino acid sequence of SEQ ID NO:308, a light chain CDR1 region comprising the amino acid sequence of SEQ ID NO:309, a light chain CDR2 region comprising the amino acid sequence of SEQ ID NO:310, and a light chain CDR3 region comprising the amino acid sequence of SEQ ID NO:311; or (l) a heavy chain CDR1 region comprising the amino acid sequence of SEQ ID NO:312, a heavy chain CDR2 region comprising the amino acid sequence of SEQ ID NO:313, a heavy chain CDR3 region comprising the amino acid sequence of SEQ ID NO:314, a light chain CDR1 region comprising the amino acid sequence of SEQ ID NO:315, a light chain CDR2 region comprising the amino acid sequence of SEQ ID NO:316, and a light chain CDR3 region comprising the amino acid sequence of SEQ ID NO:317; or (li) a heavy chain CDR1 region comprising the amino acid sequence of SEQ ID NO:318, a heavy chain CDR2 region comprising the amino acid sequence of SEQ ID NO:319, a heavy chain CDR3 region comprising the amino acid sequence of SEQ ID NO:320, a light chain CDR1 region comprising the amino acid sequence of SEQ ID NO:321, a light chain CDR2 region comprising the amino acid sequence of SEQ ID NO:322, and a light chain CDR3 region comprising the amino acid sequence of SEQ ID NO:323; or (lii) a heavy chain CDR1 region comprising the amino acid sequence of SEQ ID NO:324, a heavy chain CDR2 region comprising the amino acid sequence of SEQ ID NO:325, a heavy chain CDR3 region comprising the amino acid sequence of SEQ ID NO:326, a light chain CDR1 region comprising the amino acid sequence of SEQ ID NO:327, a light chain CDR2 region comprising the amino acid sequence of SEQ ID NO:328, and a light chain CDR3 region comprising the amino acid sequence of SEQ ID NO:329.

2. The antigen-binding peptide according to claim 1, wherein the antigen-binding peptide binds to more than one of SEQ ID NOs: 1, 2, 5 and 6.

3. The antigen-binding peptide according to claim 1, wherein said perilipin-1 epitope is a human perilipin-1 epitope.

4. The antigen-binding peptide according to claim 1, wherein said antigen-binding peptide is not a perilipin-1 targeting autoantibody of a human patient having lipoatrophy.

5. The antigen-binding peptide according to claim 1, wherein said antigen-binding peptide competes for binding with a perilipin-1 targeting autoantibody of a human patient having lipoatrophy.

6. The antigen-binding peptide according to claim 1, wherein said antigen-binding peptide binds to perilipin-1 in a binding assay with an affinity (Kp) of at least $10^{-4}$ M.

7. The antigen-binding peptide according to claim 1, wherein said antigen-binding peptide is an antibody.

8. The antigen-binding peptide according to claim 1, wherein said antigen-binding peptide, when incubated in the presence of complement, with 3T3-L1-cells that have been differentiated into adipocytes, causes a complement-mediated cell death of said 3T3-L1-cells and/or said differentiated adipocytes.

9. The antigen-binding peptide according to claim 1, wherein said antigen-binding peptide binds to the surface(s) of adipocytes, when said antigen-binding peptide is incubated with said adipocytes.

10. The antigen-binding peptide according to claim 1, wherein said antigen-binding peptide is a human antibody, a humanised antibody, or a chimeric-human antibody.

11. The antigen-binding peptide according to claim 1, wherein said antigen-binding peptide is an intact antibody, a Fab fragment, a $F(ab')_2$ fragment, or a single chain Fv fragment.

12. The antigen-binding peptide according to claim 1, wherein said antigen-binding peptide binds to a perilipin-1 fragment presented on an adipocyte, and wherein said binding of said antigen-binding peptide to a perilipin-1 fragment on said adipocyte activates an immune effector system to target and/or eliminate said adipocyte.

13. The antigen-binding peptide according to claim 1, wherein said antigen-binding peptide comprises an Fc region that is optimized by protein engineering for higher binding affinity to an effector cell compared to a binding affinity of an Fc region which has not been optimized.

14. The antigen-binding peptide according to claim 1, wherein said antigen-binding peptide does not cross-react with any other perilipin protein.

15. A composition comprising an antigen-binding peptide according to claim 1.

16. The composition according to claim 15, comprising more than one of said antigen-binding peptides.

17. The composition according to claim 16, wherein said more than one antigen-binding peptide are a set of peptides, each of which peptides bind to a different perilipin-1 epitope.

* * * * *

SEQUENCE LISTING

```
<160> NUMBER OF SEQ ID NOS: 439

<210> SEQ ID NO 1
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: epitope

<400> SEQUENCE: 1

Leu Thr Leu Leu Asp Gly Asp Leu Pro Glu
1               5                   10


<210> SEQ ID NO 2
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: epitope

<400> SEQUENCE: 2

Glu Lys Ile Ala Ser Glu Leu Lys
1               5
```

```
<210> SEQ ID NO 3
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: epitope

<400> SEQUENCE: 3

Val Pro Ile Ala Ser Thr Ser Asp Lys Val
1               5                   10


<210> SEQ ID NO 4
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: epitope

<400> SEQUENCE: 4

Pro Ala Pro Gly His Gln Gln Ala Gln Lys
1               5                   10


<210> SEQ ID NO 5
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: epitope

<400> SEQUENCE: 5

Pro Ser Leu Leu Ser Arg Val Gly Ala Leu Thr Asn
1               5                   10


<210> SEQ ID NO 6
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: epitope

<400> SEQUENCE: 6

Pro Trp Leu His Ser Leu Ala Ala
1               5


<210> SEQ ID NO 7
<211> LENGTH: 522
<212> TYPE: PRT
<213> ORGANISM: Homo sapiens
<220> FEATURE:
<221> NAME/KEY: MISC_FEATURE
<222> LOCATION: (1)..(522)
<223> OTHER INFORMATION: full-length human perilipin-1

<400> SEQUENCE: 7

Met Ala Val Asn Lys Gly Leu Thr Leu Leu Asp Gly Asp Leu Pro Glu
1               5                   10                  15

Gln Glu Asn Val Leu Gln Arg Val Leu Gln Leu Pro Val Val Ser Gly
            20                  25                  30

Thr Cys Glu Cys Phe Gln Lys Thr Tyr Thr Ser Thr Lys Glu Ala His
```

```
        35                  40                  45

Pro Leu Val Ala Ser Val Cys Asn Ala Tyr Glu Lys Gly Val Gln Ser
    50                  55                  60

Ala Ser Ser Leu Ala Ala Trp Ser Met Glu Pro Val Val Arg Arg Leu
65                  70                  75                  80

Ser Thr Gln Phe Thr Ala Ala Asn Glu Leu Ala Cys Arg Gly Leu Asp
                85                  90                  95

His Leu Glu Glu Lys Ile Pro Ala Leu Gln Tyr Pro Pro Glu Lys Ile
            100                 105                 110

Ala Ser Glu Leu Lys Asp Thr Ile Ser Thr Arg Leu Arg Ser Ala Arg
        115                 120                 125

Asn Ser Ile Ser Val Pro Ile Ala Ser Thr Ser Asp Lys Val Leu Gly
    130                 135                 140

Ala Ala Leu Ala Gly Cys Glu Leu Ala Trp Gly Val Ala Arg Asp Thr
145                 150                 155                 160

Ala Glu Phe Ala Ala Asn Thr Arg Ala Gly Arg Leu Ala Ser Gly Gly
                165                 170                 175

Ala Asp Leu Ala Leu Gly Ser Ile Glu Lys Val Val Glu Tyr Leu Leu
            180                 185                 190

Pro Pro Asp Lys Glu Glu Ser Ala Pro Ala Pro Gly His Gln Gln Ala
        195                 200                 205

Gln Lys Ser Pro Lys Ala Lys Pro Ser Leu Leu Ser Arg Val Gly Ala
    210                 215                 220

Leu Thr Asn Thr Leu Ser Arg Tyr Thr Val Gln Thr Met Ala Arg Ala
225                 230                 235                 240

Leu Glu Gln Gly His Thr Val Ala Met Trp Ile Pro Gly Val Val Pro
                245                 250                 255

Leu Ser Ser Leu Ala Gln Trp Gly Ala Ser Val Ala Met Gln Ala Val
            260                 265                 270

Ser Arg Arg Arg Ser Glu Val Arg Val Pro Trp Leu His Ser Leu Ala
        275                 280                 285

Ala Ala Gln Glu Glu Asp His Glu Asp Gln Thr Asp Thr Glu Gly Glu
    290                 295                 300

Asp Thr Glu Glu Glu Glu Glu Leu Glu Thr Glu Glu Asn Lys Phe Ser
305                 310                 315                 320

Glu Val Ala Ala Leu Pro Gly Pro Arg Gly Leu Leu Gly Gly Val Ala
                325                 330                 335

His Thr Leu Gln Lys Thr Leu Gln Thr Thr Ile Ser Ala Val Thr Trp
            340                 345                 350

Ala Pro Ala Ala Val Leu Gly Met Ala Gly Arg Val Leu His Leu Thr
        355                 360                 365

Pro Ala Pro Ala Val Ser Ser Thr Lys Gly Arg Ala Met Ser Leu Ser
    370                 375                 380

Asp Ala Leu Lys Gly Val Thr Asp Asn Val Val Asp Thr Val Val His
385                 390                 395                 400

Tyr Val Pro Leu Pro Arg Leu Ser Leu Met Glu Pro Glu Ser Glu Phe
                405                 410                 415

Arg Asp Ile Asp Asn Pro Pro Ala Glu Val Glu Arg Arg Glu Ala Glu
            420                 425                 430

Arg Arg Ala Ser Gly Ala Pro Ser Ala Gly Pro Glu Pro Ala Pro Arg
        435                 440                 445

Leu Ala Gln Pro Arg Arg Ser Leu Arg Ser Ala Gln Ser Pro Gly Ala
    450                 455                 460
```

```
Pro Pro Gly Pro Gly Leu Glu Asp Glu Val Ala Thr Pro Ala Ala Pro
465                 470                 475                 480

Arg Pro Gly Phe Pro Ala Val Pro Arg Glu Lys Pro Lys Arg Arg Val
                485                 490                 495

Ser Asp Ser Phe Phe Arg Pro Ser Val Met Glu Pro Ile Leu Gly Arg
            500                 505                 510

Thr His Tyr Ser Gln Leu Arg Lys Lys Ser
        515                 520


<210> SEQ ID NO 8
<211> LENGTH: 8
<212> TYPE: PRT
<213> ORGANISM: Homo sapiens

<400> SEQUENCE: 8

Pro Glu Lys Glu Pro Pro Lys Pro
1               5


<210> SEQ ID NO 9
<211> LENGTH: 9
<212> TYPE: PRT
<213> ORGANISM: Homo sapiens

<400> SEQUENCE: 9

Pro Ile Leu Val Glu Arg Pro Glu Pro
1               5


<210> SEQ ID NO 10
<211> LENGTH: 8
<212> TYPE: PRT
<213> ORGANISM: Homo sapiens

<400> SEQUENCE: 10

Glu Lys Ile Ala Ser Glu Leu Lys
1               5


<210> SEQ ID NO 11
<211> LENGTH: 10
<212> TYPE: PRT
<213> ORGANISM: Homo sapiens

<400> SEQUENCE: 11

Val Pro Ile Ala Ser Thr Ser Asp Lys Val
1               5                   10


<210> SEQ ID NO 12
<211> LENGTH: 10
<212> TYPE: PRT
<213> ORGANISM: Homo sapiens

<400> SEQUENCE: 12

Pro Ala Pro Gly His Gln Gln Ala Gln Lys
1               5                   10


<210> SEQ ID NO 13
<211> LENGTH: 12
<212> TYPE: PRT
<213> ORGANISM: Homo sapiens

<400> SEQUENCE: 13

Pro Ser Leu Leu Ser Arg Val Gly Ala Leu Thr Asn
1               5                   10
```

<210> SEQ ID NO 14
<211> LENGTH: 8
<212> TYPE: PRT
<213> ORGANISM: Homo sapiens

<400> SEQUENCE: 14

Pro Trp Leu His Ser Leu Ala Ala
1 5

<210> SEQ ID NO 15
<211> LENGTH: 10
<212> TYPE: PRT
<213> ORGANISM: Homo sapiens

<400> SEQUENCE: 15

Leu Thr Leu Leu Asp Gly Asp Leu Pro Glu
1 5 10

<210> SEQ ID NO 16
<211> LENGTH: 8
<212> TYPE: PRT
<213> ORGANISM: Homo sapiens

<400> SEQUENCE: 16

Pro Glu Lys Glu Pro Pro Lys Pro
1 5

<210> SEQ ID NO 17
<211> LENGTH: 9
<212> TYPE: PRT
<213> ORGANISM: Homo sapiens

<400> SEQUENCE: 17

Pro Ile Leu Val Glu Arg Pro Glu Pro
1 5

<210> SEQ ID NO 18
<211> LENGTH: 5
<212> TYPE: PRT
<213> ORGANISM: Artificial Sequence
<220> FEATURE:
<223> OTHER INFORMATION: HCDR 1

<400> SEQUENCE: 18

Ser Tyr Ala Met His
1 5

<210> SEQ ID NO 19
<211> LENGTH: 17
<212> TYPE: PRT
<213> ORGANISM: Artificial Sequence
<220> FEATURE:
<223> OTHER INFORMATION: HCDR 2

<400> SEQUENCE: 19

Val Ile Ser Tyr Asp Gly Ser Asn Lys Tyr Tyr Ala Asp Ser Val Lys
1 5 10 15

Gly

<210> SEQ ID NO 20
<211> LENGTH: 9
<212> TYPE: PRT
<213> ORGANISM: Artificial Sequence
<220> FEATURE:
<223> OTHER INFORMATION: HCDR 3

<400> SEQUENCE: 20

Ile Ala Ala Ala Gly Pro Phe Asp Tyr
1 5

<210> SEQ ID NO 21
<211> LENGTH: 13
<212> TYPE: PRT
<213> ORGANISM: Artificial Sequence
<220> FEATURE:
<223> OTHER INFORMATION: LCDR 1

<400> SEQUENCE: 21

Ser Gly Ser Ser Ser Asn Ile Gly Asn Asn Ala Val Asn
1 5 10

<210> SEQ ID NO 22
<211> LENGTH: 7
<212> TYPE: PRT
<213> ORGANISM: Artificial Sequence
<220> FEATURE:
<223> OTHER INFORMATION: LCDR 2

<400> SEQUENCE: 22

Tyr Asp Asp Leu Leu Pro Ser
1 5

<210> SEQ ID NO 23
<211> LENGTH: 11
<212> TYPE: PRT
<213> ORGANISM: Artificial Sequence
<220> FEATURE:
<223> OTHER INFORMATION: LCDR 3

<400> SEQUENCE: 23

Ala Ala Trp Asp Asp Ser Leu Asn Gly Val Val
1 5 10

<210> SEQ ID NO 24
<211> LENGTH: 5
<212> TYPE: PRT
<213> ORGANISM: Artificial Sequence
<220> FEATURE:
<223> OTHER INFORMATION: HCDR 1

<400> SEQUENCE: 24

Ser Tyr Ala Met Ser
1 5

<210> SEQ ID NO 25
<211> LENGTH: 17
<212> TYPE: PRT
<213> ORGANISM: Artificial Sequence
<220> FEATURE:
<223> OTHER INFORMATION: HCDR 2

<400> SEQUENCE: 25

Ala Ile Ser Gly Ser Gly Gly Ser Thr Tyr Tyr Ala Asp Ser Val Lys
1 5 10 15

Gly

<210> SEQ ID NO 26
<211> LENGTH: 8
<212> TYPE: PRT
<213> ORGANISM: Artificial Sequence
<220> FEATURE:

<223> OTHER INFORMATION: HCDR 3

<400> SEQUENCE: 26

Gly Phe Arg Arg Leu Phe Asp Pro
1               5

<210> SEQ ID NO 27
<211> LENGTH: 14
<212> TYPE: PRT
<213> ORGANISM: Artificial Sequence
<220> FEATURE:
<223> OTHER INFORMATION: LCDR 1

<400> SEQUENCE: 27

Thr Gly Thr Ser Ser Asp Val Gly Gly Tyr Asn Tyr Val Ser
1               5                   10

<210> SEQ ID NO 28
<211> LENGTH: 7
<212> TYPE: PRT
<213> ORGANISM: Artificial Sequence
<220> FEATURE:
<223> OTHER INFORMATION: LCDR 2

<400> SEQUENCE: 28

Asp Val Ser Asn Arg Pro Ser
1               5

<210> SEQ ID NO 29
<211> LENGTH: 11
<212> TYPE: PRT
<213> ORGANISM: Artificial Sequence
<220> FEATURE:
<223> OTHER INFORMATION: LCDR 3

<400> SEQUENCE: 29

Ser Ser Tyr Thr Ser Ser Ser Thr His Val Val
1               5                   10

<210> SEQ ID NO 30
<211> LENGTH: 5
<212> TYPE: PRT
<213> ORGANISM: Artificial Sequence
<220> FEATURE:
<223> OTHER INFORMATION: HCDR 1

<400> SEQUENCE: 30

Ser Tyr Ala Met His
1               5

<210> SEQ ID NO 31
<211> LENGTH: 17
<212> TYPE: PRT
<213> ORGANISM: Artificial Sequence
<220> FEATURE:
<223> OTHER INFORMATION: HCDR 2

<400> SEQUENCE: 31

Val Ile Ser Tyr Asp Gly Ser Asn Lys Tyr Tyr Ala Asp Ser Val Lys
1               5                   10                  15

Gly

<210> SEQ ID NO 32
<211> LENGTH: 11
<212> TYPE: PRT
<213> ORGANISM: Artificial Sequence

<220> FEATURE:
<223> OTHER INFORMATION: HCDR 3

<400> SEQUENCE: 32

Phe Ala Ser Ile Ala Ala Arg Pro Phe Asp Tyr
1 5 10

<210> SEQ ID NO 33
<211> LENGTH: 13
<212> TYPE: PRT
<213> ORGANISM: Artificial Sequence
<220> FEATURE:
<223> OTHER INFORMATION: LCDR 1

<400> SEQUENCE: 33

Ser Gly Ser Ser Ser Asn Ile Gly Ser Asn Thr Val Asn
1 5 10

<210> SEQ ID NO 34
<211> LENGTH: 7
<212> TYPE: PRT
<213> ORGANISM: Artificial Sequence
<220> FEATURE:
<223> OTHER INFORMATION: LCDR 2

<400> SEQUENCE: 34

Ser Asn Asn Gln Arg Pro Ser
1 5

<210> SEQ ID NO 35
<211> LENGTH: 12
<212> TYPE: PRT
<213> ORGANISM: Artificial Sequence
<220> FEATURE:
<223> OTHER INFORMATION: LCDR 3

<400> SEQUENCE: 35

Ala Ala Trp Asp Asp Ser Leu Asn Gly Arg Tyr Val
1 5 10

<210> SEQ ID NO 36
<211> LENGTH: 5
<212> TYPE: PRT
<213> ORGANISM: Artificial Sequence
<220> FEATURE:
<223> OTHER INFORMATION: HCDR 1

<400> SEQUENCE: 36

Ser Tyr Gly Ile Ser
1 5

<210> SEQ ID NO 37
<211> LENGTH: 17
<212> TYPE: PRT
<213> ORGANISM: Artificial Sequence
<220> FEATURE:
<223> OTHER INFORMATION: HCDR 2

<400> SEQUENCE: 37

Trp Ile Ser Ala Tyr Asn Gly Asn Thr Asn Tyr Ala Gln Lys Leu Gln
1 5 10 15

Gly

<210> SEQ ID NO 38
<211> LENGTH: 7
<212> TYPE: PRT

<213> ORGANISM: Artificial Sequence
<220> FEATURE:
<223> OTHER INFORMATION: HCDR 3

<400> SEQUENCE: 38

Gly Gly Ser Ser Ser Asn Tyr
1 5

<210> SEQ ID NO 39
<211> LENGTH: 14
<212> TYPE: PRT
<213> ORGANISM: Artificial Sequence
<220> FEATURE:
<223> OTHER INFORMATION: LCDR 1

<400> SEQUENCE: 39

Thr Gly Thr Ser Ser Asp Val Gly Gly Tyr Asn Tyr Val Ser
1 5 10

<210> SEQ ID NO 40
<211> LENGTH: 7
<212> TYPE: PRT
<213> ORGANISM: Artificial Sequence
<220> FEATURE:
<223> OTHER INFORMATION: LCDR 2

<400> SEQUENCE: 40

Glu Val Ser Asn Arg Pro Ser
1 5

<210> SEQ ID NO 41
<211> LENGTH: 10
<212> TYPE: PRT
<213> ORGANISM: Artificial Sequence
<220> FEATURE:
<223> OTHER INFORMATION: LCDR 3

<400> SEQUENCE: 41

Ser Ser Tyr Thr Ser Ser Ser Thr Leu Val
1 5 10

<210> SEQ ID NO 42
<211> LENGTH: 5
<212> TYPE: PRT
<213> ORGANISM: Artificial Sequence
<220> FEATURE:
<223> OTHER INFORMATION: HCDR 1

<400> SEQUENCE: 42

Ser Tyr Gly Met His
1 5

<210> SEQ ID NO 43
<211> LENGTH: 17
<212> TYPE: PRT
<213> ORGANISM: Artificial Sequence
<220> FEATURE:
<223> OTHER INFORMATION: HCDR 2

<400> SEQUENCE: 43

Val Ile Ser Tyr Asp Gly Ser Asn Lys Tyr Tyr Ala Asp Ser Val Lys
1 5 10 15

Gly

<210> SEQ ID NO 44
<211> LENGTH: 8

<212> TYPE: PRT
<213> ORGANISM: Artificial Sequence
<220> FEATURE:
<223> OTHER INFORMATION: HCDR 3

<400> SEQUENCE: 44

Asn Pro Ser Ser Gly Ala Asp Tyr
1 5

<210> SEQ ID NO 45
<211> LENGTH: 13
<212> TYPE: PRT
<213> ORGANISM: Artificial Sequence
<220> FEATURE:
<223> OTHER INFORMATION: LCDR 1

<400> SEQUENCE: 45

Ser Gly Ser Ser Ser Asn Ile Gly Ser Asn Tyr Val Tyr
1 5 10

<210> SEQ ID NO 46
<211> LENGTH: 7
<212> TYPE: PRT
<213> ORGANISM: Artificial Sequence
<220> FEATURE:
<223> OTHER INFORMATION: LCDR 2

<400> SEQUENCE: 46

Arg Asn Asn Gln Arg Pro Ser
1 5

<210> SEQ ID NO 47
<211> LENGTH: 12
<212> TYPE: PRT
<213> ORGANISM: Artificial Sequence
<220> FEATURE:
<223> OTHER INFORMATION: LCDR 3

<400> SEQUENCE: 47

Ala Ala Trp Asp Asp Ser Leu Ser Gly Ala Trp Val
1 5 10

<210> SEQ ID NO 48
<211> LENGTH: 5
<212> TYPE: PRT
<213> ORGANISM: Artificial Sequence
<220> FEATURE:
<223> OTHER INFORMATION: HCDR 1

<400> SEQUENCE: 48

Ser Tyr Ala Ile Ser
1 5

<210> SEQ ID NO 49
<211> LENGTH: 17
<212> TYPE: PRT
<213> ORGANISM: Artificial Sequence
<220> FEATURE:
<223> OTHER INFORMATION: HCDR 2

<400> SEQUENCE: 49

Gly Ile Ile Pro Ile Phe Gly Thr Ala Asn Tyr Ala Gln Lys Phe Gln
1 5 10 15

Gly

<210> SEQ ID NO 50

<211> LENGTH: 8
<212> TYPE: PRT
<213> ORGANISM: Artificial Sequence
<220> FEATURE:
<223> OTHER INFORMATION: HCDR 3

<400> SEQUENCE: 50

Ser His Ser Ser Gly Trp Glu Trp
1               5

<210> SEQ ID NO 51
<211> LENGTH: 13
<212> TYPE: PRT
<213> ORGANISM: Artificial Sequence
<220> FEATURE:
<223> OTHER INFORMATION: LCDR 1

<400> SEQUENCE: 51

Ser Gly Ser Ser Ser Asn Ile Gly Ser Asn Tyr Val Tyr
1               5                   10

<210> SEQ ID NO 52
<211> LENGTH: 7
<212> TYPE: PRT
<213> ORGANISM: Artificial Sequence
<220> FEATURE:
<223> OTHER INFORMATION: LCDR 2

<400> SEQUENCE: 52

Arg Asn Asn Gln Arg Pro Ser
1               5

<210> SEQ ID NO 53
<211> LENGTH: 11
<212> TYPE: PRT
<213> ORGANISM: Artificial Sequence
<220> FEATURE:
<223> OTHER INFORMATION: LCDR 3

<400> SEQUENCE: 53

Ala Ala Trp Asp Asp Ser Leu Ser Gly Val Val
1               5                   10

<210> SEQ ID NO 54
<211> LENGTH: 5
<212> TYPE: PRT
<213> ORGANISM: Artificial Sequence
<220> FEATURE:
<223> OTHER INFORMATION: HCDR 1

<400> SEQUENCE: 54

Ser Tyr Gly Ile Ser
1               5

<210> SEQ ID NO 55
<211> LENGTH: 17
<212> TYPE: PRT
<213> ORGANISM: Artificial Sequence
<220> FEATURE:
<223> OTHER INFORMATION: HCDR 2

<400> SEQUENCE: 55

Trp Ile Ser Ala Tyr Asn Gly Asn Thr Asn Tyr Ala Gln Lys Leu Gln
1               5                   10                  15

Gly

<210> SEQ ID NO 56
<211> LENGTH: 14
<212> TYPE: PRT
<213> ORGANISM: Artificial Sequence
<220> FEATURE:
<223> OTHER INFORMATION: HCDR 3

<400> SEQUENCE: 56

Leu Tyr Cys Ser Gly Gly Ser Cys Tyr Ser Ala Leu Asp Pro
1 5 10

<210> SEQ ID NO 57
<211> LENGTH: 14
<212> TYPE: PRT
<213> ORGANISM: Artificial Sequence
<220> FEATURE:
<223> OTHER INFORMATION: LCDR 1

<400> SEQUENCE: 57

Thr Gly Ser Ser Ser Asn Ile Gly Ala Gly Tyr Asp Val His
1 5 10

<210> SEQ ID NO 58
<211> LENGTH: 7
<212> TYPE: PRT
<213> ORGANISM: Artificial Sequence
<220> FEATURE:
<223> OTHER INFORMATION: LCDR 2

<400> SEQUENCE: 58

Gly Asn Ser Asn Arg Pro Ser
1 5

<210> SEQ ID NO 59
<211> LENGTH: 11
<212> TYPE: PRT
<213> ORGANISM: Artificial Sequence
<220> FEATURE:
<223> OTHER INFORMATION: LCDR 3

<400> SEQUENCE: 59

Gln Ser Tyr Asp Ser Ser Leu Arg Tyr Val Val
1 5 10

<210> SEQ ID NO 60
<211> LENGTH: 5
<212> TYPE: PRT
<213> ORGANISM: Artificial Sequence
<220> FEATURE:
<223> OTHER INFORMATION: HCDR 1

<400> SEQUENCE: 60

Asp Tyr Ala Met His
1 5

<210> SEQ ID NO 61
<211> LENGTH: 17
<212> TYPE: PRT
<213> ORGANISM: Artificial Sequence
<220> FEATURE:
<223> OTHER INFORMATION: HCDR 2

<400> SEQUENCE: 61

Gly Ile Ser Trp Asn Ser Gly Ser Ile Gly Tyr Ala Asp Ser Val Lys
1 5 10 15

Gly

<210> SEQ ID NO 62
<211> LENGTH: 9
<212> TYPE: PRT
<213> ORGANISM: Artificial Sequence
<220> FEATURE:
<223> OTHER INFORMATION: HCDR 3

<400> SEQUENCE: 62

Glu Asp Gly Ser Tyr Ala Leu Asp Tyr
1 5

<210> SEQ ID NO 63
<211> LENGTH: 11
<212> TYPE: PRT
<213> ORGANISM: Artificial Sequence
<220> FEATURE:
<223> OTHER INFORMATION: LCDR 1

<400> SEQUENCE: 63

Arg Ala Ser Gln Ser Ile Ser Ser Tyr Leu Asn
1 5 10

<210> SEQ ID NO 64
<211> LENGTH: 7
<212> TYPE: PRT
<213> ORGANISM: Artificial Sequence
<220> FEATURE:
<223> OTHER INFORMATION: LCDR 2

<400> SEQUENCE: 64

Ala Ala Ser Ser Leu Gln Ser
1 5

<210> SEQ ID NO 65
<211> LENGTH: 9
<212> TYPE: PRT
<213> ORGANISM: Artificial Sequence
<220> FEATURE:
<223> OTHER INFORMATION: LCDR 3

<400> SEQUENCE: 65

Gln Gln Ser Tyr Ser Thr Pro Pro Thr
1 5

<210> SEQ ID NO 66
<211> LENGTH: 5
<212> TYPE: PRT
<213> ORGANISM: Artificial Sequence
<220> FEATURE:
<223> OTHER INFORMATION: HCDR 1

<400> SEQUENCE: 66

Asp Tyr Ala Met His
1 5

<210> SEQ ID NO 67
<211> LENGTH: 17
<212> TYPE: PRT
<213> ORGANISM: Artificial Sequence
<220> FEATURE:
<223> OTHER INFORMATION: HCDR 2

<400> SEQUENCE: 67

Gly Ile Ser Trp Asn Ser Gly Ser Ile Gly Tyr Ala Asp Ser Val Lys
1 5 10 15

Gly

<210> SEQ ID NO 68
<211> LENGTH: 10
<212> TYPE: PRT
<213> ORGANISM: Artificial Sequence
<220> FEATURE:
<223> OTHER INFORMATION: HCDR 3

<400> SEQUENCE: 68

Glu Gly Tyr Gly Asn Asp Ala Phe Asp Ile
1               5                   10

<210> SEQ ID NO 69
<211> LENGTH: 11
<212> TYPE: PRT
<213> ORGANISM: Artificial Sequence
<220> FEATURE:
<223> OTHER INFORMATION: LCDR 1

<400> SEQUENCE: 69

Arg Ala Ser Gln Ser Ile Ser Ser Tyr Leu Asn
1               5                   10

<210> SEQ ID NO 70
<211> LENGTH: 7
<212> TYPE: PRT
<213> ORGANISM: Artificial Sequence
<220> FEATURE:
<223> OTHER INFORMATION: LCDR 2

<400> SEQUENCE: 70

Ala Ala Ser Ser Leu Gln Ser
1               5

<210> SEQ ID NO 71
<211> LENGTH: 9
<212> TYPE: PRT
<213> ORGANISM: Artificial Sequence
<220> FEATURE:
<223> OTHER INFORMATION: LCDR 3

<400> SEQUENCE: 71

Gln Gln Ser Tyr Ser Thr Pro Pro Thr
1               5

<210> SEQ ID NO 72
<211> LENGTH: 5
<212> TYPE: PRT
<213> ORGANISM: Artificial Sequence
<220> FEATURE:
<223> OTHER INFORMATION: HCDR 1

<400> SEQUENCE: 72

Ser Tyr Gly Met His
1               5

<210> SEQ ID NO 73
<211> LENGTH: 17
<212> TYPE: PRT
<213> ORGANISM: Artificial Sequence
<220> FEATURE:
<223> OTHER INFORMATION: HCDR 2

<400> SEQUENCE: 73

Ala Ile Ser Tyr Asp Gly Ser Asn Lys Tyr Tyr Ala Asp Ser Val Lys
1               5                   10                  15

Gly

<210> SEQ ID NO 74
<211> LENGTH: 12
<212> TYPE: PRT
<213> ORGANISM: Artificial Sequence
<220> FEATURE:
<223> OTHER INFORMATION: HCDR 3

<400> SEQUENCE: 74

Asp Met Gly Leu Ser Trp Tyr Gly Glu Phe Asp Tyr
1 5 10

<210> SEQ ID NO 75
<211> LENGTH: 13
<212> TYPE: PRT
<213> ORGANISM: Artificial Sequence
<220> FEATURE:
<223> OTHER INFORMATION: LCDR 1

<400> SEQUENCE: 75

Ser Gly Ser Ser Ser Asn Ile Gly Asn Asn Ala Val Ser
1 5 10

<210> SEQ ID NO 76
<211> LENGTH: 7
<212> TYPE: PRT
<213> ORGANISM: Artificial Sequence
<220> FEATURE:
<223> OTHER INFORMATION: LCDR 2

<400> SEQUENCE: 76

Tyr Asp Asp Leu Leu Pro Ser
1 5

<210> SEQ ID NO 77
<211> LENGTH: 10
<212> TYPE: PRT
<213> ORGANISM: Artificial Sequence
<220> FEATURE:
<223> OTHER INFORMATION: LCDR 3

<400> SEQUENCE: 77

Ala Ala Trp Asp Asp Ser Leu Asn Trp Val
1 5 10

<210> SEQ ID NO 78
<211> LENGTH: 5
<212> TYPE: PRT
<213> ORGANISM: Artificial Sequence
<220> FEATURE:
<223> OTHER INFORMATION: HCDR 1

<400> SEQUENCE: 78

Ser Tyr Gly Met His
1 5

<210> SEQ ID NO 79
<211> LENGTH: 17
<212> TYPE: PRT
<213> ORGANISM: Artificial Sequence
<220> FEATURE:
<223> OTHER INFORMATION: HCDR 2

<400> SEQUENCE: 79

Val Ile Ser Tyr Asp Gly Ser Asn Lys Tyr Tyr Ala Asp Ser Val Lys
1 5 10 15

Gly

<210> SEQ ID NO 80
<211> LENGTH: 6
<212> TYPE: PRT
<213> ORGANISM: Artificial Sequence
<220> FEATURE:
<223> OTHER INFORMATION: HCDR 3

<400> SEQUENCE: 80

Asp Ile Phe Met Asp Val
1 5

<210> SEQ ID NO 81
<211> LENGTH: 14
<212> TYPE: PRT
<213> ORGANISM: Artificial Sequence
<220> FEATURE:
<223> OTHER INFORMATION: LCDR 1

<400> SEQUENCE: 81

Thr Gly Thr Ser Ser Asp Val Gly Gly Tyr Asn Tyr Val Ser
1 5 10

<210> SEQ ID NO 82
<211> LENGTH: 7
<212> TYPE: PRT
<213> ORGANISM: Artificial Sequence
<220> FEATURE:
<223> OTHER INFORMATION: LCDR 2

<400> SEQUENCE: 82

Asp Val Ser Asn Arg Pro Ser
1 5

<210> SEQ ID NO 83
<211> LENGTH: 11
<212> TYPE: PRT
<213> ORGANISM: Artificial Sequence
<220> FEATURE:
<223> OTHER INFORMATION: LCDR 3

<400> SEQUENCE: 83

Ser Ser Tyr Thr Ser Ser Ser Thr Leu Val Val
1 5 10

<210> SEQ ID NO 84
<211> LENGTH: 5
<212> TYPE: PRT
<213> ORGANISM: Artificial Sequence
<220> FEATURE:
<223> OTHER INFORMATION: HCDR 1

<400> SEQUENCE: 84

Asp Tyr Gly Met His
1 5

<210> SEQ ID NO 85
<211> LENGTH: 17
<212> TYPE: PRT
<213> ORGANISM: Artificial Sequence
<220> FEATURE:
<223> OTHER INFORMATION: HCDR 2

<400> SEQUENCE: 85

Val Ile Ser Tyr Asp Gly Ser Asn Lys Tyr Tyr Ala Asp Ser Val Lys 1 5 10 15

Gly

<210> SEQ ID NO 86
<211> LENGTH: 9
<212> TYPE: PRT
<213> ORGANISM: Artificial Sequence
<220> FEATURE:
<223> OTHER INFORMATION: HCDR 3

<400> SEQUENCE: 86

Ala Tyr Gly Glu Gly Gly Phe Asp Pro
1 5

<210> SEQ ID NO 87
<211> LENGTH: 14
<212> TYPE: PRT
<213> ORGANISM: Artificial Sequence
<220> FEATURE:
<223> OTHER INFORMATION: LCDR 1

<400> SEQUENCE: 87

Thr Gly Thr Ser Ser Asp Val Gly Gly Tyr Asn Tyr Val Ser
1 5 10

<210> SEQ ID NO 88
<211> LENGTH: 7
<212> TYPE: PRT
<213> ORGANISM: Artificial Sequence
<220> FEATURE:
<223> OTHER INFORMATION: LCDR 2

<400> SEQUENCE: 88

Glu Val Ser Asn Arg Pro Ser
1 5

<210> SEQ ID NO 89
<211> LENGTH: 11
<212> TYPE: PRT
<213> ORGANISM: Artificial Sequence
<220> FEATURE:
<223> OTHER INFORMATION: LCDR 3

<400> SEQUENCE: 89

Ser Ser Tyr Thr Ser Ser Ser Thr Thr Trp Val
1 5 10

<210> SEQ ID NO 90
<211> LENGTH: 5
<212> TYPE: PRT
<213> ORGANISM: Artificial Sequence
<220> FEATURE:
<223> OTHER INFORMATION: HCDR 1

<400> SEQUENCE: 90

Ser Tyr Ala Met His
1 5

<210> SEQ ID NO 91
<211> LENGTH: 17
<212> TYPE: PRT
<213> ORGANISM: Artificial Sequence
<220> FEATURE:
<223> OTHER INFORMATION: HCDR 2

<400> SEQUENCE: 91

Val Ile Ser Tyr Asp Gly Ser Asn Lys Tyr Tyr Ala Asp Pro Val Lys
1 5 10 15

Gly

<210> SEQ ID NO 92
<211> LENGTH: 12
<212> TYPE: PRT
<213> ORGANISM: Artificial Sequence
<220> FEATURE:
<223> OTHER INFORMATION: HCDR 3

<400> SEQUENCE: 92

Gly Gly Asp Gly Tyr Asn Trp Asp Ala Phe Asp Ile
1 5 10

<210> SEQ ID NO 93
<211> LENGTH: 13
<212> TYPE: PRT
<213> ORGANISM: Artificial Sequence
<220> FEATURE:
<223> OTHER INFORMATION: LCDR 1

<400> SEQUENCE: 93

Ser Gly Ser Ser Ser Asn Ile Gly Ser Asn Thr Val Asn
1 5 10

<210> SEQ ID NO 94
<211> LENGTH: 7
<212> TYPE: PRT
<213> ORGANISM: Artificial Sequence
<220> FEATURE:
<223> OTHER INFORMATION: LCDR 2

<400> SEQUENCE: 94

Ser Asn Asn Gln Arg Pro Ser
1 5

<210> SEQ ID NO 95
<211> LENGTH: 11
<212> TYPE: PRT
<213> ORGANISM: Artificial Sequence
<220> FEATURE:
<223> OTHER INFORMATION: LCDR 3

<400> SEQUENCE: 95

Ala Ala Trp Asp Asp Ser Leu Asn Ala Leu Val
1 5 10

<210> SEQ ID NO 96
<211> LENGTH: 5
<212> TYPE: PRT
<213> ORGANISM: Artificial Sequence
<220> FEATURE:
<223> OTHER INFORMATION: HCDR 1

<400> SEQUENCE: 96

Asp Tyr Ala Met His
1 5

<210> SEQ ID NO 97
<211> LENGTH: 17
<212> TYPE: PRT
<213> ORGANISM: Artificial Sequence
<220> FEATURE:
<223> OTHER INFORMATION: HCDR 2

<400> SEQUENCE: 97

Gly Ile Ser Trp Asn Ser Gly Ser Ile Gly Tyr Ala Asp Ser Val Lys
1 5 10 15

Gly

<210> SEQ ID NO 98
<211> LENGTH: 9
<212> TYPE: PRT
<213> ORGANISM: Artificial Sequence
<220> FEATURE:
<223> OTHER INFORMATION: HCDR 3

<400> SEQUENCE: 98

Glu Gly Arg Tyr Gly Gly Phe Asp Tyr
1 5

<210> SEQ ID NO 99
<211> LENGTH: 11
<212> TYPE: PRT
<213> ORGANISM: Artificial Sequence
<220> FEATURE:
<223> OTHER INFORMATION: LCDR 1

<400> SEQUENCE: 99

Gln Ala Ser Gln Asp Ile Ser Asn Tyr Leu Asn
1 5 10

<210> SEQ ID NO 100
<211> LENGTH: 7
<212> TYPE: PRT
<213> ORGANISM: Artificial Sequence
<220> FEATURE:
<223> OTHER INFORMATION: LCDR 2

<400> SEQUENCE: 100

Asp Ala Ser Asn Leu Glu Thr
1 5

<210> SEQ ID NO 101
<211> LENGTH: 9
<212> TYPE: PRT
<213> ORGANISM: Artificial Sequence
<220> FEATURE:
<223> OTHER INFORMATION: LCDR 3

<400> SEQUENCE: 101

Gln Gln Tyr Asp Asn Leu Pro Leu Thr
1 5

<210> SEQ ID NO 102
<211> LENGTH: 5
<212> TYPE: PRT
<213> ORGANISM: Artificial Sequence
<220> FEATURE:
<223> OTHER INFORMATION: HCDR 1

<400> SEQUENCE: 102

Asp Tyr Ala Met His
1 5

<210> SEQ ID NO 103
<211> LENGTH: 17
<212> TYPE: PRT
<213> ORGANISM: Artificial Sequence
<220> FEATURE:
<223> OTHER INFORMATION: HCDR 2

<400> SEQUENCE: 103

Gly Ile Ser Trp Asn Ser Gly Ser Ile Gly Tyr Ala Asp Ser Val Lys
1 5 10 15

Gly

<210> SEQ ID NO 104
<211> LENGTH: 13
<212> TYPE: PRT
<213> ORGANISM: Artificial Sequence
<220> FEATURE:
<223> OTHER INFORMATION: HCDR 3

<400> SEQUENCE: 104

Glu Gly Glu Tyr Ser Tyr Gly Gly Gly Glu Phe Asp Pro
1 5 10

<210> SEQ ID NO 105
<211> LENGTH: 14
<212> TYPE: PRT
<213> ORGANISM: Artificial Sequence
<220> FEATURE:
<223> OTHER INFORMATION: LCDR 1

<400> SEQUENCE: 105

Thr Gly Thr Ser Ser Asp Val Gly Gly Tyr Asn Tyr Val Ser
1 5 10

<210> SEQ ID NO 106
<211> LENGTH: 7
<212> TYPE: PRT
<213> ORGANISM: Artificial Sequence
<220> FEATURE:
<223> OTHER INFORMATION: LCDR 2

<400> SEQUENCE: 106

Asp Val Ser Asn Arg Pro Ser
1 5

<210> SEQ ID NO 107
<211> LENGTH: 10
<212> TYPE: PRT
<213> ORGANISM: Artificial Sequence
<220> FEATURE:
<223> OTHER INFORMATION: LCDR 3

<400> SEQUENCE: 107

Ser Ser Tyr Thr Ser Ser Ser Thr Trp Val
1 5 10

<210> SEQ ID NO 108
<211> LENGTH: 5
<212> TYPE: PRT
<213> ORGANISM: Artificial Sequence
<220> FEATURE:
<223> OTHER INFORMATION: HCDR 1

<400> SEQUENCE: 108

Ser Tyr Gly Met His
1 5

<210> SEQ ID NO 109
<211> LENGTH: 17
<212> TYPE: PRT
<213> ORGANISM: Artificial Sequence
<220> FEATURE:
<223> OTHER INFORMATION: HCDR 2

<400> SEQUENCE: 109

Val Ile Ser Tyr Asp Gly Ser Asn Lys Tyr Tyr Ala Asp Ser Val Lys
1 5 10 15

Gly

<210> SEQ ID NO 110
<211> LENGTH: 10
<212> TYPE: PRT
<213> ORGANISM: Artificial Sequence
<220> FEATURE:
<223> OTHER INFORMATION: HCDR 3

<400> SEQUENCE: 110

Thr Pro Gly Gly Leu Thr Pro Phe Asp Tyr
1 5 10

<210> SEQ ID NO 111
<211> LENGTH: 13
<212> TYPE: PRT
<213> ORGANISM: Artificial Sequence
<220> FEATURE:
<223> OTHER INFORMATION: LCDR 1

<400> SEQUENCE: 111

Ser Gly Ser Ser Ser Asn Ile Gly Gly Asn Thr Val Asn
1 5 10

<210> SEQ ID NO 112
<211> LENGTH: 7
<212> TYPE: PRT
<213> ORGANISM: Artificial Sequence
<220> FEATURE:
<223> OTHER INFORMATION: LCDR 2

<400> SEQUENCE: 112

Ser Asn Asn Gln Arg Pro Ser
1 5

<210> SEQ ID NO 113
<211> LENGTH: 13
<212> TYPE: PRT
<213> ORGANISM: Artificial Sequence
<220> FEATURE:
<223> OTHER INFORMATION: LCDR 3

<400> SEQUENCE: 113

Ala Ala Trp Asp Asp Ser Leu Asn Gly Pro Asn Val Val
1 5 10

<210> SEQ ID NO 114
<211> LENGTH: 5
<212> TYPE: PRT
<213> ORGANISM: Artificial Sequence
<220> FEATURE:
<223> OTHER INFORMATION: HCDR 1

<400> SEQUENCE: 114

Asp Tyr Ala Met His
1 5

<210> SEQ ID NO 115
<211> LENGTH: 17
<212> TYPE: PRT
<213> ORGANISM: Artificial Sequence
<220> FEATURE:

<223> OTHER INFORMATION: HCDR 2

<400> SEQUENCE: 115

Gly Ile Ser Trp Asn Ser Gly Ser Ile Gly Tyr Ala Asp Ser Val Lys
1 5 10 15

Gly

<210> SEQ ID NO 116
<211> LENGTH: 12
<212> TYPE: PRT
<213> ORGANISM: Artificial Sequence
<220> FEATURE:
<223> OTHER INFORMATION: HCDR 3

<400> SEQUENCE: 116

Asp Ile Ala Gly Gly Asp Tyr Pro Val Phe Asp Tyr
1 5 10

<210> SEQ ID NO 117
<211> LENGTH: 11
<212> TYPE: PRT
<213> ORGANISM: Artificial Sequence
<220> FEATURE:
<223> OTHER INFORMATION: LCDR 1

<400> SEQUENCE: 117

Arg Ala Ser Gln Ser Ile Ser Ser Trp Leu Ala
1 5 10

<210> SEQ ID NO 118
<211> LENGTH: 7
<212> TYPE: PRT
<213> ORGANISM: Artificial Sequence
<220> FEATURE:
<223> OTHER INFORMATION: LCDR 2

<400> SEQUENCE: 118

Lys Ala Ser Ser Leu Glu Ser
1 5

<210> SEQ ID NO 119
<211> LENGTH: 10
<212> TYPE: PRT
<213> ORGANISM: Artificial Sequence
<220> FEATURE:
<223> OTHER INFORMATION: LCDR 3

<400> SEQUENCE: 119

Gln Gln Tyr Asn Ser Tyr Ser Pro Trp Thr
1 5 10

<210> SEQ ID NO 120
<211> LENGTH: 5
<212> TYPE: PRT
<213> ORGANISM: Artificial Sequence
<220> FEATURE:
<223> OTHER INFORMATION: HCDR 1

<400> SEQUENCE: 120

Ser Tyr Ala Met Ser
1 5

<210> SEQ ID NO 121
<211> LENGTH: 17
<212> TYPE: PRT
<213> ORGANISM: Artificial Sequence

<220> FEATURE:
<223> OTHER INFORMATION: HCDR 2

<400> SEQUENCE: 121

Ala Ile Ser Gly Ser Gly Gly Ser Thr Tyr Tyr Ala Asp Ser Val Lys
1 5 10 15

Gly

<210> SEQ ID NO 122
<211> LENGTH: 11
<212> TYPE: PRT
<213> ORGANISM: Artificial Sequence
<220> FEATURE:
<223> OTHER INFORMATION: HCDR 3

<400> SEQUENCE: 122

Glu Ser Tyr Tyr Asp Ser Ser Gly Tyr Thr Thr
1 5 10

<210> SEQ ID NO 123
<211> LENGTH: 14
<212> TYPE: PRT
<213> ORGANISM: Artificial Sequence
<220> FEATURE:
<223> OTHER INFORMATION: LCDR 1

<400> SEQUENCE: 123

Thr Gly Ser Ser Ser Asn Ile Gly Ala Gly Tyr Asp Val His
1 5 10

<210> SEQ ID NO 124
<211> LENGTH: 7
<212> TYPE: PRT
<213> ORGANISM: Artificial Sequence
<220> FEATURE:
<223> OTHER INFORMATION: LCDR 2

<400> SEQUENCE: 124

Gly Asn Ser Asn Arg Pro Ser
1 5

<210> SEQ ID NO 125
<211> LENGTH: 11
<212> TYPE: PRT
<213> ORGANISM: Artificial Sequence
<220> FEATURE:
<223> OTHER INFORMATION: LCDR 3

<400> SEQUENCE: 125

Gln Ser Tyr Asp Ser Ser Leu Ser Gly Tyr Val
1 5 10

<210> SEQ ID NO 126
<211> LENGTH: 5
<212> TYPE: PRT
<213> ORGANISM: Artificial Sequence
<220> FEATURE:
<223> OTHER INFORMATION: HCDR 1

<400> SEQUENCE: 126

Asp Tyr Ala Met His
1 5

<210> SEQ ID NO 127
<211> LENGTH: 17
<212> TYPE: PRT

<213> ORGANISM: Artificial Sequence
<220> FEATURE:
<223> OTHER INFORMATION: HCDR 2

<400> SEQUENCE: 127

Gly Ile Ser Trp Asn Ser Gly Ser Ile Gly Tyr Ala Asp Ser Val Lys
1 5 10 15

Gly

<210> SEQ ID NO 128
<211> LENGTH: 18
<212> TYPE: PRT
<213> ORGANISM: Artificial Sequence
<220> FEATURE:
<223> OTHER INFORMATION: HCDR 3

<400> SEQUENCE: 128

Ala Gln Tyr Tyr Tyr Asp Ser Ser Gly Ser Tyr Val Gly Glu Ser Phe
1 5 10 15

Asp Tyr

<210> SEQ ID NO 129
<211> LENGTH: 11
<212> TYPE: PRT
<213> ORGANISM: Artificial Sequence
<220> FEATURE:
<223> OTHER INFORMATION: LCDR 1

<400> SEQUENCE: 129

Arg Ala Ser Gln Ser Ile Ser Ser Tyr Leu Asn
1 5 10

<210> SEQ ID NO 130
<211> LENGTH: 7
<212> TYPE: PRT
<213> ORGANISM: Artificial Sequence
<220> FEATURE:
<223> OTHER INFORMATION: LCDR 2

<400> SEQUENCE: 130

Ala Ala Ser Ser Leu Gln Ser
1 5

<210> SEQ ID NO 131
<211> LENGTH: 8
<212> TYPE: PRT
<213> ORGANISM: Artificial Sequence
<220> FEATURE:
<223> OTHER INFORMATION: LCDR 3

<400> SEQUENCE: 131

Gln Gln Ser Tyr Ser Thr Pro Thr
1 5

<210> SEQ ID NO 132
<211> LENGTH: 5
<212> TYPE: PRT
<213> ORGANISM: Artificial Sequence
<220> FEATURE:
<223> OTHER INFORMATION: HCDR 1

<400> SEQUENCE: 132

Ser Tyr Ala Met His
1 5

<210> SEQ ID NO 133
<211> LENGTH: 17
<212> TYPE: PRT
<213> ORGANISM: Artificial Sequence
<220> FEATURE:
<223> OTHER INFORMATION: HCDR 2

<400> SEQUENCE: 133

Val Ile Ser Tyr Asp Gly Ser Asn Lys Tyr Tyr Ala Asp Ser Val Lys
1 5 10 15

Gly

<210> SEQ ID NO 134
<211> LENGTH: 11
<212> TYPE: PRT
<213> ORGANISM: Artificial Sequence
<220> FEATURE:
<223> OTHER INFORMATION: HCDR 3

<400> SEQUENCE: 134

Glu Leu Tyr Tyr Gly Pro Gly Gly Met Asp Val
1 5 10

<210> SEQ ID NO 135
<211> LENGTH: 14
<212> TYPE: PRT
<213> ORGANISM: Artificial Sequence
<220> FEATURE:
<223> OTHER INFORMATION: LCDR 1

<400> SEQUENCE: 135

Thr Gly Ser Ser Ser Asn Ile Gly Ala Gly Tyr Asp Val His
1 5 10

<210> SEQ ID NO 136
<211> LENGTH: 7
<212> TYPE: PRT
<213> ORGANISM: Artificial Sequence
<220> FEATURE:
<223> OTHER INFORMATION: LCDR 2

<400> SEQUENCE: 136

Gly Asn Ser Asn Arg Pro Ser
1 5

<210> SEQ ID NO 137
<211> LENGTH: 11
<212> TYPE: PRT
<213> ORGANISM: Artificial Sequence
<220> FEATURE:
<223> OTHER INFORMATION: LCDR 3

<400> SEQUENCE: 137

Gln Ser Tyr Asp Ser Ser Leu Ser Gly Ser Val
1 5 10

<210> SEQ ID NO 138
<211> LENGTH: 5
<212> TYPE: PRT
<213> ORGANISM: Artificial Sequence
<220> FEATURE:
<223> OTHER INFORMATION: HCDR 1

<400> SEQUENCE: 138

Asn Tyr Ala Met Ser
1 5

<210> SEQ ID NO 139
<211> LENGTH: 17
<212> TYPE: PRT
<213> ORGANISM: Artificial Sequence
<220> FEATURE:
<223> OTHER INFORMATION: HCDR 2

<400> SEQUENCE: 139

Ala Ile Ser Gly Ser Gly Gly Ser Thr Tyr Tyr Ala Asp Ser Val Lys
1 5 10 15

Gly

<210> SEQ ID NO 140
<211> LENGTH: 13
<212> TYPE: PRT
<213> ORGANISM: Artificial Sequence
<220> FEATURE:
<223> OTHER INFORMATION: HCDR 3

<400> SEQUENCE: 140

Val Glu Val Ser Ser Trp Tyr Glu Asn Trp Phe Asp Pro
1 5 10

<210> SEQ ID NO 141
<211> LENGTH: 11
<212> TYPE: PRT
<213> ORGANISM: Artificial Sequence
<220> FEATURE:
<223> OTHER INFORMATION: LCDR 1

<400> SEQUENCE: 141

Arg Ala Ser Gln Ser Ile Ser Ser Tyr Leu Asn
1 5 10

<210> SEQ ID NO 142
<211> LENGTH: 7
<212> TYPE: PRT
<213> ORGANISM: Artificial Sequence
<220> FEATURE:
<223> OTHER INFORMATION: LCDR 2

<400> SEQUENCE: 142

Ala Ala Ser Ser Leu Gln Ser
1 5

<210> SEQ ID NO 143
<211> LENGTH: 9
<212> TYPE: PRT
<213> ORGANISM: Artificial Sequence
<220> FEATURE:
<223> OTHER INFORMATION: LCDR 3

<400> SEQUENCE: 143

Gln Gln Ser Tyr Ser Thr Pro Leu Thr
1 5

<210> SEQ ID NO 144
<211> LENGTH: 5
<212> TYPE: PRT
<213> ORGANISM: Artificial Sequence
<220> FEATURE:
<223> OTHER INFORMATION: HCDR 1

<400> SEQUENCE: 144

Ser Tyr Ala Met His
1 5

<210> SEQ ID NO 145
<211> LENGTH: 17
<212> TYPE: PRT
<213> ORGANISM: Artificial Sequence
<220> FEATURE:
<223> OTHER INFORMATION: HCDR 2

<400> SEQUENCE: 145

Val Ile Ser Tyr Asp Gly Ser Asn Lys Tyr Tyr Ala Asp Ser Val Lys
1 5 10 15

Gly

<210> SEQ ID NO 146
<211> LENGTH: 8
<212> TYPE: PRT
<213> ORGANISM: Artificial Sequence
<220> FEATURE:
<223> OTHER INFORMATION: HCDR 3

<400> SEQUENCE: 146

Asp Ser Gly Val Val Met Asp Tyr
1 5

<210> SEQ ID NO 147
<211> LENGTH: 14
<212> TYPE: PRT
<213> ORGANISM: Artificial Sequence
<220> FEATURE:
<223> OTHER INFORMATION: LCDR 1

<400> SEQUENCE: 147

Thr Gly Thr Ser Ser Asp Val Gly Gly Tyr Asn Tyr Val Ser
1 5 10

<210> SEQ ID NO 148
<211> LENGTH: 7
<212> TYPE: PRT
<213> ORGANISM: Artificial Sequence
<220> FEATURE:
<223> OTHER INFORMATION: LCDR 2

<400> SEQUENCE: 148

Asp Val Ser Asn Arg Pro Ser
1 5

<210> SEQ ID NO 149
<211> LENGTH: 10
<212> TYPE: PRT
<213> ORGANISM: Artificial Sequence
<220> FEATURE:
<223> OTHER INFORMATION: LCDR 3

<400> SEQUENCE: 149

Ser Ser Tyr Thr Ser Ser Ser Thr Leu Val
1 5 10

<210> SEQ ID NO 150
<211> LENGTH: 5
<212> TYPE: PRT
<213> ORGANISM: Artificial Sequence
<220> FEATURE:
<223> OTHER INFORMATION: HCDR 1

<400> SEQUENCE: 150

Ser Tyr Ala Met Ser 1 5

<210> SEQ ID NO 151
<211> LENGTH: 17
<212> TYPE: PRT
<213> ORGANISM: Artificial Sequence
<220> FEATURE:
<223> OTHER INFORMATION: HCDR 2

<400> SEQUENCE: 151

Ala Ile Ser Gly Ser Gly Gly Ser Ala Tyr Tyr Ala Asp Ser Val Lys
1 5 10 15

Gly

<210> SEQ ID NO 152
<211> LENGTH: 13
<212> TYPE: PRT
<213> ORGANISM: Artificial Sequence
<220> FEATURE:
<223> OTHER INFORMATION: HCDR 3

<400> SEQUENCE: 152

Val Gly Met Val Gln Gly Ala Arg Asn Trp Phe Asp Pro
1 5 10

<210> SEQ ID NO 153
<211> LENGTH: 11
<212> TYPE: PRT
<213> ORGANISM: Artificial Sequence
<220> FEATURE:
<223> OTHER INFORMATION: LCDR 1

<400> SEQUENCE: 153

Arg Ala Ser Gln Ser Ile Ser Ser Tyr Leu Asn
1 5 10

<210> SEQ ID NO 154
<211> LENGTH: 7
<212> TYPE: PRT
<213> ORGANISM: Artificial Sequence
<220> FEATURE:
<223> OTHER INFORMATION: LCDR 2

<400> SEQUENCE: 154

Ala Ala Ser Ser Leu Gln Ser
1 5

<210> SEQ ID NO 155
<211> LENGTH: 9
<212> TYPE: PRT
<213> ORGANISM: Artificial Sequence
<220> FEATURE:
<223> OTHER INFORMATION: LCDR 3

<400> SEQUENCE: 155

Gln Gln Ser Tyr Ser Thr Pro Leu Thr
1 5

<210> SEQ ID NO 156
<211> LENGTH: 5
<212> TYPE: PRT
<213> ORGANISM: Artificial Sequence
<220> FEATURE:
<223> OTHER INFORMATION: HCDR 1

<400> SEQUENCE: 156

Ser Tyr Ala Met Ser
1 5

<210> SEQ ID NO 157
<211> LENGTH: 17
<212> TYPE: PRT
<213> ORGANISM: Artificial Sequence
<220> FEATURE:
<223> OTHER INFORMATION: HCDR 2

<400> SEQUENCE: 157

Ala Ile Ser Gly Ser Gly Gly Ser Thr Tyr Tyr Ala Asp Ser Val Lys
1 5 10 15

Gly

<210> SEQ ID NO 158
<211> LENGTH: 10
<212> TYPE: PRT
<213> ORGANISM: Artificial Sequence
<220> FEATURE:
<223> OTHER INFORMATION: HCDR 3

<400> SEQUENCE: 158

Val Arg Val Ser Asp Gly Arg Phe Asp Tyr
1 5 10

<210> SEQ ID NO 159
<211> LENGTH: 17
<212> TYPE: PRT
<213> ORGANISM: Artificial Sequence
<220> FEATURE:
<223> OTHER INFORMATION: LCDR 1

<400> SEQUENCE: 159

Lys Ser Ser Gln Ser Val Leu Tyr Ser Ser Asn Asn Lys Asn Tyr Leu
1 5 10 15

Ala

<210> SEQ ID NO 160
<211> LENGTH: 7
<212> TYPE: PRT
<213> ORGANISM: Artificial Sequence
<220> FEATURE:
<223> OTHER INFORMATION: LCDR 2

<400> SEQUENCE: 160

Trp Ala Ser Thr Arg Glu Ser
1 5

<210> SEQ ID NO 161
<211> LENGTH: 8
<212> TYPE: PRT
<213> ORGANISM: Artificial Sequence
<220> FEATURE:
<223> OTHER INFORMATION: LCDR 3

<400> SEQUENCE: 161

Gln Gln Tyr Tyr Ser Thr Pro Thr
1 5

<210> SEQ ID NO 162
<211> LENGTH: 5
<212> TYPE: PRT
<213> ORGANISM: Artificial Sequence
<220> FEATURE:
<223> OTHER INFORMATION: HCDR 1

<400> SEQUENCE: 162

Ser Tyr Ala Met His
1               5

<210> SEQ ID NO 163
<211> LENGTH: 17
<212> TYPE: PRT
<213> ORGANISM: Artificial Sequence
<220> FEATURE:
<223> OTHER INFORMATION: HCDR 2

<400> SEQUENCE: 163

Val Ile Ser Tyr Asp Gly Ser Asn Lys Tyr Tyr Ala Asp Ser Val Lys
1               5                   10                  15

Gly

<210> SEQ ID NO 164
<211> LENGTH: 6
<212> TYPE: PRT
<213> ORGANISM: Artificial Sequence
<220> FEATURE:
<223> OTHER INFORMATION: HCDR 3

<400> SEQUENCE: 164

Asp Thr Ile Leu Ile Asp
1               5

<210> SEQ ID NO 165
<211> LENGTH: 16
<212> TYPE: PRT
<213> ORGANISM: Artificial Sequence
<220> FEATURE:
<223> OTHER INFORMATION: LCDR 1

<400> SEQUENCE: 165

Arg Ser Ser Gln Ser Leu Leu Tyr Ser Asn Gly Tyr Asn Tyr Leu Asp
1               5                   10                  15

<210> SEQ ID NO 166
<211> LENGTH: 7
<212> TYPE: PRT
<213> ORGANISM: Artificial Sequence
<220> FEATURE:
<223> OTHER INFORMATION: LCDR 2

<400> SEQUENCE: 166

Leu Gly Ser Asn Arg Ala Ser
1               5

<210> SEQ ID NO 167
<211> LENGTH: 9
<212> TYPE: PRT
<213> ORGANISM: Artificial Sequence
<220> FEATURE:
<223> OTHER INFORMATION: LCDR 3

<400> SEQUENCE: 167

Met Gln Ala Leu Gln Thr Pro Ile Thr
1               5

<210> SEQ ID NO 168
<211> LENGTH: 5
<212> TYPE: PRT
<213> ORGANISM: Artificial Sequence
<220> FEATURE:

<223> OTHER INFORMATION: HCDR 1

<400> SEQUENCE: 168

Ser Tyr Ala Met His
1 5

<210> SEQ ID NO 169
<211> LENGTH: 17
<212> TYPE: PRT
<213> ORGANISM: Artificial Sequence
<220> FEATURE:
<223> OTHER INFORMATION: HCDR 2

<400> SEQUENCE: 169

Val Ile Ser Tyr Asp Gly Ser Asn Lys Tyr Tyr Ala Asp Ser Val Lys
1 5 10 15

Gly

<210> SEQ ID NO 170
<211> LENGTH: 15
<212> TYPE: PRT
<213> ORGANISM: Artificial Sequence
<220> FEATURE:
<223> OTHER INFORMATION: HCDR 3

<400> SEQUENCE: 170

Asp Val His His Pro Asp Tyr Gly Gly Asn Ser Ala Phe Asp Tyr
1 5 10 15

<210> SEQ ID NO 171
<211> LENGTH: 11
<212> TYPE: PRT
<213> ORGANISM: Artificial Sequence
<220> FEATURE:
<223> OTHER INFORMATION: LCDR 1

<400> SEQUENCE: 171

Gln Ala Ser Gln Asp Ile Ser Asn Tyr Leu Asn
1 5 10

<210> SEQ ID NO 172
<211> LENGTH: 7
<212> TYPE: PRT
<213> ORGANISM: Artificial Sequence
<220> FEATURE:
<223> OTHER INFORMATION: LCDR 2

<400> SEQUENCE: 172

Asp Ala Ser Asn Leu Glu Thr
1 5

<210> SEQ ID NO 173
<211> LENGTH: 9
<212> TYPE: PRT
<213> ORGANISM: Artificial Sequence
<220> FEATURE:
<223> OTHER INFORMATION: LCDR 3

<400> SEQUENCE: 173

Gln Gln Tyr Asp Asn Leu Pro Leu Thr
1 5

<210> SEQ ID NO 174
<211> LENGTH: 5
<212> TYPE: PRT
<213> ORGANISM: Artificial Sequence

<220> FEATURE:
<223> OTHER INFORMATION: HCDR 1

<400> SEQUENCE: 174

Ser Tyr Ala Met His
1 5

<210> SEQ ID NO 175
<211> LENGTH: 17
<212> TYPE: PRT
<213> ORGANISM: Artificial Sequence
<220> FEATURE:
<223> OTHER INFORMATION: HCDR 2

<400> SEQUENCE: 175

Val Ile Ser Tyr Asp Gly Ser Asn Lys Tyr Tyr Ala Asp Ser Val Lys
1 5 10 15

Gly

<210> SEQ ID NO 176
<211> LENGTH: 13
<212> TYPE: PRT
<213> ORGANISM: Artificial Sequence
<220> FEATURE:
<223> OTHER INFORMATION: HCDR 3

<400> SEQUENCE: 176

Asp Arg Tyr Gly Asp Tyr Asp Gly Ser Ala Phe Asp Ile
1 5 10

<210> SEQ ID NO 177
<211> LENGTH: 11
<212> TYPE: PRT
<213> ORGANISM: Artificial Sequence
<220> FEATURE:
<223> OTHER INFORMATION: LCDR 1

<400> SEQUENCE: 177

Gln Ala Ser Gln Asp Ile Ser Asn Tyr Leu Asn
1 5 10

<210> SEQ ID NO 178
<211> LENGTH: 7
<212> TYPE: PRT
<213> ORGANISM: Artificial Sequence
<220> FEATURE:
<223> OTHER INFORMATION: LCDR 2

<400> SEQUENCE: 178

Asp Ala Ser Asn Leu Glu Thr
1 5

<210> SEQ ID NO 179
<211> LENGTH: 9
<212> TYPE: PRT
<213> ORGANISM: Artificial Sequence
<220> FEATURE:
<223> OTHER INFORMATION: LCDR 3

<400> SEQUENCE: 179

Gln Gln Tyr Asp Asn Leu Pro Leu Thr
1 5

<210> SEQ ID NO 180
<211> LENGTH: 5
<212> TYPE: PRT

<213> ORGANISM: Artificial Sequence
<220> FEATURE:
<223> OTHER INFORMATION: HCDR 1

<400> SEQUENCE: 180

Asp Tyr Ala Met His
1 5

<210> SEQ ID NO 181
<211> LENGTH: 17
<212> TYPE: PRT
<213> ORGANISM: Artificial Sequence
<220> FEATURE:
<223> OTHER INFORMATION: HCDR 2

<400> SEQUENCE: 181

Gly Ile Ser Trp Asn Ser Gly Ser Ile Gly Tyr Ala Asp Ser Val Lys
1 5 10 15

Gly

<210> SEQ ID NO 182
<211> LENGTH: 9
<212> TYPE: PRT
<213> ORGANISM: Artificial Sequence
<220> FEATURE:
<223> OTHER INFORMATION: HCDR 3

<400> SEQUENCE: 182

Glu Gly Gly Asp Ser Asp Phe Asp Tyr
1 5

<210> SEQ ID NO 183
<211> LENGTH: 11
<212> TYPE: PRT
<213> ORGANISM: Artificial Sequence
<220> FEATURE:
<223> OTHER INFORMATION: LCDR 1

<400> SEQUENCE: 183

Arg Ala Ser Gln Ser Ile Ser Ser Tyr Leu Asn
1 5 10

<210> SEQ ID NO 184
<211> LENGTH: 7
<212> TYPE: PRT
<213> ORGANISM: Artificial Sequence
<220> FEATURE:
<223> OTHER INFORMATION: LCDR 2

<400> SEQUENCE: 184

Ala Ala Ser Ser Leu Gln Ser
1 5

<210> SEQ ID NO 185
<211> LENGTH: 9
<212> TYPE: PRT
<213> ORGANISM: Artificial Sequence
<220> FEATURE:
<223> OTHER INFORMATION: LCDR 3

<400> SEQUENCE: 185

Gln Gln Ser Tyr Ser Thr Pro Val Thr
1 5

<210> SEQ ID NO 186
<211> LENGTH: 5

<212> TYPE: PRT
<213> ORGANISM: Artificial Sequence
<220> FEATURE:
<223> OTHER INFORMATION: HCDR 1

<400> SEQUENCE: 186

Asp Tyr Tyr Met His
1 5

<210> SEQ ID NO 187
<211> LENGTH: 17
<212> TYPE: PRT
<213> ORGANISM: Artificial Sequence
<220> FEATURE:
<223> OTHER INFORMATION: HCDR 2

<400> SEQUENCE: 187

Leu Val Asp Pro Glu Asp Gly Glu Thr Leu Tyr Ala Glu Lys Phe Gln
1 5 10 15

Gly

<210> SEQ ID NO 188
<211> LENGTH: 13
<212> TYPE: PRT
<213> ORGANISM: Artificial Sequence
<220> FEATURE:
<223> OTHER INFORMATION: HCDR 3

<400> SEQUENCE: 188

Glu Pro Gln Met Val Gln Gly Pro Ser Pro Pro Asp Tyr
1 5 10

<210> SEQ ID NO 189
<211> LENGTH: 14
<212> TYPE: PRT
<213> ORGANISM: Artificial Sequence
<220> FEATURE:
<223> OTHER INFORMATION: LCDR 1

<400> SEQUENCE: 189

Thr Gly Thr Ser Ser Asp Val Gly Gly Tyr Ser Tyr Val Ser
1 5 10

<210> SEQ ID NO 190
<211> LENGTH: 7
<212> TYPE: PRT
<213> ORGANISM: Artificial Sequence
<220> FEATURE:
<223> OTHER INFORMATION: LCDR 2

<400> SEQUENCE: 190

Asp Val Ser Asn Arg Pro Ser
1 5

<210> SEQ ID NO 191
<211> LENGTH: 10
<212> TYPE: PRT
<213> ORGANISM: Artificial Sequence
<220> FEATURE:
<223> OTHER INFORMATION: LCDR 3

<400> SEQUENCE: 191

Ser Ser Tyr Thr Ser Ser Ser Thr Leu Leu
1 5 10

<210> SEQ ID NO 192

<211> LENGTH: 5
<212> TYPE: PRT
<213> ORGANISM: Artificial Sequence
<220> FEATURE:
<223> OTHER INFORMATION: HCDR 1

<400> SEQUENCE: 192

Ser Tyr Ala Met His
1               5

<210> SEQ ID NO 193
<211> LENGTH: 17
<212> TYPE: PRT
<213> ORGANISM: Artificial Sequence
<220> FEATURE:
<223> OTHER INFORMATION: HCDR 2

<400> SEQUENCE: 193

Val Ile Ser Tyr Asp Gly Ser Asn Lys Tyr Tyr Ala Asp Ser Val Lys
1               5                   10                  15

Gly

<210> SEQ ID NO 194
<211> LENGTH: 8
<212> TYPE: PRT
<213> ORGANISM: Artificial Sequence
<220> FEATURE:
<223> OTHER INFORMATION: HCDR 3

<400> SEQUENCE: 194

Asp Pro Leu Tyr Gly Met Asp Val
1               5

<210> SEQ ID NO 195
<211> LENGTH: 14
<212> TYPE: PRT
<213> ORGANISM: Artificial Sequence
<220> FEATURE:
<223> OTHER INFORMATION: LCDR 1

<400> SEQUENCE: 195

Thr Gly Thr Ser Ser Asp Val Gly Asn Tyr Asn Tyr Val Ser
1               5                   10

<210> SEQ ID NO 196
<211> LENGTH: 7
<212> TYPE: PRT
<213> ORGANISM: Artificial Sequence
<220> FEATURE:
<223> OTHER INFORMATION: LCDR 2

<400> SEQUENCE: 196

Glu Val Ser Lys Arg Pro Ser
1               5

<210> SEQ ID NO 197
<211> LENGTH: 11
<212> TYPE: PRT
<213> ORGANISM: Artificial Sequence
<220> FEATURE:
<223> OTHER INFORMATION: LCDR 3

<400> SEQUENCE: 197

Ala Ser Tyr Ala Asp Ser Asn Asn Leu Tyr Val
1               5                   10

<210> SEQ ID NO 198
<211> LENGTH: 5
<212> TYPE: PRT
<213> ORGANISM: Artificial Sequence
<220> FEATURE:
<223> OTHER INFORMATION: HCDR 1

<400> SEQUENCE: 198

Ser Tyr Tyr Met His
1               5

<210> SEQ ID NO 199
<211> LENGTH: 17
<212> TYPE: PRT
<213> ORGANISM: Artificial Sequence
<220> FEATURE:
<223> OTHER INFORMATION: HCDR 2

<400> SEQUENCE: 199

Ile Ile Asn Pro Ser Gly Gly Ser Thr Ser Tyr Ala Gln Lys Phe Gln
1               5                   10                  15

Gly

<210> SEQ ID NO 200
<211> LENGTH: 17
<212> TYPE: PRT
<213> ORGANISM: Artificial Sequence
<220> FEATURE:
<223> OTHER INFORMATION: HCDR 3

<400> SEQUENCE: 200

Asp Ser Tyr Tyr Asp Ser Ser Gly Tyr Tyr Tyr Ala Asp Ala Phe Asp
1               5                   10                  15

Ile

<210> SEQ ID NO 201
<211> LENGTH: 14
<212> TYPE: PRT
<213> ORGANISM: Artificial Sequence
<220> FEATURE:
<223> OTHER INFORMATION: LCDR 1

<400> SEQUENCE: 201

Thr Gly Ser Ser Ser Asn Ile Gly Ala Gly Tyr Asp Val His
1               5                   10

<210> SEQ ID NO 202
<211> LENGTH: 7
<212> TYPE: PRT
<213> ORGANISM: Artificial Sequence
<220> FEATURE:
<223> OTHER INFORMATION: LCDR 2

<400> SEQUENCE: 202

Gly Asn Ser Asn Arg Pro Ser
1               5

<210> SEQ ID NO 203
<211> LENGTH: 12
<212> TYPE: PRT
<213> ORGANISM: Artificial Sequence
<220> FEATURE:
<223> OTHER INFORMATION: LCDR 3

<400> SEQUENCE: 203

Gln Ser Tyr Asp Ser Ser Leu Ser Gly Asp Val Val

```
1               5                   10


<210> SEQ ID NO 204
<211> LENGTH: 5
<212> TYPE: PRT
<213> ORGANISM: Artificial Sequence
<220> FEATURE:
<223> OTHER INFORMATION: HCDR 1

<400> SEQUENCE: 204

Ser Tyr Tyr Met His
1               5


<210> SEQ ID NO 205
<211> LENGTH: 17
<212> TYPE: PRT
<213> ORGANISM: Artificial Sequence
<220> FEATURE:
<223> OTHER INFORMATION: HCDR 2

<400> SEQUENCE: 205

Ile Ile Asn Pro Ser Gly Gly Ser Thr Ser Tyr Ala Gln Lys Phe Gln
1               5                   10                  15

Gly


<210> SEQ ID NO 206
<211> LENGTH: 12
<212> TYPE: PRT
<213> ORGANISM: Artificial Sequence
<220> FEATURE:
<223> OTHER INFORMATION: HCDR 3

<400> SEQUENCE: 206

Asn Val Pro Gly Asp Tyr Glu Val Gly Phe Asp Tyr
1               5                   10


<210> SEQ ID NO 207
<211> LENGTH: 14
<212> TYPE: PRT
<213> ORGANISM: Artificial Sequence
<220> FEATURE:
<223> OTHER INFORMATION: LCDR 1

<400> SEQUENCE: 207

Thr Gly Ser Ser Ser Asn Ile Gly Ala Gly Tyr Asp Val His
1               5                   10


<210> SEQ ID NO 208
<211> LENGTH: 7
<212> TYPE: PRT
<213> ORGANISM: Artificial Sequence
<220> FEATURE:
<223> OTHER INFORMATION: LCDR 2

<400> SEQUENCE: 208

Gly Asn Ser Asn Arg Pro Ser
1               5


<210> SEQ ID NO 209
<211> LENGTH: 11
<212> TYPE: PRT
<213> ORGANISM: Artificial Sequence
<220> FEATURE:
<223> OTHER INFORMATION: LCDR 3

<400> SEQUENCE: 209
```

Gln Ser Tyr Asp Ser Ser Leu Ser Ala Val Val
1 5 10

<210> SEQ ID NO 210
<211> LENGTH: 5
<212> TYPE: PRT
<213> ORGANISM: Artificial Sequence
<220> FEATURE:
<223> OTHER INFORMATION: HCDR 1

<400> SEQUENCE: 210

Asp Tyr Ala Met His
1 5

<210> SEQ ID NO 211
<211> LENGTH: 17
<212> TYPE: PRT
<213> ORGANISM: Artificial Sequence
<220> FEATURE:
<223> OTHER INFORMATION: HCDR 2

<400> SEQUENCE: 211

Gly Ile Ser Trp Asn Ser Gly Ser Ile Gly Tyr Ala Asp Ser Val Lys
1 5 10 15

Gly

<210> SEQ ID NO 212
<211> LENGTH: 13
<212> TYPE: PRT
<213> ORGANISM: Artificial Sequence
<220> FEATURE:
<223> OTHER INFORMATION: HCDR 3

<400> SEQUENCE: 212

Asp Thr Thr Trp Gly Gly Ser Tyr Pro Tyr Phe Asp Tyr
1 5 10

<210> SEQ ID NO 213
<211> LENGTH: 11
<212> TYPE: PRT
<213> ORGANISM: Artificial Sequence
<220> FEATURE:
<223> OTHER INFORMATION: LCDR 1

<400> SEQUENCE: 213

Arg Ala Ser Gln Ser Ile Ser Ser Trp Leu Ala
1 5 10

<210> SEQ ID NO 214
<211> LENGTH: 7
<212> TYPE: PRT
<213> ORGANISM: Artificial Sequence
<220> FEATURE:
<223> OTHER INFORMATION: LCDR 2

<400> SEQUENCE: 214

Lys Ala Ser Ser Leu Glu Ser
1 5

<210> SEQ ID NO 215
<211> LENGTH: 10
<212> TYPE: PRT
<213> ORGANISM: Artificial Sequence
<220> FEATURE:
<223> OTHER INFORMATION: LCDR 3

<400> SEQUENCE: 215

Gln Gln Tyr Asn Ser Tyr Ser Pro Leu Ala
1 5 10

<210> SEQ ID NO 216
<211> LENGTH: 5
<212> TYPE: PRT
<213> ORGANISM: Artificial Sequence
<220> FEATURE:
<223> OTHER INFORMATION: HCDR 1

<400> SEQUENCE: 216

Asp Tyr Tyr Met Ser
1 5

<210> SEQ ID NO 217
<211> LENGTH: 17
<212> TYPE: PRT
<213> ORGANISM: Artificial Sequence
<220> FEATURE:
<223> OTHER INFORMATION: HCDR 2

<400> SEQUENCE: 217

Tyr Ile Ser Ser Ser Ser Ser Tyr Thr Asn Tyr Ala Asp Ser Val Lys
1 5 10 15

Gly

<210> SEQ ID NO 218
<211> LENGTH: 10
<212> TYPE: PRT
<213> ORGANISM: Artificial Sequence
<220> FEATURE:
<223> OTHER INFORMATION: HCDR 3

<400> SEQUENCE: 218

Leu Ser Thr Val Thr Arg Ala Phe Asp Ile
1 5 10

<210> SEQ ID NO 219
<211> LENGTH: 11
<212> TYPE: PRT
<213> ORGANISM: Artificial Sequence
<220> FEATURE:
<223> OTHER INFORMATION: LCDR 1

<400> SEQUENCE: 219

Arg Ala Ser Gln Gly Ile Ser Ser Trp Leu Ala
1 5 10

<210> SEQ ID NO 220
<211> LENGTH: 7
<212> TYPE: PRT
<213> ORGANISM: Artificial Sequence
<220> FEATURE:
<223> OTHER INFORMATION: LCDR 2

<400> SEQUENCE: 220

Ala Ala Ser Ser Leu Gln Ser
1 5

<210> SEQ ID NO 221
<211> LENGTH: 9
<212> TYPE: PRT
<213> ORGANISM: Artificial Sequence
<220> FEATURE:
<223> OTHER INFORMATION: LCDR 3

<400> SEQUENCE: 221

Gln Gln Ala Asn Ser Phe Pro Pro Thr
1 5

<210> SEQ ID NO 222
<211> LENGTH: 5
<212> TYPE: PRT
<213> ORGANISM: Artificial Sequence
<220> FEATURE:
<223> OTHER INFORMATION: HCDR 1

<400> SEQUENCE: 222

Asn Ala Trp Met Ser
1 5

<210> SEQ ID NO 223
<211> LENGTH: 17
<212> TYPE: PRT
<213> ORGANISM: Artificial Sequence
<220> FEATURE:
<223> OTHER INFORMATION: HCDR 2

<400> SEQUENCE: 223

Ala Ile Ser Gly Ser Gly Gly Ser Thr Tyr Tyr Ala Asp Ser Val Lys
1 5 10 15

Gly

<210> SEQ ID NO 224
<211> LENGTH: 9
<212> TYPE: PRT
<213> ORGANISM: Artificial Sequence
<220> FEATURE:
<223> OTHER INFORMATION: HCDR 3

<400> SEQUENCE: 224

Asn Glu Gly Gly Asp Ala Phe Asp Ile
1 5

<210> SEQ ID NO 225
<211> LENGTH: 16
<212> TYPE: PRT
<213> ORGANISM: Artificial Sequence
<220> FEATURE:
<223> OTHER INFORMATION: LCDR 1

<400> SEQUENCE: 225

Arg Ser Ser Gln Ser Leu Val Tyr Ser Asp Gly Asn Thr Tyr Leu Asn
1 5 10 15

<210> SEQ ID NO 226
<211> LENGTH: 7
<212> TYPE: PRT
<213> ORGANISM: Artificial Sequence
<220> FEATURE:
<223> OTHER INFORMATION: LCDR 2

<400> SEQUENCE: 226

Lys Val Ser Asn Arg Asp Ser
1 5

<210> SEQ ID NO 227
<211> LENGTH: 9
<212> TYPE: PRT
<213> ORGANISM: Artificial Sequence
<220> FEATURE:
<223> OTHER INFORMATION: LCDR 3

<400> SEQUENCE: 227

Met Gln Gly Thr His Trp Pro Leu Thr
1 5

<210> SEQ ID NO 228
<211> LENGTH: 5
<212> TYPE: PRT
<213> ORGANISM: Artificial Sequence
<220> FEATURE:
<223> OTHER INFORMATION: HCDR 1

<400> SEQUENCE: 228

Asn Tyr Ala Met His
1 5

<210> SEQ ID NO 229
<211> LENGTH: 17
<212> TYPE: PRT
<213> ORGANISM: Artificial Sequence
<220> FEATURE:
<223> OTHER INFORMATION: HCDR 2

<400> SEQUENCE: 229

Val Ile Ser Tyr Asp Gly Ser Lys Lys Tyr Tyr Ala Asp Ser Val Lys
1 5 10 15

Gly

<210> SEQ ID NO 230
<211> LENGTH: 10
<212> TYPE: PRT
<213> ORGANISM: Artificial Sequence
<220> FEATURE:
<223> OTHER INFORMATION: HCDR 3

<400> SEQUENCE: 230

Glu Asp Pro Arg Arg Gly Gly Ile Asp Tyr
1 5 10

<210> SEQ ID NO 231
<211> LENGTH: 14
<212> TYPE: PRT
<213> ORGANISM: Artificial Sequence
<220> FEATURE:
<223> OTHER INFORMATION: LCDR 1

<400> SEQUENCE: 231

Thr Gly Ser Ser Ser Asn Ile Gly Ala Gly Tyr Asp Val His
1 5 10

<210> SEQ ID NO 232
<211> LENGTH: 7
<212> TYPE: PRT
<213> ORGANISM: Artificial Sequence
<220> FEATURE:
<223> OTHER INFORMATION: LCDR 2

<400> SEQUENCE: 232

Gly Asn Ser Asn Arg Pro Ser
1 5

<210> SEQ ID NO 233
<211> LENGTH: 11
<212> TYPE: PRT
<213> ORGANISM: Artificial Sequence
<220> FEATURE:

<223> OTHER INFORMATION: LCDR 3

<400> SEQUENCE: 233

Gln Ser Tyr Asp Ser Ser Leu Ser Gly Tyr Val
1 5 10

<210> SEQ ID NO 234
<211> LENGTH: 5
<212> TYPE: PRT
<213> ORGANISM: Artificial Sequence
<220> FEATURE:
<223> OTHER INFORMATION: HCDR 1

<400> SEQUENCE: 234

Ser Tyr Ala Ile Ser
1 5

<210> SEQ ID NO 235
<211> LENGTH: 17
<212> TYPE: PRT
<213> ORGANISM: Artificial Sequence
<220> FEATURE:
<223> OTHER INFORMATION: HCDR 2

<400> SEQUENCE: 235

Gly Ile Ile Pro Ile Phe Gly Thr Ala Asn Tyr Ala Gln Lys Ser Gln
1 5 10 15

Gly

<210> SEQ ID NO 236
<211> LENGTH: 14
<212> TYPE: PRT
<213> ORGANISM: Artificial Sequence
<220> FEATURE:
<223> OTHER INFORMATION: HCDR 3

<400> SEQUENCE: 236

Glu Ser Gly Ser Gly Asn Arg Ile Pro Tyr Gly Met Asp Val
1 5 10

<210> SEQ ID NO 237
<211> LENGTH: 14
<212> TYPE: PRT
<213> ORGANISM: Artificial Sequence
<220> FEATURE:
<223> OTHER INFORMATION: LCDR 1

<400> SEQUENCE: 237

Thr Gly Ser Ser Ser Asn Ile Gly Ala Gly Tyr Asp Val His
1 5 10

<210> SEQ ID NO 238
<211> LENGTH: 7
<212> TYPE: PRT
<213> ORGANISM: Artificial Sequence
<220> FEATURE:
<223> OTHER INFORMATION: LCDR 2

<400> SEQUENCE: 238

Gly Asn Ser Asn Arg Pro Ser
1 5

<210> SEQ ID NO 239
<211> LENGTH: 12
<212> TYPE: PRT
<213> ORGANISM: Artificial Sequence

<220> FEATURE:
<223> OTHER INFORMATION: LCDR 3

<400> SEQUENCE: 239

Gln Ser Tyr Asp Ser Ser Leu Ser Gly Pro Val Val
1 5 10

<210> SEQ ID NO 240
<211> LENGTH: 5
<212> TYPE: PRT
<213> ORGANISM: Artificial Sequence
<220> FEATURE:
<223> OTHER INFORMATION: HCDR 1

<400> SEQUENCE: 240

Ser Tyr Ala Met His
1 5

<210> SEQ ID NO 241
<211> LENGTH: 17
<212> TYPE: PRT
<213> ORGANISM: Artificial Sequence
<220> FEATURE:
<223> OTHER INFORMATION: HCDR 2

<400> SEQUENCE: 241

Val Ile Ser Tyr Asp Gly Ser Asn Lys Tyr Tyr Ala Asp Ser Val Lys
1 5 10 15

Gly

<210> SEQ ID NO 242
<211> LENGTH: 15
<212> TYPE: PRT
<213> ORGANISM: Artificial Sequence
<220> FEATURE:
<223> OTHER INFORMATION: HCDR 3

<400> SEQUENCE: 242

Asp Ala Leu Tyr Asn Tyr Tyr Gly Ser Gly Ser His Phe Asp Tyr
1 5 10 15

<210> SEQ ID NO 243
<211> LENGTH: 11
<212> TYPE: PRT
<213> ORGANISM: Artificial Sequence
<220> FEATURE:
<223> OTHER INFORMATION: LCDR 1

<400> SEQUENCE: 243

Gln Ala Ser Gln Asp Ile Ser Asn Tyr Leu Asn
1 5 10

<210> SEQ ID NO 244
<211> LENGTH: 7
<212> TYPE: PRT
<213> ORGANISM: Artificial Sequence
<220> FEATURE:
<223> OTHER INFORMATION: LCDR 2

<400> SEQUENCE: 244

Asp Ala Ser Asn Leu Glu Thr
1 5

<210> SEQ ID NO 245
<211> LENGTH: 9
<212> TYPE: PRT

<213> ORGANISM: Artificial Sequence
<220> FEATURE:
<223> OTHER INFORMATION: LCDR 3

<400> SEQUENCE: 245

Gln Gln Tyr Asp Asn Leu Pro Leu Thr
1               5

<210> SEQ ID NO 246
<211> LENGTH: 5
<212> TYPE: PRT
<213> ORGANISM: Artificial Sequence
<220> FEATURE:
<223> OTHER INFORMATION: HCDR 1

<400> SEQUENCE: 246

Ser Tyr Ala Met His
1               5

<210> SEQ ID NO 247
<211> LENGTH: 17
<212> TYPE: PRT
<213> ORGANISM: Artificial Sequence
<220> FEATURE:
<223> OTHER INFORMATION: HCDR 2

<400> SEQUENCE: 247

Val Ile Ser Tyr Asp Gly Ser Asn Lys Tyr Tyr Ala Asp Ser Val Lys
1               5                   10                  15

Gly

<210> SEQ ID NO 248
<211> LENGTH: 9
<212> TYPE: PRT
<213> ORGANISM: Artificial Sequence
<220> FEATURE:
<223> OTHER INFORMATION: HCDR 3

<400> SEQUENCE: 248

Asp Lys Gly Asp Ser Ser Phe Asp Tyr
1               5

<210> SEQ ID NO 249
<211> LENGTH: 14
<212> TYPE: PRT
<213> ORGANISM: Artificial Sequence
<220> FEATURE:
<223> OTHER INFORMATION: LCDR 1

<400> SEQUENCE: 249

Thr Gly Ser Ser Ser Asn Ile Gly Ala Gly Tyr Asp Val His
1               5                   10

<210> SEQ ID NO 250
<211> LENGTH: 7
<212> TYPE: PRT
<213> ORGANISM: Artificial Sequence
<220> FEATURE:
<223> OTHER INFORMATION: LCDR 2

<400> SEQUENCE: 250

Gly Asn Ser Asn Arg Pro Ser
1               5

<210> SEQ ID NO 251
<211> LENGTH: 11

<212> TYPE: PRT
<213> ORGANISM: Artificial Sequence
<220> FEATURE:
<223> OTHER INFORMATION: LCDR 3

<400> SEQUENCE: 251

Gln Ser Tyr Asp Ser Ser Leu Ser Gly Val Val
1               5                   10

<210> SEQ ID NO 252
<211> LENGTH: 5
<212> TYPE: PRT
<213> ORGANISM: Artificial Sequence
<220> FEATURE:
<223> OTHER INFORMATION: HCDR 1

<400> SEQUENCE: 252

Ser Tyr Ala Met His
1               5

<210> SEQ ID NO 253
<211> LENGTH: 17
<212> TYPE: PRT
<213> ORGANISM: Artificial Sequence
<220> FEATURE:
<223> OTHER INFORMATION: HCDR 2

<400> SEQUENCE: 253

Val Ile Ser Tyr Asp Gly Ser Asn Lys Tyr Tyr Ala Asp Ser Val Lys
1               5                   10                  15

Gly

<210> SEQ ID NO 254
<211> LENGTH: 16
<212> TYPE: PRT
<213> ORGANISM: Artificial Sequence
<220> FEATURE:
<223> OTHER INFORMATION: HCDR 3

<400> SEQUENCE: 254

Asp Gln Tyr Asp Ile Leu Thr Gly Tyr Gly Gly Thr Ala Leu Asp Tyr
1               5                   10                  15

<210> SEQ ID NO 255
<211> LENGTH: 14
<212> TYPE: PRT
<213> ORGANISM: Artificial Sequence
<220> FEATURE:
<223> OTHER INFORMATION: LCDR 1

<400> SEQUENCE: 255

Thr Gly Thr Ser Ser Asp Val Gly Gly Tyr Asn Tyr Val Ser
1               5                   10

<210> SEQ ID NO 256
<211> LENGTH: 7
<212> TYPE: PRT
<213> ORGANISM: Artificial Sequence
<220> FEATURE:
<223> OTHER INFORMATION: LCDR 2

<400> SEQUENCE: 256

Glu Val Ser Lys Arg Pro Ser
1               5

<210> SEQ ID NO 257

<211> LENGTH: 10
<212> TYPE: PRT
<213> ORGANISM: Artificial Sequence
<220> FEATURE:
<223> OTHER INFORMATION: LCDR 3

<400> SEQUENCE: 257

Ser Ser Tyr Ala Gly Ser Asn Asn Leu Val
1 5 10

<210> SEQ ID NO 258
<211> LENGTH: 5
<212> TYPE: PRT
<213> ORGANISM: Artificial Sequence
<220> FEATURE:
<223> OTHER INFORMATION: HCDR 1

<400> SEQUENCE: 258

Ser Tyr Ala Met His
1 5

<210> SEQ ID NO 259
<211> LENGTH: 17
<212> TYPE: PRT
<213> ORGANISM: Artificial Sequence
<220> FEATURE:
<223> OTHER INFORMATION: HCDR 2

<400> SEQUENCE: 259

Val Ile Ser Tyr Asp Gly Ser Asn Lys Tyr Tyr Ala Asp Ser Val Lys
1 5 10 15

Gly

<210> SEQ ID NO 260
<211> LENGTH: 8
<212> TYPE: PRT
<213> ORGANISM: Artificial Sequence
<220> FEATURE:
<223> OTHER INFORMATION: HCDR 3

<400> SEQUENCE: 260

Glu Ala Gly Glu Gly Val Asp Tyr
1 5

<210> SEQ ID NO 261
<211> LENGTH: 14
<212> TYPE: PRT
<213> ORGANISM: Artificial Sequence
<220> FEATURE:
<223> OTHER INFORMATION: LCDR 1

<400> SEQUENCE: 261

Thr Gly Ser Ser Ser Asn Ile Gly Ala Gly Tyr Asp Val His
1 5 10

<210> SEQ ID NO 262
<211> LENGTH: 7
<212> TYPE: PRT
<213> ORGANISM: Artificial Sequence
<220> FEATURE:
<223> OTHER INFORMATION: LCDR 2

<400> SEQUENCE: 262

Gly Asn Ser Asn Arg Pro Ser
1 5

<210> SEQ ID NO 263
<211> LENGTH: 11
<212> TYPE: PRT
<213> ORGANISM: Artificial Sequence
<220> FEATURE:
<223> OTHER INFORMATION: LCDR 3

<400> SEQUENCE: 263

Gln Ser Tyr Asp Ser Ser Leu Ser Gly Tyr Val
1 5 10

<210> SEQ ID NO 264
<211> LENGTH: 5
<212> TYPE: PRT
<213> ORGANISM: Artificial Sequence
<220> FEATURE:
<223> OTHER INFORMATION: HCDR 1

<400> SEQUENCE: 264

Ser Tyr Ala Met His
1 5

<210> SEQ ID NO 265
<211> LENGTH: 17
<212> TYPE: PRT
<213> ORGANISM: Artificial Sequence
<220> FEATURE:
<223> OTHER INFORMATION: HCDR 2

<400> SEQUENCE: 265

Val Ile Ser Tyr Asp Gly Ser Asn Lys Tyr Tyr Ala Asp Ser Val Lys
1 5 10 15

Gly

<210> SEQ ID NO 266
<211> LENGTH: 15
<212> TYPE: PRT
<213> ORGANISM: Artificial Sequence
<220> FEATURE:
<223> OTHER INFORMATION: HCDR 3

<400> SEQUENCE: 266

Glu Ser Ala Tyr Ser Ser Ser Trp Ser Gly Leu Arg Phe Asp Pro
1 5 10 15

<210> SEQ ID NO 267
<211> LENGTH: 14
<212> TYPE: PRT
<213> ORGANISM: Artificial Sequence
<220> FEATURE:
<223> OTHER INFORMATION: LCDR 1

<400> SEQUENCE: 267

Thr Gly Ser Ser Ser Asn Ile Gly Ala Gly Tyr Asp Val His
1 5 10

<210> SEQ ID NO 268
<211> LENGTH: 7
<212> TYPE: PRT
<213> ORGANISM: Artificial Sequence
<220> FEATURE:
<223> OTHER INFORMATION: LCDR 2

<400> SEQUENCE: 268

Gly Asn Ser Asn Arg Pro Ser
1 5

```
<210> SEQ ID NO 269
<211> LENGTH: 11
<212> TYPE: PRT
<213> ORGANISM: Artificial Sequence
<220> FEATURE:
<223> OTHER INFORMATION: LCDR 3

<400> SEQUENCE: 269

Gln Ser Tyr Asp Ser Ser Leu Ser Gly Tyr Val
1               5                   10


<210> SEQ ID NO 270
<211> LENGTH: 5
<212> TYPE: PRT
<213> ORGANISM: Artificial Sequence
<220> FEATURE:
<223> OTHER INFORMATION: HCDR 1

<400> SEQUENCE: 270

Ser Tyr Ala Met His
1               5


<210> SEQ ID NO 271
<211> LENGTH: 17
<212> TYPE: PRT
<213> ORGANISM: Artificial Sequence
<220> FEATURE:
<223> OTHER INFORMATION: HCDR 2

<400> SEQUENCE: 271

Val Ile Ser Tyr Asp Gly Ser Asn Lys Tyr Tyr Ala Asp Ser Val Lys
1               5                   10                  15

Gly


<210> SEQ ID NO 272
<211> LENGTH: 12
<212> TYPE: PRT
<213> ORGANISM: Artificial Sequence
<220> FEATURE:
<223> OTHER INFORMATION: HCDR 3

<400> SEQUENCE: 272

Gly Gly Ala Val Ala Gly Gly Trp Tyr Phe Asp Tyr
1               5                   10


<210> SEQ ID NO 273
<211> LENGTH: 11
<212> TYPE: PRT
<213> ORGANISM: Artificial Sequence
<220> FEATURE:
<223> OTHER INFORMATION: LCDR 1

<400> SEQUENCE: 273

Arg Ala Ser Gln Gly Ile Ser Ser Trp Leu Ala
1               5                   10


<210> SEQ ID NO 274
<211> LENGTH: 7
<212> TYPE: PRT
<213> ORGANISM: Artificial Sequence
<220> FEATURE:
<223> OTHER INFORMATION: LCDR 2

<400> SEQUENCE: 274

Ala Ala Ser Ser Leu Gln Ser
1               5
```

<210> SEQ ID NO 275
<211> LENGTH: 9
<212> TYPE: PRT
<213> ORGANISM: Artificial Sequence
<220> FEATURE:
<223> OTHER INFORMATION: LCDR 3

<400> SEQUENCE: 275

Gln Gln Ala Asn Ser Phe Pro Pro Thr
1 5

<210> SEQ ID NO 276
<211> LENGTH: 5
<212> TYPE: PRT
<213> ORGANISM: Artificial Sequence
<220> FEATURE:
<223> OTHER INFORMATION: HCDR 1

<400> SEQUENCE: 276

Ser Tyr Ala Met His
1 5

<210> SEQ ID NO 277
<211> LENGTH: 17
<212> TYPE: PRT
<213> ORGANISM: Artificial Sequence
<220> FEATURE:
<223> OTHER INFORMATION: HCDR 2

<400> SEQUENCE: 277

Val Ile Ser Tyr Asp Gly Ser Asn Lys Tyr Tyr Ala Asp Ser Val Lys
1 5 10 15

Gly

<210> SEQ ID NO 278
<211> LENGTH: 9
<212> TYPE: PRT
<213> ORGANISM: Artificial Sequence
<220> FEATURE:
<223> OTHER INFORMATION: HCDR 3

<400> SEQUENCE: 278

Ser Gly Ser Tyr Phe Gly Phe Asp Tyr
1 5

<210> SEQ ID NO 279
<211> LENGTH: 16
<212> TYPE: PRT
<213> ORGANISM: Artificial Sequence
<220> FEATURE:
<223> OTHER INFORMATION: LCDR 1

<400> SEQUENCE: 279

Arg Ser Ser Gln Ser Leu Leu His Ser Asn Gly Tyr Asn Tyr Leu Asp
1 5 10 15

<210> SEQ ID NO 280
<211> LENGTH: 7
<212> TYPE: PRT
<213> ORGANISM: Artificial Sequence
<220> FEATURE:
<223> OTHER INFORMATION: LCDR 2

<400> SEQUENCE: 280

Leu Gly Ser Asn Arg Ala Ser 1 5

<210> SEQ ID NO 281
<211> LENGTH: 9
<212> TYPE: PRT
<213> ORGANISM: Artificial Sequence
<220> FEATURE:
<223> OTHER INFORMATION: LCDR 3

<400> SEQUENCE: 281

Met Gln Ala Leu Gln Thr Pro Leu Thr
1 5

<210> SEQ ID NO 282
<211> LENGTH: 5
<212> TYPE: PRT
<213> ORGANISM: Artificial Sequence
<220> FEATURE:
<223> OTHER INFORMATION: HCDR 1

<400> SEQUENCE: 282

Ser Tyr Ala Met His
1 5

<210> SEQ ID NO 283
<211> LENGTH: 17
<212> TYPE: PRT
<213> ORGANISM: Artificial Sequence
<220> FEATURE:
<223> OTHER INFORMATION: HCDR 2

<400> SEQUENCE: 283

Val Ile Ser Tyr Asp Gly Ser Asn Lys Tyr Tyr Ala Gly Ser Val Lys
1 5 10 15

Gly

<210> SEQ ID NO 284
<211> LENGTH: 9
<212> TYPE: PRT
<213> ORGANISM: Artificial Sequence
<220> FEATURE:
<223> OTHER INFORMATION: HCDR 3

<400> SEQUENCE: 284

Asp Trp Arg Gly Val Tyr Phe Asp Tyr
1 5

<210> SEQ ID NO 285
<211> LENGTH: 14
<212> TYPE: PRT
<213> ORGANISM: Artificial Sequence
<220> FEATURE:
<223> OTHER INFORMATION: LCDR 1

<400> SEQUENCE: 285

Thr Gly Thr Ser Ser Asp Val Gly Gly Tyr Asn Tyr Val Ser
1 5 10

<210> SEQ ID NO 286
<211> LENGTH: 7
<212> TYPE: PRT
<213> ORGANISM: Artificial Sequence
<220> FEATURE:
<223> OTHER INFORMATION: LCDR 2

<400> SEQUENCE: 286

Glu Val Ser Asn Arg Pro Ser
1 5

<210> SEQ ID NO 287
<211> LENGTH: 10
<212> TYPE: PRT
<213> ORGANISM: Artificial Sequence
<220> FEATURE:
<223> OTHER INFORMATION: LCDR 3

<400> SEQUENCE: 287

Ser Ser Tyr Thr Ser Ser Ser Thr Leu Val
1 5 10

<210> SEQ ID NO 288
<211> LENGTH: 5
<212> TYPE: PRT
<213> ORGANISM: Artificial Sequence
<220> FEATURE:
<223> OTHER INFORMATION: HCDR 1

<400> SEQUENCE: 288

Ser Tyr Gly Ile Ser
1 5

<210> SEQ ID NO 289
<211> LENGTH: 17
<212> TYPE: PRT
<213> ORGANISM: Artificial Sequence
<220> FEATURE:
<223> OTHER INFORMATION: HCDR 2

<400> SEQUENCE: 289

Trp Ile Ser Ala Tyr Asn Gly Asn Thr Asn Tyr Ala Gln Lys Leu Gln
1 5 10 15

Gly

<210> SEQ ID NO 290
<211> LENGTH: 9
<212> TYPE: PRT
<213> ORGANISM: Artificial Sequence
<220> FEATURE:
<223> OTHER INFORMATION: HCDR 3

<400> SEQUENCE: 290

Trp Gly Val Val Gly Gly Met Asp Val
1 5

<210> SEQ ID NO 291
<211> LENGTH: 11
<212> TYPE: PRT
<213> ORGANISM: Artificial Sequence
<220> FEATURE:
<223> OTHER INFORMATION: LCDR 1

<400> SEQUENCE: 291

Arg Ala Ser Gln Gly Ile Ser Ser Trp Leu Ala
1 5 10

<210> SEQ ID NO 292
<211> LENGTH: 7
<212> TYPE: PRT
<213> ORGANISM: Artificial Sequence
<220> FEATURE:
<223> OTHER INFORMATION: LCDR 2

<400> SEQUENCE: 292

```
Ala Ala Ser Ser Leu Gln Ser
1               5


<210> SEQ ID NO 293
<211> LENGTH: 9
<212> TYPE: PRT
<213> ORGANISM: Artificial Sequence
<220> FEATURE:
<223> OTHER INFORMATION: LCDR 3

<400> SEQUENCE: 293

Gln Gln Ala Asn Ser Phe Pro Leu Thr
1               5


<210> SEQ ID NO 294
<211> LENGTH: 5
<212> TYPE: PRT
<213> ORGANISM: Artificial Sequence
<220> FEATURE:
<223> OTHER INFORMATION: HCDR 1

<400> SEQUENCE: 294

Ser Tyr Gly Met His
1               5


<210> SEQ ID NO 295
<211> LENGTH: 17
<212> TYPE: PRT
<213> ORGANISM: Artificial Sequence
<220> FEATURE:
<223> OTHER INFORMATION: HCDR 2

<400> SEQUENCE: 295

Val Ile Ser Tyr Asp Gly Ser Asn Lys Tyr Tyr Ala Asp Ser Val Lys
1               5                   10                  15

Gly


<210> SEQ ID NO 296
<211> LENGTH: 8
<212> TYPE: PRT
<213> ORGANISM: Artificial Sequence
<220> FEATURE:
<223> OTHER INFORMATION: HCDR 3

<400> SEQUENCE: 296

Asp Phe Ser Asp Ala Phe Asp Ile
1               5


<210> SEQ ID NO 297
<211> LENGTH: 13
<212> TYPE: PRT
<213> ORGANISM: Artificial Sequence
<220> FEATURE:
<223> OTHER INFORMATION: LCDR 1

<400> SEQUENCE: 297

Ser Gly Ser Ser Ser Asn Ile Gly Asn Asn Tyr Val Ser
1               5                   10


<210> SEQ ID NO 298
<211> LENGTH: 7
<212> TYPE: PRT
<213> ORGANISM: Artificial Sequence
<220> FEATURE:
<223> OTHER INFORMATION: LCDR 2
```

<400> SEQUENCE: 298

Asp Asn Asn Lys Arg Pro Ser
1 5

<210> SEQ ID NO 299
<211> LENGTH: 11
<212> TYPE: PRT
<213> ORGANISM: Artificial Sequence
<220> FEATURE:
<223> OTHER INFORMATION: LCDR 3

<400> SEQUENCE: 299

Gly Thr Trp Asp Ser Ser Leu Ser Ala Val Val
1 5 10

<210> SEQ ID NO 300
<211> LENGTH: 5
<212> TYPE: PRT
<213> ORGANISM: Artificial Sequence
<220> FEATURE:
<223> OTHER INFORMATION: HCDR 1

<400> SEQUENCE: 300

Ser Tyr Gly Met His
1 5

<210> SEQ ID NO 301
<211> LENGTH: 17
<212> TYPE: PRT
<213> ORGANISM: Artificial Sequence
<220> FEATURE:
<223> OTHER INFORMATION: HCDR 2

<400> SEQUENCE: 301

Val Ile Ser Tyr Asp Gly Ser Asn Lys Tyr Tyr Ala Asp Ser Val Lys
1 5 10 15

Gly

<210> SEQ ID NO 302
<211> LENGTH: 8
<212> TYPE: PRT
<213> ORGANISM: Artificial Sequence
<220> FEATURE:
<223> OTHER INFORMATION: HCDR 3

<400> SEQUENCE: 302

Gly Ser Gly Trp Tyr Phe Asp Tyr
1 5

<210> SEQ ID NO 303
<211> LENGTH: 11
<212> TYPE: PRT
<213> ORGANISM: Artificial Sequence
<220> FEATURE:
<223> OTHER INFORMATION: LCDR 1

<400> SEQUENCE: 303

Arg Ala Ser Gln Ser Ile Ser Ser Trp Leu Ala
1 5 10

<210> SEQ ID NO 304
<211> LENGTH: 7
<212> TYPE: PRT
<213> ORGANISM: Artificial Sequence
<220> FEATURE:
<223> OTHER INFORMATION: LCDR 2

<400> SEQUENCE: 304

Lys Ala Ser Ser Leu Glu Ser
1 5

<210> SEQ ID NO 305
<211> LENGTH: 9
<212> TYPE: PRT
<213> ORGANISM: Artificial Sequence
<220> FEATURE:
<223> OTHER INFORMATION: LCDR 3

<400> SEQUENCE: 305

Gln Gln Tyr Asn Ser Tyr Ser Trp Thr
1 5

<210> SEQ ID NO 306
<211> LENGTH: 5
<212> TYPE: PRT
<213> ORGANISM: Artificial Sequence
<220> FEATURE:
<223> OTHER INFORMATION: HCDR 1

<400> SEQUENCE: 306

Ser Tyr Tyr Met His
1 5

<210> SEQ ID NO 307
<211> LENGTH: 17
<212> TYPE: PRT
<213> ORGANISM: Artificial Sequence
<220> FEATURE:
<223> OTHER INFORMATION: HCDR 2

<400> SEQUENCE: 307

Ile Ile Asn Pro Ser Gly Gly Ser Thr Ser Tyr Ala Gln Lys Phe Gln
1 5 10 15

Gly

<210> SEQ ID NO 308
<211> LENGTH: 6
<212> TYPE: PRT
<213> ORGANISM: Artificial Sequence
<220> FEATURE:
<223> OTHER INFORMATION: HCDR 3

<400> SEQUENCE: 308

Asp Asp Tyr Gly Asp Tyr
1 5

<210> SEQ ID NO 309
<211> LENGTH: 14
<212> TYPE: PRT
<213> ORGANISM: Artificial Sequence
<220> FEATURE:
<223> OTHER INFORMATION: LCDR 1

<400> SEQUENCE: 309

Thr Gly Thr Ser Ser Asp Val Gly Gly Tyr Asn Tyr Val Ser
1 5 10

<210> SEQ ID NO 310
<211> LENGTH: 7
<212> TYPE: PRT
<213> ORGANISM: Artificial Sequence
<220> FEATURE:

<223> OTHER INFORMATION: LCDR 2

<400> SEQUENCE: 310

Glu Val Ser Asn Arg Pro Ser
1 5

<210> SEQ ID NO 311
<211> LENGTH: 9
<212> TYPE: PRT
<213> ORGANISM: Artificial Sequence
<220> FEATURE:
<223> OTHER INFORMATION: LCDR 3

<400> SEQUENCE: 311

Ser Ser Tyr Thr Ser Ser Ser Phe Ser
1 5

<210> SEQ ID NO 312
<211> LENGTH: 5
<212> TYPE: PRT
<213> ORGANISM: Artificial Sequence
<220> FEATURE:
<223> OTHER INFORMATION: HCDR 1

<400> SEQUENCE: 312

Ser Tyr Tyr Met His
1 5

<210> SEQ ID NO 313
<211> LENGTH: 17
<212> TYPE: PRT
<213> ORGANISM: Artificial Sequence
<220> FEATURE:
<223> OTHER INFORMATION: HCDR 2

<400> SEQUENCE: 313

Ile Ile Asn Pro Ser Gly Gly Ser Thr Ser Tyr Ala Gln Lys Phe Gln
1 5 10 15

Gly

<210> SEQ ID NO 314
<211> LENGTH: 12
<212> TYPE: PRT
<213> ORGANISM: Artificial Sequence
<220> FEATURE:
<223> OTHER INFORMATION: HCDR 3

<400> SEQUENCE: 314

Asp Ser Ser Ser Gly Trp Ser Ser Tyr Phe Asp Tyr
1 5 10

<210> SEQ ID NO 315
<211> LENGTH: 11
<212> TYPE: PRT
<213> ORGANISM: Artificial Sequence
<220> FEATURE:
<223> OTHER INFORMATION: LCDR 1

<400> SEQUENCE: 315

Gln Ala Ser Gln Asp Ile Ser Asn Tyr Leu Asn
1 5 10

<210> SEQ ID NO 316
<211> LENGTH: 7
<212> TYPE: PRT
<213> ORGANISM: Artificial Sequence

<220> FEATURE:
<223> OTHER INFORMATION: LCDR 2

<400> SEQUENCE: 316

Asp Ala Ser Asn Leu Glu Thr
1 5

<210> SEQ ID NO 317
<211> LENGTH: 9
<212> TYPE: PRT
<213> ORGANISM: Artificial Sequence
<220> FEATURE:
<223> OTHER INFORMATION: LCDR 3

<400> SEQUENCE: 317

Gln Gln Tyr Asp Asn Leu Pro Leu Thr
1 5

<210> SEQ ID NO 318
<211> LENGTH: 5
<212> TYPE: PRT
<213> ORGANISM: Artificial Sequence
<220> FEATURE:
<223> OTHER INFORMATION: HCDR 1

<400> SEQUENCE: 318

Ser Tyr Tyr Met His
1 5

<210> SEQ ID NO 319
<211> LENGTH: 17
<212> TYPE: PRT
<213> ORGANISM: Artificial Sequence
<220> FEATURE:
<223> OTHER INFORMATION: HCDR 2

<400> SEQUENCE: 319

Ile Ile Asn Pro Ser Gly Gly Ser Thr Ser Tyr Ala Gln Lys Phe Gln
1 5 10 15

Gly

<210> SEQ ID NO 320
<211> LENGTH: 9
<212> TYPE: PRT
<213> ORGANISM: Artificial Sequence
<220> FEATURE:
<223> OTHER INFORMATION: HCDR 3

<400> SEQUENCE: 320

Met Thr Thr Ser Leu Gly Phe Asp Tyr
1 5

<210> SEQ ID NO 321
<211> LENGTH: 11
<212> TYPE: PRT
<213> ORGANISM: Artificial Sequence
<220> FEATURE:
<223> OTHER INFORMATION: LCDR 1

<400> SEQUENCE: 321

Arg Ala Ser Gln Gly Ile Ser Asn Trp Leu Ala
1 5 10

<210> SEQ ID NO 322
<211> LENGTH: 7
<212> TYPE: PRT

<213> ORGANISM: Artificial Sequence
<220> FEATURE:
<223> OTHER INFORMATION: LCDR 2

<400> SEQUENCE: 322

Ala Ala Ser Ser Leu Gln Ser
1 5

<210> SEQ ID NO 323
<211> LENGTH: 9
<212> TYPE: PRT
<213> ORGANISM: Artificial Sequence
<220> FEATURE:
<223> OTHER INFORMATION: LCDR 3

<400> SEQUENCE: 323

Gln Gln Ala Asn Ser Leu Pro Leu Thr
1 5

<210> SEQ ID NO 324
<211> LENGTH: 5
<212> TYPE: PRT
<213> ORGANISM: Artificial Sequence
<220> FEATURE:
<223> OTHER INFORMATION: HCDR 1

<400> SEQUENCE: 324

Ser Tyr Tyr Met His
1 5

<210> SEQ ID NO 325
<211> LENGTH: 17
<212> TYPE: PRT
<213> ORGANISM: Artificial Sequence
<220> FEATURE:
<223> OTHER INFORMATION: HCDR 2

<400> SEQUENCE: 325

Ile Ile Asn Pro Ser Gly Gly Ser Thr Ser Tyr Ala Gln Lys Phe Gln
1 5 10 15

Gly

<210> SEQ ID NO 326
<211> LENGTH: 9
<212> TYPE: PRT
<213> ORGANISM: Artificial Sequence
<220> FEATURE:
<223> OTHER INFORMATION: HCDR 3

<400> SEQUENCE: 326

Ser Arg Gly Gly Ser Ala Phe Asp Ile
1 5

<210> SEQ ID NO 327
<211> LENGTH: 16
<212> TYPE: PRT
<213> ORGANISM: Artificial Sequence
<220> FEATURE:
<223> OTHER INFORMATION: LCDR 1

<400> SEQUENCE: 327

Arg Ser Ser Gln Ser Leu Leu His Ser Asn Gly Tyr Asn Tyr Leu Asp
1 5 10 15

<210> SEQ ID NO 328
<211> LENGTH: 7

<212> TYPE: PRT
<213> ORGANISM: Artificial Sequence
<220> FEATURE:
<223> OTHER INFORMATION: LCDR 2

<400> SEQUENCE: 328

Leu Gly Ser Asn Arg Ala Ser
1               5

<210> SEQ ID NO 329
<211> LENGTH: 9
<212> TYPE: PRT
<213> ORGANISM: Artificial Sequence
<220> FEATURE:
<223> OTHER INFORMATION: LCDR 3

<400> SEQUENCE: 329

Met Gln Ala Leu Gln Thr Pro Leu Thr
1               5

<210> SEQ ID NO 330
<211> LENGTH: 15
<212> TYPE: PRT
<213> ORGANISM: Artificial Sequence
<220> FEATURE:
<223> OTHER INFORMATION: Epitope 1

<400> SEQUENCE: 330

Asn Lys Gly Leu Thr Leu Leu Asp Gly Asp Leu Pro Glu Gln Glu
1               5                   10                  15

<210> SEQ ID NO 331
<211> LENGTH: 15
<212> TYPE: PRT
<213> ORGANISM: Artificial Sequence
<220> FEATURE:
<223> OTHER INFORMATION: Epitope 2

<400> SEQUENCE: 331

Gln Tyr Pro Pro Glu Lys Ile Ala Ser Glu Leu Lys Asp Thr Ile
1               5                   10                  15

<210> SEQ ID NO 332
<211> LENGTH: 15
<212> TYPE: PRT
<213> ORGANISM: Artificial Sequence
<220> FEATURE:
<223> OTHER INFORMATION: Epitope 5

<400> SEQUENCE: 332

Ala Lys Pro Ser Leu Leu Ser Arg Val Gly Ala Leu Thr Asn Thr
1               5                   10                  15

<210> SEQ ID NO 333
<211> LENGTH: 15
<212> TYPE: PRT
<213> ORGANISM: Artificial Sequence
<220> FEATURE:
<223> OTHER INFORMATION: Epitope 6

<400> SEQUENCE: 333

Glu Val Arg Val Pro Trp Leu His Ser Leu Ala Ala Ala Gln Glu
1               5                   10                  15

<210> SEQ ID NO 334
<211> LENGTH: 118
<212> TYPE: PRT

```
<213> ORGANISM: Artificial Sequence
<220> FEATURE:
<223> OTHER INFORMATION: VH

<400> SEQUENCE: 334

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Ala Ala Ala Gly Pro Phe Asp Tyr Trp Gly Gln Gly Thr
            100                 105                 110

Leu Val Thr Val Ser Ser
        115


<210> SEQ ID NO 335
<211> LENGTH: 110
<212> TYPE: PRT
<213> ORGANISM: Artificial Sequence
<220> FEATURE:
<223> OTHER INFORMATION: VL

<400> SEQUENCE: 335

Ser Tyr Val Leu Thr Gln Pro Pro Ser Val Ser Glu Ala Pro Arg Gln
1               5                   10                  15

Arg Val Thr Ile Ser Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
            100                 105                 110


<210> SEQ ID NO 336
<211> LENGTH: 117
<212> TYPE: PRT
<213> ORGANISM: Artificial Sequence
<220> FEATURE:
<223> OTHER INFORMATION: VH

<400> SEQUENCE: 336

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Gly Phe Arg Arg Leu Phe Asp Pro Trp Gly Gln Gly Thr Leu
            100                 105                 110

Val Thr Val Ser Ser
        115


<210> SEQ ID NO 337
<211> LENGTH: 111
<212> TYPE: PRT
<213> ORGANISM: Artificial Sequence
<220> FEATURE:
<223> OTHER INFORMATION: VL

<400> SEQUENCE: 337

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr His Val Val Phe Gly Gly Gly Thr Lys Leu Thr Val Leu
            100                 105                 110


<210> SEQ ID NO 338
<211> LENGTH: 120
<212> TYPE: PRT
<213> ORGANISM: Artificial Sequence
<220> FEATURE:
<223> OTHER INFORMATION: VH

<400> SEQUENCE: 338

Gln Val Gln Leu Val Gln Ser Gly Gly Ser Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Ala Ser Ile Ala Ala Arg Pro Phe Asp Tyr Trp Gly Gln
            100                 105                 110

Gly Thr Leu Val Thr Val Ser Ser
```

115 120

<210> SEQ ID NO 339
<211> LENGTH: 111
<212> TYPE: PRT
<213> ORGANISM: Artificial Sequence
<220> FEATURE:
<223> OTHER INFORMATION: VL

<400> SEQUENCE: 339

Gln Ser Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Ser Asn
20 25 30

Thr Val Asn Trp Tyr Gln Gln Leu Pro Gly Thr Ala Pro Lys Leu Leu
35 40 45

Ile Tyr Ser Asn Asn Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ala Ala Trp Asp Asp Ser Leu
85 90 95

Asn Gly Arg Tyr Val Phe Gly Thr Gly Thr Lys Leu Thr Val Leu
100 105 110

<210> SEQ ID NO 340
<211> LENGTH: 116
<212> TYPE: PRT
<213> ORGANISM: Artificial Sequence
<220> FEATURE:
<223> OTHER INFORMATION: VH

<400> SEQUENCE: 340

Gln Val Gln Leu Val Glu Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Gly Ile Ser Trp Val Arg Gln Ala Pro Gly Gln Gly Leu Glu Trp Met
35 40 45

Gly Trp Ile Ser Ala Tyr Asn Gly Asn Thr Asn Tyr Ala Gln Lys Leu
50 55 60

Gln Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Gly Gly Ser Ser Ser Asn Tyr Trp Gly Gln Gly Thr Leu Val
100 105 110

Thr Val Ser Ser
115

<210> SEQ ID NO 341
<211> LENGTH: 110
<212> TYPE: PRT
<213> ORGANISM: Artificial Sequence
<220> FEATURE:
<223> OTHER INFORMATION: VL

<400> SEQUENCE: 341

Gln Ser Ala Leu Thr Gln Pro Ala Ser Val Ser Gly Ser Pro Gly Gln
1 5 10 15

```
Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Val Phe Gly Gly Gly Thr Lys Leu Thr Val Leu
            100                 105                 110


<210> SEQ ID NO 342
<211> LENGTH: 117
<212> TYPE: PRT
<213> ORGANISM: Artificial Sequence
<220> FEATURE:
<223> OTHER INFORMATION: VH

<400> SEQUENCE: 342

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Asn Pro Ser Ser Gly Ala Asp Tyr Trp Gly Gln Gly Thr Leu
            100                 105                 110

Val Thr Val Ser Ser
        115


<210> SEQ ID NO 343
<211> LENGTH: 111
<212> TYPE: PRT
<213> ORGANISM: Artificial Sequence
<220> FEATURE:
<223> OTHER INFORMATION: VL

<400> SEQUENCE: 343

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
```

```
                85                  90                  95

Ser Gly Ala Trp Val Phe Gly Gly Gly Thr Lys Leu Thr Val Leu
            100                 105                 110


<210> SEQ ID NO 344
<211> LENGTH: 117
<212> TYPE: PRT
<213> ORGANISM: Artificial Sequence
<220> FEATURE:
<223> OTHER INFORMATION: VH

<400> SEQUENCE: 344

Glu Val Gln Leu Val Gln Ser Gly Ala Glu Val Lys Lys Pro Gly Ser
1               5                   10                  15

Ser Val Lys Ile Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Ser Ser Gly Trp Glu Trp Trp Gly Gln Gly Thr Leu
            100                 105                 110

Val Thr Val Ser Ser
        115


<210> SEQ ID NO 345
<211> LENGTH: 110
<212> TYPE: PRT
<213> ORGANISM: Artificial Sequence
<220> FEATURE:
<223> OTHER INFORMATION: VL

<400> SEQUENCE: 345

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Val Val Phe Gly Gly Gly Thr Lys Leu Thr Val Leu
            100                 105                 110


<210> SEQ ID NO 346
<211> LENGTH: 123
<212> TYPE: PRT
<213> ORGANISM: Artificial Sequence
<220> FEATURE:
<223> OTHER INFORMATION: VH

<400> SEQUENCE: 346
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Ser Leu Tyr Cys Ser Gly Gly Ser Cys Tyr Ser Ala Leu Asp Pro
            100                 105                 110

Trp Gly Gln Gly Thr Leu Val Thr Val Ser Ser
        115                 120


<210> SEQ ID NO 347
<211> LENGTH: 111
<212> TYPE: PRT
<213> ORGANISM: Artificial Sequence
<220> FEATURE:
<223> OTHER INFORMATION: VL

<400> SEQUENCE: 347

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Arg Tyr Val Val Phe Gly Gly Gly Thr Lys Val Thr Val Leu
            100                 105                 110


<210> SEQ ID NO 348
<211> LENGTH: 118
<212> TYPE: PRT
<213> ORGANISM: Artificial Sequence
<220> FEATURE:
<223> OTHER INFORMATION: VH

<400> SEQUENCE: 348

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
```

```
65                  70                  75                  80

Leu Gln Met Asn Ser Leu Arg Ala Glu Asp Thr Ala Leu Tyr Tyr Cys
                85                  90                  95

Ala Lys Glu Asp Gly Ser Tyr Ala Leu Asp Tyr Trp Gly Gln Gly Thr
            100                 105                 110

Leu Val Thr Val Ser Ser
        115


<210> SEQ ID NO 349
<211> LENGTH: 107
<212> TYPE: PRT
<213> ORGANISM: Artificial Sequence
<220> FEATURE:
<223> OTHER INFORMATION: VL

<400> SEQUENCE: 349

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gly Gly Thr Lys Leu Glu Ile Lys
            100                 105


<210> SEQ ID NO 350
<211> LENGTH: 119
<212> TYPE: PRT
<213> ORGANISM: Artificial Sequence
<220> FEATURE:
<223> OTHER INFORMATION: VH

<400> SEQUENCE: 350

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Gly Tyr Gly Asn Asp Ala Phe Asp Ile Trp Gly Gln Gly
            100                 105                 110

Thr Met Val Thr Val Ser Ser
        115


<210> SEQ ID NO 351
<211> LENGTH: 107
```

```
<212> TYPE: PRT
<213> ORGANISM: Artificial Sequence
<220> FEATURE:
<223> OTHER INFORMATION: VL

<400> SEQUENCE: 351

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys
            100                 105


<210> SEQ ID NO 352
<211> LENGTH: 121
<212> TYPE: PRT
<213> ORGANISM: Artificial Sequence
<220> FEATURE:
<223> OTHER INFORMATION: VH

<400> SEQUENCE: 352

Gln Val Gln Leu Val Glu Phe Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Met Gly Leu Ser Trp Tyr Gly Glu Phe Asp Tyr Trp Gly
            100                 105                 110

Gln Gly Thr Leu Val Thr Val Ser Ser
        115                 120


<210> SEQ ID NO 353
<211> LENGTH: 109
<212> TYPE: PRT
<213> ORGANISM: Artificial Sequence
<220> FEATURE:
<223> OTHER INFORMATION: VL

<400> SEQUENCE: 353

Gln Ser Val Leu Thr Gln Pro Pro Ser Val Ser Glu Ala Pro Arg Gln
1               5                   10                  15

Arg Val Thr Ile Ser Cys Ser Gly Ser Ser Ser Asn Ile Gly Asn Asn
            20                  25                  30

Ala Val Ser Trp Tyr Gln Gln Leu Pro Gly Lys Ala Pro Lys Leu Leu
```

35 40 45

Ile Tyr Tyr Asp Asp Leu Leu Pro Ser Gly Val Ser Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ala Ala Trp Asp Asp Ser Leu
85 90 95

Asn Trp Val Phe Gly Gly Gly Thr Lys Leu Thr Val Leu
100 105

<210> SEQ ID NO 354
<211> LENGTH: 115
<212> TYPE: PRT
<213> ORGANISM: Artificial Sequence
<220> FEATURE:
<223> OTHER INFORMATION: VH

<400> SEQUENCE: 354

Glu Val Gln Leu Val Gln Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Ile Phe Met Asp Val Trp Gly Gln Gly Thr Met Val Thr
100 105 110

Val Ser Ser
115

<210> SEQ ID NO 355
<211> LENGTH: 111
<212> TYPE: PRT
<213> ORGANISM: Artificial Sequence
<220> FEATURE:
<223> OTHER INFORMATION: VL

<400> SEQUENCE: 355

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Tyr Val Ser Trp Tyr Gln Gln His Pro Gly Lys Ala Pro Lys Leu
35 40 45

Met Ile Tyr Asp Val Ser Asn Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Ser Ser Tyr Thr Ser Ser
85 90 95

Ser Thr Leu Val Val Phe Gly Gly Gly Thr Lys Leu Thr Val Leu
100 105 110

<210> SEQ ID NO 356
<211> LENGTH: 118
<212> TYPE: PRT
<213> ORGANISM: Artificial Sequence
<220> FEATURE:
<223> OTHER INFORMATION: VH

<400> SEQUENCE: 356

Glu Val Gln Leu Leu Glu Ser Gly Gly Gly Leu Val Gln Pro Gly Arg
1               5                   10                  15

Ser Leu Arg Leu Ala Cys Val Ala Ser Gly Phe Thr Phe Asp Asp Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Tyr Gly Glu Gly Gly Phe Asp Pro Trp Gly Gln Gly Thr
            100                 105                 110

Leu Val Thr Val Ser Ser
        115

<210> SEQ ID NO 357
<211> LENGTH: 111
<212> TYPE: PRT
<213> ORGANISM: Artificial Sequence
<220> FEATURE:
<223> OTHER INFORMATION: VL

<400> SEQUENCE: 357

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Thr Trp Val Phe Gly Gly Gly Thr Lys Val Thr Val Leu
            100                 105                 110

<210> SEQ ID NO 358
<211> LENGTH: 121
<212> TYPE: PRT
<213> ORGANISM: Artificial Sequence
<220> FEATURE:
<223> OTHER INFORMATION: VH

<400> SEQUENCE: 358

Gln Val Gln Leu Val Gln Ser Gly Gly Gly Val Val Gln Pro Arg Arg
1               5                   10                  15

Ser Leu Arg Leu Ser Cys Ala Ala Ser Gly Phe Thr Phe Ser Ser Tyr

```
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Asn Trp Asp Ala Phe Asp Ile Trp Gly
            100                 105                 110

Gln Gly Thr Met Val Thr Val Ser Ser
        115                 120


<210> SEQ ID NO 359
<211> LENGTH: 110
<212> TYPE: PRT
<213> ORGANISM: Artificial Sequence
<220> FEATURE:
<223> OTHER INFORMATION: VL

<400> SEQUENCE: 359

Ser Tyr Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Ala Leu Val Phe Gly Gly Gly Thr Lys Leu Thr Val Leu
            100                 105                 110


<210> SEQ ID NO 360
<211> LENGTH: 118
<212> TYPE: PRT
<213> ORGANISM: Artificial Sequence
<220> FEATURE:
<223> OTHER INFORMATION: VH

<400> SEQUENCE: 360

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95
```

```
Ala Lys Glu Gly Arg Tyr Gly Gly Phe Asp Tyr Trp Gly Gln Gly Thr
            100                 105                 110

Leu Val Thr Val Ser Ser
        115


<210> SEQ ID NO 361
<211> LENGTH: 107
<212> TYPE: PRT
<213> ORGANISM: Artificial Sequence
<220> FEATURE:
<223> OTHER INFORMATION: VL

<400> SEQUENCE: 361

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Gly Gly Thr Lys Val Glu Ile Lys
            100                 105


<210> SEQ ID NO 362
<211> LENGTH: 122
<212> TYPE: PRT
<213> ORGANISM: Artificial Sequence
<220> FEATURE:
<223> OTHER INFORMATION: VH

<400> SEQUENCE: 362

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Gly Glu Tyr Ser Tyr Gly Gly Gly Glu Phe Asp Pro Trp
            100                 105                 110

Gly Gln Gly Thr Leu Val Thr Val Ser Ser
        115                 120


<210> SEQ ID NO 363
<211> LENGTH: 110
<212> TYPE: PRT
<213> ORGANISM: Artificial Sequence
<220> FEATURE:
<223> OTHER INFORMATION: VL
```

<400> SEQUENCE: 363

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Trp Val Phe Gly Gly Gly Thr Lys Leu Thr Val Leu
            100                 105                 110
```

<210> SEQ ID NO 364
<211> LENGTH: 119
<212> TYPE: PRT
<213> ORGANISM: Artificial Sequence
<220> FEATURE:
<223> OTHER INFORMATION: VH

<400> SEQUENCE: 364

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Thr Pro Gly Gly Leu Thr Pro Phe Asp Tyr Trp Gly Gln Gly
            100                 105                 110

Thr Leu Val Thr Val Ser Ser
        115
```

<210> SEQ ID NO 365
<211> LENGTH: 112
<212> TYPE: PRT
<213> ORGANISM: Artificial Sequence
<220> FEATURE:
<223> OTHER INFORMATION: VL

<400> SEQUENCE: 365

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Gly Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60
```

```
Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Asn Val Val Phe Gly Gly Gly Thr Lys Leu Thr Val Leu
            100                 105                 110


<210> SEQ ID NO 366
<211> LENGTH: 121
<212> TYPE: PRT
<213> ORGANISM: Artificial Sequence
<220> FEATURE:
<223> OTHER INFORMATION: VH

<400> SEQUENCE: 366

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Ala Gly Gly Asp Tyr Pro Val Phe Asp Tyr Trp Gly
            100                 105                 110

Gln Gly Thr Leu Val Thr Val Ser Ser
        115                 120


<210> SEQ ID NO 367
<211> LENGTH: 108
<212> TYPE: PRT
<213> ORGANISM: Artificial Sequence
<220> FEATURE:
<223> OTHER INFORMATION: VL

<400> SEQUENCE: 367

Asp Ile Gln Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Pro
                85                  90                  95

Trp Thr Phe Gly Gln Gly Thr Lys Leu Glu Ile Lys
            100                 105


<210> SEQ ID NO 368
<211> LENGTH: 120
<212> TYPE: PRT
<213> ORGANISM: Artificial Sequence
```

<220> FEATURE:
<223> OTHER INFORMATION: VH

<400> SEQUENCE: 368

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Glu Ser Tyr Tyr Asp Ser Ser Gly Tyr Thr Thr Trp Gly Gln
100 105 110

Gly Thr Leu Val Thr Val Ser Ser
115 120

<210> SEQ ID NO 369
<211> LENGTH: 111
<212> TYPE: PRT
<213> ORGANISM: Artificial Sequence
<220> FEATURE:
<223> OTHER INFORMATION: VL

<400> SEQUENCE: 369

Gln Ser Val Leu Thr Gln Pro Pro Ser Val Ser Gly Ala Pro Gly Gln
1 5 10 15

Arg Val Thr Ile Ser Cys Thr Gly Ser Ser Ser Asn Ile Gly Ala Gly
20 25 30

Tyr Asp Val His Trp Tyr Gln Gln Leu Pro Gly Thr Ala Pro Lys Leu
35 40 45

Leu Ile Tyr Gly Asn Ser Asn Arg Pro Ser Gly Val Pro Asp Arg Phe
50 55 60

Ser Gly Ser Lys Ser Gly Thr Ser Ala Ser Leu Ala Ile Thr Gly Leu
65 70 75 80

Gln Ala Glu Asp Glu Ala Asp Tyr Tyr Cys Gln Ser Tyr Asp Ser Ser
85 90 95

Leu Ser Gly Tyr Val Phe Gly Thr Gly Thr Lys Leu Thr Val Leu
100 105 110

<210> SEQ ID NO 370
<211> LENGTH: 127
<212> TYPE: PRT
<213> ORGANISM: Artificial Sequence
<220> FEATURE:
<223> OTHER INFORMATION: VH

<400> SEQUENCE: 370

Gln Val Gln Leu Val Gln Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Ala Pro Gly Lys Gly Leu Glu Trp Val
35 40 45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Ala Gln Tyr Tyr Tyr Asp Ser Ser Gly Ser Tyr Val Gly Glu
            100                 105                 110

Ser Phe Asp Tyr Trp Gly Gln Gly Thr Leu Val Thr Val Ser Ser
        115                 120                 125

<210> SEQ ID NO 371
<211> LENGTH: 106
<212> TYPE: PRT
<213> ORGANISM: Artificial Sequence
<220> FEATURE:
<223> OTHER INFORMATION: VL

<400> SEQUENCE: 371

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Thr
                85                  90                  95

Phe Gly Gln Gly Thr Lys Val Glu Ile Lys
            100                 105

<210> SEQ ID NO 372
<211> LENGTH: 120
<212> TYPE: PRT
<213> ORGANISM: Artificial Sequence
<220> FEATURE:
<223> OTHER INFORMATION: VH

<400> SEQUENCE: 372

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Tyr Tyr Gly Pro Gly Gly Met Asp Val Trp Gly Gln
            100                 105                 110

Gly Thr Leu Val Thr Val Ser Ser
        115                 120

<210> SEQ ID NO 373
<211> LENGTH: 111
<212> TYPE: PRT
<213> ORGANISM: Artificial Sequence
<220> FEATURE:
<223> OTHER INFORMATION: VL

<400> SEQUENCE: 373

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Gly Thr Lys Leu Thr Val Leu
            100                 105                 110
```

<210> SEQ ID NO 374
<211> LENGTH: 122
<212> TYPE: PRT
<213> ORGANISM: Artificial Sequence
<220> FEATURE:
<223> OTHER INFORMATION: VH

<400> SEQUENCE: 374

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Ile Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Glu Val Ser Ser Trp Tyr Glu Asn Trp Phe Asp Pro Trp
            100                 105                 110

Gly Gln Gly Thr Leu Val Thr Val Ser Ser
        115                 120
```

<210> SEQ ID NO 375
<211> LENGTH: 107
<212> TYPE: PRT
<213> ORGANISM: Artificial Sequence
<220> FEATURE:
<223> OTHER INFORMATION: VL

<400> SEQUENCE: 375

```
Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Arg Leu Glu Ile Lys
            100                 105


<210> SEQ ID NO 376
<211> LENGTH: 117
<212> TYPE: PRT
<213> ORGANISM: Artificial Sequence
<220> FEATURE:
<223> OTHER INFORMATION: VH

<400> SEQUENCE: 376

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Gly Val Val Met Asp Tyr Trp Gly Gln Gly Thr Leu
            100                 105                 110

Val Thr Val Ser Ser
        115


<210> SEQ ID NO 377
<211> LENGTH: 110
<212> TYPE: PRT
<213> ORGANISM: Artificial Sequence
<220> FEATURE:
<223> OTHER INFORMATION: VL

<400> SEQUENCE: 377

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95
```

```
Ser Thr Leu Val Phe Gly Gly Gly Thr Lys Val Thr Val Leu
            100                 105                 110


<210> SEQ ID NO 378
<211> LENGTH: 122
<212> TYPE: PRT
<213> ORGANISM: Artificial Sequence
<220> FEATURE:
<223> OTHER INFORMATION: VH

<400> SEQUENCE: 378

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Ala Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Gly Met Val Gln Gly Ala Arg Asn Trp Phe Asp Pro Trp
            100                 105                 110

Gly Gln Gly Thr Thr Val Thr Val Ser Ser
        115                 120


<210> SEQ ID NO 379
<211> LENGTH: 107
<212> TYPE: PRT
<213> ORGANISM: Artificial Sequence
<220> FEATURE:
<223> OTHER INFORMATION: VL

<400> SEQUENCE: 379

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105


<210> SEQ ID NO 380
<211> LENGTH: 119
<212> TYPE: PRT
<213> ORGANISM: Artificial Sequence
<220> FEATURE:
<223> OTHER INFORMATION: VH

<400> SEQUENCE: 380
```

```
Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Arg Val Ser Asp Gly Arg Phe Asp Tyr Trp Gly Gln Gly
            100                 105                 110

Thr Leu Val Thr Val Ser Ser
        115
```

<210> SEQ ID NO 381
<211> LENGTH: 112
<212> TYPE: PRT
<213> ORGANISM: Artificial Sequence
<220> FEATURE:
<223> OTHER INFORMATION: VL

<400> SEQUENCE: 381

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Thr Phe Gly Gly Gly Thr Lys Leu Glu Ile Lys
            100                 105                 110
```

<210> SEQ ID NO 382
<211> LENGTH: 115
<212> TYPE: PRT
<213> ORGANISM: Artificial Sequence
<220> FEATURE:
<223> OTHER INFORMATION: VH

<400> SEQUENCE: 382

```
Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Val Ser
65                  70                  75                  80
```

```
Leu Gln Met Ser Ser Leu Arg Ala Asp Asp Thr Ala Ile Tyr Tyr Cys
                85                  90                  95

Val Lys Asp Thr Ile Leu Ile Asp Trp Gly Gln Gly Thr Leu Val Thr
            100                 105                 110

Val Ser Ser
        115


<210> SEQ ID NO 383
<211> LENGTH: 112
<212> TYPE: PRT
<213> ORGANISM: Artificial Sequence
<220> FEATURE:
<223> OTHER INFORMATION: VL

<400> SEQUENCE: 383

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Gln Thr Pro Ile Thr Phe Gly Gln Gly Thr Arg Leu Glu Ile Lys
            100                 105                 110


<210> SEQ ID NO 384
<211> LENGTH: 124
<212> TYPE: PRT
<213> ORGANISM: Artificial Sequence
<220> FEATURE:
<223> OTHER INFORMATION: VH

<400> SEQUENCE: 384

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Tyr Cys
                85                  90                  95

Ala Arg Asp Val His His Pro Asp Tyr Gly Gly Asn Ser Ala Phe Asp
            100                 105                 110

Tyr Trp Gly Gln Gly Thr Leu Val Thr Val Ser Ser
        115                 120


<210> SEQ ID NO 385
<211> LENGTH: 107
<212> TYPE: PRT
```

<213> ORGANISM: Artificial Sequence
<220> FEATURE:
<223> OTHER INFORMATION: VL

<400> SEQUENCE: 385

Asp Ile Val Met Thr Gln Ser Pro Ser Ser Leu Ser Ala Ser Val Gly
1 5 10 15

Asp Arg Val Thr Ile Thr Cys Gln Ala Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Asp Ala Ser Asn Leu Glu Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Tyr Asp Asn Leu Pro Leu
85 90 95

Thr Phe Gly Gly Gly Thr Lys Leu Glu Ile Lys
100 105

<210> SEQ ID NO 386
<211> LENGTH: 122
<212> TYPE: PRT
<213> ORGANISM: Artificial Sequence
<220> FEATURE:
<223> OTHER INFORMATION: VH

<400> SEQUENCE: 386

Glu Val Gln Leu Leu Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Ala Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Arg Tyr Gly Asp Tyr Asp Gly Ser Ala Phe Asp Ile Trp
100 105 110

Gly Gln Gly Thr Met Val Thr Val Ser Ser
115 120

<210> SEQ ID NO 387
<211> LENGTH: 107
<212> TYPE: PRT
<213> ORGANISM: Artificial Sequence
<220> FEATURE:
<223> OTHER INFORMATION: VL

<400> SEQUENCE: 387

Asp Ile Val Met Thr Gln Ser Pro Ser Ser Leu Ser Ala Ser Val Gly
1 5 10 15

Asp Arg Val Thr Ile Thr Cys Gln Ala Ser Gln Asp Ile Ser Asn Tyr
20 25 30

Leu Asn Trp Tyr Gln Gln Lys Pro Gly Lys Ala Pro Lys Leu Leu Ile
35 40 45

```
Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Gly Gly Thr Arg Leu Glu Ile Lys
            100                 105


<210> SEQ ID NO 388
<211> LENGTH: 118
<212> TYPE: PRT
<213> ORGANISM: Artificial Sequence
<220> FEATURE:
<223> OTHER INFORMATION: VH

<400> SEQUENCE: 388

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Gly Gly Asp Ser Asp Phe Asp Tyr Trp Gly Gln Gly Thr
            100                 105                 110

Leu Val Thr Val Ser Ser
        115


<210> SEQ ID NO 389
<211> LENGTH: 107
<212> TYPE: PRT
<213> ORGANISM: Artificial Sequence
<220> FEATURE:
<223> OTHER INFORMATION: VL

<400> SEQUENCE: 389

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Val
                85                  90                  95

Thr Phe Gly Gly Gly Thr Lys Val Asp Ile Lys
            100                 105
```

<210> SEQ ID NO 390
<211> LENGTH: 122
<212> TYPE: PRT
<213> ORGANISM: Artificial Sequence
<220> FEATURE:
<223> OTHER INFORMATION: VH

<400> SEQUENCE: 390

```
Gln Val Gln Leu Val Gln Ser Gly Ala Glu Val Lys Lys Pro Gly Thr
1               5                   10                  15

Thr Val Lys Ile Ser Cys Lys Val Ser Gly Tyr Ser Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Leu Tyr Ala Glu Lys Phe
    50                  55                  60

Gln Gly Arg Val Thr Ile Thr Val Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Ala Glu Pro Gln Met Val Gln Gly Pro Ser Pro Pro Asp Tyr Trp
            100                 105                 110

Gly Gln Gly Thr Leu Val Thr Val Ser Ser
        115                 120
```

<210> SEQ ID NO 391
<211> LENGTH: 110
<212> TYPE: PRT
<213> ORGANISM: Artificial Sequence
<220> FEATURE:
<223> OTHER INFORMATION: VL

<400> SEQUENCE: 391

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Ser Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Leu Phe Gly Gly Gly Thr Lys Leu Thr Val Leu
            100                 105                 110
```

<210> SEQ ID NO 392
<211> LENGTH: 117
<212> TYPE: PRT
<213> ORGANISM: Artificial Sequence
<220> FEATURE:
<223> OTHER INFORMATION: VH

<400> SEQUENCE: 392

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30
```

```
Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Leu Tyr Gly Met Asp Val Trp Gly Gln Gly Thr Leu
            100                 105                 110

Val Thr Val Ser Ser
        115


<210> SEQ ID NO 393
<211> LENGTH: 111
<212> TYPE: PRT
<213> ORGANISM: Artificial Sequence
<220> FEATURE:
<223> OTHER INFORMATION: VL

<400> SEQUENCE: 393

Gln Ser Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Asn Tyr
            20                  25                  30

Asn Tyr Val Ser Trp Phe Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ala Ser Tyr Ala Asp Ser
                85                  90                  95

Asn Asn Leu Tyr Val Phe Gly Thr Gly Thr Lys Leu Thr Val Leu
            100                 105                 110


<210> SEQ ID NO 394
<211> LENGTH: 126
<212> TYPE: PRT
<213> ORGANISM: Artificial Sequence
<220> FEATURE:
<223> OTHER INFORMATION: VH

<400> SEQUENCE: 394

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ser Tyr Tyr Asp Ser Ser Gly Tyr Tyr Tyr Ala Asp Ala
```

```
            100                 105                 110

Phe Asp Ile Trp Gly Gln Gly Thr Met Val Thr Val Ser Ser
        115                 120                 125


<210> SEQ ID NO 395
<211> LENGTH: 112
<212> TYPE: PRT
<213> ORGANISM: Artificial Sequence
<220> FEATURE:
<223> OTHER INFORMATION: VL

<400> SEQUENCE: 395

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Asp Val Val Phe Gly Gly Gly Thr Lys Leu Thr Val Leu
            100                 105                 110


<210> SEQ ID NO 396
<211> LENGTH: 121
<212> TYPE: PRT
<213> ORGANISM: Artificial Sequence
<220> FEATURE:
<223> OTHER INFORMATION: VH

<400> SEQUENCE: 396

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asn Val Pro Gly Asp Tyr Glu Val Gly Phe Asp Tyr Trp Gly
            100                 105                 110

Gln Gly Thr Leu Val Thr Val Ser Ser
        115                 120


<210> SEQ ID NO 397
<211> LENGTH: 111
<212> TYPE: PRT
<213> ORGANISM: Artificial Sequence
<220> FEATURE:
<223> OTHER INFORMATION: VL

<400> SEQUENCE: 397
```

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Ala Val Val Phe Gly Gly Gly Thr Lys Leu Thr Val Leu
            100                 105                 110


<210> SEQ ID NO 398
<211> LENGTH: 122
<212> TYPE: PRT
<213> ORGANISM: Artificial Sequence
<220> FEATURE:
<223> OTHER INFORMATION: VH

<400> SEQUENCE: 398

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Thr Thr Trp Gly Gly Ser Tyr Pro Tyr Phe Asp Tyr Trp
            100                 105                 110

Gly Gln Gly Thr Leu Val Thr Val Ser Ser
        115                 120


<210> SEQ ID NO 399
<211> LENGTH: 108
<212> TYPE: PRT
<213> ORGANISM: Artificial Sequence
<220> FEATURE:
<223> OTHER INFORMATION: VL

<400> SEQUENCE: 399

Asp Ile Gln Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
```

```
65                  70                  75                  80

Asp Asp Phe Ala Thr Tyr Tyr Cys Gln Gln Tyr Asn Ser Tyr Ser Pro
                85                  90                  95

Leu Ala Phe Gly Gly Gly Thr Lys Leu Glu Ile Lys
            100                 105


<210> SEQ ID NO 400
<211> LENGTH: 119
<212> TYPE: PRT
<213> ORGANISM: Artificial Sequence
<220> FEATURE:
<223> OTHER INFORMATION: VH

<400> SEQUENCE: 400

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Ser Ser Tyr Thr Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Ser Thr Val Thr Arg Ala Phe Asp Ile Trp Gly Gln Gly
            100                 105                 110

Thr Met Val Thr Val Ser Ser
        115


<210> SEQ ID NO 401
<211> LENGTH: 107
<212> TYPE: PRT
<213> ORGANISM: Artificial Sequence
<220> FEATURE:
<223> OTHER INFORMATION: VL

<400> SEQUENCE: 401

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
                85                  90                  95

Thr Phe Gly Gln Gly Thr Lys Leu Glu Ile Lys
            100                 105


<210> SEQ ID NO 402
<211> LENGTH: 118
<212> TYPE: PRT
<213> ORGANISM: Artificial Sequence
<220> FEATURE:
```

<223> OTHER INFORMATION: VH

<400> SEQUENCE: 402

Gln Val Gln Leu Val Gln Ser Gly Gly Gly Val Val Gln Pro Gly Arg
1 5 10 15

Ser Gln Arg Leu Ser Cys Ala Ala Ser Gly Phe Thr Phe Ser Asn Ala
20 25 30

Trp Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Ala Asn Glu Gly Gly Asp Ala Phe Asp Ile Trp Gly Gln Gly Thr
100 105 110

Met Val Thr Val Ser Ser
115

<210> SEQ ID NO 403
<211> LENGTH: 112
<212> TYPE: PRT
<213> ORGANISM: Artificial Sequence
<220> FEATURE:
<223> OTHER INFORMATION: VL

<400> SEQUENCE: 403

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val Tyr Ser
20 25 30

Asp Gly Asn Thr Tyr Leu Asn Trp Phe Gln Gln Arg Pro Gly Gln Ser
35 40 45

Pro Arg Arg Leu Ile Tyr Lys Val Ser Asn Arg Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Gly
85 90 95

Thr His Trp Pro Leu Thr Phe Gly Gly Gly Thr Lys Leu Glu Ile Lys
100 105 110

<210> SEQ ID NO 404
<211> LENGTH: 119
<212> TYPE: PRT
<213> ORGANISM: Artificial Sequence
<220> FEATURE:
<223> OTHER INFORMATION: VH

<400> SEQUENCE: 404

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Asn Tyr
20 25 30

Ala Met His Trp Val Arg Gln Ala Pro Gly Lys Gly Leu Glu Trp Val
35 40 45

Ala Val Ile Ser Tyr Asp Gly Ser Lys Lys Tyr Tyr Ala Asp Ser Val

```
    50                  55                  60

Lys Gly Arg Phe Thr Ile Ser Arg Asp Asn Ser Lys Asn Thr Leu Tyr
65                  70                  75                  80

Leu Gln Met Asn Ser Leu Gly Ala Glu Asp Met Ala Val Tyr Tyr Cys
                85                  90                  95

Ala Arg Glu Asp Pro Arg Arg Gly Gly Ile Asp Tyr Trp Gly Gln Gly
            100                 105                 110

Thr Leu Val Thr Val Ser Ser
        115


<210> SEQ ID NO 405
<211> LENGTH: 111
<212> TYPE: PRT
<213> ORGANISM: Artificial Sequence
<220> FEATURE:
<223> OTHER INFORMATION: VL

<400> SEQUENCE: 405

Gln Ser Val Leu Thr Gln Pro Pro Pro Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu
            100                 105                 110


<210> SEQ ID NO 406
<211> LENGTH: 123
<212> TYPE: PRT
<213> ORGANISM: Artificial Sequence
<220> FEATURE:
<223> OTHER INFORMATION: VH

<400> SEQUENCE: 406

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Ser
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Gly Ser Gly Asn Arg Ile Pro Tyr Gly Met Asp Val
            100                 105                 110

Trp Gly Gln Gly Thr Met Val Thr Val Ser Ser
        115                 120
```

<210> SEQ ID NO 407
<211> LENGTH: 112
<212> TYPE: PRT
<213> ORGANISM: Artificial Sequence
<220> FEATURE:
<223> OTHER INFORMATION: VL

<400> SEQUENCE: 407

Gln Ser Val Leu Thr Gln Pro Pro Ser Val Ser Gly Ala Pro Gly Gln
1 5 10 15

Arg Val Thr Ile Ser Cys Thr Gly Ser Ser Ser Asn Ile Gly Ala Gly
20 25 30

Tyr Asp Val His Trp Tyr Gln Gln Leu Pro Gly Thr Ala Pro Lys Leu
35 40 45

Leu Ile Tyr Gly Asn Ser Asn Arg Pro Ser Gly Val Pro Asp Arg Phe
50 55 60

Ser Gly Ser Lys Ser Gly Thr Ser Ala Ser Leu Ala Ile Thr Gly Leu
65 70 75 80

Gln Ala Glu Asp Glu Ala Asp Tyr Tyr Cys Gln Ser Tyr Asp Ser Ser
85 90 95

Leu Ser Gly Pro Val Val Phe Gly Gly Gly Thr Gln Val Thr Val Leu
100 105 110

<210> SEQ ID NO 408
<211> LENGTH: 124
<212> TYPE: PRT
<213> ORGANISM: Artificial Sequence
<220> FEATURE:
<223> OTHER INFORMATION: VH

<400> SEQUENCE: 408

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Ala Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Ala Leu Tyr Asn Tyr Tyr Gly Ser Gly Ser His Phe Asp
100 105 110

Tyr Trp Gly Gln Gly Thr Leu Val Thr Val Ser Ser
115 120

<210> SEQ ID NO 409
<211> LENGTH: 107
<212> TYPE: PRT
<213> ORGANISM: Artificial Sequence
<220> FEATURE:
<223> OTHER INFORMATION: VL

<400> SEQUENCE: 409

Asp Ile Val Met Thr Gln Ser Pro Ser Ser Leu Ser Ala Ser Val Gly
1 5 10 15

Asp Arg Val Thr Ile Thr Cys Gln Ala Ser Gln Asp Ile Ser Asn Tyr 20 25 30

Leu Asn Trp Tyr Gln Gln Lys Pro Gly Lys Ala Pro Lys Leu Leu Ile
35 40 45

Tyr Asp Ala Ser Asn Leu Glu Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Tyr Asp Asn Leu Pro Leu
85 90 95

Thr Phe Gly Gly Gly Thr Arg Leu Glu Ile Lys
100 105

<210> SEQ ID NO 410
<211> LENGTH: 118
<212> TYPE: PRT
<213> ORGANISM: Artificial Sequence
<220> FEATURE:
<223> OTHER INFORMATION: VH

<400> SEQUENCE: 410

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Ala Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Lys Gly Asp Ser Ser Phe Asp Tyr Trp Gly Gln Gly Thr
100 105 110

Leu Val Thr Val Ser Ser
115

<210> SEQ ID NO 411
<211> LENGTH: 111
<212> TYPE: PRT
<213> ORGANISM: Artificial Sequence
<220> FEATURE:
<223> OTHER INFORMATION: VL

<400> SEQUENCE: 411

Gln Ser Val Leu Thr Gln Pro Pro Ser Val Ser Gly Ala Pro Gly Gln
1 5 10 15

Arg Val Thr Ile Ser Cys Thr Gly Ser Ser Ser Asn Ile Gly Ala Gly
20 25 30

Tyr Asp Val His Trp Tyr Gln Gln Leu Pro Gly Thr Ala Pro Lys Leu
35 40 45

Leu Ile Tyr Gly Asn Ser Asn Arg Pro Ser Gly Val Pro Asp Arg Phe
50 55 60

Ser Gly Ser Lys Ser Gly Thr Ser Ala Ser Leu Ala Ile Thr Gly Leu
65 70 75 80

Gln Ala Glu Asp Glu Ala Asp Tyr Tyr Cys Gln Ser Tyr Asp Ser Ser
85 90 95

```
Leu Ser Gly Val Val Phe Gly Gly Gly Thr Lys Val Thr Val Leu
            100                 105                 110


<210> SEQ ID NO 412
<211> LENGTH: 125
<212> TYPE: PRT
<213> ORGANISM: Artificial Sequence
<220> FEATURE:
<223> OTHER INFORMATION: VH

<400> SEQUENCE: 412

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Tyr Asp Ile Leu Thr Gly Tyr Gly Gly Thr Ala Leu
            100                 105                 110

Asp Tyr Trp Gly Gln Gly Thr Leu Val Thr Val Ser Ser
        115                 120                 125


<210> SEQ ID NO 413
<211> LENGTH: 110
<212> TYPE: PRT
<213> ORGANISM: Artificial Sequence
<220> FEATURE:
<223> OTHER INFORMATION: VL

<400> SEQUENCE: 413

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Glu Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Leu Val Phe Gly Gly Gly Thr Lys Leu Thr Val Leu
            100                 105                 110


<210> SEQ ID NO 414
<211> LENGTH: 117
<212> TYPE: PRT
<213> ORGANISM: Artificial Sequence
<220> FEATURE:
<223> OTHER INFORMATION: VH

<400> SEQUENCE: 414

Gln Val Gln Leu Val Gln Ser Gly Gly Gly Val Val Gln Pro Gly Arg
```

```
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Gly Glu Gly Val Asp Tyr Trp Gly Gln Gly Thr Leu
            100                 105                 110

Val Thr Val Ser Ser
        115


<210> SEQ ID NO 415
<211> LENGTH: 111
<212> TYPE: PRT
<213> ORGANISM: Artificial Sequence
<220> FEATURE:
<223> OTHER INFORMATION: VL

<400> SEQUENCE: 415

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Leu Thr Val Leu
            100                 105                 110


<210> SEQ ID NO 416
<211> LENGTH: 124
<212> TYPE: PRT
<213> ORGANISM: Artificial Sequence
<220> FEATURE:
<223> OTHER INFORMATION: VH

<400> SEQUENCE: 416

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Ala Glu Ser Ala Tyr Ser Ser Ser Trp Ser Gly Leu Arg Phe Asp
            100                 105                 110

Pro Trp Gly Gln Gly Thr Leu Val Thr Val Ser Ser
        115                 120


<210> SEQ ID NO 417
<211> LENGTH: 111
<212> TYPE: PRT
<213> ORGANISM: Artificial Sequence
<220> FEATURE:
<223> OTHER INFORMATION: VL

<400> SEQUENCE: 417

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Leu Thr Val Leu
            100                 105                 110


<210> SEQ ID NO 418
<211> LENGTH: 121
<212> TYPE: PRT
<213> ORGANISM: Artificial Sequence
<220> FEATURE:
<223> OTHER INFORMATION: VH

<400> SEQUENCE: 418

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ala Val Ala Gly Gly Trp Tyr Phe Asp Tyr Trp Gly
            100                 105                 110

Gln Gly Thr Leu Val Thr Val Ser Ser
        115                 120


<210> SEQ ID NO 419
<211> LENGTH: 107
<212> TYPE: PRT
<213> ORGANISM: Artificial Sequence
```

<220> FEATURE:
<223> OTHER INFORMATION: VL

<400> SEQUENCE: 419

Asp Ile Val Met Thr Gln Ser Pro Ser Ser Val Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ala Asn Ser Phe Pro Pro
85 90 95

Thr Phe Gly Gln Gly Thr Lys Leu Glu Ile Lys
100 105

<210> SEQ ID NO 420
<211> LENGTH: 118
<212> TYPE: PRT
<213> ORGANISM: Artificial Sequence
<220> FEATURE:
<223> OTHER INFORMATION: VH

<400> SEQUENCE: 420

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Ala Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Gly Ser Tyr Phe Gly Phe Asp Tyr Trp Gly Gln Gly Thr
100 105 110

Leu Val Thr Val Ser Ser
115

<210> SEQ ID NO 421
<211> LENGTH: 112
<212> TYPE: PRT
<213> ORGANISM: Artificial Sequence
<220> FEATURE:
<223> OTHER INFORMATION: VL

<400> SEQUENCE: 421

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Tyr Leu Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro Leu Thr Phe Gly Gly Gly Thr Lys Leu Glu Ile Lys
100 105 110

<210> SEQ ID NO 422
<211> LENGTH: 118
<212> TYPE: PRT
<213> ORGANISM: Artificial Sequence
<220> FEATURE:
<223> OTHER INFORMATION: VH

<400> SEQUENCE: 422

Gln Val Gln Leu Gln Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Ala Met His Trp Val Arg Gln Ala Pro Gly Lys Gly Leu Glu Trp Val
35 40 45

Ala Val Ile Ser Tyr Asp Gly Ser Asn Lys Tyr Tyr Ala Gly Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Trp Arg Gly Val Tyr Phe Asp Tyr Trp Gly Gln Gly Thr
100 105 110

Leu Val Thr Val Ser Ser
115

<210> SEQ ID NO 423
<211> LENGTH: 110
<212> TYPE: PRT
<213> ORGANISM: Artificial Sequence
<220> FEATURE:
<223> OTHER INFORMATION: VL

<400> SEQUENCE: 423

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Tyr Val Ser Trp Tyr Gln Gln His Pro Gly Lys Ala Pro Lys Leu
35 40 45

Met Ile Tyr Glu Val Ser Asn Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Ser Ser Tyr Thr Ser Ser
85 90 95

Ser Thr Leu Val Phe Gly Gly Gly Thr Lys Leu Thr Val Leu
100 105 110

<210> SEQ ID NO 424

<211> LENGTH: 118
<212> TYPE: PRT
<213> ORGANISM: Artificial Sequence
<220> FEATURE:
<223> OTHER INFORMATION: VH

<400> SEQUENCE: 424

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Ser Trp Gly Val Val Gly Gly Met Asp Val Trp Gly Gln Gly Thr
            100                 105                 110

Leu Val Thr Val Ser Ser
        115
```

<210> SEQ ID NO 425
<211> LENGTH: 107
<212> TYPE: PRT
<213> ORGANISM: Artificial Sequence
<220> FEATURE:
<223> OTHER INFORMATION: VL

<400> SEQUENCE: 425

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Asp Ile Lys
            100                 105
```

<210> SEQ ID NO 426
<211> LENGTH: 117
<212> TYPE: PRT
<213> ORGANISM: Artificial Sequence
<220> FEATURE:
<223> OTHER INFORMATION: VH

<400> SEQUENCE: 426

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30
```

```
Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Ser Asp Ala Phe Asp Ile Trp Gly Gln Gly Thr Met
            100                 105                 110

Val Thr Val Ser Ser
        115


<210> SEQ ID NO 427
<211> LENGTH: 110
<212> TYPE: PRT
<213> ORGANISM: Artificial Sequence
<220> FEATURE:
<223> OTHER INFORMATION: VL

<400> SEQUENCE: 427

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Val Thr Val Leu
            100                 105                 110


<210> SEQ ID NO 428
<211> LENGTH: 117
<212> TYPE: PRT
<213> ORGANISM: Artificial Sequence
<220> FEATURE:
<223> OTHER INFORMATION: VH

<400> SEQUENCE: 428

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Trp Tyr Phe Asp Tyr Trp Gly Gln Gly Thr Leu
            100                 105                 110
```

```
Val Thr Val Ser Ser
        115


<210> SEQ ID NO 429
<211> LENGTH: 107
<212> TYPE: PRT
<213> ORGANISM: Artificial Sequence
<220> FEATURE:
<223> OTHER INFORMATION: VL

<400> SEQUENCE: 429

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Trp
                85                  90                  95

Thr Phe Gly Gln Gly Thr Lys Leu Glu Ile Lys
            100                 105


<210> SEQ ID NO 430
<211> LENGTH: 115
<212> TYPE: PRT
<213> ORGANISM: Artificial Sequence
<220> FEATURE:
<223> OTHER INFORMATION: VH

<400> SEQUENCE: 430

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Tyr Gly Asp Tyr Trp Gly Gln Gly Thr Leu Val Thr
            100                 105                 110

Val Ser Ser
        115


<210> SEQ ID NO 431
<211> LENGTH: 109
<212> TYPE: PRT
<213> ORGANISM: Artificial Sequence
<220> FEATURE:
<223> OTHER INFORMATION: VL

<400> SEQUENCE: 431
```

```
Gln Ser Ala Leu Thr Gln Pro Ala Ser Val Ser Gly Ser Pro Gly Gln
1               5                   10                  15

Ser Ile Thr Ile Pro Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Phe Ser Phe Gly Thr Gly Thr Lys Leu Thr Val Leu
            100                 105


<210> SEQ ID NO 432
<211> LENGTH: 121
<212> TYPE: PRT
<213> ORGANISM: Artificial Sequence
<220> FEATURE:
<223> OTHER INFORMATION: VH

<400> SEQUENCE: 432

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ser Ser Ser Gly Trp Ser Ser Tyr Phe Asp Tyr Trp Gly
            100                 105                 110

Gln Gly Thr Leu Val Thr Val Ser Ser
        115                 120


<210> SEQ ID NO 433
<211> LENGTH: 107
<212> TYPE: PRT
<213> ORGANISM: Artificial Sequence
<220> FEATURE:
<223> OTHER INFORMATION: VL

<400> SEQUENCE: 433

Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80
```

```
Glu Asp Ile Ala Thr Tyr Tyr Cys Gln Gln Tyr Asp Asn Leu Pro Leu
                85                  90                  95

Thr Phe Gly Gly Gly Thr Lys Val Glu Ile Lys
            100                 105
```

<210> SEQ ID NO 434
<211> LENGTH: 118
<212> TYPE: PRT
<213> ORGANISM: Artificial Sequence
<220> FEATURE:
<223> OTHER INFORMATION: VH

<400> SEQUENCE: 434

```
Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Met Thr Thr Ser Leu Gly Phe Asp Tyr Trp Gly Gln Gly Thr
            100                 105                 110

Leu Val Thr Val Ser Ser
        115
```

<210> SEQ ID NO 435
<211> LENGTH: 107
<212> TYPE: PRT
<213> ORGANISM: Artificial Sequence
<220> FEATURE:
<223> OTHER INFORMATION: VL

<400> SEQUENCE: 435

```
Asp Ile Gln Leu Thr Gln Ser Pro Ser Ser Val Ser Ala Ser Val Gly
1               5                   10                  15

Asp Lys Val Thr Ile Thr Cys Arg Ala Ser Gln Gly Ile Ser Asn Trp
            20                  25                  30

Leu Ala Trp Tyr Gln Leu Lys Pro Gly Lys Ala Pro Lys Leu Leu Val
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Cys Gln Gln Ala Asn Ser Leu Pro Leu
                85                  90                  95

Thr Phe Gly Gly Gly Thr Arg Leu Glu Ile Lys
            100                 105
```

<210> SEQ ID NO 436
<211> LENGTH: 118
<212> TYPE: PRT
<213> ORGANISM: Artificial Sequence
<220> FEATURE:
<223> OTHER INFORMATION: VH

<400> SEQUENCE: 436

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Arg Gly Gly Ser Ala Phe Asp Ile Trp Gly Gln Gly Thr
            100                 105                 110

Leu Val Thr Val Ser Ser
        115
```

<210> SEQ ID NO 437
<211> LENGTH: 112
<212> TYPE: PRT
<213> ORGANISM: Artificial Sequence
<220> FEATURE:
<223> OTHER INFORMATION: VL

<400> SEQUENCE: 437

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Asp Ile Lys
            100                 105                 110
```

<210> SEQ ID NO 438
<211> LENGTH: 6
<212> TYPE: PRT
<213> ORGANISM: Artificial Sequence
<220> FEATURE:
<223> OTHER INFORMATION: Linker

<400> SEQUENCE: 438

```
Gly Gly Ser Gly Gly Ser
1               5
```

<210> SEQ ID NO 439
<211> LENGTH: 5
<212> TYPE: PRT
<213> ORGANISM: Artificial Sequence
<220> FEATURE:
<223> OTHER INFORMATION: Linker

```
<400> SEQUENCE: 439

Ala Ala Ala Ala Ala
1               5
```